US012649799B2

(12) United States Patent
Furusako et al.

(10) Patent No.: US 12,649,799 B2
(45) Date of Patent: Jun. 9, 2026

(54) CROSSLINKED ALGINIC ACID

(71) Applicant: MOCHIDA PHARMACEUTICAL CO., LTD., Tokyo (JP)

(72) Inventors: Shoji Furusako, Tokyo (JP); Tomohiro Narumi, Tokyo (JP); Tsutomu Satoh, Tokyo (JP)

(73) Assignee: MOCHIDA PHARMACEUTICAL CO., LTD., Tokyo (JP)

(*) Notice: Subject to any disclaimer, the term of this patent is extended or adjusted under 35 U.S.C. 154(b) by 0 days.

(21) Appl. No.: 18/428,348

(22) Filed: Jan. 31, 2024

(65) Prior Publication Data

US 2024/0174772 A1 May 30, 2024

Related U.S. Application Data

(63) Continuation of application No. 17/119,681, filed on Dec. 11, 2020, now Pat. No. 11,932,708, which is a continuation-in-part of application No. PCT/JP2019/023478, filed on Jun. 13, 2019.

(30) Foreign Application Priority Data

Jun. 14, 2018 (JP) ................................ 2018-113767
Oct. 31, 2018 (JP) ................................ 2018-205668

(51) Int. Cl.

| | |
|---|---|
| ***C08B 37/00*** | (2006.01) |
| ***A61L 15/28*** | (2006.01) |
| ***A61L 26/00*** | (2006.01) |
| ***A61L 27/20*** | (2006.01) |
| ***C08J 3/24*** | (2006.01) |
| ***C12N 5/00*** | (2006.01) |

(52) U.S. Cl.

CPC .......... *C08B 37/0084* (2013.01); *A61L 15/28* (2013.01); *A61L 26/0023* (2013.01); *A61L 27/20* (2013.01); *C08J 3/24* (2013.01); *C12N 5/0068* (2013.01); *C08J 2305/04* (2013.01); *C12N 2533/74* (2013.01)

(58) Field of Classification Search

CPC .. C08B 37/0084; A61L 15/28; A61L 26/0023; A61L 27/20; C08J 3/24; C08J 2305/04; C12N 5/0068; C12N 2533/74
USPC ........................................................... 536/3
See application file for complete search history.

(56) References Cited

U.S. PATENT DOCUMENTS

| | | | |
|---|---|---|---|
| 5,144,016 A | 9/1992 | Skjak-Braek et al. | |
| 5,354,657 A | 10/1994 | Höltke et al. | |
| 8,133,515 B2 | 3/2012 | Boons et al. | |
| 10,487,103 B2 | 11/2019 | Kitade et al. | |
| 11,932,708 B2 * | 3/2024 | Furusako | C08L 5/04 |
| 12,312,574 B2 * | 5/2025 | Furusako | C12N 11/10 |
| 2007/0009579 A1 | 1/2007 | Sato | |
| 2010/0152423 A1 | 6/2010 | Song | |
| 2010/0297250 A1 | 11/2010 | Boons et al. | |
| 2012/0095203 A1 | 4/2012 | Bernardin | |
| 2012/0308650 A1 | 12/2012 | Vegas et al. | |
| 2013/0137763 A1 | 5/2013 | van Delft et al. | |
| 2014/0256831 A1 | 9/2014 | Tto et al. | |
| 2015/0125904 A1 | 5/2015 | Ting et al. | |
| 2016/0280723 A1 | 9/2016 | Zhang et al. | |
| 2018/0094017 A1 | 4/2018 | Kitade et al. | |
| 2019/0233878 A1 * | 8/2019 | Delaney | B01J 13/18 |

FOREIGN PATENT DOCUMENTS

| | | |
|---|---|---|
| CN | 102408496 A | 4/2012 |
| CN | 106140040 A | 11/2016 |
| CN | 105713106 A | 6/2018 |
| EP | 0 713 859 A2 | 5/1996 |
| JP | 1-215300 A | 8/1989 |
| JP | 5-105701 A | 4/1993 |
| JP | 9-87236 A | 3/1997 |
| JP | 2011-504507 A | 2/2011 |
| JP | 2013-525425 A | 6/2013 |
| WO | WO 89/10941 A1 | 11/1969 |

(Continued)

OTHER PUBLICATIONS

Uttamapinant et al. Fast, Cell-Compatible Click Chemistry with Copper-Chelating Azides for Biomolecular Labeling. Angew. Chem. Int. Ed. 2012, 51, 5852-5856. (Year: 2012).*

(Continued)

*Primary Examiner* — Yih-Horng Shiao

(74) *Attorney, Agent, or Firm* — Birch, Stewart, Kolasch & Birch, LLP

(57) ABSTRACT

The present invention provides alginic acid derivatives represented by formula (I) and formula (II), and a novel crosslinked alginic acid obtained by carrying out a Huisgen reaction using an alginic acid derivative of formula (I) and an alginic acid derivative of formula (II). There are thereby provided novel alginic acid derivatives and a novel cross-linked alginic acid.

(I)

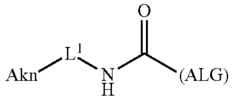

(II)

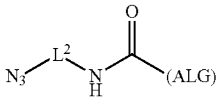

18 Claims, 9 Drawing Sheets

(56) References Cited

FOREIGN PATENT DOCUMENTS

| | | | |
|---|---|---|---|
| WO | WO 2005/026214 | A1 | 3/2005 |
| WO | WO 2008/031525 | A1 | 3/2008 |
| WO | WO 2008/071058 | A1 | 6/2008 |
| WO | WO 2009/073437 | A1 | 6/2009 |
| WO | WO 2011/028031 | A2 | 3/2011 |
| WO | WO 2012/165462 | A1 | 12/2012 |
| WO | WO 2013/181697 | A1 | 12/2013 |
| WO | WO 2014/111344 | A1 | 7/2014 |
| WO | WO 2015/020206 | A1 | 2/2015 |
| WO | WO 2016/152980 | A1 | 9/2016 |
| WO | WO 2017/165389 | A2 | 9/2017 |

OTHER PUBLICATIONS

Clark et al. In situ crosslinked hydrogels formed using Cu(I)-free Huisgen cycloaddition reaction. Polym Int 2009; 58: 1190-1195. (Year: 2009).*

Chinese Ofice Action and Search Report for Chinese Application No. 201980038664.8. dated May 25, 2022, with English Translation.

Desai et al., "Versatile click alginate hydrogels crosslinked via tetrazine-norbornene chemistry", Biomaterials, 2015, vol. 50, pp. 30-37.

Dommerholt et al., "Highly accelerated inverse electron-demand cycloaddition of electron-deficient azides with aliphatic cyclooctynes." Nature Communications, 2014, pp. 1-7.

Evans et al., "Copper-free click—a promising tool for pre-targeted PET imaging", Chemical Communications (Cambridge, United Kingdom), 2012, vol. 48, No. 7, pp. 991-993.

Extended European Search Report for European Application No. 19819436.7, dated Feb. 16, 2022.

Indian Office Action for Indian Application No. 202017053492, dated Dec. 13, 2022, with English translation.

International Search Report (PCT/ISA/210) issued in PCT/JP2019/023478 mailed on Sep. 3, 2019.

Japanese Office Action for Japanese Application No. 2020-211438, dated Jan. 18, 2022, with English translation.

Nagahama et al., "Development of cell cross-linked hydrogels and quest of their characteristic functions", Polymer Preprints, Japan, 2017, vol. 66, No. 2, 3M04, Total 9 pages.

Nagahama et al., "Living functional hydrogels generated by bioorthogonal cross-linking reactions of azide-modified cells with alkyne-modified polymers", Nat. Commun., 2016, vol. 9, No. 1, p. 2195-, pp. 1-11.

Office Action issued Apr. 4, 2023, In Japanese Patent Application No. 2022-094133.

Rostovtsev et al., "A Stepwise Huisgen Cycloaddition Process: Copper(I)-Catalyzed Regioselective "Ligation" of Azides and Terminal Alkynes", Angew. Chem. Int. Ed. Engl., 2002, vol. 41, No. 14, pp. 2596-2599.

Tornøe et al., "Peptidotriazoles on Solid Phase: [1,2,3]-Triazoles by Regiospecific Copper(1)-Catalyzed 1,3-Dipolar Cycloadditions of Terminal Alkynes to Azides", J. Org. Chem., 2002, vol. 67, No. 9, pp. 3057-3064.

Written Opinion (PCT/ISA/237) issued in PCT/JP2019/023478 mailed on Sep. 3, 2019.

Japanese Office Action for Japanese Application No. 2023-147261, dated Aug. 27, 2024, with an English translation.

Japanese Office Action for Japanese Application No. 2023-147261, dated Jan. 7, 2025, with an English translation.

Chinese Office Action and Search Report for Chinese Application No. 202310971621.3, dated Mar. 18, 2025, with English translation.

Canadian Office Action for Canadian Application No. 3,103,227, dated Sep. 25, 2025.

Chinese Office Action for Chinese Application No. 202310971621.3, dated Aug. 11, 2025, with English translation.

Gattás-Asfura et al., "Chemoselective cross-linking and functionalization of alginate via Staudinger ligation", Biomacromolecules, 10(11), Nov. 9, 2009, pp. 3122-3129 (23 pages total).

Office Action issued in Indian Patent Application No. 202318077595, mailed Mar. 18, 2026.

Office Action issued in Indian Patent Application No. 202318077596, mailed Mar. 19, 2026.

* cited by examiner

CROSSLINKED ALGINIC ACID

CROSS REFERENCE TO RELATED APPLICATIONS

This application is a Continuation of Ser. No. 17/119,681, filed on Dec. 11, 2020, which is a continuation-in-part of PCT International Application No. PCT/JP2019/023478, filed on Jun. 13, 2019, which claims priority under 35 U.S.C. 119(a) to Patent Application No. 2018-113767, filed in Japan on Jun. 14, 2018, and Patent Application No. 2018-205668, filed in Japan on Oct. 31, 2018, all of which are hereby expressly incorporated by reference into the present application.

TECHNICAL FIELD

The present invention relates to novel alginic acid derivatives, to a novel crosslinked alginic acid, and to methods of manufacturing these.

BACKGROUND ART

Alginic acid, a high-molecular-weight acidic polysaccharide molecule that is extracted from the cell walls of natural brown algae such as *Lessonia, Macrocystis, Laminaria, Ascophyllum, Durvillea, Ecklonia cava, Eisenia bicyclis* and *Saccharina japonica*, is a linear heteropolymer of two kinds of uronic acid, β-D-mannuronate (M component) and its C-5 epimer α-L-guluronate (G component), connected by 1-4 linkages. Specifically, in terms of its chemical structure it is a block copolymer made up of homopolymer blocks of mannuronic acid (MM), homopolymer blocks of guluronic acid (GG), and randomly arranged blocks of mannuronic acid and guluronic acid (MG), in complex combination with arbitrary permutations and proportions. Alginic acid is widely used in such fields as medicine, biotechnology, cosmetics, fibers, paper and foodstuffs.

While monovalent alkali metal salts of alginic acid (such as sodium alginate) are water soluble, divalent alkali earth metal salts of alginic acid (such as calcium alginate) have the property of being gelled (insolubilized) by crosslinking with metal ions, and these properties have been used to modify or mold these into suitable forms for various applications.

To investigate ways of modifying or molding polysaccharides (such as hyaluronic acid, chondroitin sulfate and alginic acid) into various materials and improving their physical properties (such as strength and swelling properties), much research has already been done into crosslinked polysaccharides crosslinked by covalent bonds.

Methods of obtaining crosslinked polysaccharides include (1) crosslinking methods using aldehyde crosslinking agents such as formaldehyde (Patent Literature 1: WO 2011/028031A), (2) self-crosslinking methods via carboxyl groups and hydroxyl groups in polysaccharides (Patent Literature 2: WO 1989/10941A), and (3) crosslinking methods using homo-bifunctional crosslinking agents (diepoxides, divinylsulfones, diamines, dihydrazines, etc.) or hetero-bifunctional crosslinking agents (epihalohydrins, etc.) (Patent Literature 3: WO 2009/073437A).

Other known methods include (4) methods of crosslinking by light exposure after introduction of a photoreactive group (such as cinnamic acid, substituted cinnamic acid, acrylic acid, maleic acid, fumaric acid, furyl acrylic acid, thiophen acrylic acid, cinnamylidene acetic acid, sorbic acid, thymine or coumarin) (Patent Literatures 4 and 5: WO 2005/026214A, and JP H 09-87236A) and (5) methods of crosslinking by disulfide bonds between polysaccharides having introduced thiol groups, and methods of crosslinking by a Michael addition reaction using a polysaccharide having an introduced thiol group and a polysaccharide having an introduced maleimide group (Patent Literature 6: WO 2008/071058A).

Another method of crosslinking by covalent binding between polysaccharides is (6) a method of crosslinking by a Huisgen reaction (1,3-dipolar cycloaddition reaction) using a polysaccharide having an introduced alkyne group and a polysaccharide having an introduced azide.

Crosslinked polysaccharides obtained by subjecting polysaccharides to a Huisgen reaction are disclosed in (i) WO 2008/031525A (Patent Literature 7), (ii), WO 2012/165462A (Patent Literature 8), (iii) WO 2015/020206A (Patent Literature 9) and (iv) CN 106140040A (Patent Literature 10).

However, (i) Patent Literature 7 relates to a crosslinked polysaccharide obtained by performing a Huisgen reaction in the presence of a copper catalyst on a chain-like alkyne group and azide group introduced via linkers into a first polysaccharide (hyaluronic acid) and a second polysaccharide selected from chondroitin, sulfated dermatan, alginic acid or its salt and the like, and does not disclose the novel crosslinked alginic acid described below.

Meanwhile, (ii) Patent Literature 8 relates to a crosslinked polysaccharide obtained using polysaccharides selected from hyaluronic acid, carboxymethyl dextran, cellulose derivatives and chitosan as first and second polysaccharides (the first and second polysaccharide may be the same or different) by performing a Huisgen reaction on a cyclic alkyne group and azide group introduced into the respective polysaccharides via linkers (by ester bonds between the polysaccharides and the linkers), and does not disclose the novel crosslinked alginic acid described below.

Furthermore, (iii) Patent Literature 9 relates to a crosslinked polysaccharide obtained using hyaluronic acid as a first polysaccharide and chondroitin sulfate as a second polysaccharide by performing a Huisgen reaction on a cyclic alkyne group and azide group introduced into the respective polysaccharides via linkers, and does not disclose the novel crosslinked alginic acid described below.

Moreover, (iv) Patent Literature 10 relates to a crosslinked polysaccharide obtained using chitosan as a first polysaccharide and sodium alginate as a second polysaccharide by performing a Huisgen reaction on a cyclic alkyne group and azide group introduced into the respective polysaccharides via linkers (by ester bonds between the polysaccharides and the linkers), and does not disclose the novel crosslinked alginic acid described below.

(v) Patent Literature 11 relates to a method of derivatizing a sugar by binding an 8-membered cycloalkyne group to the sugar, but the sugar in this case is a non-natural sugar (capsular saccharide from *Streptococcus agalactiae*) rather than alginic acid, and since the end of the 8-membered cycloalkyne group is also not amide bonded to a carboxyl group of the sugar, this differs from the novel alginic acid derivatives and manufacturing method described below.

(vi) Non Patent Literature 1 describes a branched alginic acid (bA1g-DBCO) having a cyclooctyne side chain introduced into the side chain, but this is obtained by reacting an aminated cyclooctyne (DBCO-PEG-amine) with a branched alginic acid (bA1g) synthesized from alginic acid and a branched polyethylene glycol (4-arm PEG-$NH_2$), and differs from the novel alginic acid derivatives described below both in structure and purpose.

CITATION LIST

Patent Literature

[Patent Literature 1] WO 2011/028031A
[Patent Literature 2] WO 1989/10941A
[Patent Literature 3] WO 2009/073437A
[Patent Literature 4] WO 2005/026214A
[Patent Literature 5] JP H 09-87236A
[Patent Literature 6] WO 2008/071058A
[Patent Literature 7] WO 2008/031525A
[Patent Literature 8] WO 2012/165462A
[Patent Literature 9] WO 2015-020206A
[Patent Literature 10] CN 106140040A
[Patent Literature 11] WO 2014/111344A Non Patent Literature

[Non Patent Literature 1] Nat. Commun. 9(1), pp. 2195-, 2018

SUMMARY OF INVENTION

Technical Problem

Under these circumstances, there is demand for novel alginic acid derivatives or a novel crosslinked alginic acid, and also for methods of manufacturing these.

Solution to Problem

As a result of earnest research aimed at solving these problems, the inventors discovered the novel alginic acid derivatives represented by formula (I) and formula (II). The inventors perfected the present invention after discovering that when a novel crosslinked alginic acid obtained by performing a Huisgen reaction on the novel alginic acid derivatives of formula (I) and formula (II) was used for being molded into a bead (dye-containing bead), namely one of crosslinked alginic acid structures, the bead was highly stable and could be used to prepare a gel having a permeability more suited to the purpose in comparison with conventional gels.

The novel alginic acid derivatives (formula (I) and formula (II)) provided here can be used in chemical crosslink formation for example, meaning that they have an introduced reactive group and a reactive group complementary to that reactive group which can be used in chemical crosslink formation.

This chemical crosslink formation is accomplished for example by crosslinking using a Huisgen reaction (1,3-dipolar cycloaddition reaction), and can be performed for example between the alginic acid derivatives of formula (I) and formula (II), or between the alginic acid derivative of formula (I) and another molecule having an azide group, or between the alginic acid derivative of formula (II) and another molecule having an alkyne group.

Because a Huisgen reaction between a terminal alkyne group and a terminal azide group normally requires heating at 100° C. or more, this reaction has not been suitable for chemical modification of biological molecules. However, reaction conditions have been found under which a cycloadduct (triazole ring) is formed with a yield of roughly 100% at room temperature when a copper catalyst (such as Cu(I)) is included in the reaction (Angew. Chem. Int. Ed. Engl., 14, pp. 2596-2599, 2002; J. Org. Chem., 9, pp. 3057-3064, 2002), allowing this reaction to be used for chemical modification of biological molecules.

However, the concern has been that when attempting to obtain a crosslinked alginic acid by a Huisgen reaction in the presence of a copper catalyst, a trace amount of the copper catalyst may remain in the crosslinked alginic acid, and copper-derived cytotoxicity may be expressed in the crosslinked alginic acid or crosslinked alginic acid structure.

In order to avoid copper-derived cytotoxity in the crosslinked alginic acid, a crosslinked alginic acid can be obtained by a Huisgen reaction that does not require a copper catalyst in a preferred embodiment. Specifically, such a reaction has been achieved without the need for a copper catalyst or high-temperature conditions of 100° ° C. or more by using a cyclooctyne derivative (high strained cyclic alkyne group) for the alkyne group introduced into the alginic acid derivative. Consequently, because the novel alginic acid of a preferred embodiment does not contain a copper catalyst, it is superior in that it does not cause copper-derived toxicity even when molded into a final formed product (crosslinked alginic acid structure).

As shown in the following embodiments, an alginic acid derivative of formula (I) or formula (II) comprising a cyclic alkyne group or azide group introduced via an amide bond and a divalent linker at any one or more carboxyl groups of alginic acid, a novel crosslinked alginic acid obtained by performing a Huisgen reaction (1,3-dipolar cycloaddition reaction) using the alginic acid derivatives of formula (I) and formula (II), and methods for manufacturing the above alginic acid derivatives and crosslinked alginic acid are provided here. For example, exemplary embodiments may be as shown in [1] to [17] below.

[1] An alginic acid derivative represented by formula (I) below [in formula (I), (ALG), $-L^1-$ and Akn are defined as in Embodiment 1 below], comprising a cyclic alkyne group (Akn) introduced via an amide bond and a divalent linker ($-L^1-$) at any one or more carboxyl groups of alginic acid:

[C1]

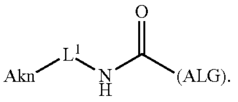

(I)

[2] The alginic acid derivative represented by formula (I) according to [1], wherein the introduction rate of the $Akn-L^1-NH_2$ group (in Akn and $-L^1-$ are defined as in Embodiment 1 below) is 0.1% to 30%.

[3] The alginic acid derivative represented by formula (I) according to [1], wherein the weight-average molecular weight as measured by gel filtration chromatography of the alginic acid derivative is 100,000 Da to 3,000,000 Da.

[4] An alginic acid derivative represented by formula (II) below [in formula (II), (ALG) and $-L^2-$ are defined as in Embodiment 4 below], comprising an azide group introduced via an amide bond and a divalent linker ($-L^2-$) at any one or more carboxyl groups of alginic acid:

[C2]

(II)

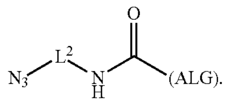

[5] The alginic acid derivative represented by formula (II) according to [4], wherein the introduction rate of the $N_3$-$L^2$-$NH_2$ group (in which -$L^2$- is defined as in Embodiment 4 below) is 0.1% to 30%.

[6] The alginic acid derivative represented by formula (II) according to [4], wherein the weight-average molecular weight as measured by gel filtration chromatography of the alginic acid derivative is 100,000 Da to 3,000,000 Da.

[7] A crosslinked alginic acid in which any carboxyl group of a first alginic acid and any carboxyl group of a second alginic acid are bound together via the following formula (III-L):

[C3]

(III-L)

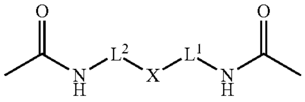

[in formula (III-L), the —CONH— and —NHCO— at either end represent amide bonds via any carboxyl group of alginic acid; and -$L^1$, -$L^2$- and X are defined as in Embodiment 7 below].

[8] A method of manufacturing a crosslinked alginic acid, comprising mixing an alginic acid derivative of formula (I) according to any one of [1] to [3] above with an alginic acid derivative of formula (II) according to any one of [4] to [6] above, and performing a Huisgen reaction to thereby obtain the crosslinked alginic acid of [7] above.

[8-1] A crosslinked alginic acid comprising as crosslinking both chemical crosslinking by triazole rings formed by a Huisgen reaction and ionic crosslinking partially formed by calcium ions.

[9] A crosslinked alginic acid structure obtained by mixing an alginic acid derivative of formula (I) according to any one of [1] to [3] above with an alginic acid derivative of formula (II) according to any one of [4] to [6] above to obtain a mixed solution of alginic acid derivatives, and dripping this solution into a calcium chloride solution.

[10] The crosslinked alginic acid structure according to [9] above, comprising as crosslinking both chemical crosslinking by triazole rings formed by a Huisgen reaction and ionic crosslinking partially formed by calcium ions.

[11] A method of manufacturing a crosslinked alginic acid structure, comprising mixing an alginic acid derivative of formula (I) according to any one of [1] to [3] above with an alginic acid derivative of formula (II) according to any one of [4] to [6] above to obtain a mixed solution of alginic acid derivatives, and dripping this solution into a calcium chloride solution to obtain a crosslinked alginic acid structure according to [9] or above.

[12] A crosslinked alginic acid structure according to [9] or above, in the form of a bead or a nearly spherical gel.

[13] A medical material containing a crosslinked alginic acid structure according to [9] or [10] above.

[14] The medical material according to [13] above, in the form of a bead or a nearly spherical gel.

[15] An alginic acid derivative according to any one of [1] to [6] above, a crosslinked alginic acid according to [7] or [8-1] above, and a crosslinked alginic acid structure according to any one of [9], [10] and [12] above, having biocompatibility.

[16] An amino compound represented by the following formula (AM-1):

[C4]

(AM-1)

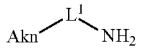

[in formula (AM-1), -$L^1$- and Akn are defined as in Embodiment 16 below], or a pharmaceutically acceptable salt thereof or a solvate of these.

[17] An amino compound represented by the following formula (AM-2):

[C5]

(AM-2)

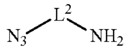

[in formula (AM-2), $L^2$ is defined as in Embodiment 17 below], or a pharmaceutically acceptable salt thereof or a solvate of these.

Effect of the Invention

The present invention provides novel alginic acid derivatives that can be used in chemical crosslink formation for example, as well as a novel crosslinked alginic acid and the like.

Preferably, the alginic acid derivatives have introduced reactive groups that do not exist in living bodies, and are expected to be safe for living organism, with no risk of ongoing crosslinking reactions with cells and other biological components even if unreacted groups remain. Moreover, the crosslinking reaction is preferably safe and easy to use because the reaction is completed at room temperature without the use of a metal catalyst.

The crosslinked alginic acid of some embodiments is chemically crosslinked by a Huisgen reaction (1,3-dipolar cycloaddition reaction). This chemical crosslinking can be used in combination with divalent metal ion crosslinking using a calcium ion for example, and preferably the reaction conditions are adjusted so that stability is improved in comparison with a non-crosslinked alginic acid or non-chemically crosslinked alginic acid (such as an alginic acid crosslinked with a calcium ion).

Moreover, preferably the gel properties of the crosslinked product can be adjusted to adjust the substance permeability.

The present invention provides at least one of the above effects.

DESCRIPTION OF EMBODIMENTS

Specific Embodiments

Figure 1:
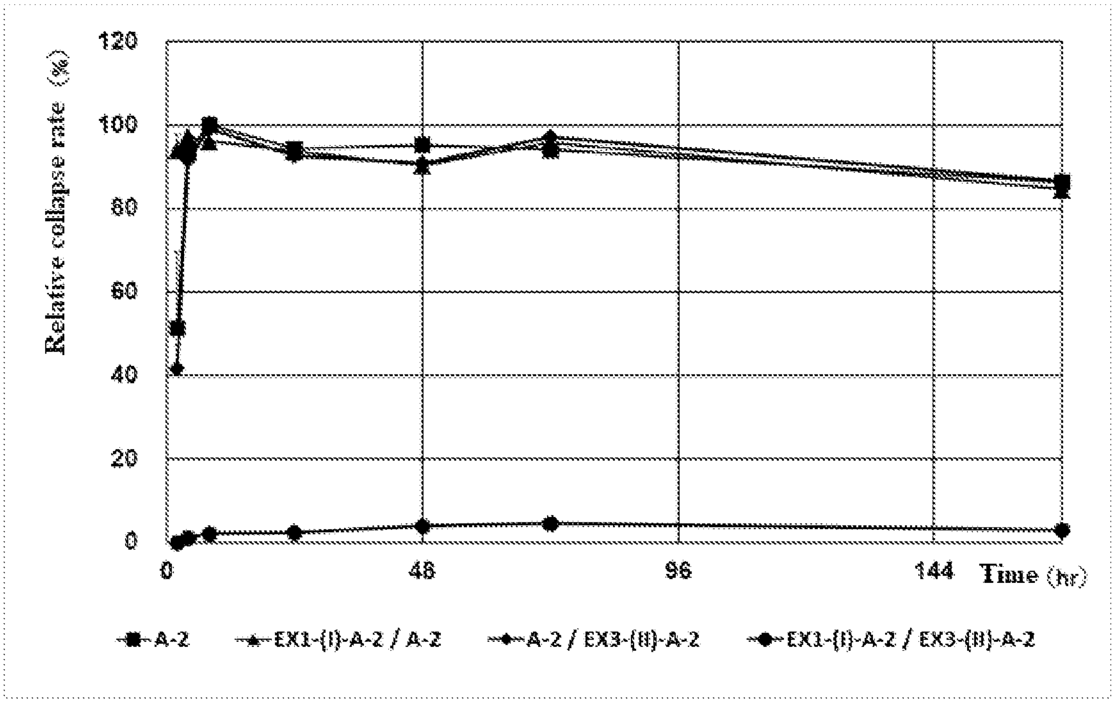
FIG. 1 shows an evaluation of the stability of gels of crosslinked alginic acid structures.

The following Embodiments [1] to may be included.

[1] Embodiment 1 is as follows: An alginic acid derivative represented by formula (I) below, comprising a cyclic alkyne group (Akn) introduced via an amide bond and a divalent linker ($-L^1-$) at any one or more carboxyl groups of alginic acid:

[C6]

(I)

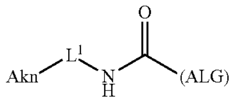

[in formula (I), (ALG) represents alginic acid; —NHCO— represents an amide bond via any carboxyl group of alginic acid; $-L^1-$ represents a divalent linker selected from the group consisting of the following partial structural formulae [excluding the parts outside the wavy lines at both ends of each formula]:

[C7]

(LN-1)

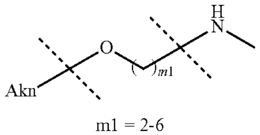

m1 = 2-6

-continued (LN-2)

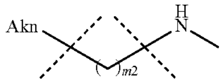

m2 = 1-6

(LN-3)

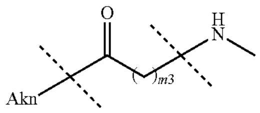

m3 = 1-6

(LN-4)

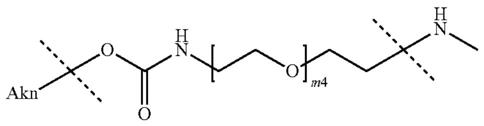

m4 = 1-6

(LN-5)

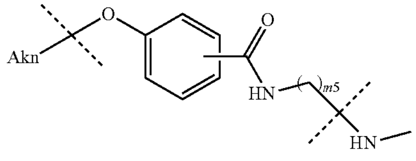

m5 = 2-6

(LN-6)

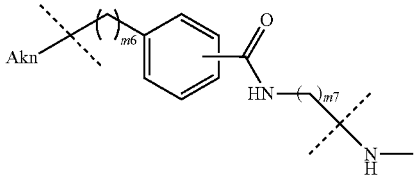

m6 = 1-6, m7 = 2-6

(LN-7)

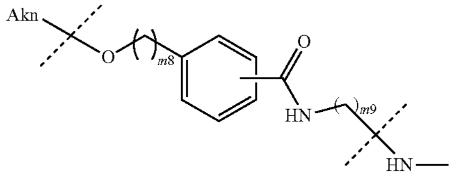

m8 = 1-6, m9 = 2-6

(LN-8)

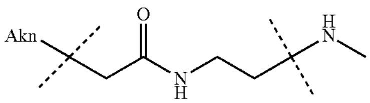

(LN-9)

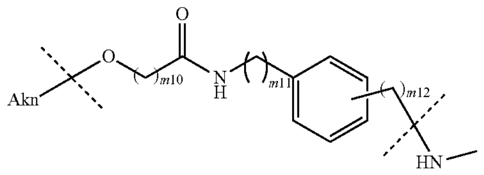

m10 = 1-4, m11 = 1-6, m12 = 1-6

-continued (LN-10)

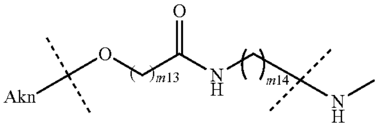

m13 = 1-4, m14 = 2~6

(LN-11)

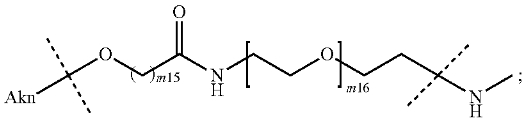

m15 = 1-4, m16 = 1-6 and Akn represents a cyclic alkyne group selected from the group consisting of the following partial structural formulae [excluding the part to the right of the wavy line in each formula]:

[C8]

(AK-1)

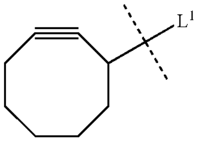

(AK-2)

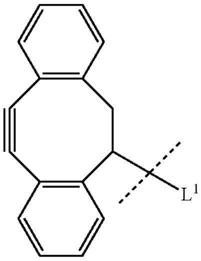

(AK-3)

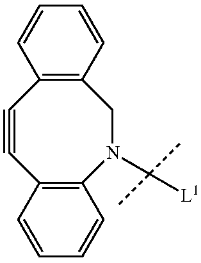

(AK-4)

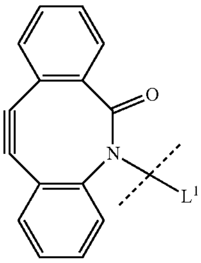

-continued (AK-5)

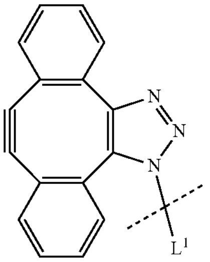

(AK-6)

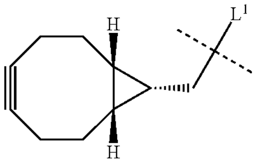

(AK-7)

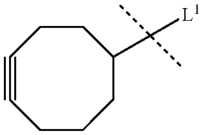

(AK-8)

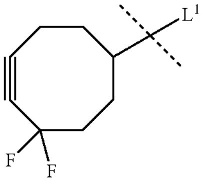

(AK-9)

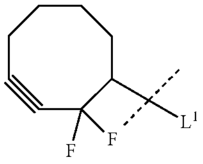

(AK-10)

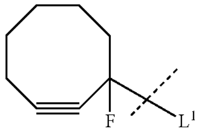

(AK-11)

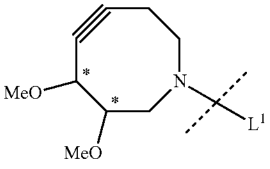

(AK-12)

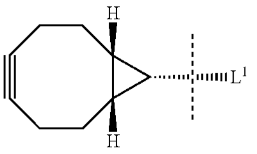

in which the asterisks represent chiral centers].

[1-1] In the alginic acid derivative of the formula (I) of the Embodiment [1], $-L^1-$ is preferably a divalent linker selected from the group consisting of the following partial structural formulae [excluding the parts outside the wavy lines at both ends of each formula]:

[C9]

(LN-1)

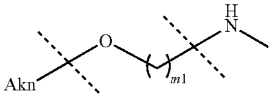

m1 = 2-6

(LN-2-1)

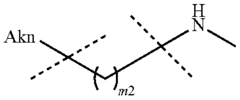

m2 = 2-6

(LN-3-1)

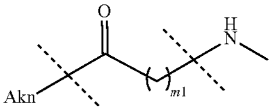

m3 = 2-6

(LN-4)

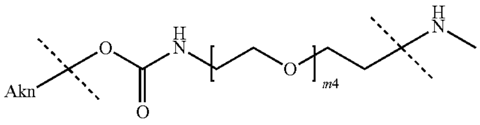

m4 = 1-6

(LN-5)

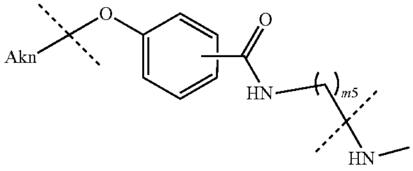

m5 = 2-6

(LN-6)

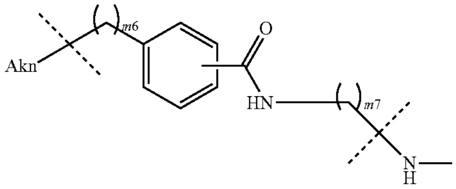

m6 = 1-6, m7 = 2-6

(LN-7)

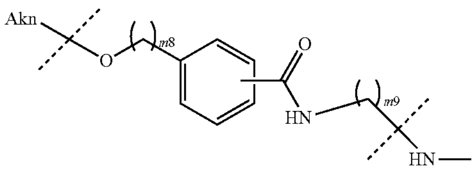

m8 = 1-6, m9 = 2-6 or more preferably a divalent linker selected from the group consisting of the following partial structural formulae [excluding the parts outside the wavy lines at both ends of each formula]:

[C10]

(LN-1)

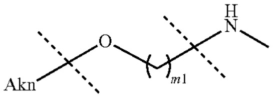

m1 = 2-6

(LN-2-1)

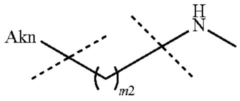

m2 = 2-6

(LN-3-1)

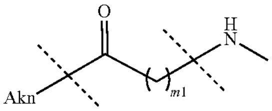

m3 = 2-6

(LN-4)

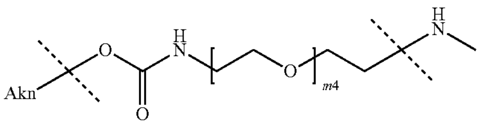

m4 = 1-6

(LN-5-p)

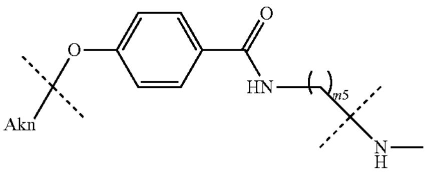

m5 = 2-6

(LN-6-p)

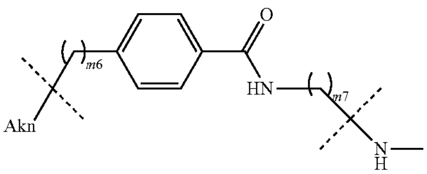

m6 = 1-6, m7 = 3-6

(LN-7-p)

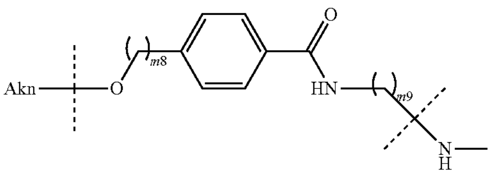

m8 = 1-6, m9 = 2-6 or still more preferably a divalent linker selected from the group consisting of the following partial structural formulae [excluding the parts outside the wavy lines at both ends of each formula]:

[C11]

(LN-3-a)

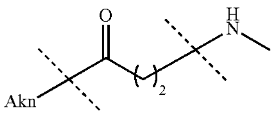

(LN-4-a)

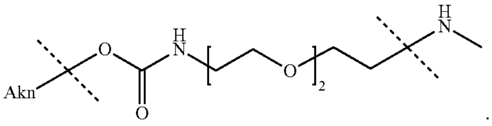

.

[1-2] In the alginic acid derivative of the formula (I) of the Embodiment [1], Akn is preferably a cyclic alkyne selected from the following partial structural formulae [excluding the part to the right of the wavy line in each formula]:

[C12]

(AK-1)

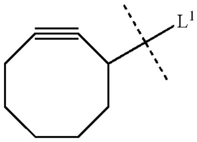

(AK-2)

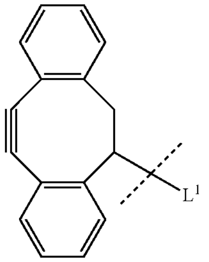

(AK-3)

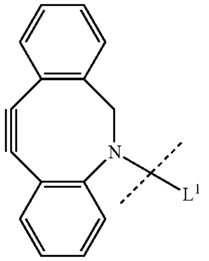

(AK-4)

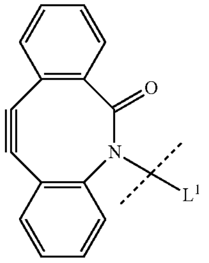

-continued (AK-5)

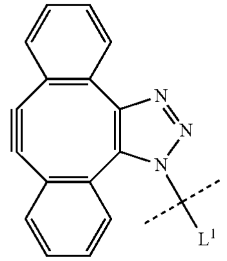

(AK-6)

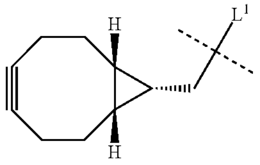

or more preferably a cyclic alkyne selected from the following partial structural formulae [excluding the part to the right of the wavy line in each formula]:

[C13]

(AK-3)

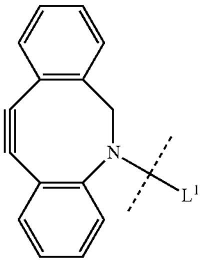

(AK-6)

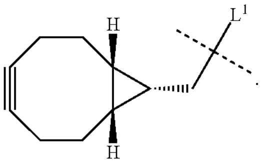

[1-3] In the alginic acid derivative of the formula (I) of the Embodiment [1], the combination of Akn and $-L^1-$ is preferably represented by a group selected from the group consisting of the following partial structural formulae [excluding the part to the right of the wavy line (imino group side) in each formula]:

[C14]

(OL-1)

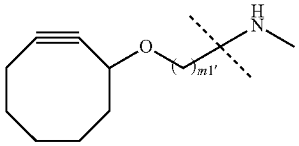

m1' = 3-6

-continued
(OL-2)
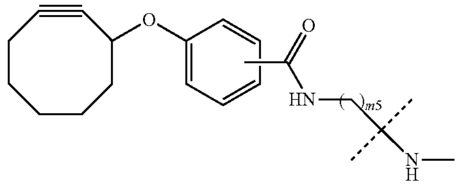
m5 = 2-6
(OL-3)
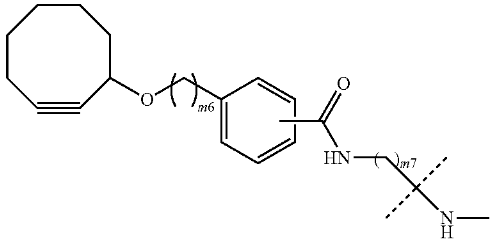
m6 = 1-6, m7 = 2-6
(OL-4)
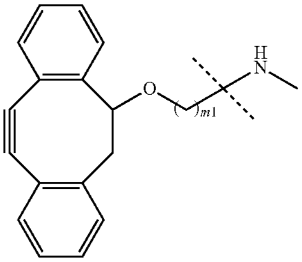
m1 = 2-6
(OL-5)
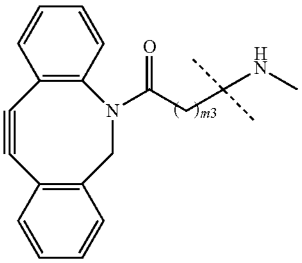
m3 = 2-6
(OL-6)
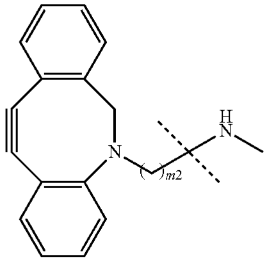
m2 = 2-6
-continued
(OL-7)
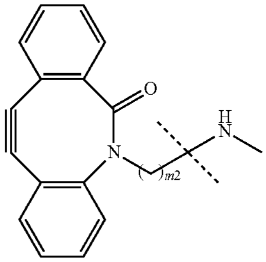
m2 = 2-6
(OL-8)
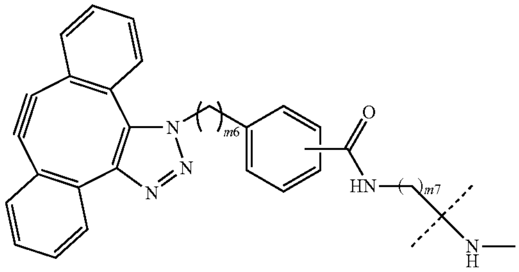
m6 = 1-6, m7 = 2-6
(OL-9)
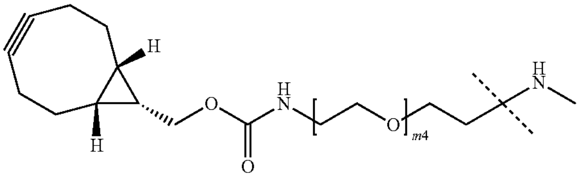
m4 = 1-6
[C15]
(OL-10)
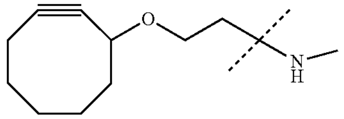
(OL-11)
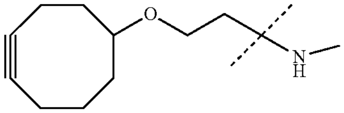
(OL-12)
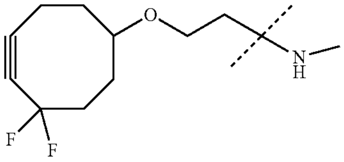
(OL-13)
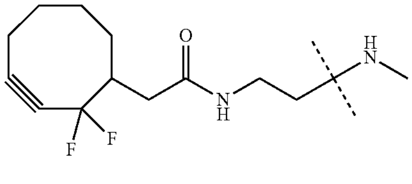

-continued
(OL-14)
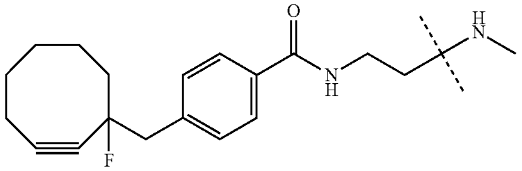
(OL-15)
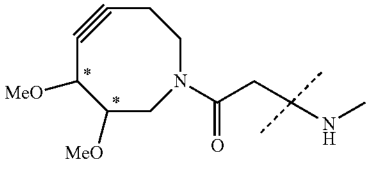
(OL-16)
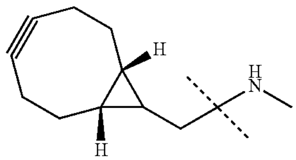
or more preferably represented by a group selected from the group consisting of the following partial structural formulae [excluding the part to the right of the wavy line (imino group side) in each formula]:
[C16]
(OL-1)
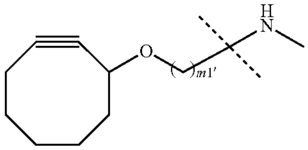
m1′ = 3-6
(OL-2-1)
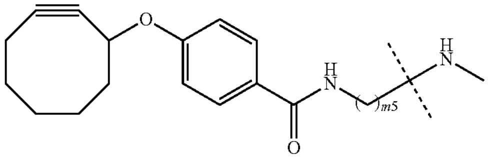
m5 = 2-6
(OL-3-1)
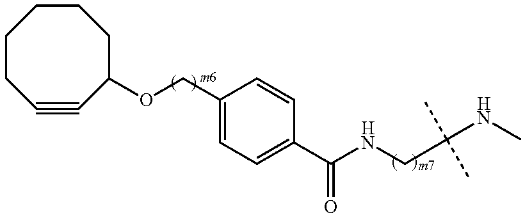
m6 = 1-6, m7 = 2-6
-continued
(OL-4)
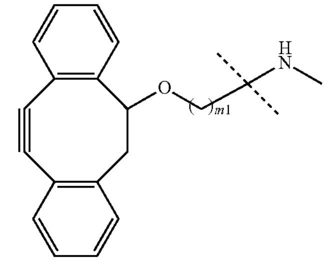
m1 = 2-6
(OL-5)
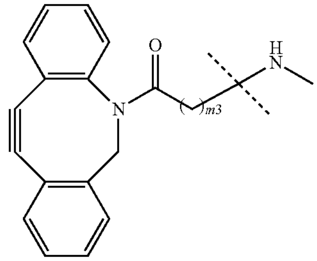
m3 = 2-6
(OL-6)
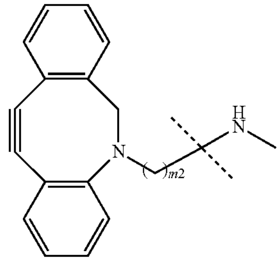
m2 = 2-6
(OL-7)
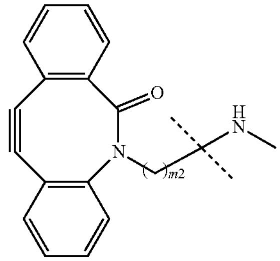
m2 = 2-6
(OL-8-1)
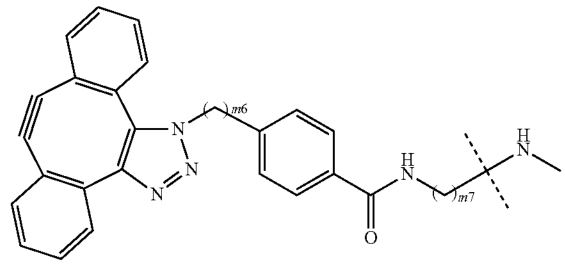
m6 = 1-6, m7 = 2-6

-continued (OL-9)

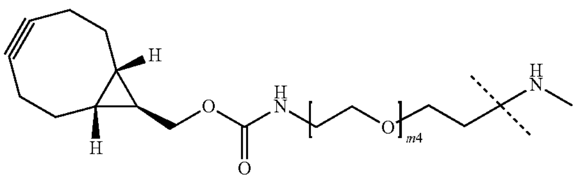

m4 = 1-6 or still more preferably represented by a group selected from the following partial structural formulae [excluding the part to the right of the wavy line (imino group side) in each formula]:

[C17]

(OL-5-1-a)

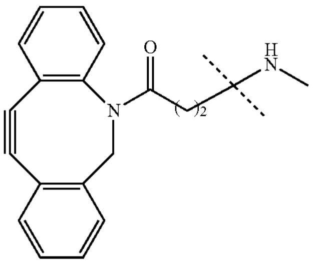

(OL-9-1-a)

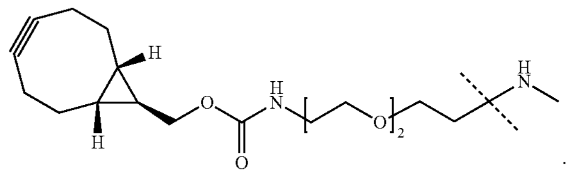

.

[1-1a] In the alginic acid derivative of the formula (I) of the Embodiment [1], $-L^1-$ is preferably a divalent linker selected from the group consisting of the following partial structural formulae [excluding the parts outside the wavy lines at both ends of each formula]:

[C18]

(LN-1)

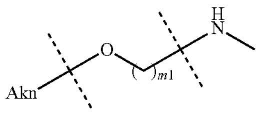

m1 = 2-1

(LN-2-1)

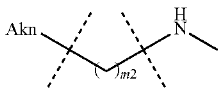

m2 = 2-6

(LN-3-1)

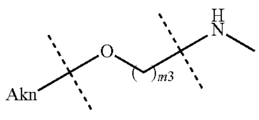

m3 = 2-6

-continued (LN-4)

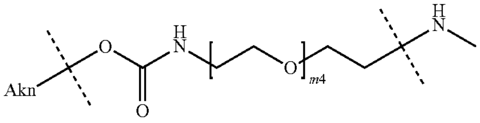

m4 = 1-6

(LN-5)

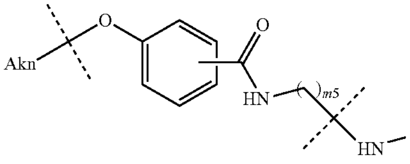

m5 = 2-6

(LN-6)

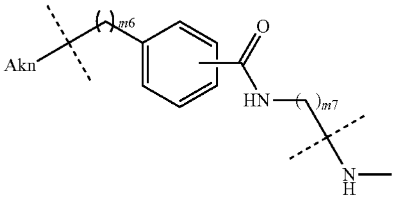

m6 = 2-6

(LN-7)

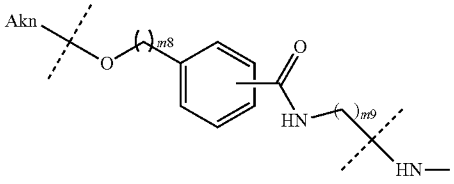

m8 =1-6, M9 = 2-6

(LN-9)

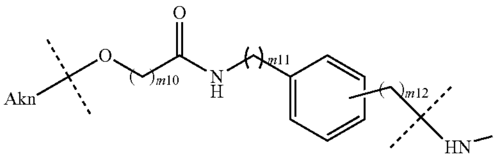

m10 = 1-4, m11 = 1-6, m12 = 1-6 or more preferably a divalent linker selected from the group consisting of the following partial structural formulae [excluding the parts outside the wavy lines at both ends of each formula]:

[C19]

(LN-1)

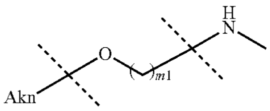

m1 = 2- 6

(LN-2-1)

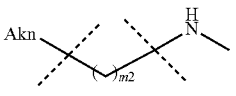

m2 = 2- 6

-continued (LN-3-1)

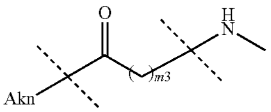

m3 = 2- 6

(LN-4)

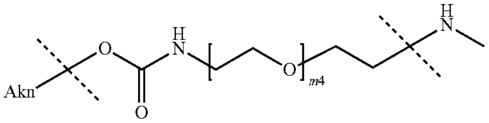

m4 = 1- 6

(LN-5-p)

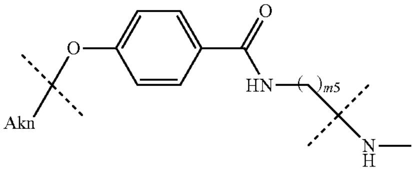

m5 = 2-6

(LN-6-p)

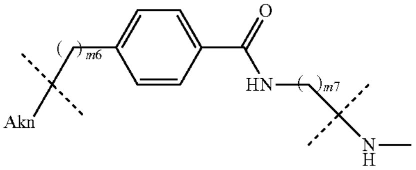

m6 = 1-6, m7 = 3-6

(LN-7-p)

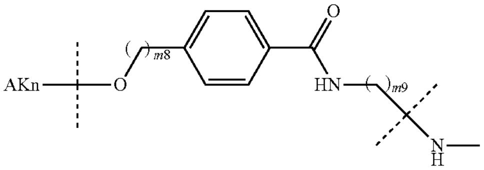

m8 = 1-6, m9 = 3-6

(LN-9-p)

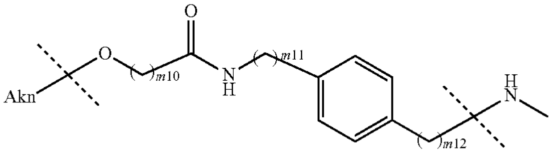

m10 = 1-4, m11 = 1-6, m12 = 1-6 or still more preferably a divalent linker selected from the following partial structural formulae [excluding the parts outside the wavy lines at both ends of each formula]:

[C20]

(LN-3-a)

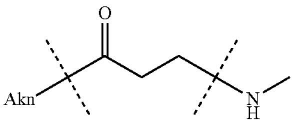

-continued (LN-3-b)

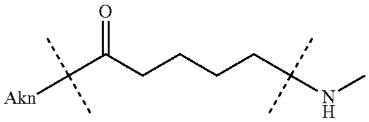

(LN-9-p-a)

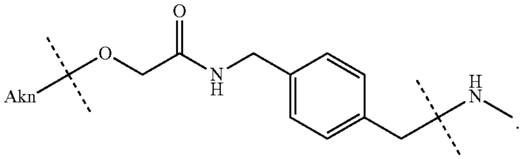

[1-2a] In the alginic acid derivative of the formula (I) of the Embodiment [1], Akn is preferably a cyclic alkyne selected from the group consisting of the following partial structural formulae [excluding the part to the right of the wavy line in each formula]:

[C21]

(AK-1)

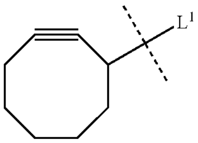

(AK-2)

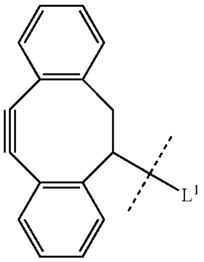

(AK-3)

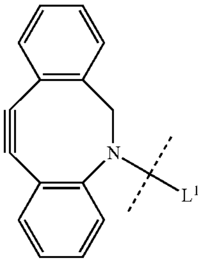

(AK-4)

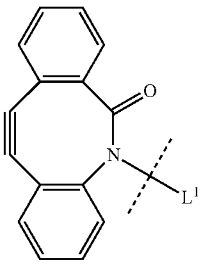

-continued (AK-5)

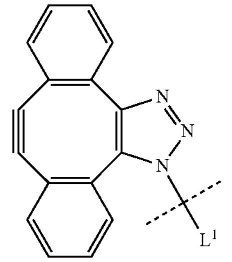

(AK-6)

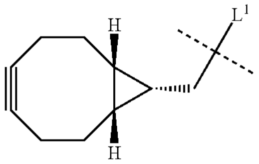

or more preferably a cyclic alkyne selected from the group consisting of the following partial structural formulae [excluding the part to the right of the wavy line in each formula]:

[C22]

(AK-1)

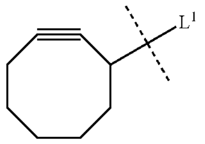

(AK-3)

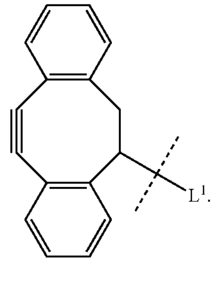

[1-3a] In the alginic acid derivative of the formula (I) of the Embodiment [1], the combination of Akn and -$L^1$- is preferably represented by a group selected from the group consisting of the following partial structural formulae [excluding the part to the right of the wavy line (imino group side) in each formula]:

[C23]

(OL-1)

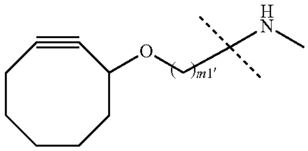

m1' = 3-6

-continued (OL-2)

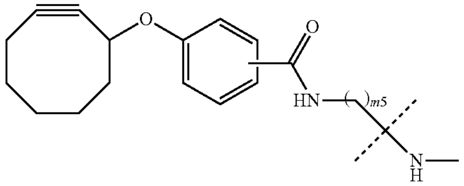

m5 = 2-6

(OL-3)

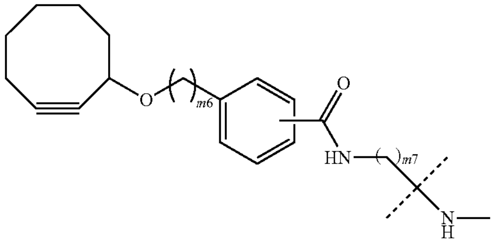

m6 = 1-6, m7 = 2-6

(OL-4)

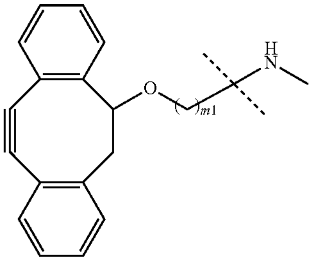

m1 = 2-6

(OL-5)

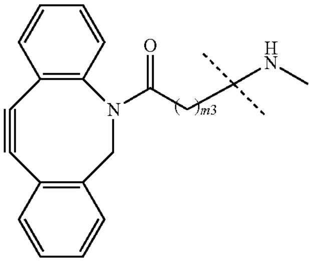

m3 = 2-6

(OL-6)

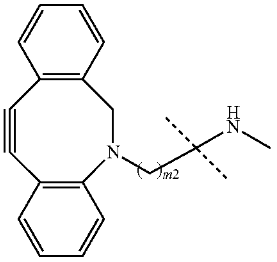

m2 = 2-6

-continued
(OL-7)
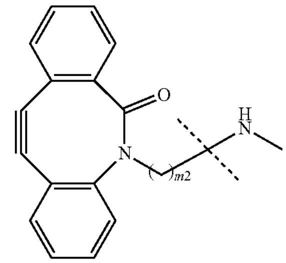
m2 = 2-6
(OL-8)
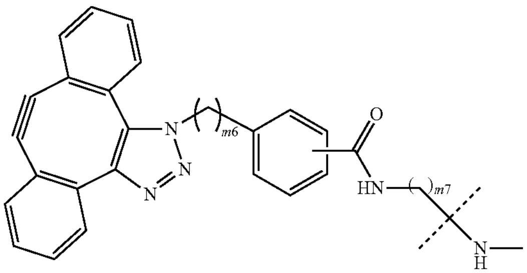
m6 = 1-6, m7 = 2-6
(OL-9)
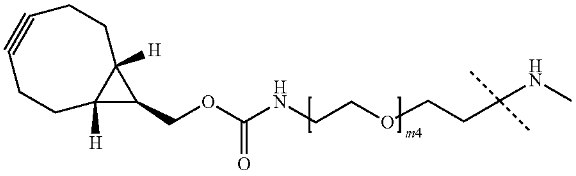
m4 = 1-6
(OL-17)
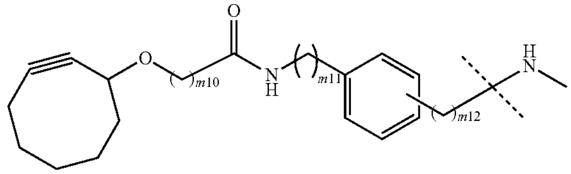
m10 = 1-4, m11 = 1-6, m12 = 1-6
[C24]
(OL-10)
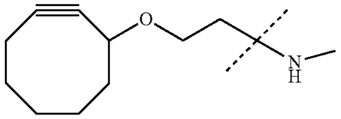
(OL-11)
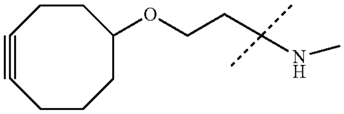
(OL-12)
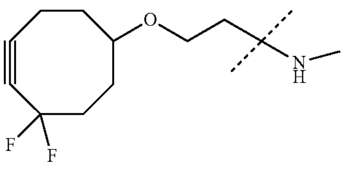
-continued
(OL-13)
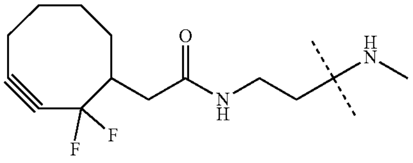
(OL-14)
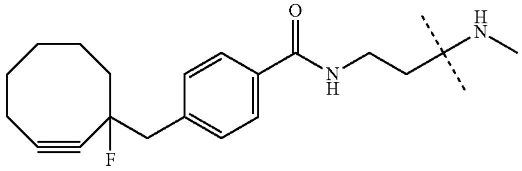
(OL-15)
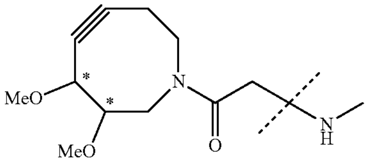
(OL-16)
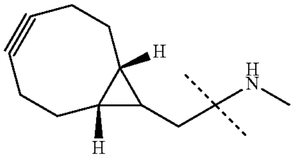
or more preferably represented by a group selected from the group consisting of the following partial structural formulae [excluding the part to the right of the wavy line (imino group side) in each formula]:
[C25]
(OL-1)
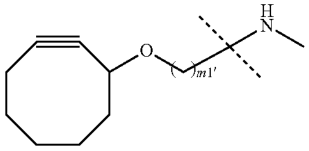
m1′ = 3-6
(OL-2-1)
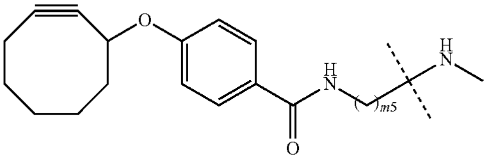
m5 = 2-6
(OL-3-1)
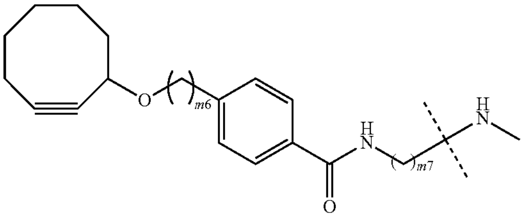
m6 = 1-6, m7 = 2-6

-continued
(OL-4)
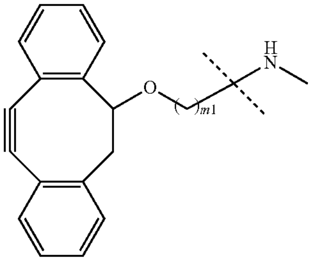
m1 = 2-6
(OL-5)
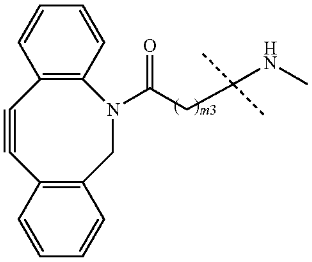
m3 = 2-6
(OL-6)
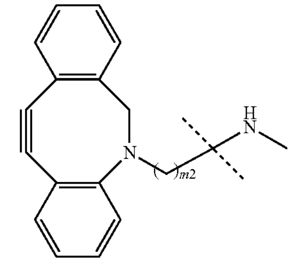
m2 = 2-6
(OL-7)
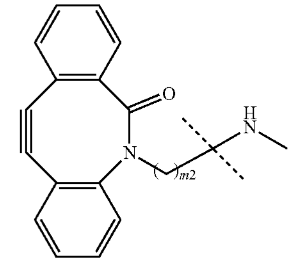
m2 = 2-6
(OL-8-1)
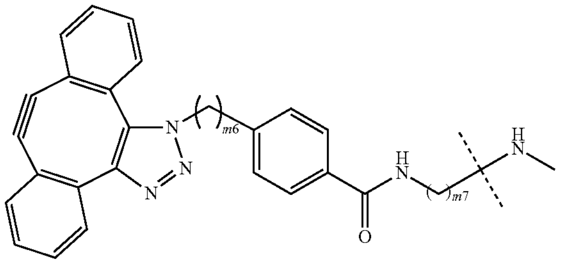
m6 = 1-6, m7 = 2-6
-continued
(OL-9)
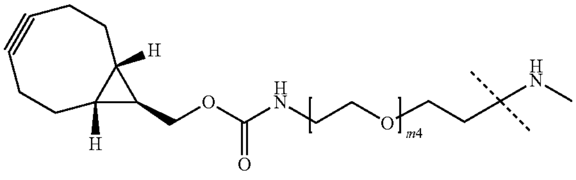
m4 = 1-6
(OL-17-1)
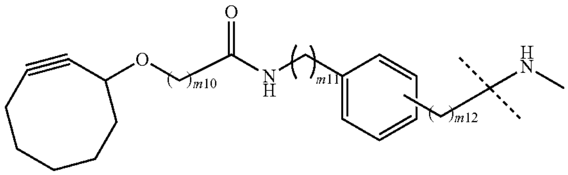
m10 = 1-4, m11 = 1-6, m12 = 1-6
[C26]
(OL-10)
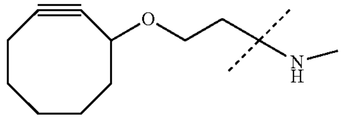
(OL-11)
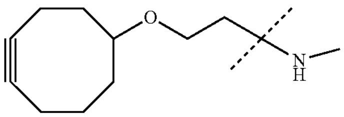
(OL-12)
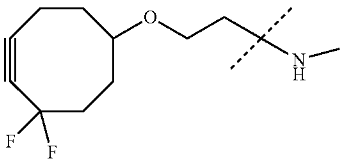
(OL-13)
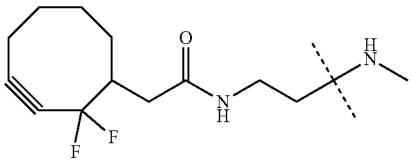
(OL-14)
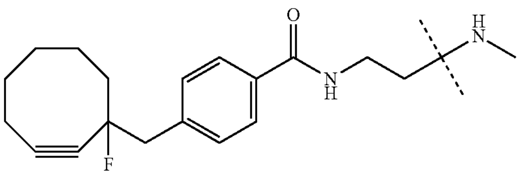
(OL-15)
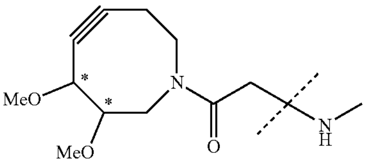

-continued (OL-16)

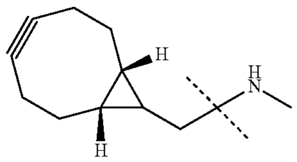

or still more preferably represented by a group selected from the group consisting of the following partial structural formulae [excluding the part to the right of the wavy line (imino group side) in each formula]:

[C27]

(OL-5-1-a)

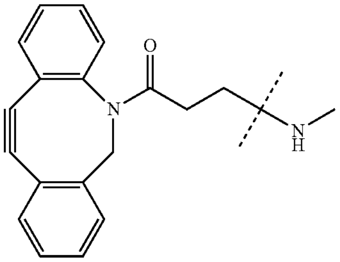

(OL-5-1-b)

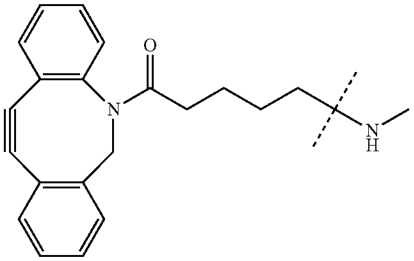

(OL-17-1-a)

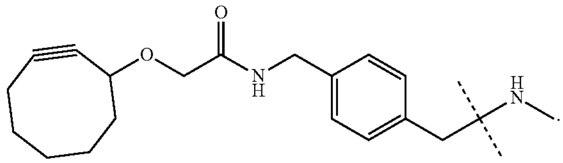

[1-1b] In the alginic acid derivative of the formula (I) of the Embodiment [1], -L[1]- is preferably a divalent linker selected from the group consisting of the following partial structural formulae [excluding the parts outside the wavy lines at both ends of each formula]:

[C28]

(LN-1)

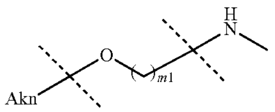

m1 = 2-6

-continued (LN-2-1)

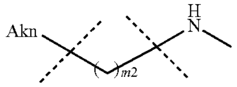

m2 = 2-6

(LN-3-1)

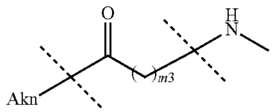

m3 = 2-6

(LN-4)

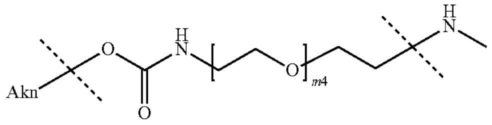

m4 = 1-6

(LN-5)

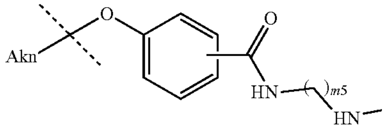

m5 = 2-6

(LN-6)

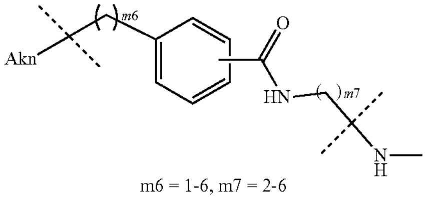

m6 = 1-6, m7 = 2-6

(LN-7)

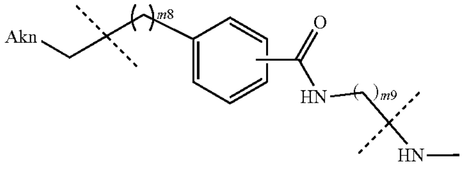

m8 = 1-6, m9 = 2-6

(LN-9)

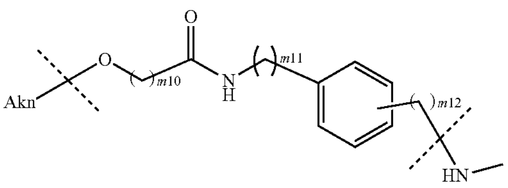

m10 = 1-4, m11 = 1-6, m12 = 1-6

(LN-10)

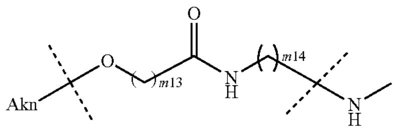

m13 = 1-4, m14 = 2-6

-continued (LN-11)

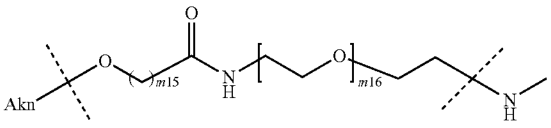

m15 = 1-4, m16 = 1-6 or more preferably a divalent linker selected from the group consisting of the following partial structural formulae [excluding the parts outside the wavy lines at both ends of each formula]:

[C29]

(LN-1)

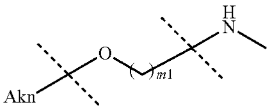

m1 = 2-6

(LN-2-1)

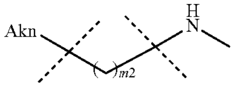

m2 = 2-6

(LN-3-1)

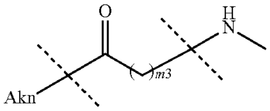

m3 = 2-6

(LN-4)

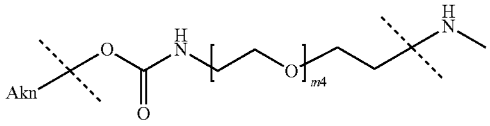

m4 = 1-6

(LN-5-p)

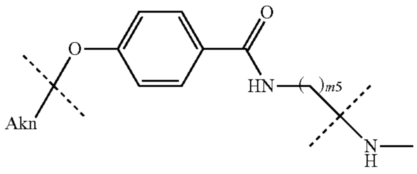

m5 = 2-6

(LN-6-p)

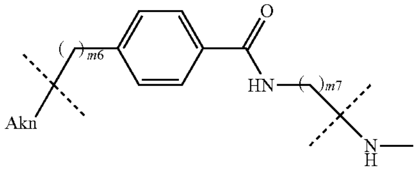

m6 = 1-6, m7 = 3-6

-continued (LN-7-p)

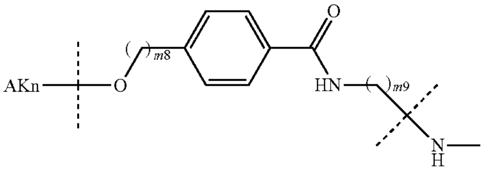

m8 = 1-6, m9 = 2-6

(LN-9-p)

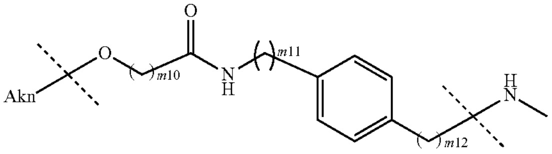

m10 = 1-4, m11 = 1-6, m12 = 1-6

(LN-10)

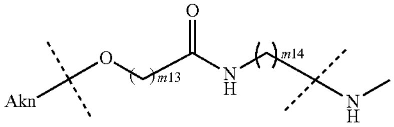

m13 = 1-4, m14 = 2-6

(LN-11)

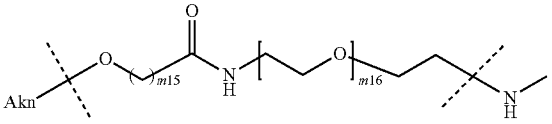

m15 = 1-4, m16 = 1-6 or still more preferably a divalent linker selected from group consisting of the following partial structural formulae [excluding the parts outside the wavy lines at both ends of each formula]:

[C30]

(LN-3-a)

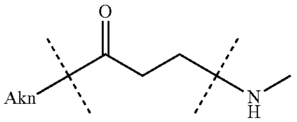

(LN-3-b)

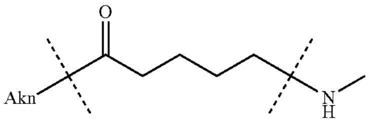

(LN-9-p-a)

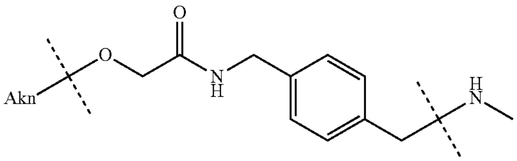

(LN-10-a)

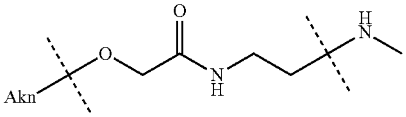

-continued (LN-11-a)

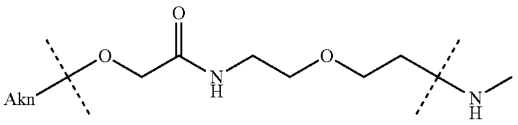

(LN-4-a)

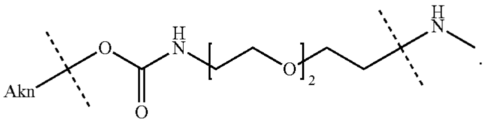

[1-2b] In the alginic acid derivative of the formula (I) of the Embodiment [1], Akn is preferably a cyclic alkyne selected from the group consisting of the following partial structural formulae [excluding the part to the right of the wavy line in each formula]:

[C31]

(AK-1)

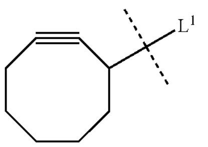

(AK-2)

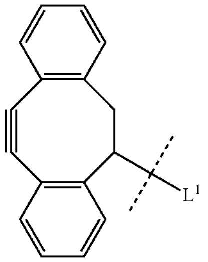

(AK-3)

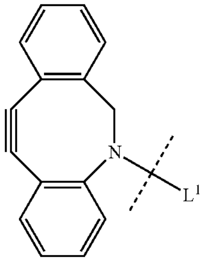

(AK-4)

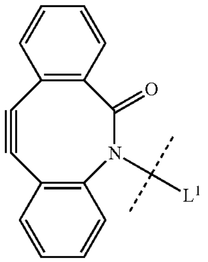

-continued (AK-5)

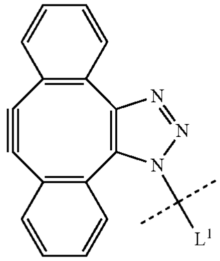

(AK-6)

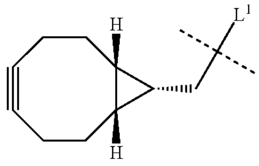

or more preferably a cyclic alkyne selected from the following partial structural formulae [excluding the part to the right of the wavy line in each formula]:

[C32]

(AK-1)

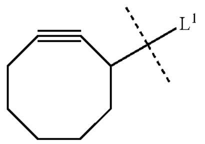

(AK-3)

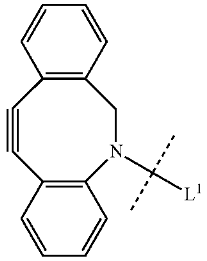

(AK-6)

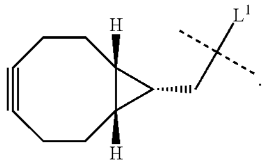

[1-3b] In the alginic acid derivative of the formula (I) of the Embodiment [1], preferably the combination of Akn and $-L^1-$ is any of the combinations shown in the following table (in which the formulae for $-L^1-$ and Akn are as described in the Embodiments [1], [1-1], [1-1a], [1-2], [1-2a] and [1-1b] above):

TABLE 1

| $—L^1—$ | Akn |
|---|---|
| LN-1 | AK-1 |
| LN-1 | AK-2 |
| LN-1 | AK-6 |
| LN-2-1 | AK-1 |
| LN-2-1 | AK-2 |

TABLE 1-continued

| —L¹— | Akn |
|---|---|
| LN-2-1 | AK-3 |
| LN-2-1 | AK-4 |
| LN-2-1 | AK-5 |
| LN-2-1 | AK-6 |
| LN-3-1 | AK-1 |
| LN-3-1 | AK-2 |
| LN-3-1 | AK-3 |
| LN-3-1 | AK-4 |
| LN-3-1 | AK-5 |
| LN-3-1 | AK-6 |
| LN-4 | AK-1 |
| LN-4 | AK-2 |
| LN-4 | AK-6 |
| LN-5 | AK-1 |
| LN-5 | AK-2 |
| LN-5 | AK-6 |
| LN-6 | AK-1 |
| LN-6 | AK-2 |
| LN-6 | AK-3 |
| LN-6 | AK-4 |
| LN-6 | AK-5 |
| LN-6 | AK-6 |
| LN-7 | AK-1 |
| LN-7 | AK-2 |
| LN-7 | AK-6 |
| LN-9 | AK-1 |
| LN-9 | AK-2 |
| LN-9 | AK-6 |
| LN-10 | AK-1 |
| LN-10 | AK-2 |
| LN-10 | AK-6 |
| LN-11 | AK-1 |
| LN-11 | AK-2 |
| LN-11 | AK-6 |

or is represented by a group selected from the group consisting of the following partial structural formulae [excluding the part to the right of the wavy line (imino group side) in each formula]:

[C33]

(OL-11)

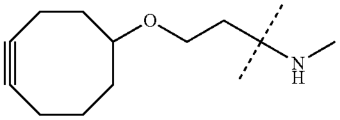

(OL-12)

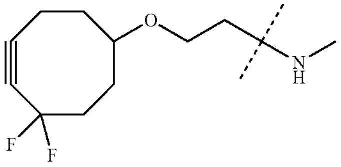

(OL-13)

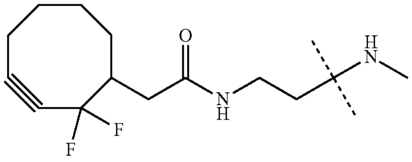

-continued (OL-14)

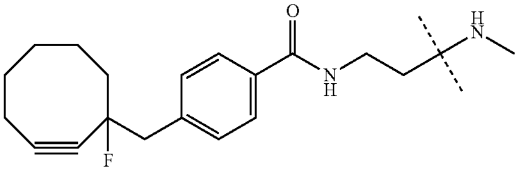

(OL-15)

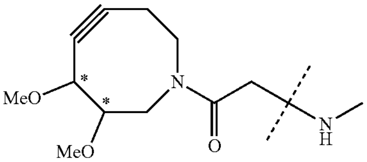

(OL-16)

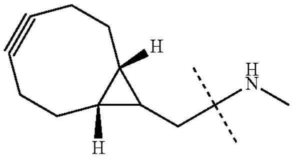

or more preferably the combination of Akn and $-L^1-$ is any of the combinations shown in the following table (in which the formulae for $-L^1-$ and Akn are as described in the Embodiments [1], [1-1], [1-1a], [1-2], [1-2a] and [1-1b] above):

TABLE 2

| —L¹— | Akn |
|---|---|
| LN-1 | AK-1 |
| LN-1 | AK-2 |
| LN-1 | AK-6 |
| LN-2-1 | AK-1 |
| LN-2-1 | AK-2 |
| LN-2-1 | AK-3 |
| LN-2-1 | AK-4 |
| LN-2-1 | AK-5 |
| LN-2-1 | AK-6 |
| LN-3-1 | AK-1 |
| LN-3-1 | AK-2 |
| LN-3-1 | AK-3 |
| LN-3-1 | AK-4 |
| LN-3-1 | AK-5 |
| LN-3-1 | AK-6 |
| LN-4 | AK-1 |
| LN-4 | AK-2 |
| LN-4 | AK-6 |
| LN-5-p | AK-1 |
| LN-5-p | AK-2 |
| LN-5-p | AK-6 |
| LN-6-p | AK-1 |
| LN-6-p | AK-2 |
| LN-6-p | AK-3 |
| LN-6-p | AK-4 |
| LN-6-p | AK-5 |
| LN-6-p | AK-6 |
| LN-7-p | AK-1 |
| LN-7-p | AK-2 |
| LN-7-p | AK-6 |
| LN-9-p | AK-1 |
| LN-9-p | AK-2 |
| LN-9-p | AK-6 |
| LN-10 | AK-1 |
| LN-10 | AK-2 |
| LN-10 | AK-6 |
| LN-11 | AK-1 |
| LN-11 | AK-2 |
| LN-11 | AK-6 |

or still more preferably the combination of Akn and -$L^1$- is any of the combinations shown in the following table (in which the formulae for -$L^1$- and Akn are as described in the Embodiments [1], [1-1], [1-1a], [1-2], [1-2a] and [1-1b] above):

TABLE 3

| —$L^1$— | Akn |
|---|---|
| LN-3-a | AK-1 |
| LN-3-a | AK-3 |
| LN-3-a | AK-6 |
| LN-3-b | AK-1 |
| LN-3-b | AK-3 |
| LN-3-b | AK-6 |
| LN-4-a | AK-1 |
| LN-4-a | AK-6 |
| LN-9-p-a | AK-1 |
| LN-9-p-a | AK-6 |
| LN-10-a | AK-1 |
| LN-10-a | AK-6 |
| LN-11-a | AK-1 |
| LN-11-a | AK-6 |

or particularly preferably the combination of Akn and -$L^1$- is represented by a group selected from the group consisting of the following partial structural formulae [excluding the part to the right of the wavy line (imino group side) in each formula]:

[C34]

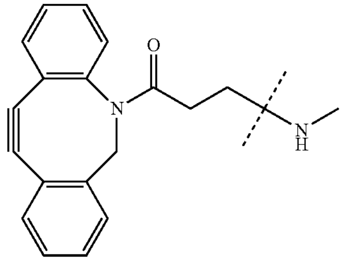

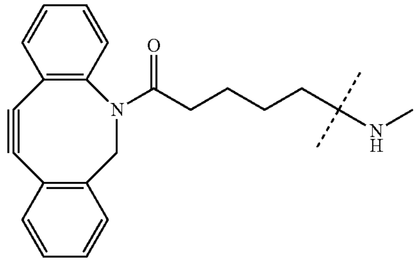

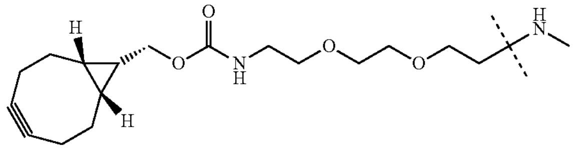

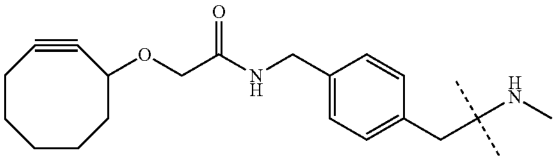

-continued

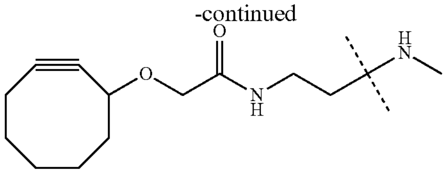

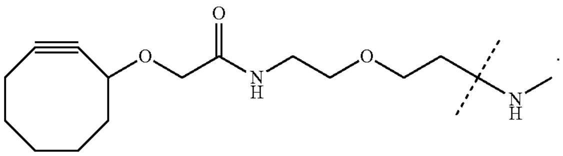

.

Preferred embodiments of the alginic acid derivative represented by the formula (I) of the Embodiment [1] can be formed at will by appropriately combining preferred embodiments of the Embodiment [1] as well as the definitions of Akn and -$L^1$-.

[2] Embodiment 2 is as follows: The alginic acid derivative of formula (I) according to the Embodiment (I), wherein the introduction rate of the Akn-$L^1$-$NH_2$ group (in which Akn and -$L^1$- are defined as in the Embodiment [1]) is from 0.1% to 30%.

[2-1] In the Embodiment [2], the introduction rate of the Akn-$L^1$-$NH_2$ group is preferably from 2% to 20%, or more preferably from 3% to 10%.

[2-1a] In the Embodiment [2], the introduction rate of the Akn-$L^1$-$NH_2$ group is preferably from 0.3% to 20%, or more preferably from 0.5% to 10%.

[3] Embodiment 3 is as follows: The alginic acid derivative of formula (I) according to the Embodiment [I], wherein the weight-average molecular weight as measured by gel filtration chromatography of the alginic acid derivative is 100,000 Da to 3,000,000 Da.

[3-1] In the Embodiment [3], the weight-average molecular weight as measured by gel filtration chromatography of the alginic acid derivative is preferably 300,000 Da to 2,500,000 Da, or more preferably 500,000 Da to 2,000,000 Da.

[3-1a] In the Embodiment [3], the weight-average molecular weight as measured by gel filtration chromatography of the alginic acid derivative is preferably 300,000 Da to 2,500,000 Da, or more preferably 1,000,000 Da to 2,000,000 Da.

[4] Embodiment 4 is as follows: An alginic acid derivative represented by formula (II) below, comprising an azide group introduced via an amide bond and a divalent linker (-$L^2$-) at any one or more carboxyl groups of alginic acid:

[C35]

(II)

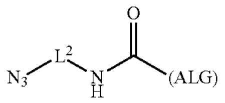

[in formula (II), (ALG) represents alginic acid; —NHCO— represents an amide bond via any carboxyl group of alginic acid; and -$L^2$- represents a divalent linker selected from the group consisting of the following partial structural formulae [excluding the parts outside the wavy lines at both ends of each formula]]:

[C36]

(LK-1)

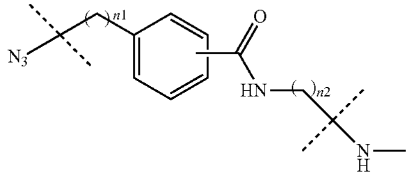

n1 = 1-6, n2 = 2-6

(LK-2)

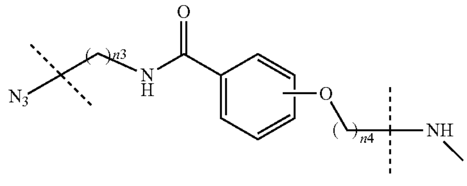

n3 = 2-6, n4 = 2-6

(LK-3)

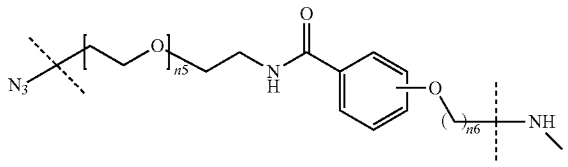

n5 = 1-6, n6 = 2-6

(LK-4)

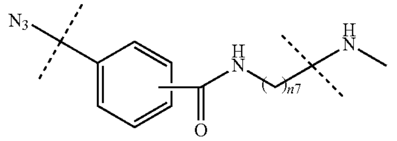

n7 = 2-6

(LK-5)

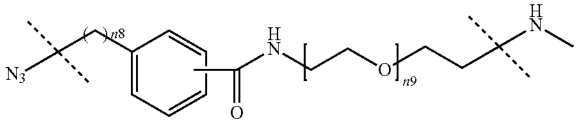

n8 = 1-4, n9 = 1-6

(LK-6)

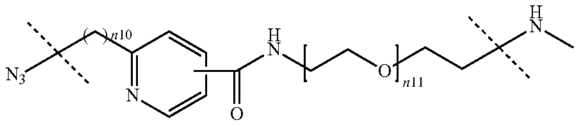

n10 = 1-4, n11 = 1-6

(LK-7)

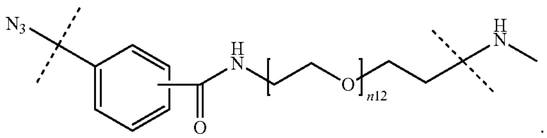

.

n12 = 1-6

[4-1] In the alginic acid derivative of the formula (II) of the Embodiment [4], $-L^2-$ is preferably a linker selected from the group consisting of the following partial structural formulae [excluding the parts outside the wavy lines at both ends of each formula]:

[C37]

(LK-1-1)

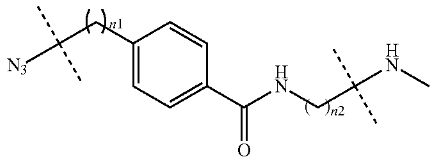

n1 = 1-6, n2 = 2-6

(LK-2-1)

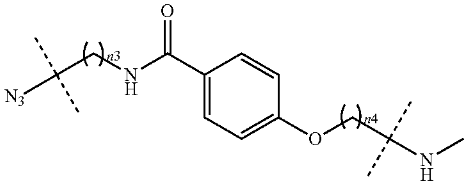

n3 = 2-6, n4 = 2-6

(LK-3-1)

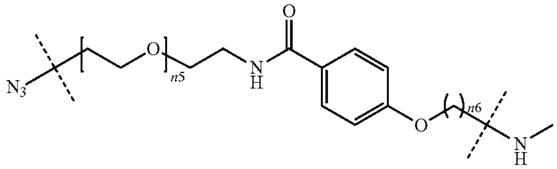

n5 = 1-6, n6 = 2-6 or more preferably a linker selected from the following partial structural formulae:

[C38]

(LK-1-1-a)

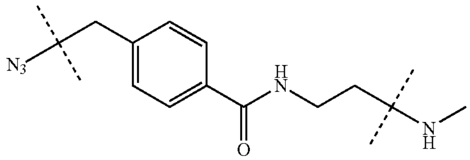

(LK-2-1-a)

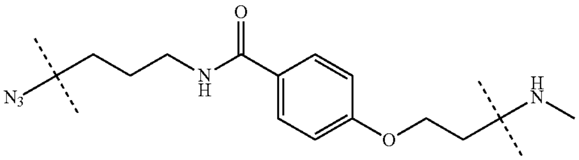

(LK-3-1-a)

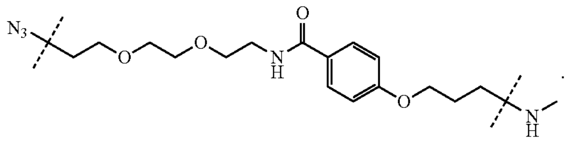

.

[4-1a] In the alginic acid derivative of the formula (II) of the Embodiment [4], $-L^2-$ is preferably a linker selected from the group consisting of the following partial structural formulae [excluding the parts outside the wavy lines at both ends of each formula]:

[C39]

(LK-1-1)

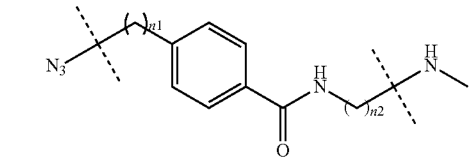

n1 = 1-6, n2 = 2-6

(LK-2-1)

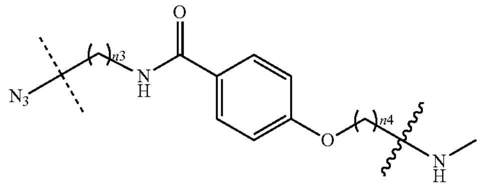

n3 = 2-6, n4 = 2-6

(LK-3-1)

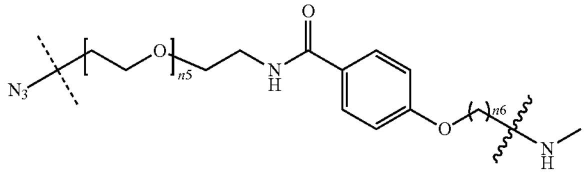

n5 = 1-6, n6 = 2-6

(LK-4-1)

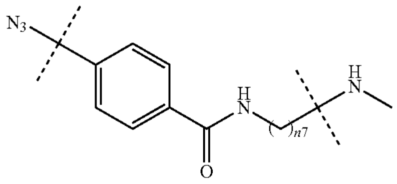

n7 = 2-6 or more preferably a linker selected from the following partial structural formulae:

[C40]

(LK-1-1-a)

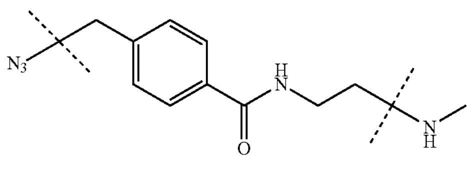

(LK-2-1-a)

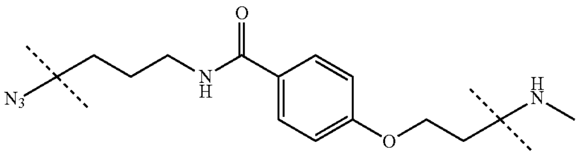

-continued (LK-4-1-a)

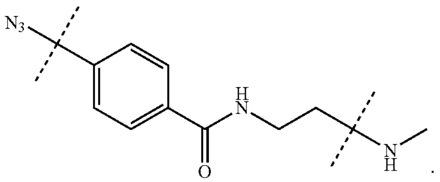

[4-1b] In the alginic acid derivative of the formula (II) of the Embodiment [4], $-L^2-$ is preferably a linker selected from the group consisting of the following partial structural formulae [excluding the parts outside the wavy lines at both ends of each formula]:

[C41]

(LK-1-1)

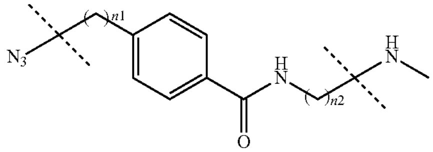

n1 = 1-6, n2 = 2-6

(LK-2-1)

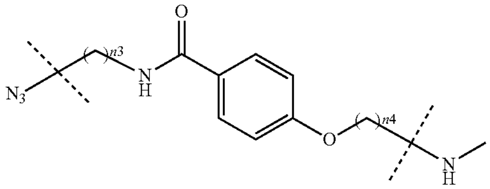

n3 = 2-6, n4 = 2-6

(LK-3-1)

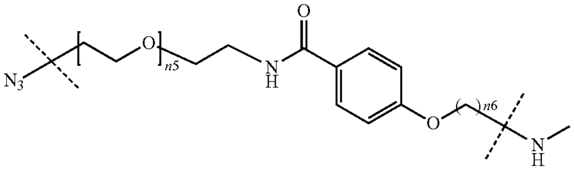

n5 = 1-6, n6 = 2-6

(LK-4-1)

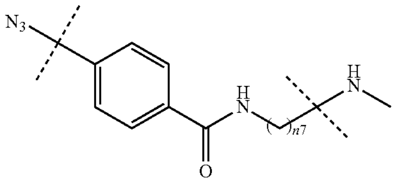

n7 = 2-6

(LK-5-1)

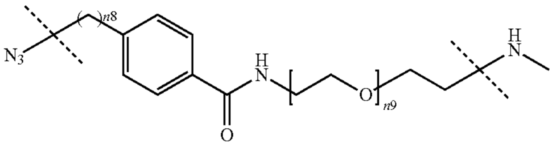

n8 = 1-4, n9 = 1-6

-continued (LK-6-1)

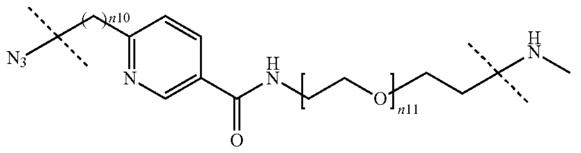

n10 = 1-4, n11 = 1-6

(LK-7-1)

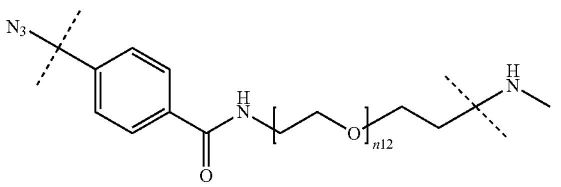

n12 = 1-6 or more preferably a linker selected from the following partial structural formulae [excluding the parts outside the wavy lines at both ends of each formula]:

[C42]

(LK-1-1-a)

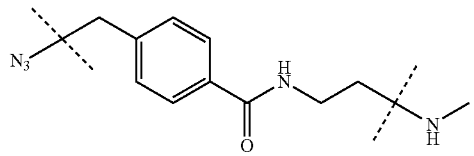

(LK-2-1-a)

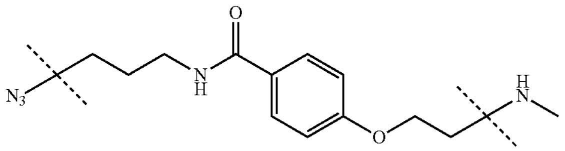

(LK-4-1-a)

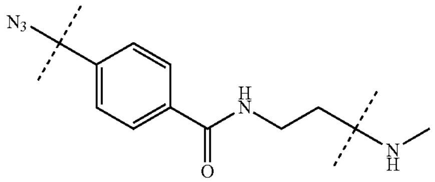

(LK-5-1-a)

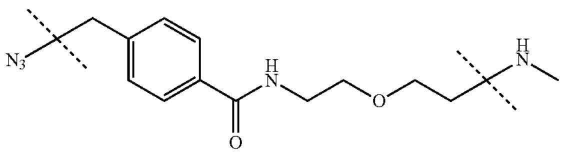

(LK-5-1-b)

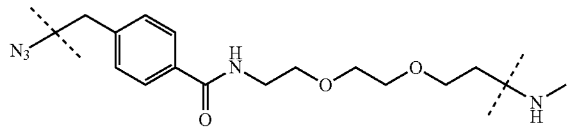

-continued (LK-6-1-a)

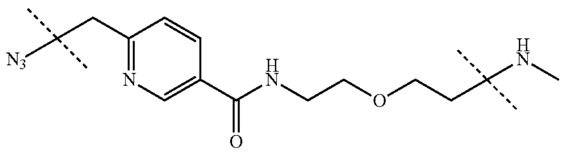

(LK-7-1-a)

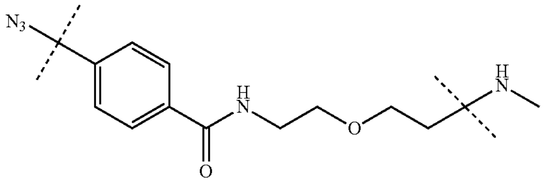

(LK-7-1-b)

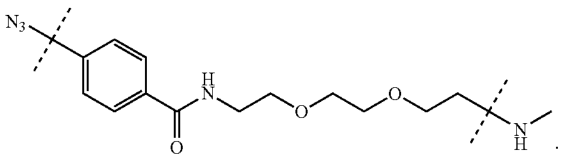

Preferred embodiments of the alginic acid derivative represented by the formula (II) of the Embodiment [4] can be formed at will by appropriately combining preferred embodiments of the Embodiment [4] as well as the definitions of the azide group and $-L^2-$.

[5] Embodiment 5 is as follows: The alginic acid derivative of formula (II) according to the Embodiment (4), wherein the introduction rate of the $N_3-L^2-NH_2$ group (in which $-L^2-$ is defined as in the Embodiment [4]) is from 0.1% to 30%.

[5-1] In the Embodiment [5], the introduction rate of the $N_3-L^2-NH_2$ group is preferably from 2% to 20%, or more preferably from 3% to 10%.

[5-1a] In the Embodiment [5], the introduction rate of the $N_3-L^2-NH_2$ group is preferably from 0.3% to 20%, or more preferably from 0.5% to 15%.

[6] Embodiment 6 is as follows: The alginic acid derivative of formula (II) according to the Embodiment [4], wherein the weight-average molecular weight as measured by gel filtration chromatography of the alginic acid derivative is 100,000 Da to 3,000,000 Da.

[6-1] In the Embodiment [6], the weight-average molecular weight as measured by gel filtration chromatography of the alginic acid derivative of formula (II) is preferably 300,000 Da to 2,500,000 Da, or more preferably 500,000 Da to 2,000,000 Da.

[6-1a] In the Embodiment [6], the weight-average molecular weight as measured by gel filtration chromatography of the alginic acid derivative of formula (II) is preferably 300,000 Da to 2,500,000 Da, or more preferably 1,000,000 Da to 2,000,000 Da.

[7] Embodiment 7 is as follows: A crosslinked alginic acid in which any carboxyl group of a first alginic acid and any carboxyl group of a second alginic acid are bound together via the following formula (III-L):

[C43]

(III-L)

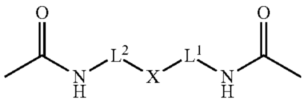

[in formula (III-L), the —CONH— and —NHCO— at either end represent amide bonds via any carboxyl group of alginic acid;

-$L^1$- is defined as in the Embodiment [1];

-$L^2$- is defined as in the Embodiment [4];

and X is a cyclic group selected from the group consisting of the following partial structural formulae [excluding the parts outside the wavy lines at both ends of each formula]:

[C44]

(TZ-1)

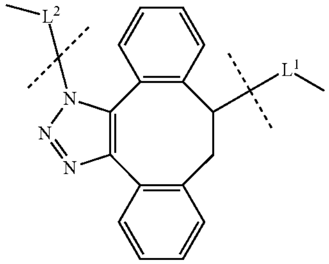

(TZ-2)

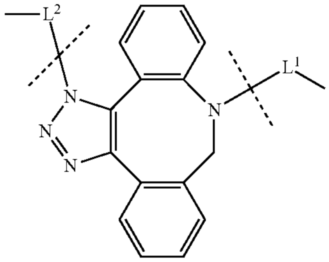

(TZ-3)

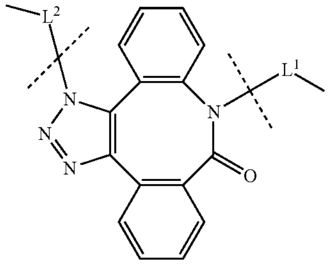

(TZ-4)

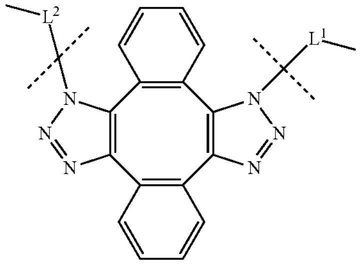

-continued (TZ-5)

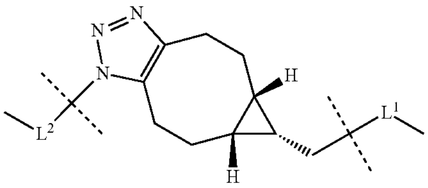

(TZ-6)

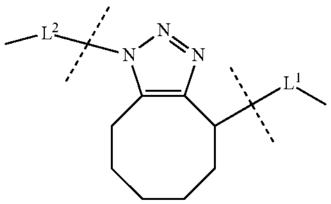

(TZ-7)

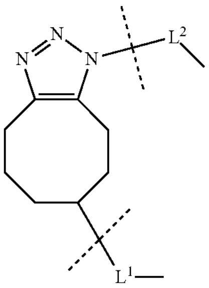

(TZ-8)

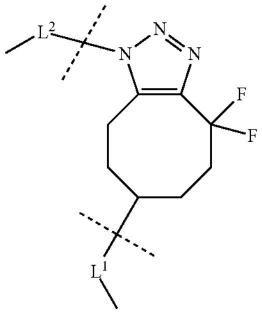

(TZ-9)

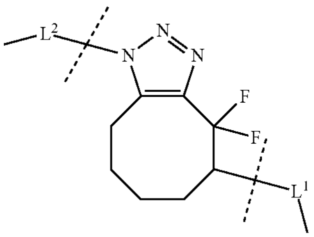

(TZ-10)

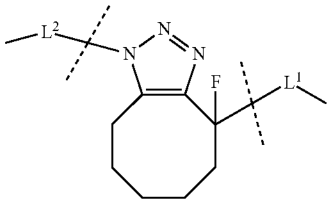

-continued
(TZ-11)
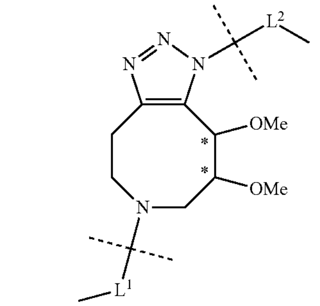
(TZ-12)
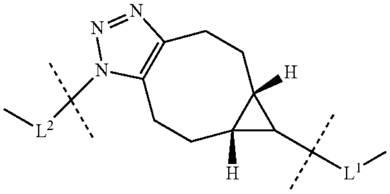
(TZ-1-r)
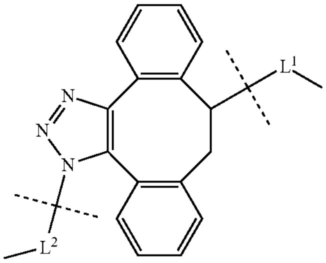
(TZ-2-r)
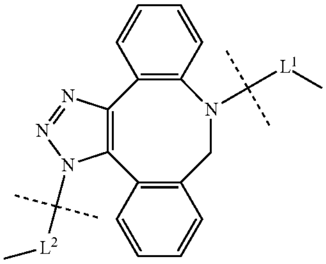
(TZ-3-r)
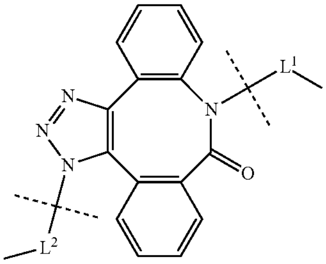
(TZ-4-r)
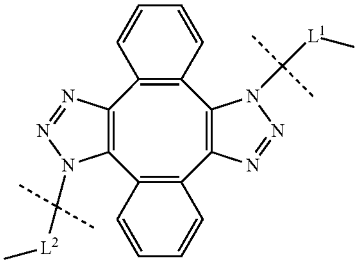
-continued
(TZ-5-r)
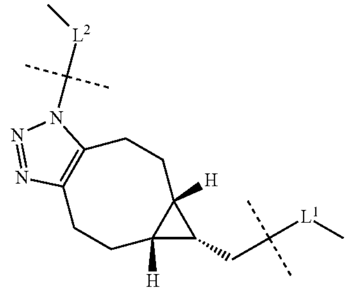
(TZ-6-r)
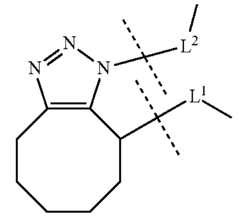
(TZ-7-r)
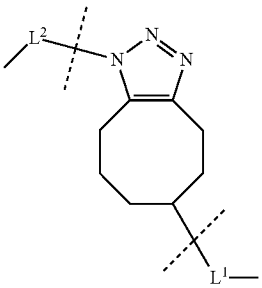
(TZ-8-r)
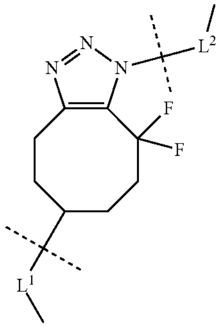
(TZ-9-r)
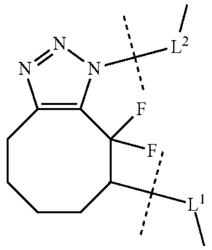
(TZ-10-r)
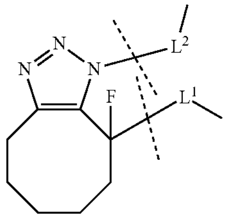

-continued (TZ-11-r)

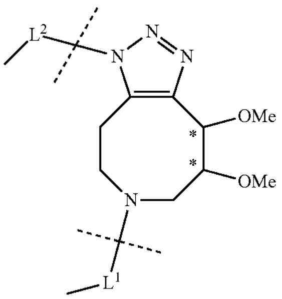

(TZ-12-r)

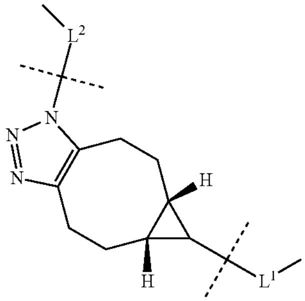

in which the asterisks represent chiral centers].

[7-1] In the formula (III-L) of the Embodiment [7], preferably -$L^1$- is a divalent linker selected from the group consisting of the following partial structural formulae [excluding the parts outside the wavy lines at both ends of each formula]:

[C45]

(LN-1)

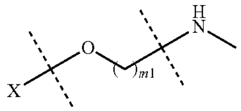

m1 = 2-6

(LN-2-1)

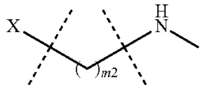

m2 = 2-6

(LN-3-1)

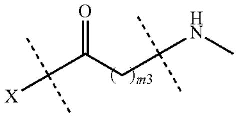

m3 = 2-6

(LN-4)

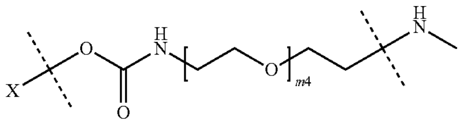

m4 = 1-6

-continued (LN-5)

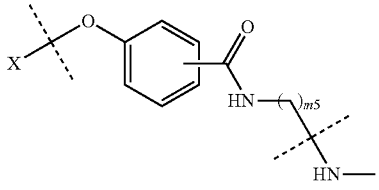

m5 = 2-6

(LN-6)

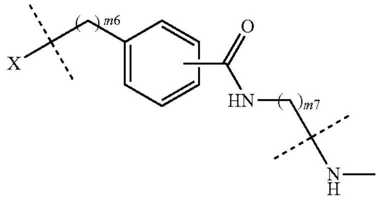

m6 = 1-6, m7 = 2-6

(LN-7)

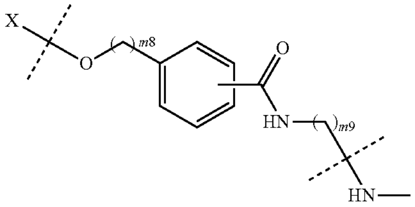

m8 = 1-6, m9 = 2-6

-$L^2$- is a divalent linker selected from the group consisting of the following partial structural formulae [excluding the parts outside the wavy lines at both ends of each formula]:

[C46]

(LK-1-1)

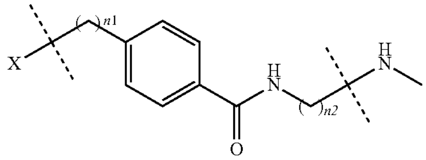

n1 = 1-6, n2 = 2-6

(LK-2-1)

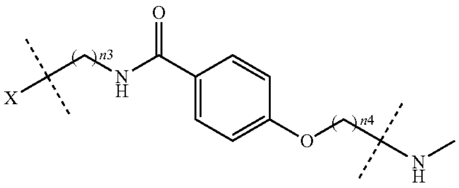

n3 = 2-6, n4 = 2-6

(LK-3-1)

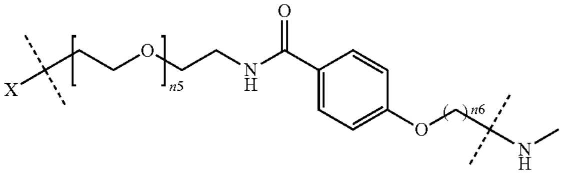

n5 = 1-6, n6 = 2-6 and X is a cyclic group selected from the group consisting of the following partial structural formulae [excluding the parts outside the wavy lines at both ends of each formula]:
[C47]
(TZ-1)
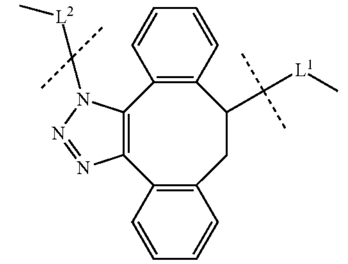
(TZ-2)
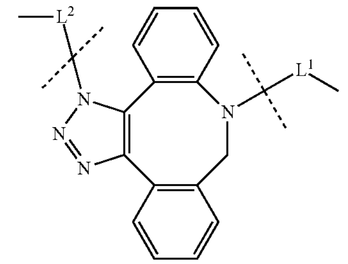
(TZ-3)
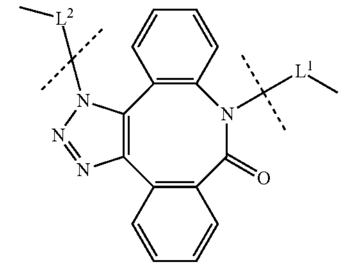
(TZ-4)
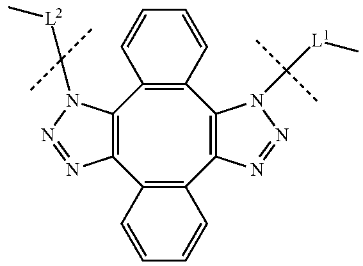
(TZ-5)
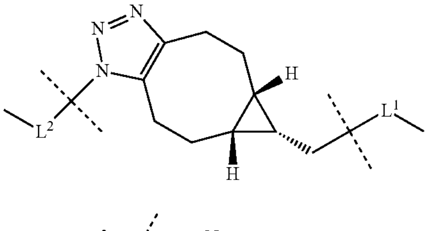
(TZ-6)
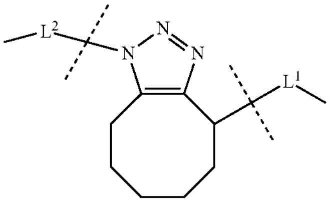
-continued
(TZ-1-r)
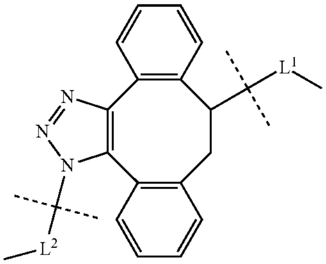
(TZ-2-r)
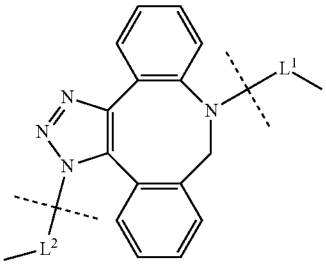
(TZ-3-r)
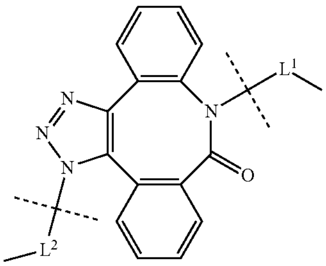
(TZ-4-r)
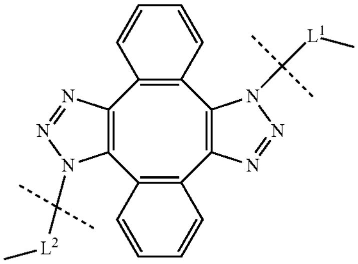
(TZ-5-r)
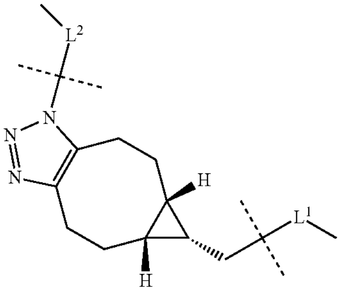
(TZ-6-r)
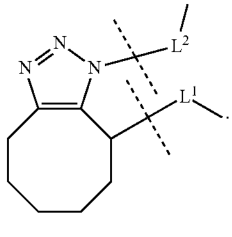
.

[7-2] In the formula (III-L) of the Embodiment [7], more preferably $-L^1-$ is a divalent linker selected from the group consisting of the following partial structural formulae [excluding the parts outside the wavy lines at both ends of each formula]:

[C48]

(LN-1)

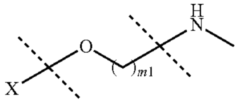

m1 = 2-6

(LN-2-1)

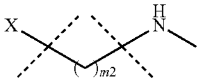

m2 = 2-6

(LN-3-1)

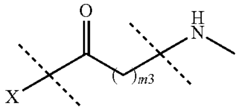

m3 = 2-6

(LN-4)

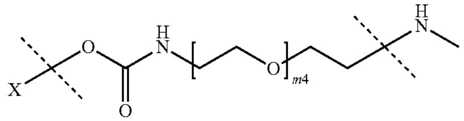

m4 = 1-6

(LN-5-p)

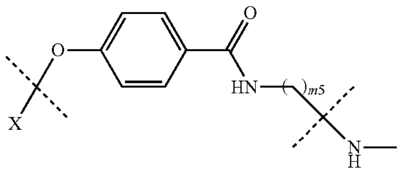

m5 = 2-6

(LN-6-p)

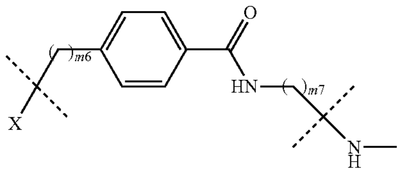

m6 = 1-6, m7 = 3-6

(LN-7-p)

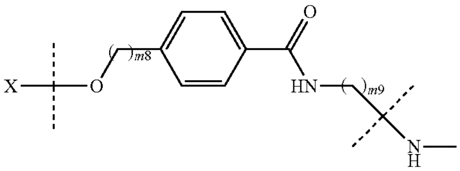

m8 = 1-6, m9 = 2-6

$-L^2-$ is a divalent linker selected from the group consisting of the following partial structural formulae [excluding the parts outside the wavy lines at both ends of each formula]:

[C49]

(LK-1-1)

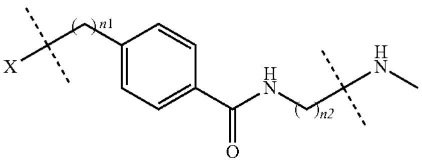

n1 = 1-6, n2 = 2-6

(LK-2-1)

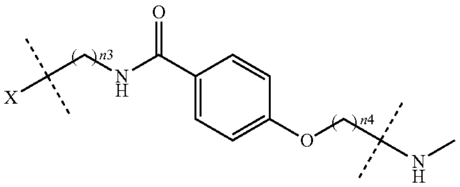

n3 = 2-6, n4 = 2-6

(LK-3-1)

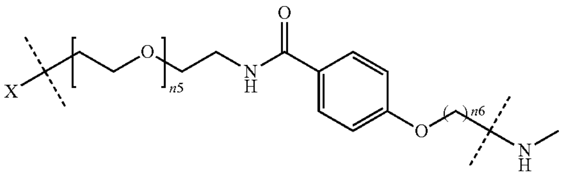

n5 = 1-6, n6 = 2-6 and X is a cyclic group selected from the group consisting of the following partial structural formulae [excluding the parts outside the wavy lines at both ends of each formula]:

[C50]

(TZ-1)

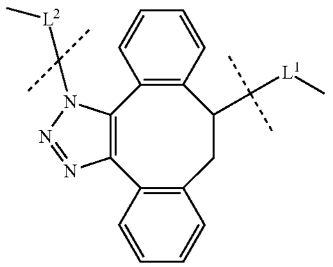

(TZ-2)

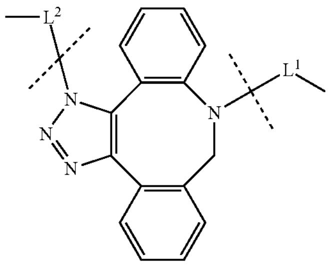

-continued (TZ-3)

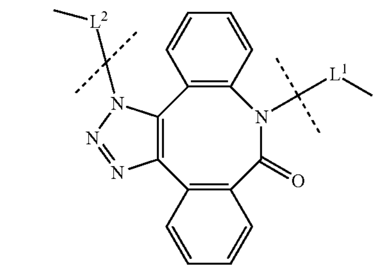

(TZ-4)

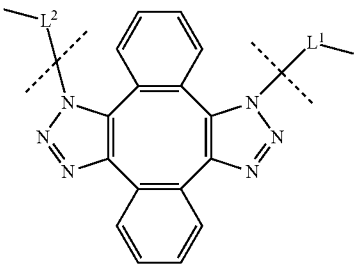

(TZ-5)

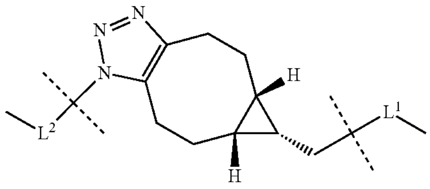

(TZ-1-r)

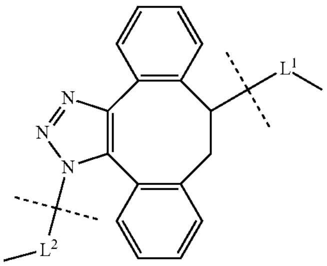

(TZ-2-r)

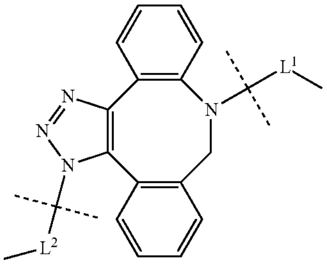

-continued (TZ-3-r)

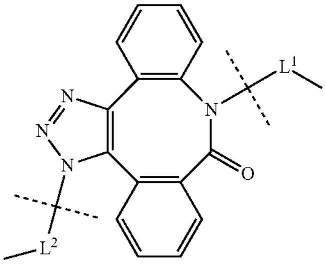

(TZ-4-r)

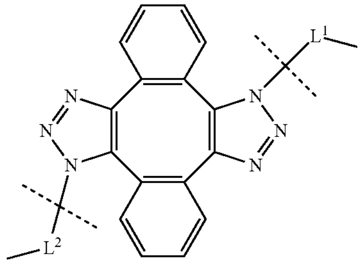

(TZ-5-r)

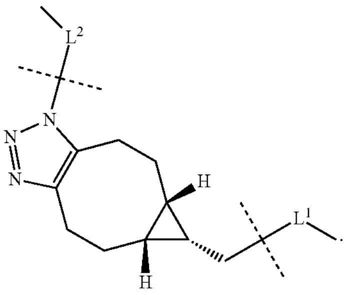

[7-3] In the formula (III-L) of the Embodiment [7], still more preferably $-L^1-$ is a divalent linker selected from the group consisting of the following partial structural formulae [excluding the parts outside the wavy lines at both ends of each formula]:

[C51]

(LN-3-a)

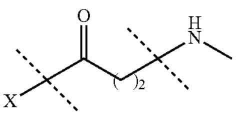

(LN-4-a)

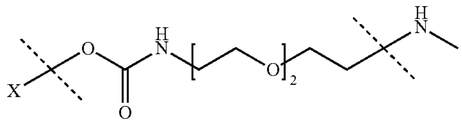

$-L^2-$ is a divalent linker selected from the group consisting of the following partial structural formulae [excluding the parts outside the wavy lines at both ends of each formula]:

[C52]

(LK-1-1-a)

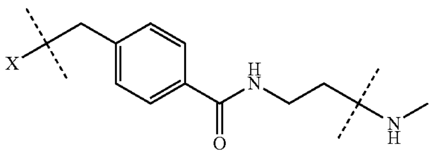

(LK-2-1-a)

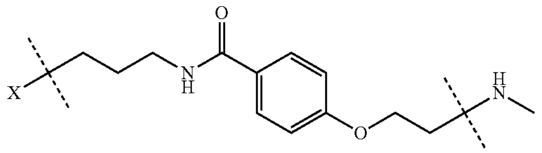

(LK-3-1-a)

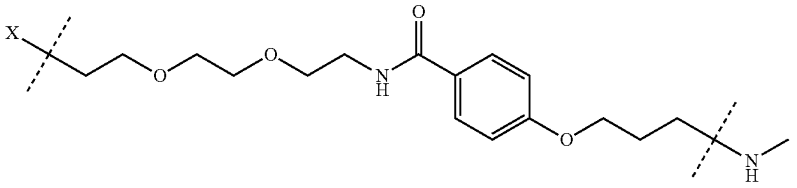

and X is a cyclic group selected from the group consisting of the following partial structural formulae [excluding the parts outside the wavy lines at both ends of each formula]:

[C53]

(TZ-2)

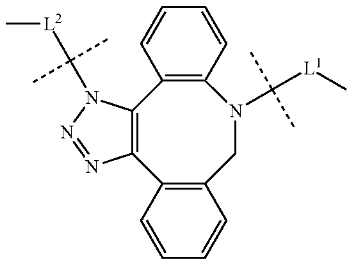

(TZ-5)

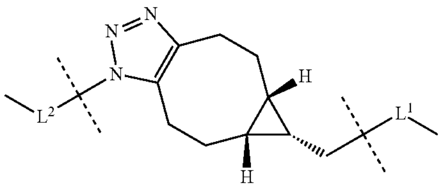

(TZ-2-r)

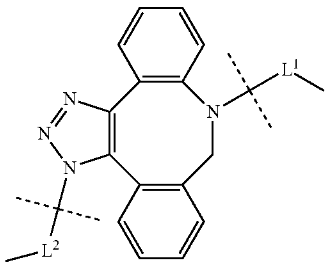

-continued (TZ-5-r)

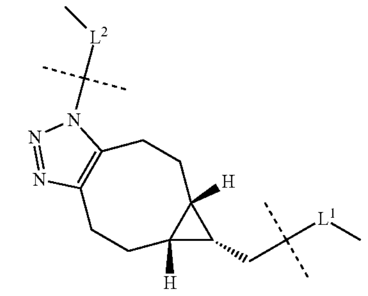

[7-3-1] In the formula (III-L) of the Embodiment [7], particularly preferably $-L^1-$ is a divalent linker represented by the following partial structural formula [excluding the parts outside the wavy lines at both ends of the formula]:

[C54]

(LN-3-a)

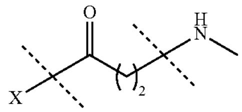

$-L^2-$ is a divalent linker represented by the following partial structural formula [excluding the parts outside the wavy lines at both ends of the formula]:

[C55]

(LK-2-1-a)

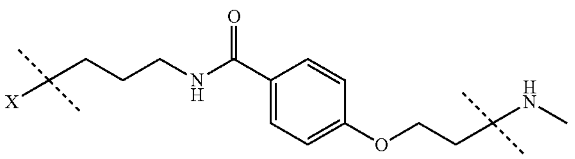

and X is a cyclic group represented by either of the following partial structural formulae [excluding the parts outside the wavy lines at both ends of each formula]:

[C56]
(TZ-2)
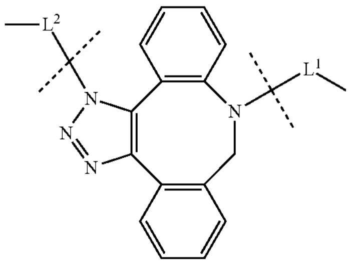
-continued
(TZ-2-r)
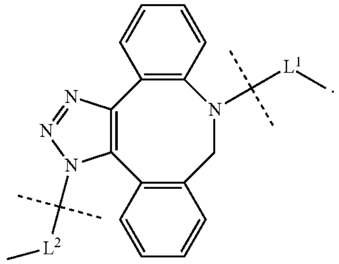
[7-4] In the formula (III-L) of the Embodiment [7], the combination of $-L^2-X-L^1$ is preferably represented by a partial structure selected from the group consisting of the following structural formulae [excluding the parts outside the wavy lines at both ends of each formula]:
[C57]
(LX-1)
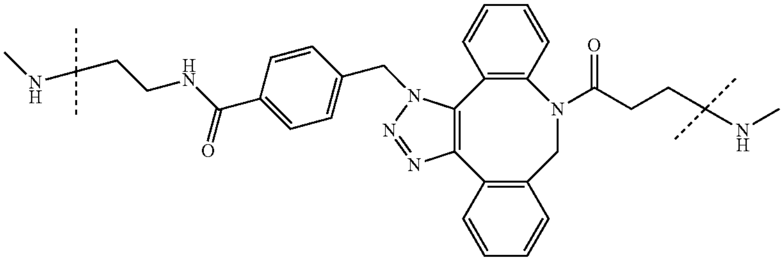
(LX-1-r)
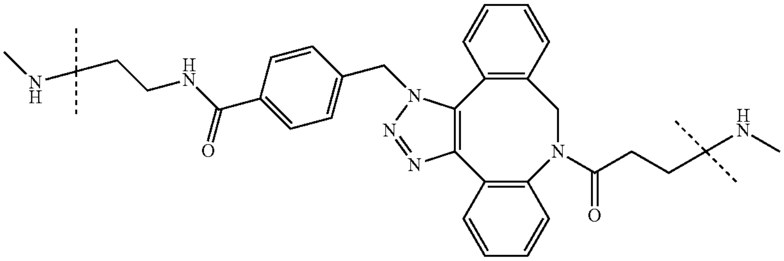
(LX-2)
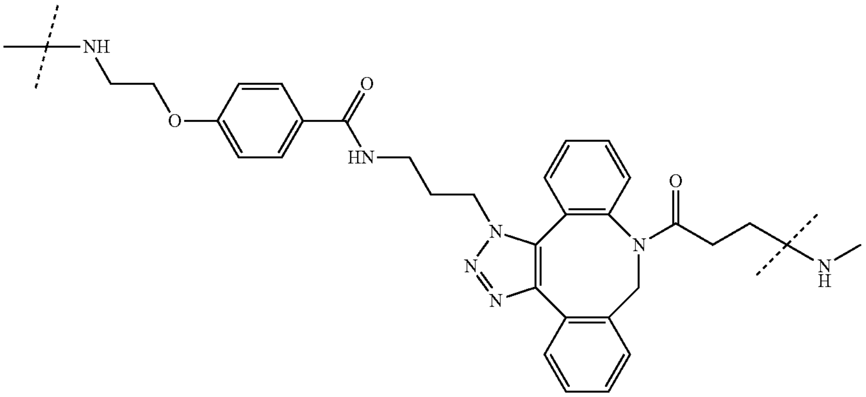

-continued
(LX-2-r)
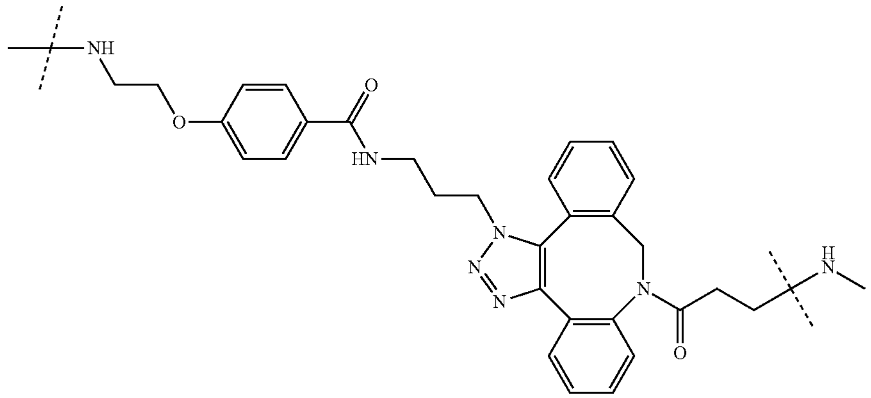
(LX-3)
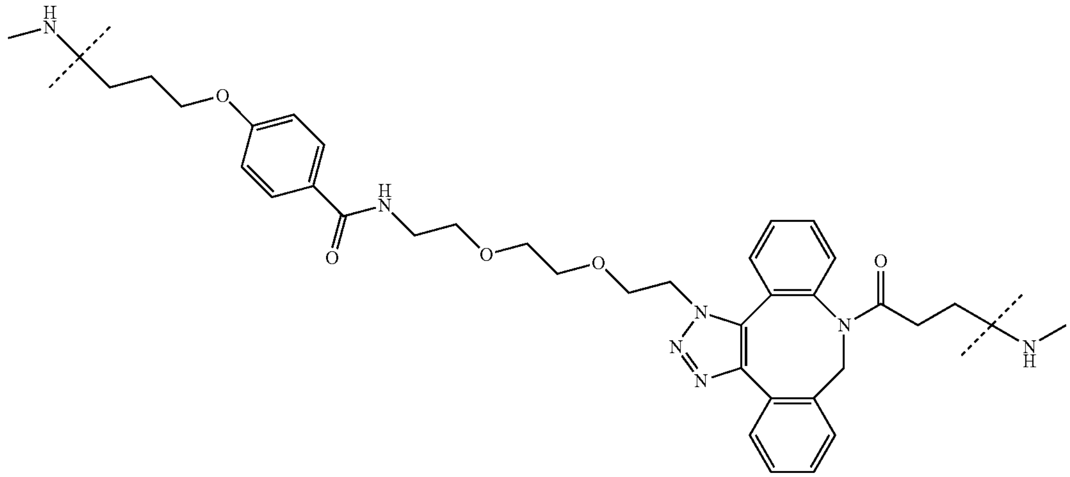
(LX-3-r)
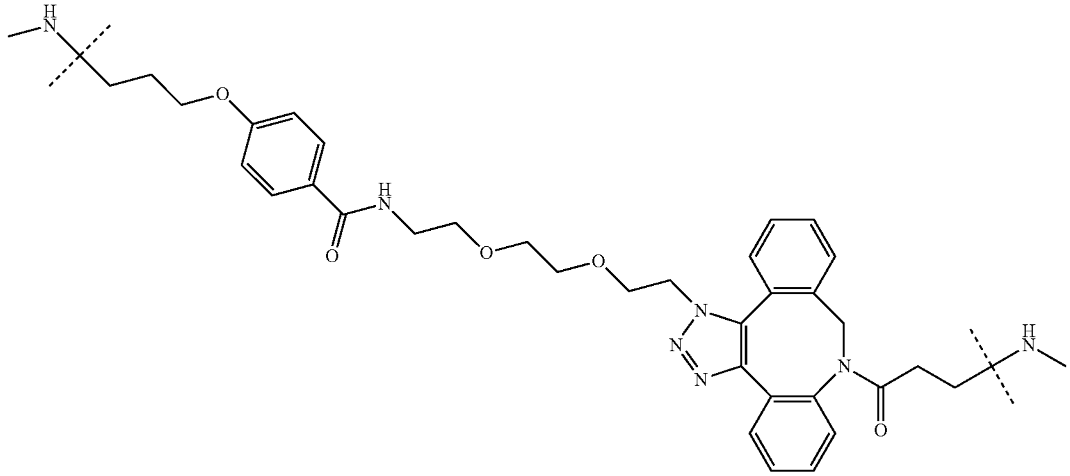
(LX-4)
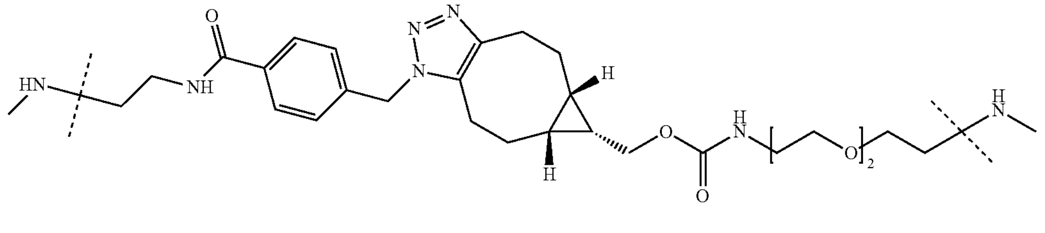

-continued
(LX-4-r)
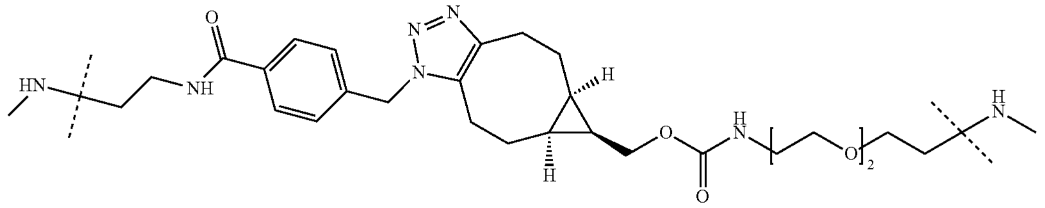
(LX-5)
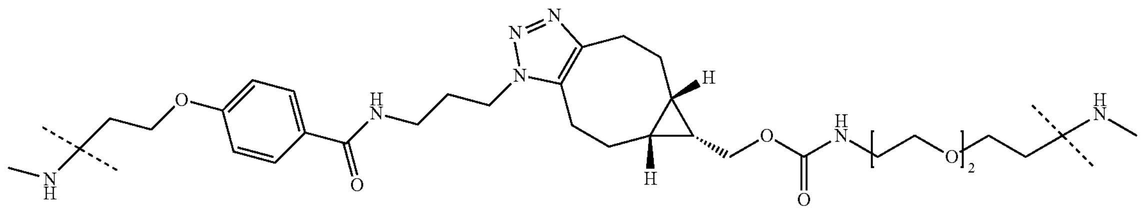
(LX-5-r)
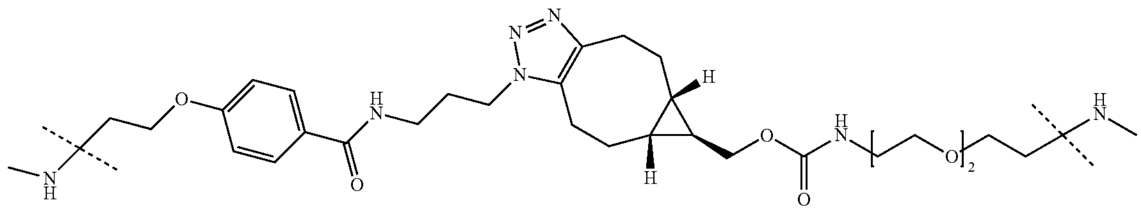
(LX-6)
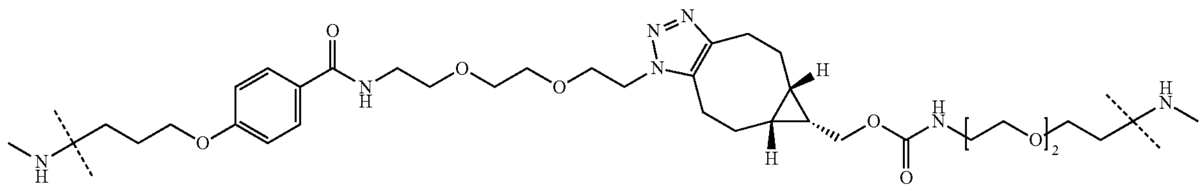
(LX-6-r)
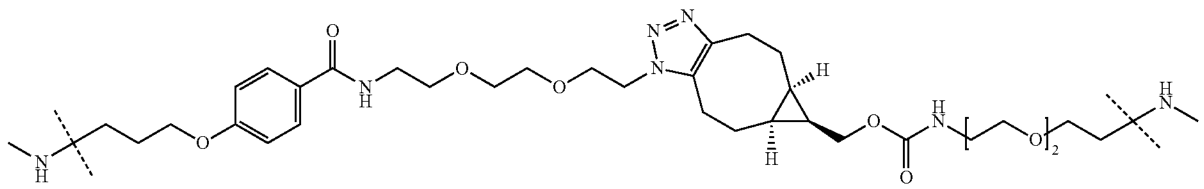

or more preferably, the combination of $-L^2-X-L^1$ is represented by either of the following structural formulae [excluding the parts outside the wavy lines at both ends of each formula]:

[C58]

(LX-2)

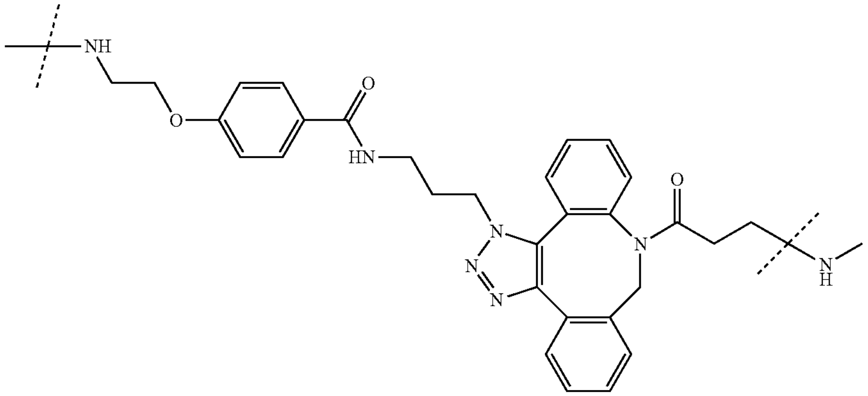

(LX-2-r)

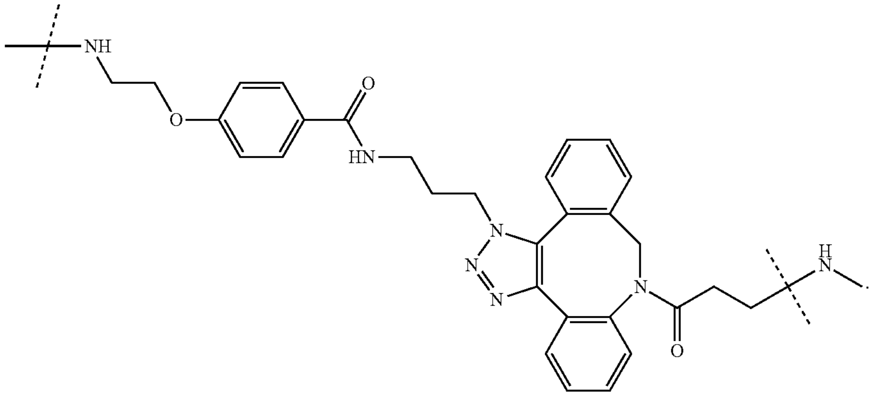

[7-1a] In the formula (III-L) of the Embodiment [7], preferably $-L^1-$ is a divalent linker selected from the following partial structural formulae [excluding the parts outside the wavy lines at both ends of each formula]:

[C59]

(LN-1)

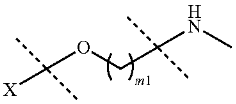

m1 = 2 - 6

(LN-2-1)

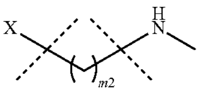

m2 = 2 - 6

-continued (LN-3-1)

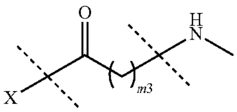

m3 = 2 - 6

(LN-4)

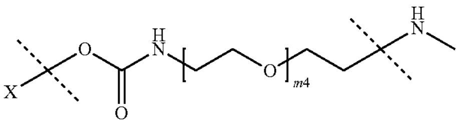

m4 = 1 - 6

(LN-5)

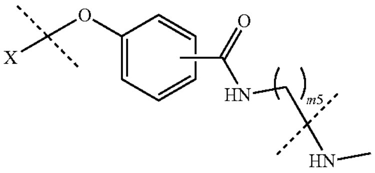

m5 = 2 - 6

-continued (LN-6)

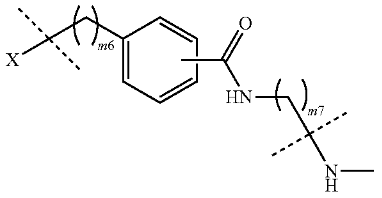

m6 = 1 - 6, m7 = 2 - 6

(LN-7)

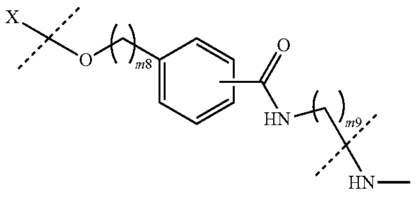

m8 = 1 - 6, m9 = 2 - 6

(LN-9)

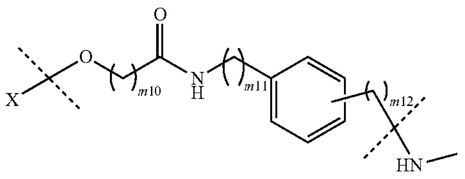

m10 = 1 - 4, m11 = 1 - 6, m12 = 1 - 6

-$L^2$- is a divalent linker selected from the group consisting of the following partial structural formulae [excluding the parts outside the wavy lines at both ends of each formula]:

[C60]

(LK-1-1)

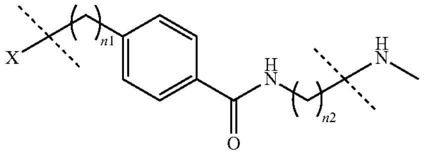

n1 = 1 - 6, n2 = 2 - 6

(LK-2-1)

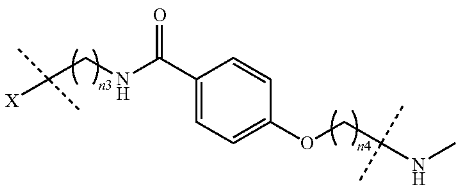

n3 = 2 - 6, n4 = 2 - 6

(LK-3-1)

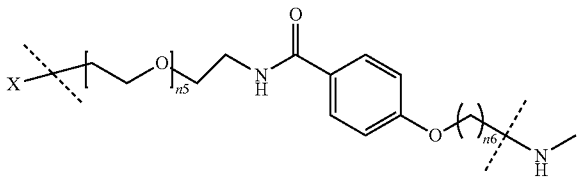

n5 = 1 - 6, n6 = 2 - 6

-continued (LK-4-1)

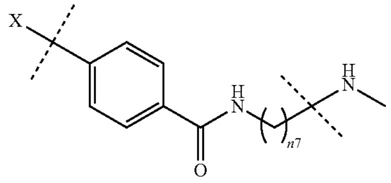

n7 = 2 - 6 and X is a cyclic group selected from the group consisting of the following partial structural formulae [excluding the parts outside the wavy lines at both ends of each formula]:

[C61]

(TZ-1)

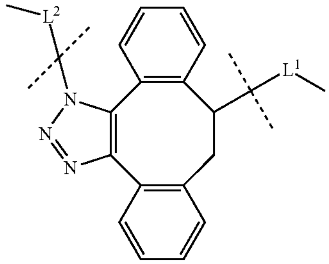

(TZ-2)

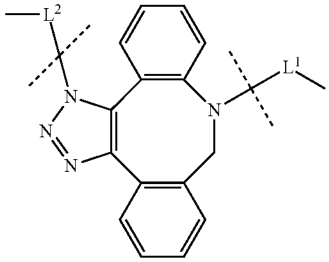

(TZ-3)

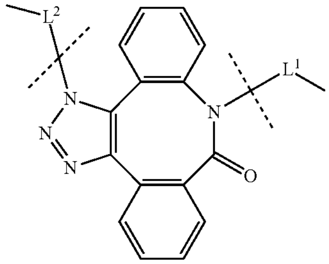

(TZ-4)

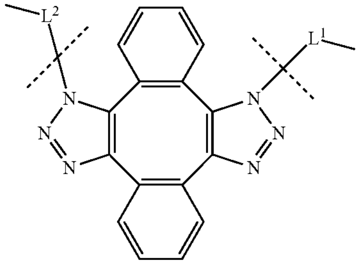

-continued
(TZ-5)
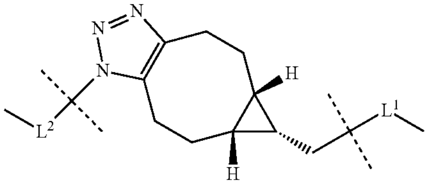
(TZ-6)
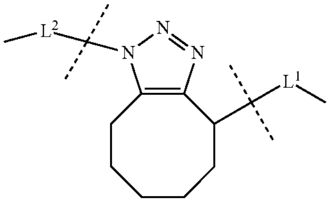
(TZ-1-r)
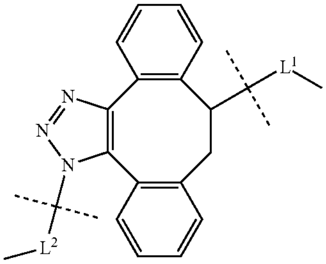
(TZ-2-r)
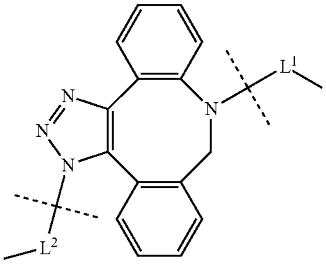
(TZ-3-r)
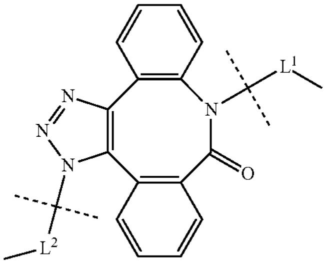
(TZ-4-r)
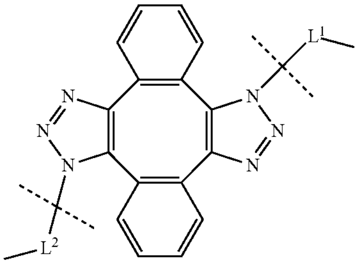
-continued
(TZ-5-r)
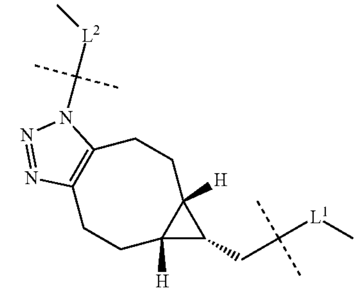
(TZ-6-r)
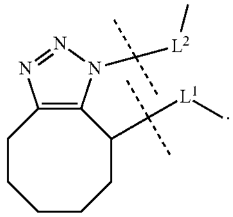
[7-2a] In the formula (III-L) of the Embodiment [7], more preferably $-L^1-$ is a divalent linker selected from the group consisting of the following partial structural formulae [excluding the parts outside the wavy lines at both ends of each formula]:
[C62]
(LN-1)
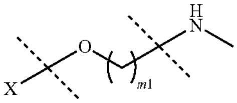
m1 = 2 - 6
(LN-2-1)
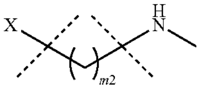
m2 = 2 - 6
(LN-3-1)
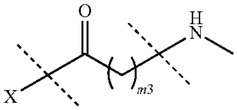
m3 = 2 - 6
(LN-4)
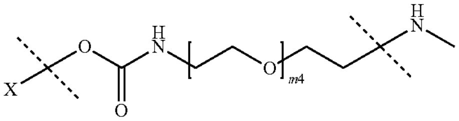
m4 = 1 - 6
(LN-5-p)
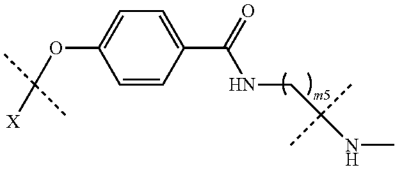
m5 = 2 - 6

-continued (LN-6-p)

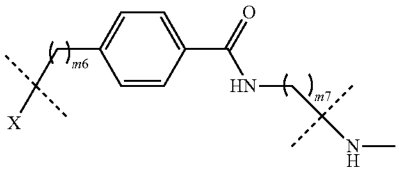

m6 = 1 - 6, m7 = 3 - 6

(LN-7-p)

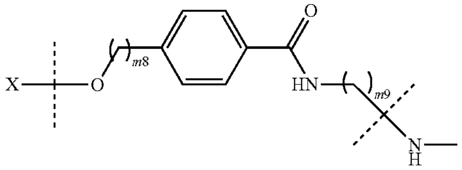

m8 = 1 - 6, m9 = 2 - 6

(LN-9-p)

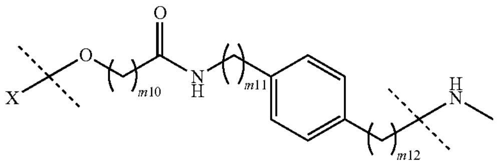

m10 = 1 - 4, m11 = 1 - 6, m12 = 1 - 6

$-L^2-$ is a divalent linker selected from the group consisting of the following partial structural formulae [excluding the parts outside the wavy lines at both ends of each formula]:

[C63]

(LK-1-1)

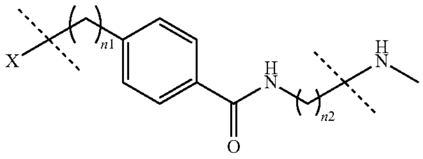

n1 = 1 - 6, n2 = 2 - 6

(LK-2-1)

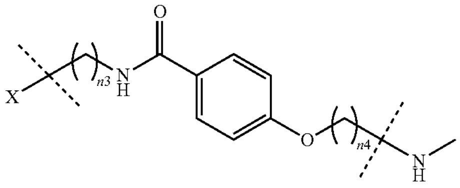

n3 = 2 - 6, n4 = 2 - 6

(LK-3-1)

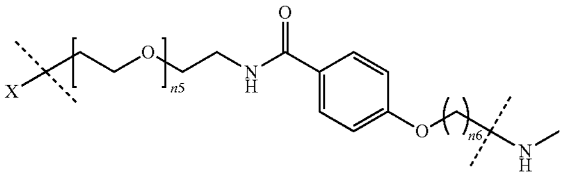

n5 = 1 - 6, n6 = 2 - 6

-continued (LK-4-1)

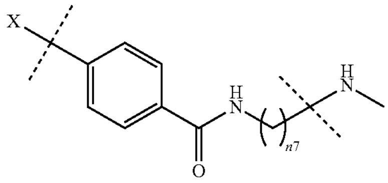

n7 = 2 - 6 and X is a cyclic group selected from the group consisting of the following partial structural formulae [excluding the parts outside the wavy lines at both ends of each formula]:

[C64]

(TZ-1)

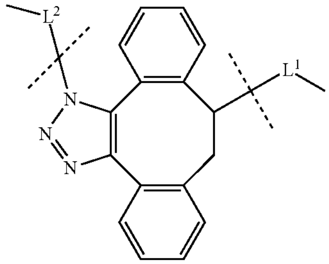

(TZ-2)

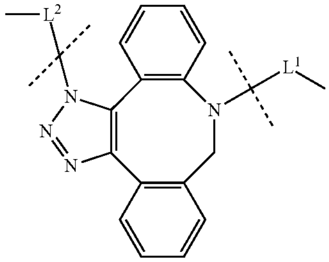

(TZ-3)

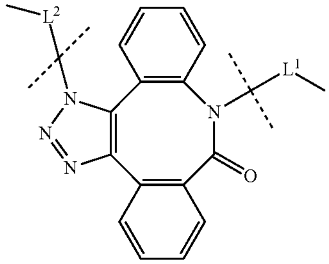

(TZ-4)

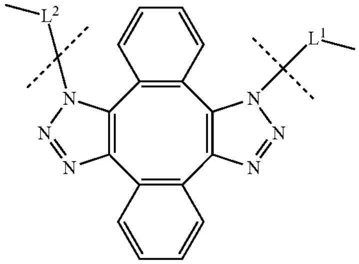

-continued (TZ-5)

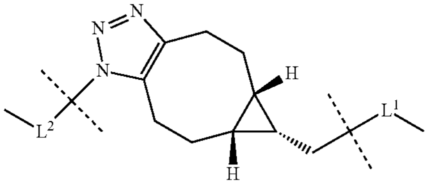

(TZ-6)

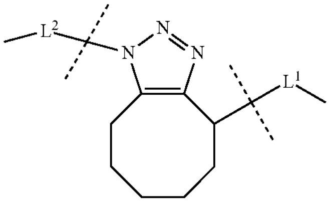

(TZ-1-r)

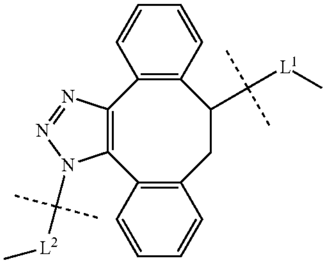

(TZ-2-r)

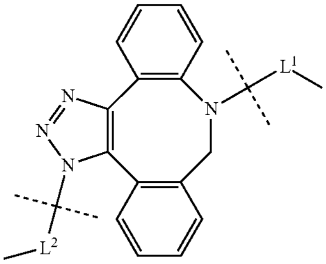

(TZ-3-r)

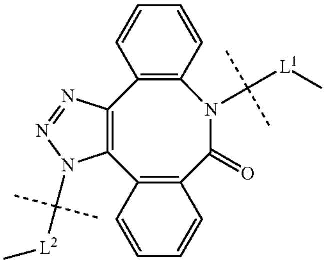

(TZ-4-r)

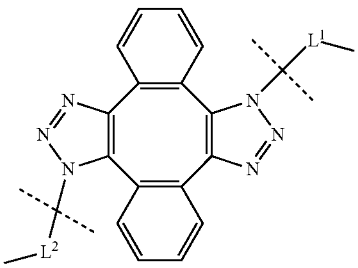

-continued (TZ-5-r)

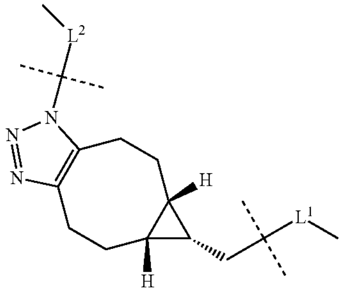

(TZ-6-r)

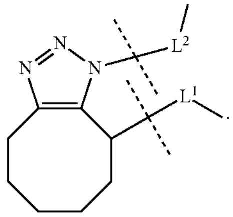

[7-3a] In the formula (III-L) of the Embodiment [7], still more preferably $-L^1-$ is a divalent linker selected from the group consisting of the following partial structural formulae [excluding the parts outside the wavy lines at both ends of each formula]:

[C65]

(LN-3-a)

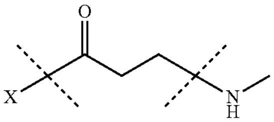

(LN-3-b)

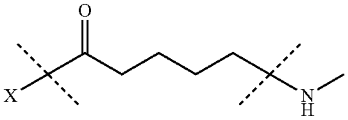

(LN-9-p-a)

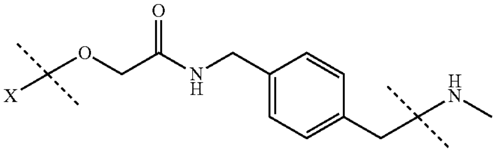

$-L^2-$ is a divalent linker selected from the group consisting of the following partial structural formulae [excluding the parts outside the wavy lines at both ends of each formula]:

[C66]

(LK-1-1-a)

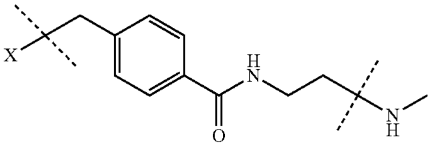

-continued (LK-2-1-a)

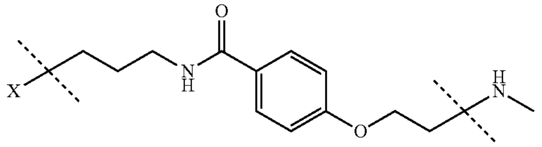

(LK-4-1-a)

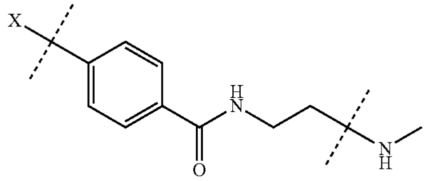

and X is a cyclic group selected from the group consisting of the following partial structural formulae [excluding the parts outside the wavy lines at both ends of each formula]:

[C67]

(TZ-2)

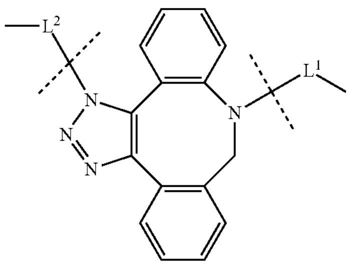

(TZ-6)

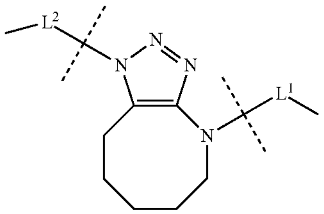

(TZ-2-r)

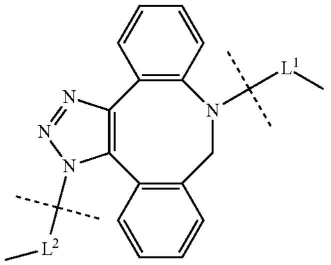

(TZ-6-r)

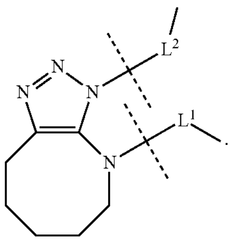

[7-3a-1] In the formula (III-L) of the Embodiment [7], particularly preferably -$L^1$- is a divalent linker selected from the following partial structural formulae [excluding the parts outside the wavy lines at both ends of each formula]:

[C68]

(LN-3-a)

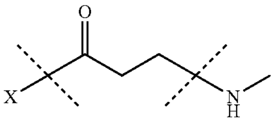

(LN-9-p)

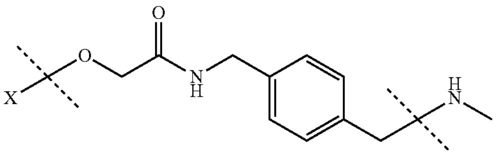

-$L^2$- is a divalent linker selected from the following partial structural formulae [excluding the parts outside the wavy lines at both ends of each formula]:

[C69]

(LK-2-1-a)

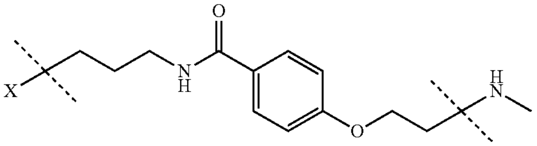

(LK-4-1-a)

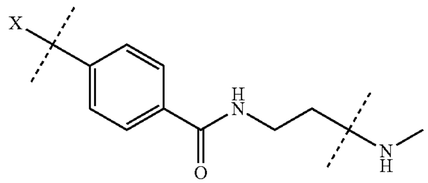

and X is a cyclic group selected from the group consisting of the following partial structural formulae [excluding the parts outside the wavy lines at both ends of each formula]:

[C70]

(TZ-2)

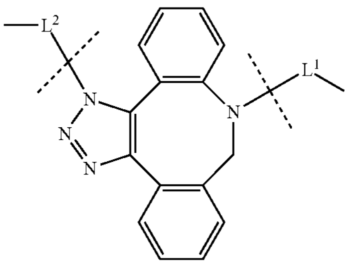

-continued (TZ-6)

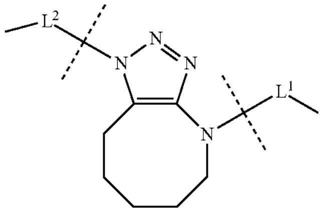

(TZ-2-r)

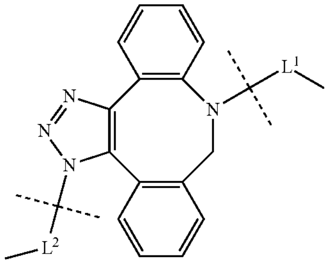

(TZ-6-r)

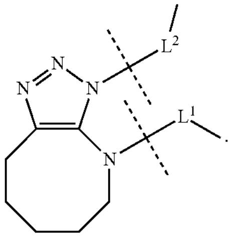

[7-4a] In the formula (III-L) of the Embodiment [7], the combination of -$L^2$-X-$L^1$ is preferably represented as a partial structure selected from the group of combinations shown in the following table (in which the formulae for -$L^1$-, -$L^2$- and —X— are as described in the Embodiments [1], [1-1], [1-1a], [1-1b], [4], [4-1], [4-1a], [4-1b], [7], [7-1], [7-2], [7-3], [7-3-1], [7-1a], [7-2a], [7-3a] and [7-3a-1] above):

TABLE 4

| | —$L^2$— | —X— | —$L^1$— |
|---|---|---|---|
| (LY-1) | (LK-1-1-a) | (TZ-2) | (LN-3-a) |
| (LY-2) | (LK-2-1-a) | (TZ-2) | (LN-3-a) |
| (LY-3) | (LK-4-1-a) | (TZ-2) | (LN-3-a) |
| (LY-4) | (LK-1-1-a) | (TZ-2) | (LN-3-b) |
| (LY-5) | (LK-2-1-a) | (TZ-2) | (LN-3-b) |
| (LY-6) | (LK-4-1-a) | (TZ-2) | (LN-3-b) |
| (LY-7) | (LK-1-1-a) | (TZ-2) | (LN-9-p) |
| (LY-8) | (LK-2-1-a) | (TZ-2) | (LN-9-p) |
| (LY-9) | (LK-4-1-a) | (TZ-2) | (LN-9-p) |
| (LY-1-r) | (LK-1-1-a) | (TZ-2-r) | (LN-3-a) |
| (LY-2-r) | (LK-2-1-a) | (TZ-2-r) | (LN-3-a) |
| (LY-3-r) | (LK-4-1-a) | (TZ-2-r) | (LN-3-a) |
| (LY-4-r) | (LK-1-1-a) | (TZ-2-r) | (LN-3-b) |
| (LY-5-r) | (LK-2-1-a) | (TZ-2-r) | (LN-3-b) |
| (LY-6-r) | (LK-4-1-a) | (TZ-2-r) | (LN-3-b) |
| (LY-7-r) | (LK-1-1-a) | (TZ-2-r) | (LN-9-p) |
| (LY-8-r) | (LK-2-1-a) | (TZ-2-r) | (LN-9-p) |
| (LY-9-r) | (LK-4-1-a) | (TZ-2-r) | (LN-9-p) |
| (LZ-1) | (LK-1-1-a) | (TZ-6) | (LN-3-a) |
| (LZ-2) | (LK-2-1-a) | (TZ-6) | (LN-3-a) |
| (LZ-3) | (LK-4-1-a) | (TZ-6) | (LN-3-a) |
| (LZ-4) | (LK-1-1-a) | (TZ-6) | (LN-3-b) |
| (LZ-5) | (LK-2-1-a) | (TZ-6) | (LN-3-b) |
| (LZ-6) | (LK-4-1-a) | (TZ-6) | (LN-3-b) |
| (LZ-7) | (LK-1-1-a) | (TZ-6) | (LN-9-p) |
| (LZ-8) | (LK-2-1-a) | (TZ-6) | (LN-9-p) |
| (LZ-9) | (LK-4-1-a) | (TZ-6) | (LN-9-p) |
| (LZ-1-r) | (LK-1-1-a) | (TZ-6-r) | (LN-3-a) |
| (LZ-2-r) | (LK-2-1-a) | (TZ-6-r) | (LN-3-a) |
| (LZ-3-r) | (LK-4-1-a) | (TZ-6-r) | (LN-3-a) |
| (LZ-4-r) | (LK-1-1-a) | (TZ-6-r) | (LN-3-b) |
| (LZ-5-r) | (LK-2-1-a) | (TZ-6-r) | (LN-3-b) |
| (LZ-6-r) | (LK-4-1-a) | (TZ-6-r) | (LN-3-b) |
| (LZ-7-r) | (LK-1-1-a) | (TZ-6-r) | (LN-9-p) |
| (LZ-8-r) | (LK-2-1-a) | (TZ-6-r) | (LN-9-p) |
| (LZ-9-r) | (LK-4-1-a) | (TZ-6-r) | (LN-9-p) |

or more preferably, the combination of -$L^2$-X-$L^1$ is represented as a partial structure selected from the group consisting of the following partial structural formulae [excluding the parts outside the wavy lines at both ends of each formula]:

[C71]

(LY-2)

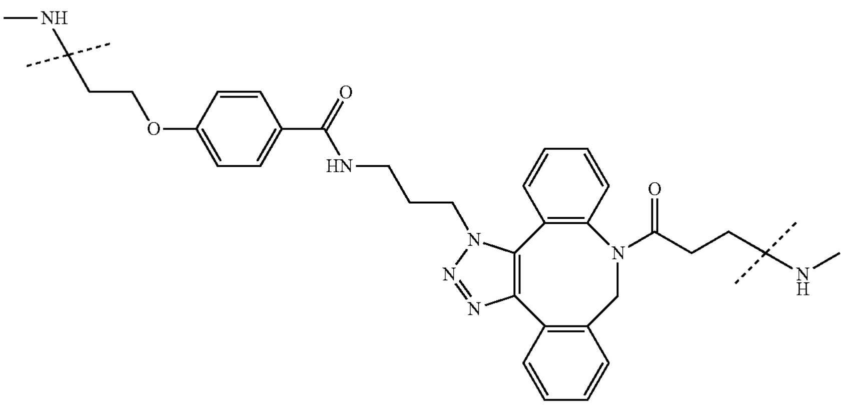

-continued
(LY-2-r)
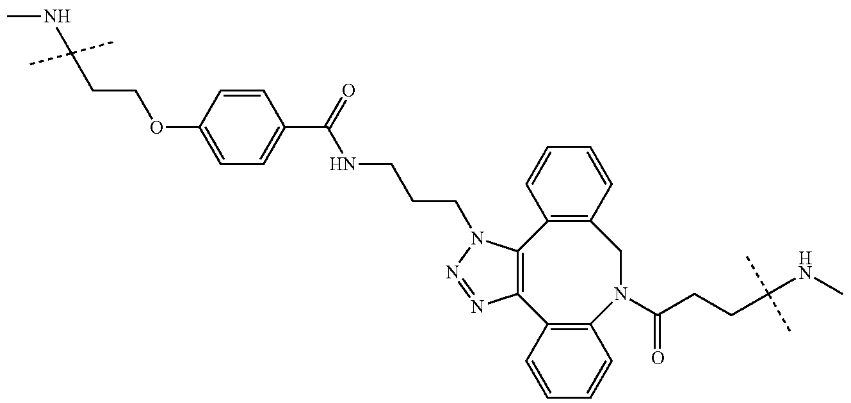
(LY-3)
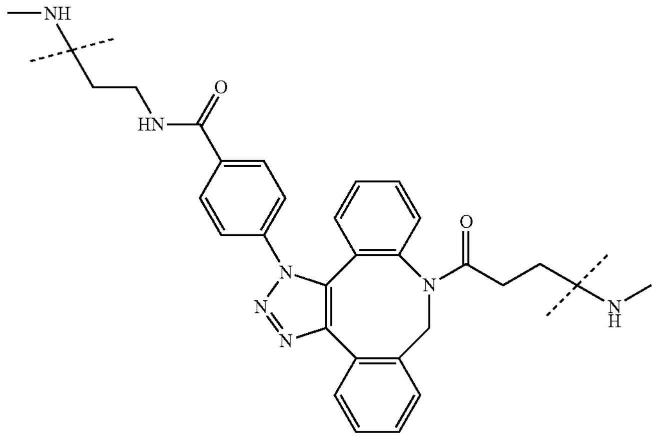
(LY-3-r)
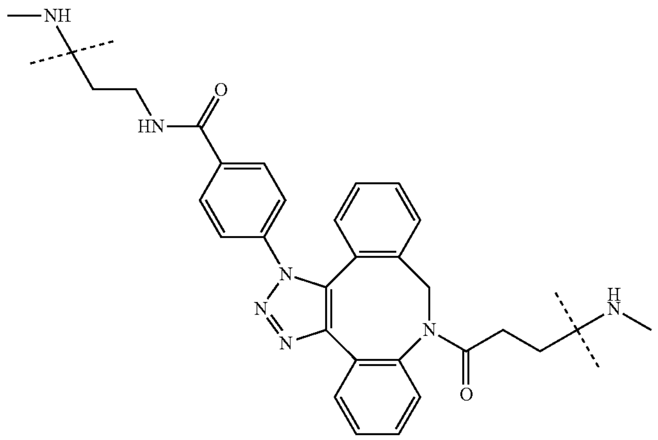
(LZ-8)
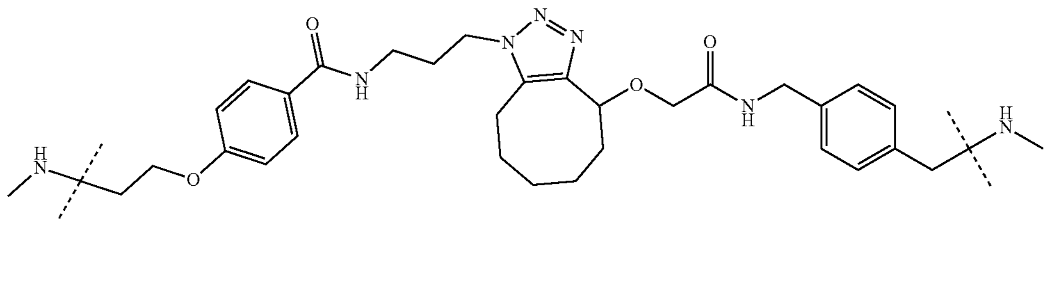

-continued
(LZ-8-r)
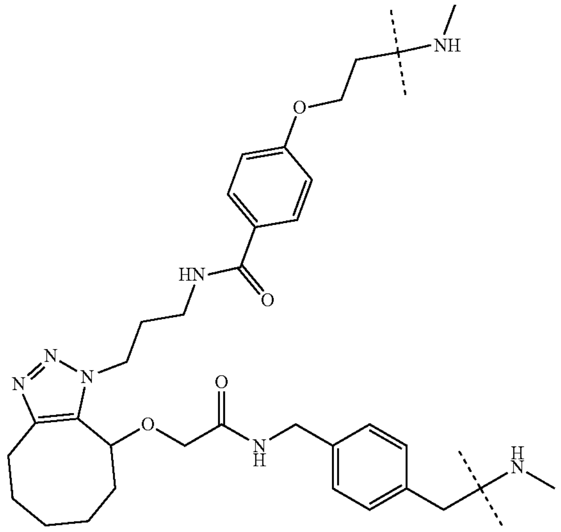
(LZ-9)
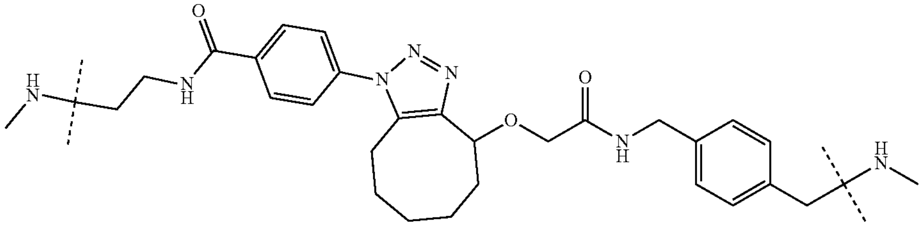
(LZ-9-r)
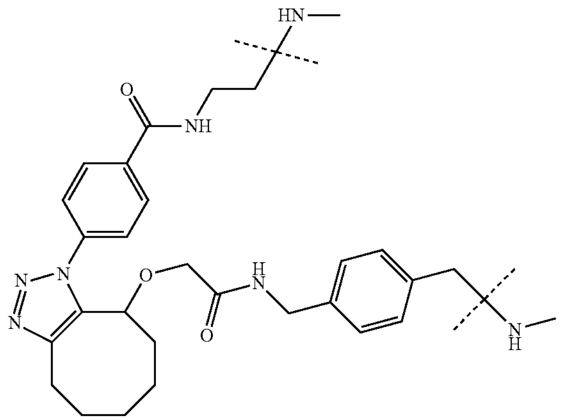
[7-1b] In the formula (III-L) of the Embodiment [7], preferably -$L^1$- is a divalent linker selected from the group consisting of the following partial structural formulae [excluding the parts outside the wavy lines at both ends of each formula]:
[C72]
(LN-1)
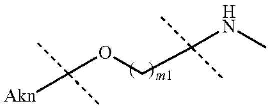
m1 = 2-6
-continued
(LN-2-1)
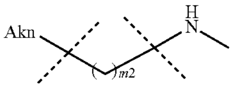
m2 = 2-6
(LN-3-1)
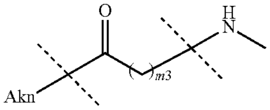
m3 = 2-6

-continued
(LN-4)
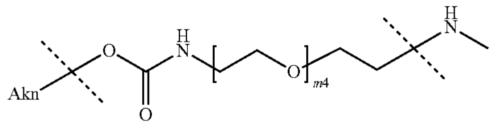
m4 = 1-6
(LN-5)
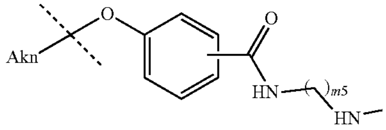
m5 = 2-6
(LN-6)
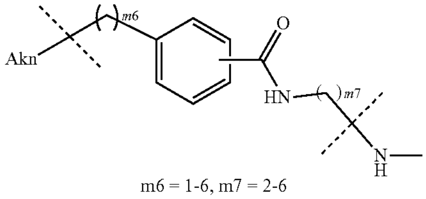
m6 = 1-6, m7 = 2-6
(LN-7)
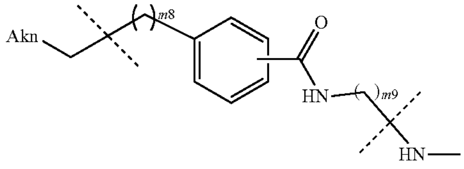
m8 = 1-6, m9 = 2-6
(LN-9)
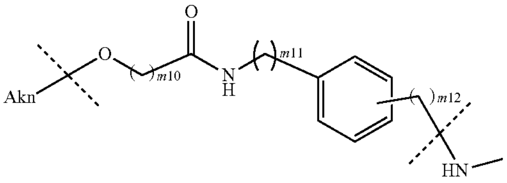
m10 = 1-4, m11 = 1-6, m12 = 1-6
(LN-10)
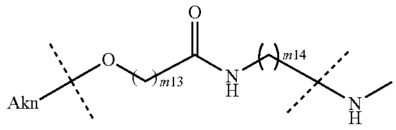
m13 = 1-4, m14 = 2-6
(LN-11)
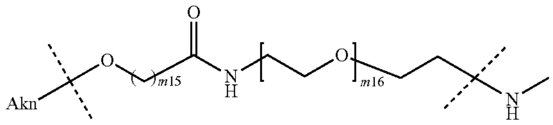
m15 = 1-4, m16 = 1-6
-$L^2$- is a divalent linker selected from the group consisting of the following partial structural formulae [excluding the parts outside the wavy lines at both ends of each formula]:
[C73]
(LK-1-1)
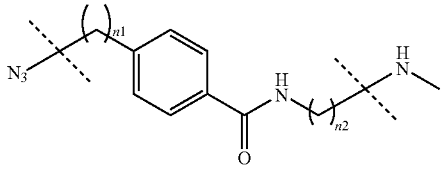
n1 = 1-6, n2 = 2-6
(LK-2-1)
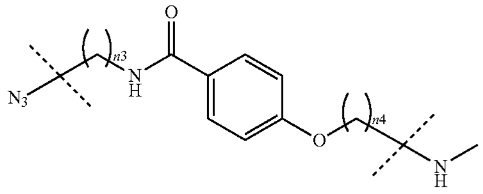
n3 = 2-6, n4 = 2-6
(LK-3-1)
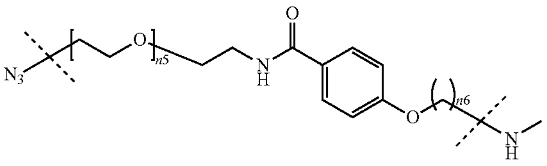
n5 = 1-6, n6 = 2-6
(LK-4-1)
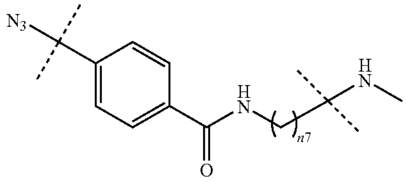
n7 = 2-6
(LK-5-1)
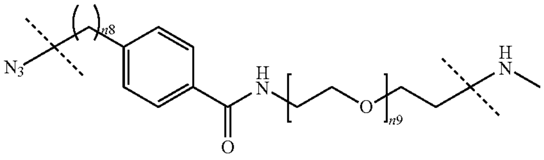
n8 = 1-4, n9 = 1-6
(LK-6-1)
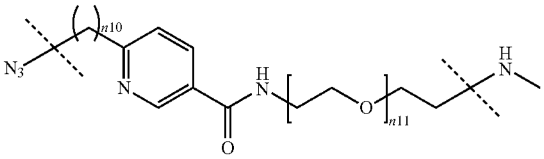
n10 = 1-4, n11 = 1-6

-continued
(LK-7-1)
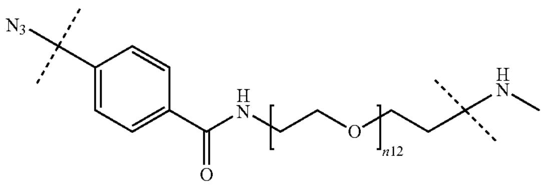
n12 = 1-6
and X is a cyclic group selected from the group consisting of the following partial structural formulae [excluding the parts outside the wavy lines at both ends of each formula]:
[C74]
(TZ-1)
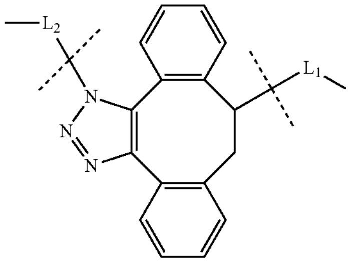
(TZ-2)
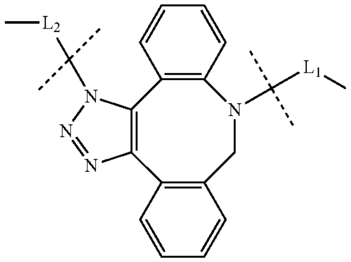
(TZ-3)
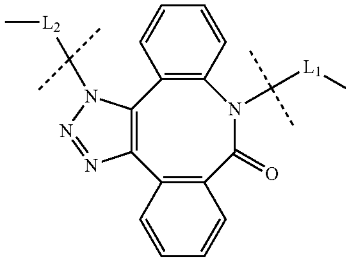
(TZ-4)
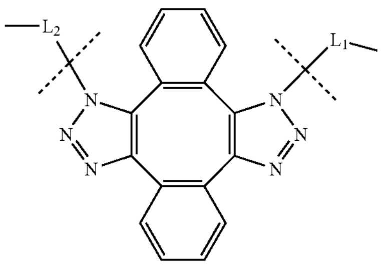
-continued
(TZ-5)
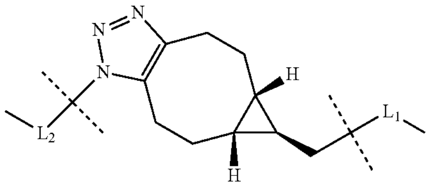
(TZ-6)
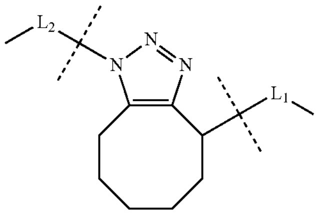
(TZ-1-r)
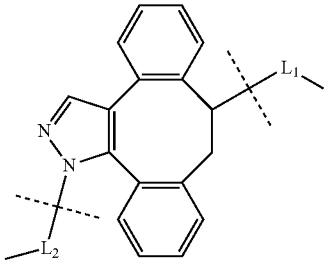
(TZ-2-r)
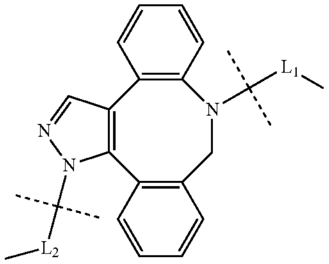
(TZ-3-r)
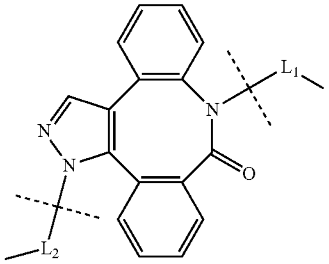
(TZ-4-r)
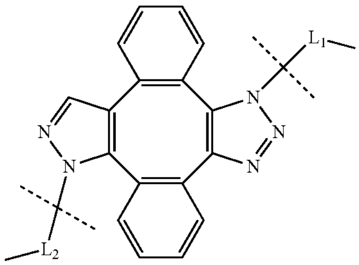

-continued (TZ-5-r)

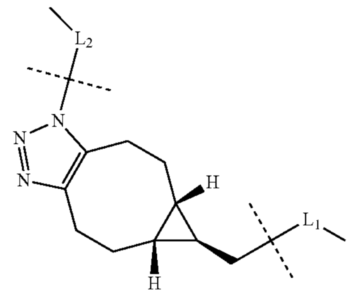

(TZ-6-r)

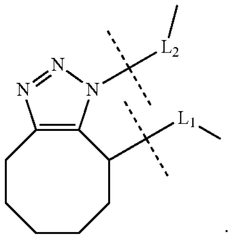

[7-2b] In the formula (III-L) of the Embodiment [7], more preferably $-L^1-$ is a divalent linker selected from the group consisting of the following partial structural formulae [excluding the parts outside the wavy lines at both ends of each formula]:

[C75]

(LN-1)

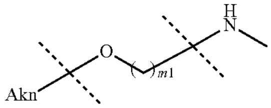

m1 = 2-6

(LN-2-1)

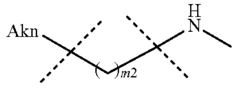

m2 = 2-6

(LN-3-1)

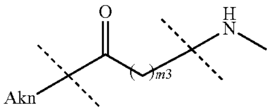

m3 = 2-6

(LN-4)

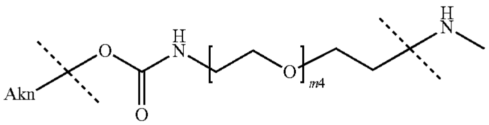

m4 = 1-6

(LN-5-p)

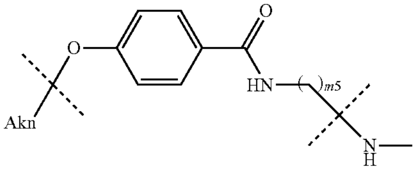

m5 = 2-6

-continued (LN-6-p)

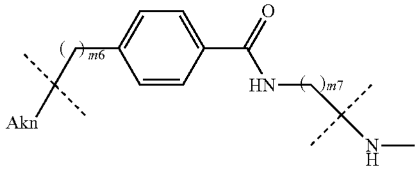

m6 = 1-6, m7 = 3-6

(LN-7-p)

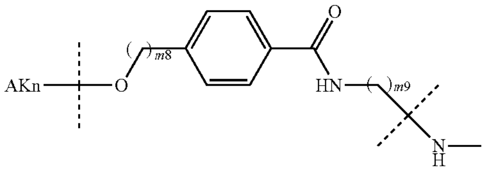

m8 = 1-6, m9 = 2-6

(LN-9-p)

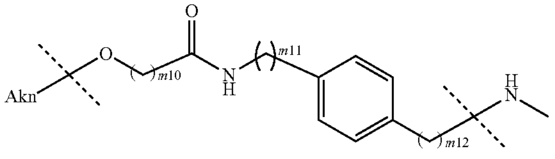

m10 = 1-4, m11 = 1-6, m12 = 1-6

(LN-10)

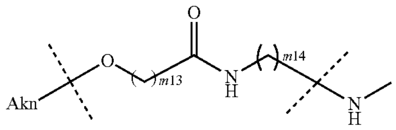

m13 = 1-4, m14 = 2-6

(LN-11)

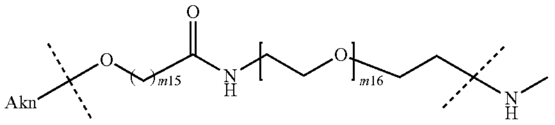

m15 = 1-4, m16 = 1-6

$-L^2-$ is a divalent linker selected from the group consisting of the following partial structural formulae [excluding the parts outside the wavy lines at both ends of each formula]:

[C76]

(LK-1-1)

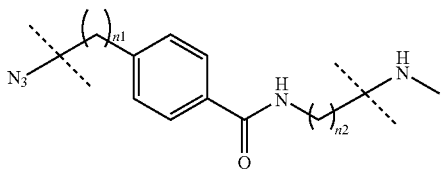

n1 = 1-6, n2 = 2-6

-continued
(LK-2-1)
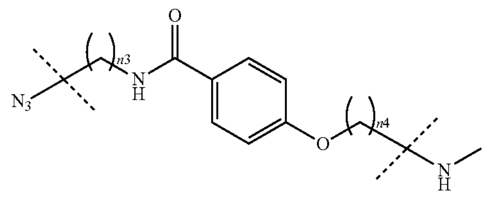
n3 = 2-6, n4 = 2-6
(LK-3-1)
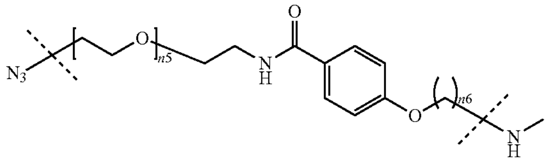
n5 = 1-6, n6 = 2-6
(LK-4-1)
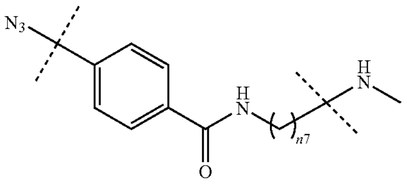
n7 = 2-6
(LK-5-1)
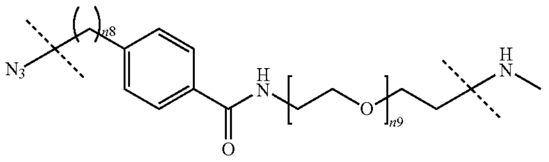
n8 = 1-4, n9 = 1-6
(LK-6-1)
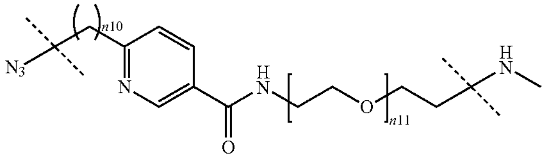
n10 = 1-4, n11 = 1-6
(LK-7-1)
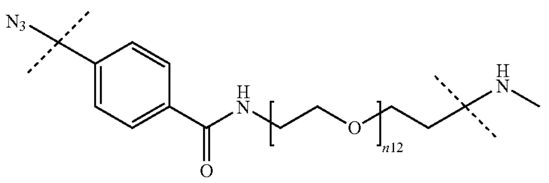
n12 = 1-6
and X is a cyclic group selected from the group consisting of the following partial structural formulae [excluding the parts outside the wavy lines at both ends of each formula]:
[C77]
(TZ-1)
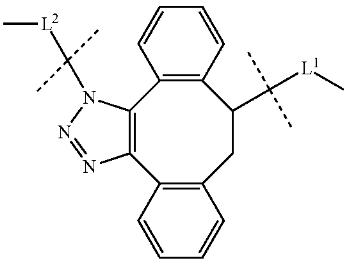
(TZ-2)
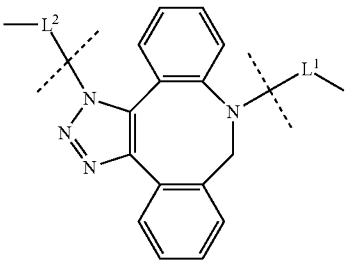
(TZ-3)
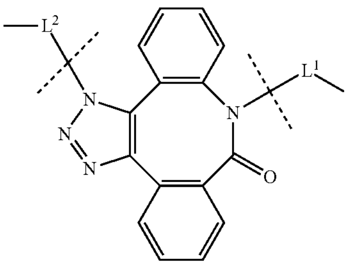
(TZ-4)
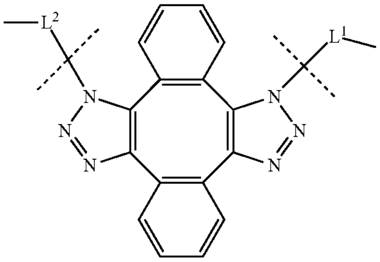
(TZ-5)
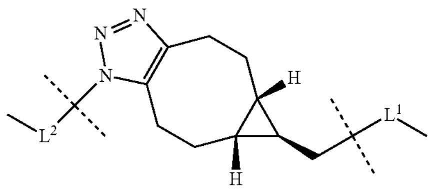
(TZ-6)
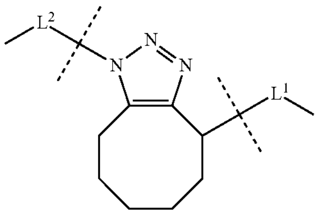

-continued (TZ-1-r)

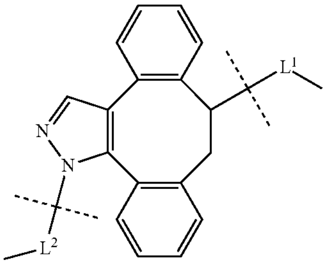

(TZ-2-r)

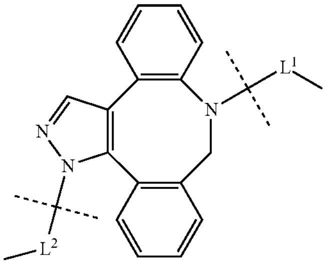

(TZ-3-r)

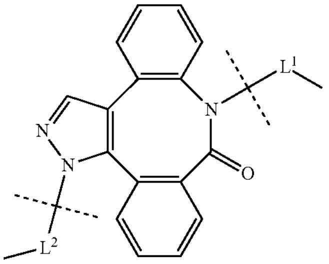

(TZ-4-r)

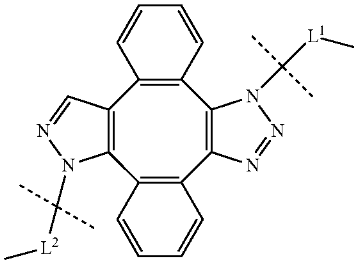

(TZ-5-r)

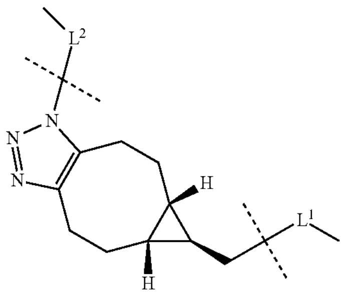

(TZ-6-r)

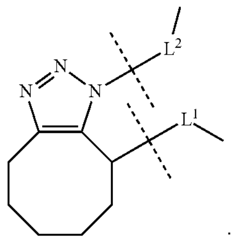

[7-3b] In the formula (III-L) of the Embodiment [7], still more preferably $-L^1-$ is a divalent linker selected from the group consisting of the following partial structural formulae [excluding the parts outside the wavy lines at both ends of each formula]:

[C78]

(LN-3-a)

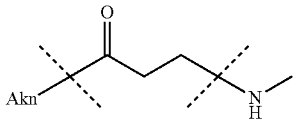

(LN-3-b)

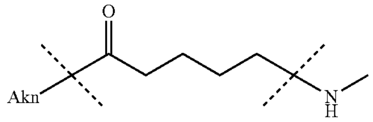

(LN-4-a)

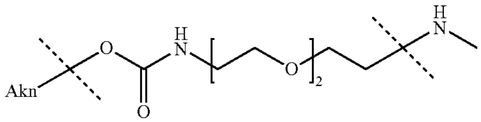

(LN-9-p-a)

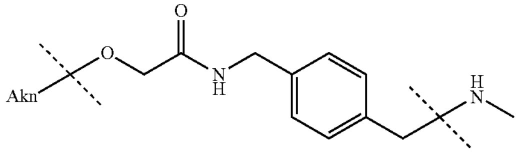

(LN-10-a)

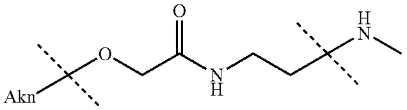

(LN-11-a)

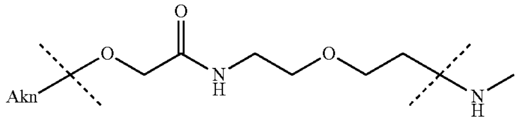

$-L^2-$ is a divalent linker selected from the group consisting of the following partial structural formulae [excluding the parts outside the wavy lines at both ends of each formula]:

[C79]

(LK-1-1-a)

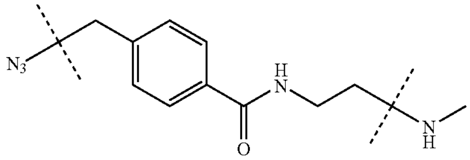

-continued (LK-2-1-a)

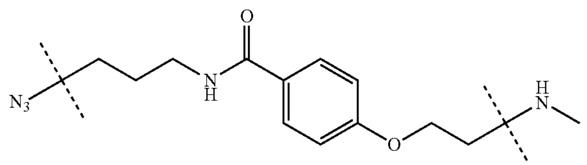

(LK-4-1-a)

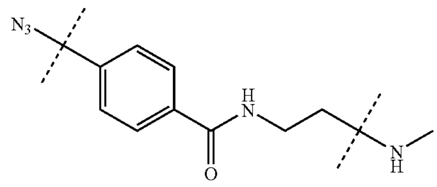

(LK-5-1-a)

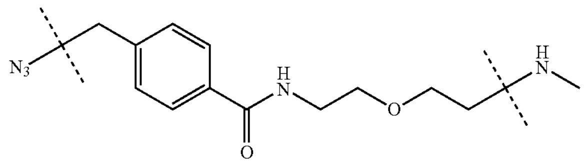

(LK-5-1-b)

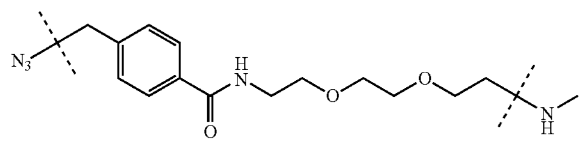

(LK-6-1-a)

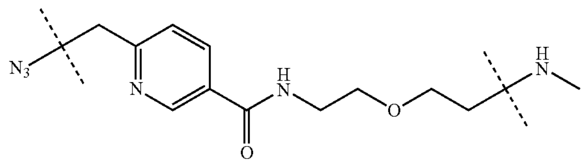

(LK-7-1-a)

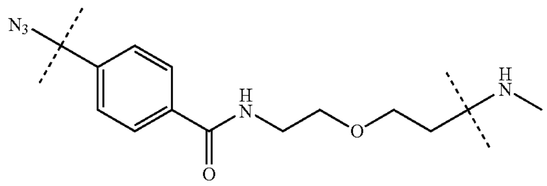

(LK-7-1-b)

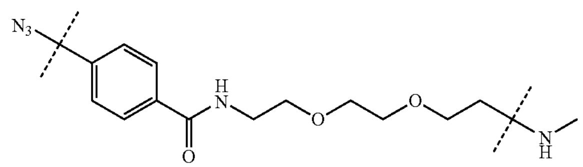

and X is a cyclic group selected from the group consisting of the following partial structural formulae [excluding the parts outside the wavy lines at both ends of each formula]:

[C80]

(TZ-2)

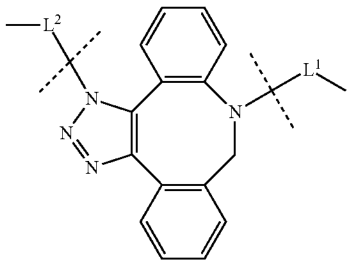

(TZ-6)

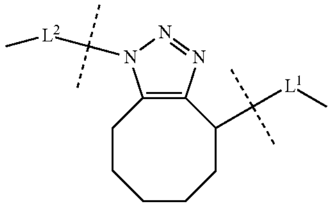

(TZ-2-r)

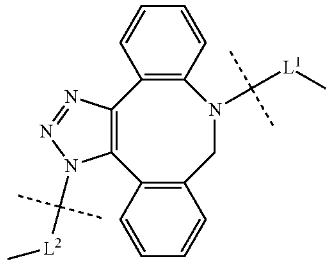

(TZ-6-r)

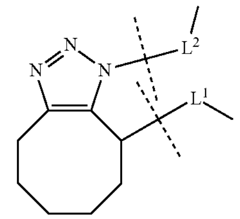

(TZ-5)

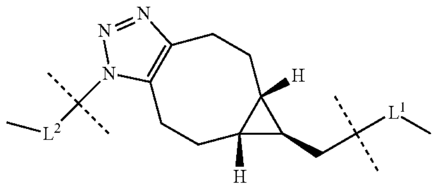

(TZ-5-r)

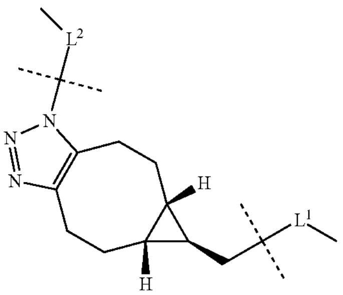

[7-4b] In the formula (III-L) of the Embodiment [7], the combination of $-L^1$-X-$L^2$ is preferably represented as a partial structure selected from the group of combinations shown in the following table (in which the formulae for $-L^1$-, $-L^2$- and —X— are as described in the Embodiments [1], [1-1], [1-1a], [1-1b], [4], [4-1], [4-1a], [4-1b], [7], [7-1], [7-2], [7-3], [7-3-1], [7-1a], [7-2a], [7-3a], [7-3a-1], [7-1b], [7-2b] and [7-3b] above):

TABLE 5-1

| —L¹— | —X— | —L²— |
|---|---|---|
| LN-3-a | TZ-2 | LK-1-1-a |
| | | LK-2-1-a |
| | | LK-4-1-a |
| | | LK-5-1-a |
| | | LK-5-1-b |
| | | LK-6-1-a |
| | | LK-7-1-a |
| | | LK-7-1-b |
| | TZ-2-r | LK-1-1-a |
| | | LK-2-1-a |
| | | LK-4-1-a |
| | | LK-5-1-a |
| | | LK-5-1-b |
| | | LK-6-1-a |
| | | LK-7-1-a |
| | | LK-7-1-b |
| | TZ-5 | LK-1-1-a |
| | | LK-2-1-a |
| | | LK-4-1-a |
| | | LK-5-1-a |
| | | LK-5-1-b |
| | | LK-6-1-a |
| | | LK-7-1-a |
| | | LK-7-1-b |
| | TZ-5-r | LK-1-1-a |
| | | LK-2-1-a |
| | | LK-4-1-a |
| | | LK-5-1-a |
| | | LK-5-1-b |
| | | LK-6-1-a |
| | | LK-7-1-a |
| | | LK-7-1-b |
| | TZ-6 | LK-1-1-a |
| | | LK-2-1-a |
| | | LK-4-1-a |
| | | LK-5-1-a |
| | | LK-5-1-b |
| | | LK-6-1-a |
| | | LK-7-1-a |
| | | LK-7-1-b |
| | TZ-6-r | LK-1-1-a |
| LN-3-b | TZ-2 | LK-1-1-a |
| | | LK-2-1-a |
| | | LK-4-1-a |
| | | LK-5-1-a |
| | | LK-5-1-b |
| | | LK-6-1-a |
| | | LK-7-1-a |
| | | LK-7-1-b |
| | TZ-2-r | LK-1-1-a |
| | | LK-2-1-a |
| | | LK-4-1-a |
| | | LK-5-1-a |
| | | LK-5-1-b |
| | | LK-6-1-a |
| | | LK-7-1-a |
| | | LK-7-1-b |
| | TZ-5 | LK-1-1-a |
| | | LK-2-1-a |
| | | LK-4-1-a |
| | | LK-5-1-a |
| | | LK-5-1-b |
| | | LK-6-1-a |
| | | LK-7-1-a |
| | | LK-7-1-b |
| | TZ-5-r | LK-1-1-a |
| | | LK-2-1-a |
| | | LK-4-1-a |
| | | LK-5-1-a |
| | | LK-5-1-b |
| | | LK-6-1-a |
| | | LK-7-1-a |

TABLE 5-1-continued

| —L¹— | —X— | —L²— |
|---|---|---|
| | | LK-7-1-b |
| | TZ-6 | LK-1-1-a |
| | | LK-2-1-a |
| | | LK-4-1-a |
| | | LK-5-1-a |
| | | LK-5-1-b |
| | | LK-6-1-a |
| | | LK-7-1-a |
| | | LK-7-1-b |
| | TZ-6-r | LK-1-1-a |

TABLE 5-2

| —L1— | —X— | —L2— | —L1— | —X— | —L2— |
|---|---|---|---|---|---|
| | | LK-2-1-a | | | LK-2-1-a |
| | | LK-4-1-a | | | LK-4-1-a |
| | | LK-5-1-a | | | LK-5-1-a |
| | | LK-5-1-b | | | LK-5-1-b |
| | | LK-6-1-a | | | LK-6-1-a |
| | | LK-7-1-a | | | LK-7-1-a |
| | | LK-7-1-b | | | LK-7-1-b |
| LN-4-a | TZ-5 | LK-1-1-a | LN-9-p-a | TZ-5 | LK-1-1-a |
| | | LK-2-1-a | | | LK-2-1-a |
| | | LK-4-1-a | | | LK-4-1-a |
| | | LK-5-1-a | | | LK-5-1-a |
| | | LK-5-1-b | | | LK-5-1-b |
| | | LK-6-1-a | | | LK-6-1-a |
| | | LK-7-1-a | | | LK-7-1-a |
| | | LK-7-1-b | | | LK-7-1-b |
| | TZ-5-r | LK-1-1-a | | TZ-5-r | LK-1-1-a |
| | | LK-2-1-a | | | LK-2-1-a |
| | | LK-4-1-a | | | LK-4-1-a |
| | | LK-5-1-a | | | LK-5-1-a |
| | | LK-5-1-b | | | LK-5-1-b |
| | | LK-6-1-a | | | LK-6-1-a |
| | | LK-7-1-a | | | LK-7-1-a |
| | | LK-7-1-b | | | LK-7-1-b |
| | TZ-6 | LK-1-1-a | | TZ-6 | LK-1-1-a |
| | | LK-2-1-a | | | LK-2-1-a |
| | | LK-4-1-a | | | LK-4-1-a |
| | | LK-5-1-a | | | LK-5-1-a |
| | | LK-5-1-b | | | LK-5-1-b |
| | | LK-6-1-a | | | LK-6-1-a |
| | | LK-7-1-a | | | LK-7-1-a |
| | | LK-7-1-b | | | LK-7-1-b |
| | TZ-6-r | LK-1-1-a | | TZ-6-r | LK-1-1-a |
| | | LK-2-1-a | | | LK-2-1-a |
| | | LK-4-1-a | | | LK-4-1-a |
| | | LK-5-1-a | | | LK-5-1-a |
| | | LK-5-1-b | | | LK-5-1-b |
| | | LK-6-1-a | | | LK-6-1-a |
| | | LK-7-1-a | | | LK-7-1-a |
| | | LK-7-1-b | | | LK-7-1-b |
| LN-10-a | TZ-5 | LK-1-1-a | LN-11-a | TZ-5 | LK-1-1-a |
| | | LK-2-1-a | | | LK-2-1-a |
| | | LK-4-1-a | | | LK-4-1-a |
| | | LK-5-1-a | | | LK-5-1-a |

TABLE 5-3

| —L1— | —X— | —L2— | —L1— | —X— | —L2— |
|---|---|---|---|---|---|
| | | LK-5-1-b | | | LK-5-1-b |
| | | LK-6-1-a | | | LK-6-1-a |
| | | LK-7-1-a | | | LK-7-1-a |
| | | LK-7-1-b | | | LK-7-1-b |
| | TZ-5-r | LK-1-1-a | | TZ-5-r | LK-1-1-a |
| | | LK-2-1-a | | | LK-2-1-a |
| | | LK-4-1-a | | | LK-4-1-a |
| | | LK-5-1-a | | | LK-5-1-a |
| | | LK-5-1-b | | | LK-5-1-b |
| | | LK-6-1-a | | | LK-6-1-a |

TABLE 5-3-continued

| —L1— | —X— | —L2— | —L1— | —X— | —L2— |
|---|---|---|---|---|---|
| | | LK-7-1-a | | | LK-7-1-a |
| | | LK-7-1-b | | | LK-7-1-b |
| | TZ-6 | LK-1-1-a | | TZ-6 | LK-1-1-a |
| | | LK-2-1-a | | | LK-2-1-a |
| | | LK-4-1-a | | | LK-4-1-a |
| | | LK-5-1-a | | | LK-5-1-a |
| | | LK-5-1-b | | | LK-5-1-b |
| | | LK-6-1-a | | | LK-6-1-a |
| | | LK-7-1-a | | | LK-7-1-a |
| | | LK-7-1-b | | | LK-7-1-b |
| | TZ-6-r | LK-1-1-a | | TZ-6-r | LK-1-1-a |
| | | LK-2-1-a | | | LK-2-1-a |
| | | LK-4-1-a | | | LK-4-1-a |

TABLE 5-3-continued

| —L1— | —X— | —L2— | —L1— | —X— | —L2— |
|---|---|---|---|---|---|
| | | LK-5-1-a | | | LK-5-1-a |
| | | LK-5-1-b | | | LK-5-1-b |
| | | LK-6-1-a | | | LK-6-1-a |
| | | LK-7-1-a | | | LK-7-1-a |
| | | LK-7-1-b | | | LK-7-1-b |

or more preferably the combination of -$L^2$-X-$L^1$ is represented as a partial structure selected from the group consisting of the following partial structural formulae [excluding the parts outside the wavy lines at both ends of each formula]:

[C81]

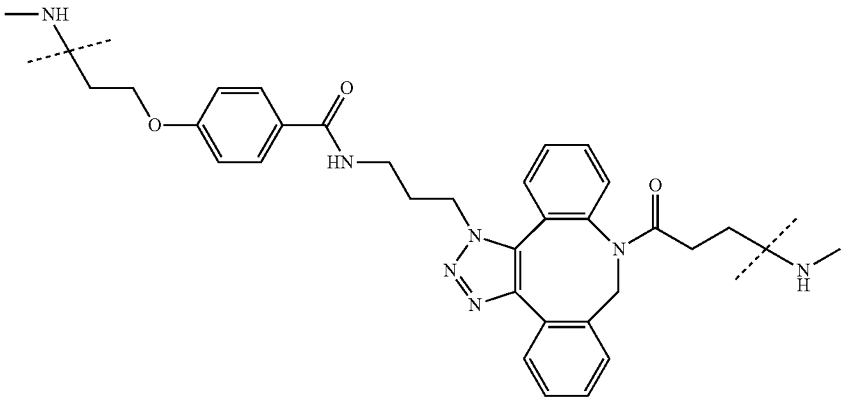

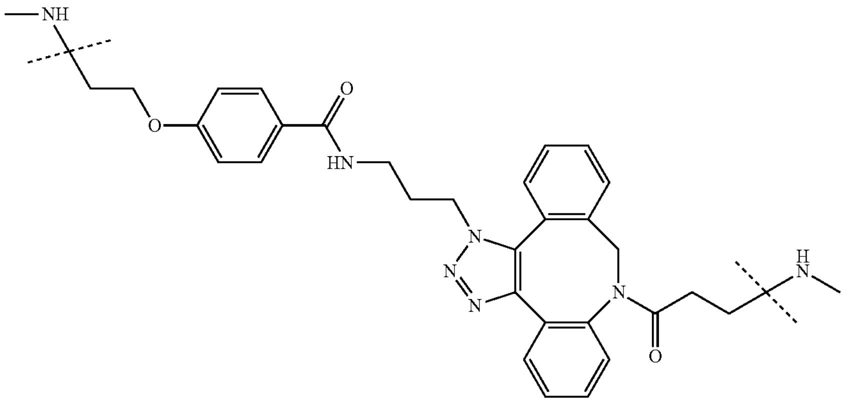

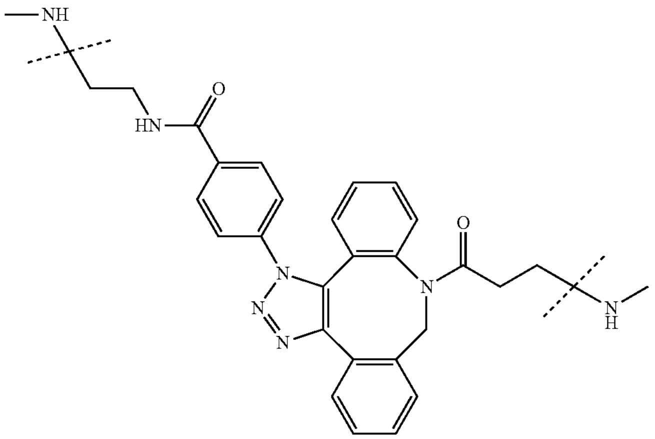

-continued
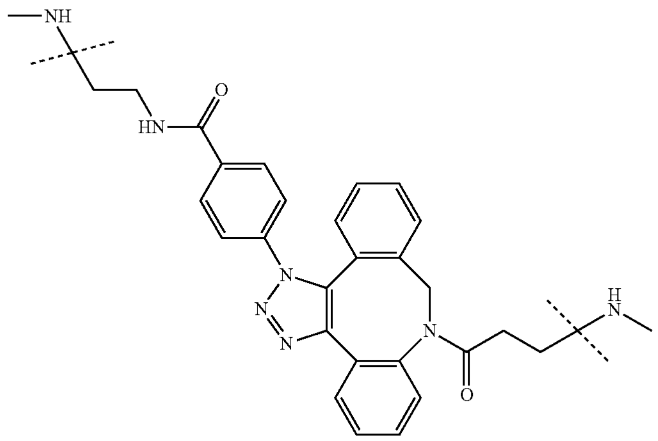
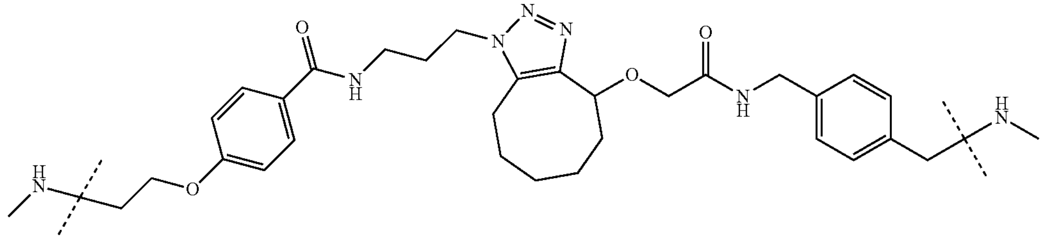
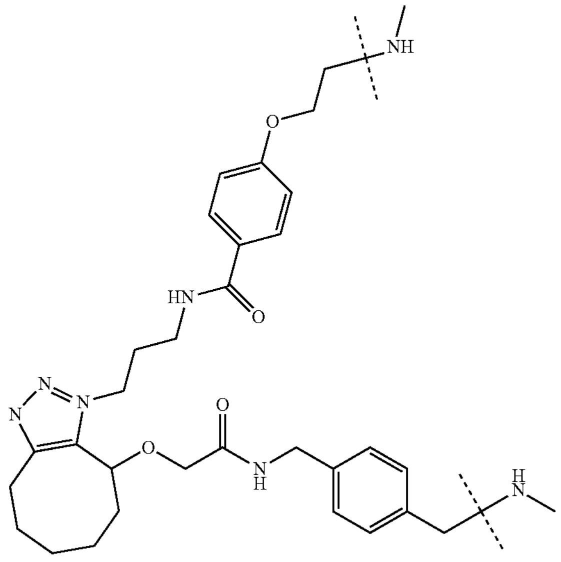
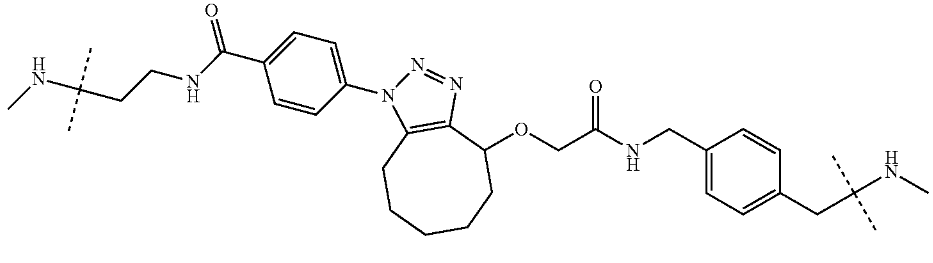

-continued
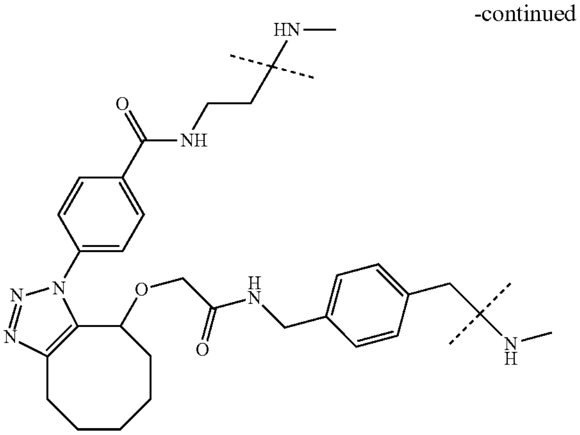
[C82]
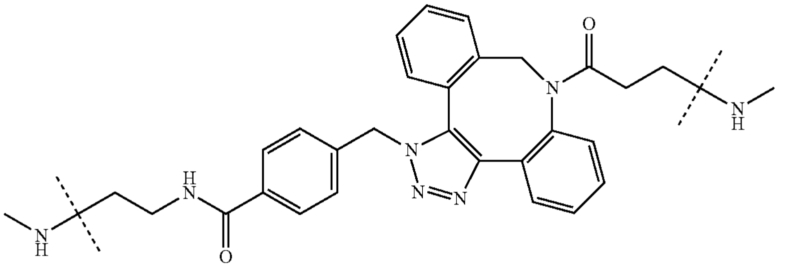
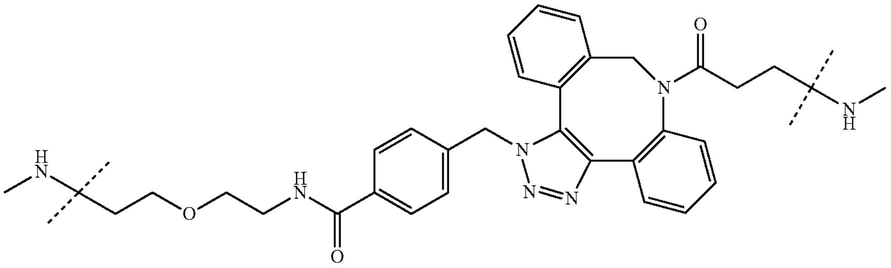
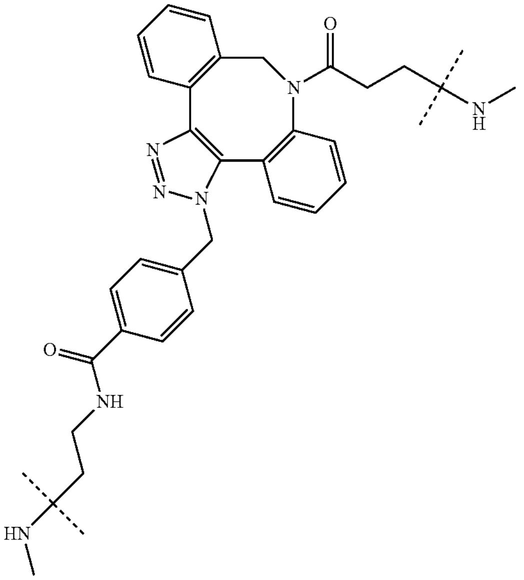
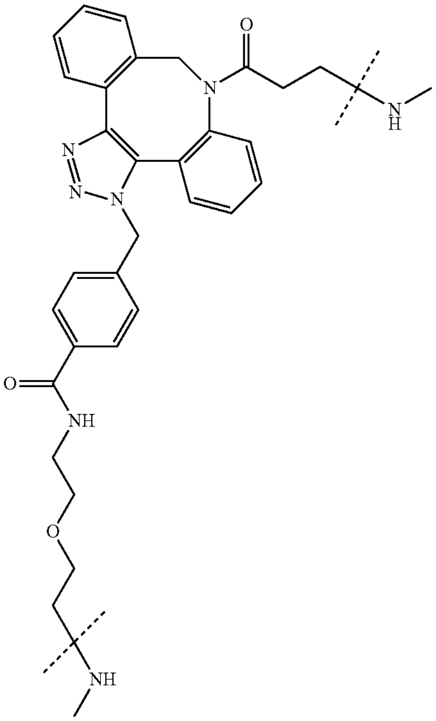

-continued
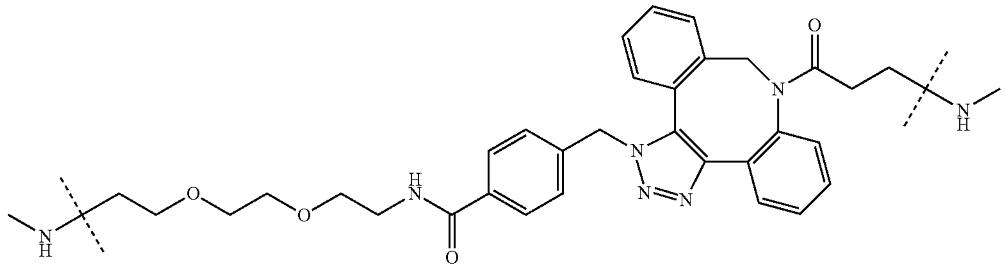
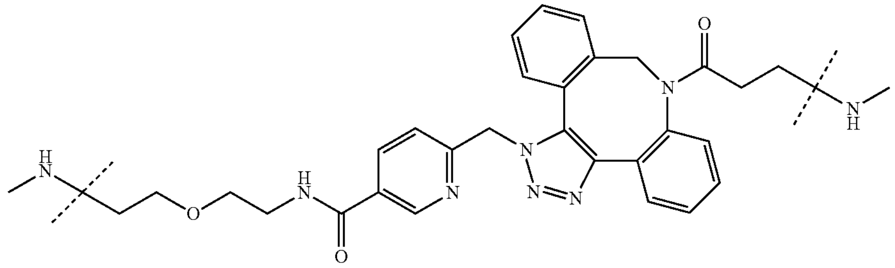
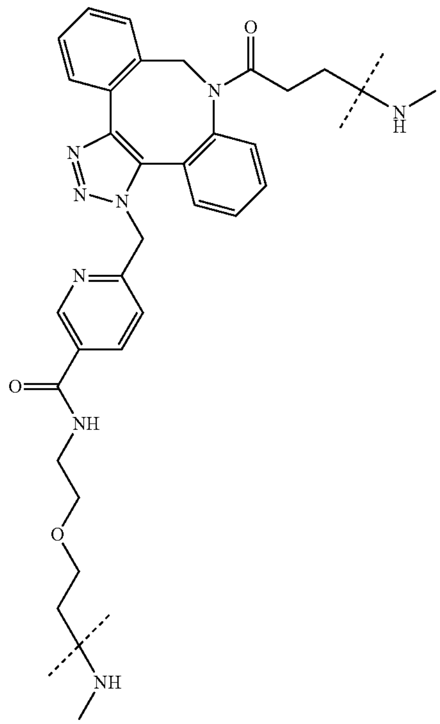
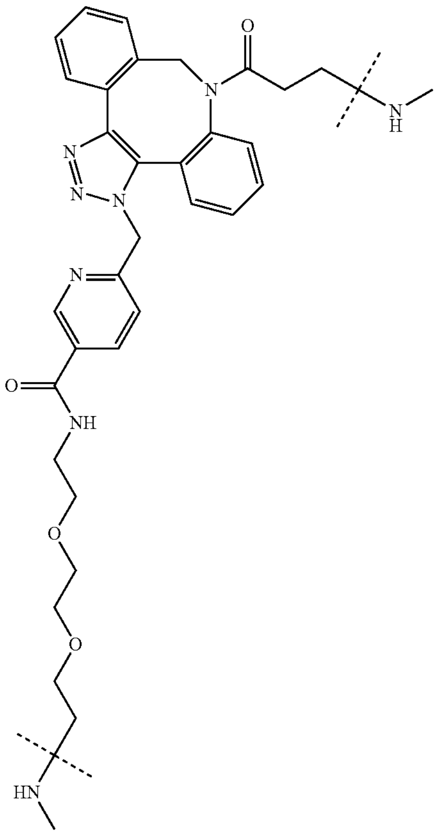

-continued
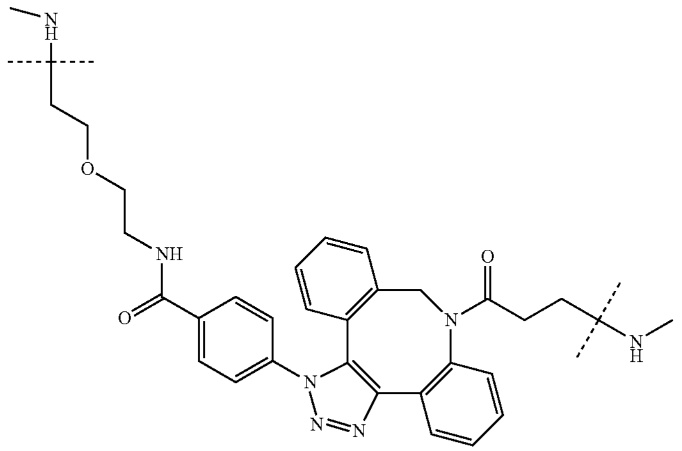
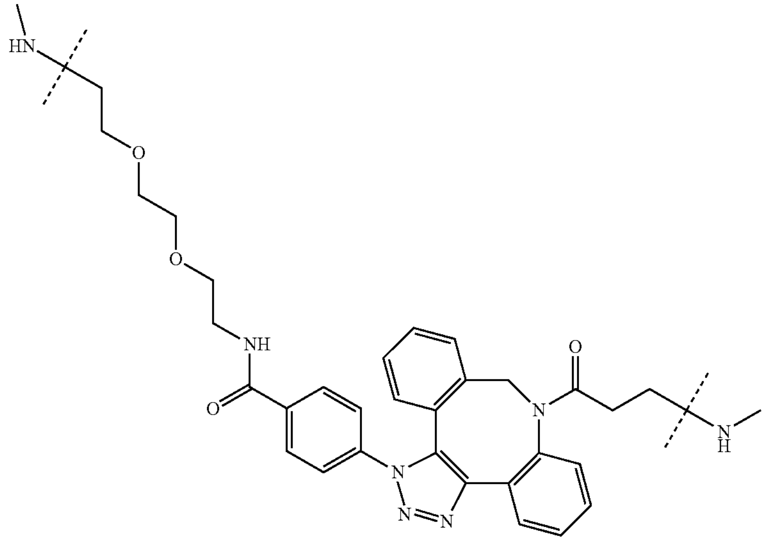
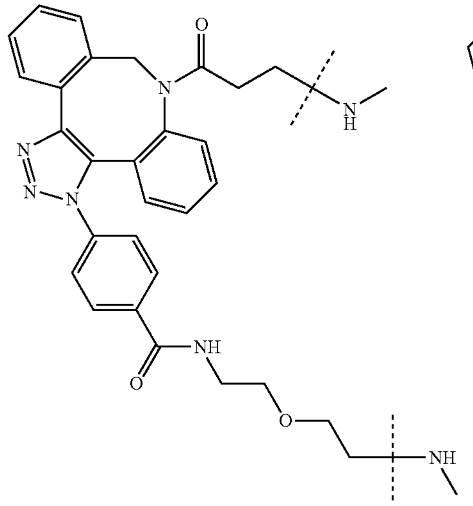
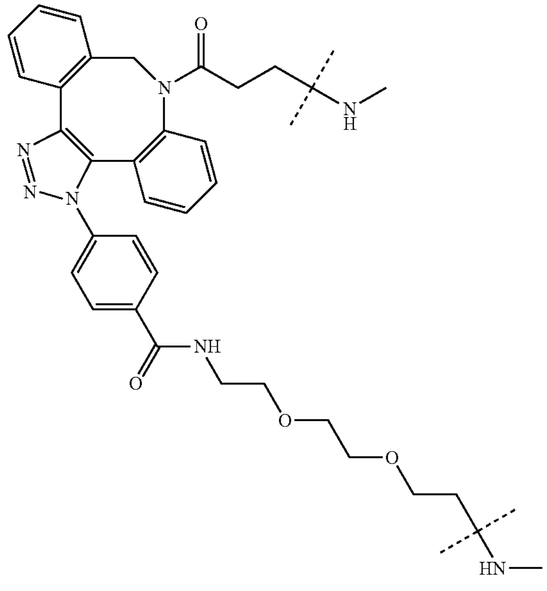

-continued

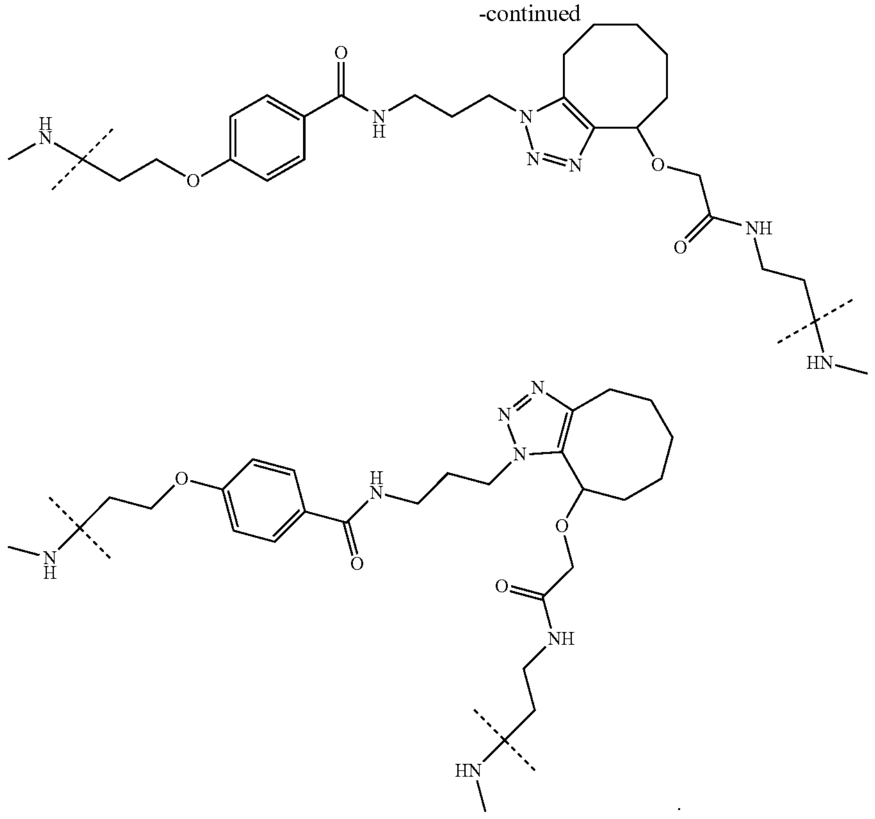

Preferred embodiments of the crosslinked alginic acid derivative of the Embodiment [7] can be formed at will by appropriately combining preferred embodiments of the Embodiment [7] as well as the definitions of $-L^1-$, $-L^2$ and X.

[8] Embodiment 8 is as follows: A method of manufacturing a crosslinked alginic acid, comprising mixing an alginic acid derivative of formula (I) according to the Embodiment [1] with an alginic acid derivative of formula (II) according to the Embodiment [4] and performing a Huisgen reaction to thereby obtain the crosslinked alginic acid according to the Embodiment [7].

[8-1] Embodiment 8-1 is as follows: A crosslinked alginic acid comprising as crosslinking both chemical crosslinking by triazole rings formed by a Huisgen reaction and ionic crosslinking partially formed by calcium ions.

[9] Embodiment 9 is as follows: A crosslinked alginic acid structure obtained by mixing an alginic acid derivative of formula (I) according to the Embodiment [1] with an alginic acid derivative of formula (II) according to the Embodiment [4] to obtain a mixed solution of alginic acid derivatives, and dripping this solution into a calcium chloride solution.

[10] Embodiment 10 is as follows: The crosslinked alginic acid structure according to the Embodiment [9], comprising as crosslinking both chemical crosslinking by triazole rings formed by a Huisgen reaction and ionic crosslinking partially formed by calcium ions.

[11] Embodiment 11 is as follows: A method of manufacturing a crosslinked alginic acid structure, comprising mixing an alginic acid derivative of formula (I) according to the Embodiment [1] with an alginic acid derivative of formula (II) according to the Embodiment [4] to obtain a mixed solution of alginic acid derivatives, and dripping this solution into a calcium chloride solution to obtain a crosslinked alginic acid structure according to the Embodiment [9] or [10].

[12] Embodiment 12 is as follows: The crosslinked alginic acid structure according to the Embodiment [9] or [10], in the form of a bead or a nearly spherical gel.

[13] Embodiment 13 is as follows: A medical material containing a crosslinked alginic acid structure according to any one of the Embodiments [9], [10], and [12].

[14] Embodiment 14 is as follows: The medical material according to the Embodiment [13], in the form of a bead or nearly spherical gel.

[15] Embodiment 15 is as follows: The alginic acid derivative according to any one of the Embodiments [1] to [6], a the crosslinked alginic acid according to the Embodiment [7] or [8-1] and the crosslinked alginic acid structure according to any one of the Embodiments [9], and [12], having biocompatibility.

[16] Embodiment 16 is as follows: An amino compound represented by the following formula (AM-1), or a pharmaceutically acceptable salt thereof or a solvate of these:

[C83]

(AM-1)

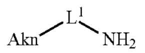

[in formula (AM-1), the combination of $-L^1-$ and Akn is any of the combinations shown in the following tables (with each formula being defined as in the Embodiment [1])]:

TABLE 6-1

| Akn | —L[1]— |
|---|---|
| AK-1 | LN-1 (excluding m1 = 2) |
| AK-2 | LN-1 (excluding m1 = 2) |
| AK-6 | LN-1 |
| AK-7 | LN-1 (excluding m1 = 2) |
| AK-8 | LN-1 |
| AK-9 | LN-1 |
| AK-10 | LN-1 |
| AK-12 | LN-1 |
| AK-1 | LN-2 |
| AK-2 | LN-2 |
| AK-3 | LN-2 |
| AK-4 | LN-2 |
| AK-5 | LN-2 |
| AK-6 | LN-2 |
| AK-7 | LN-2 |
| AK-8 | LN-2 |
| AK-9 | LN-2 |
| AK-10 | LN-2 |
| AK-11 | LN-2 |
| AK-12 | LN-2 (excluding m2 = 1) |
| AK-1 | LN-3 |
| AK-2 | LN-3 (excluding m3 = 2) |
| AK-3 | LN-3 (excluding m3 = 1, 2, 3, 5) |
| AK-4 | LN-3 (excluding m3 = 1) |
| AK-5 | LN-3 |
| AK-6 | LN-3 |
| AK-7 | LN-3 |
| AK-8 | LN-3 |
| AK-9 | LN-3 |
| AK-5 | LN-6 |
| AK-6 | LN-6 |
| AK-7 | LN-6 |
| AK-8 | LN-6 |
| AK-9 | LN-6 |
| AK-10 | LN-6 (excluding p-substitution, m6 = 1, m7 = 2) |
| AK-11 | LN-6 |
| AK-12 | LN-6 |
| AK-1 | LN-7 |
| AK-2 | LN-7 |
| AK-6 | LN-7 |
| AK-7 | LN-7 |
| AK-8 | LN-7 |
| AK-9 | LN-7 |
| AK-10 | LN-7 |
| AK-12 | LN-7 |
| AK-1 | LN-8 |
| AK-2 | LN-8 |
| AK-3 | LN-8 |
| AK-4 | LN-8 |
| AK-5 | LN-8 |
| AK-6 | LN-8 |
| AK-7 | LN-8 |
| AK-8 | LN-8 |
| AK-10 | LN-8 |
| AK-11 | LN-8 |
| AK-12 | LN-8 |
| AK-1 | LN-9 |
| AK-2 | LN-9 |

TABLE 6-2

| Akn | —L1— |
|---|---|
| AK-10 | LN-3 |
| AK-11 | LN-3 (excluding m3 = 1) |
| AK-12 | LN-3 |
| AK-1 | LN-4 (excluding m4 = 2, 3) |
| AK-2 | LN-4 (excluding m4 = 2, 4) |
| AK-6 | LN-4 (excluding m4 = 2, 3, 4) |
| AK-7 | LN-4 |
| AK-8 | LN-4 |
| AK-9 | LN-4 |
| AK-10 | LN-4 |
| AK-12 | LN-4 |
| AK-1 | LN-5 |
| AK-2 | LN-5 |
| AK-6 | LN-5 |
| AK-7 | LN-5 |
| AK-8 | LN-5 |
| AK-9 | LN-5 |
| AK-10 | LN-5 |
| AK-12 | LN-5 |
| AK-1 | LN-6 |
| AK-2 | LN-6 |
| AK-3 | LN-6 |
| AK-4 | LN-6 |
| AK-6 | LN-9 |
| AK-7 | LN-9 |
| AK-8 | LN-9 |
| AK-9 | LN-9 |
| AK-10 | LN-9 |
| AK-12 | LN-9 |
| AK-1 | LN-10 |
| AK-2 | LN-10 (excluding m13 = 1, m14 = 2) |
| AK-6 | LN-10 |
| AK-7 | LN-10 |
| AK-8 | LN-10 |
| AK-9 | LN-10 |
| AK-10 | LN-10 |
| AK-12 | LN-10 |
| AK-1 | LN-11 |
| AK-2 | LN-11 (excluding m15 = 1, m16 = 2) |
| AK-6 | LN-11 |
| AK-7 | LN-11 |
| AK-8 | LN-11 |
| AK-9 | LN-11 |
| AK-10 | LN-11 |
| AK-12 | LN-11 |

[16-1] In formula (AM-1) of the Embodiment [16], preferably the combination Akn-$L^1$ is any of the combinations shown in the following table (with each formula being as described in the Embodiments [1-1], [1-2], [1-1a], [1-2a], [1-1b] and [1-2b]):

TABLE 7

| Akn | —L[1]— |
|---|---|
| AK-1 | LN-1 (excluding m1 = 2) |
| AK-2 | LN-1 (excluding m1 = 2) |
| AK-6 | LN-1 |
| AK-1 | LN-2-1 |
| AK-2 | LN-2-1 |
| AK-3 | LN-2-1 |
| AK-4 | LN-2-1 |
| AK-5 | LN-2-1 |
| AK-6 | LN-2-1 |
| AK-1 | LN-3-1 |
| AK-2 | LN-3-1 (excluding m3 = 2) |
| AK-3 | LN-3-1 (excluding m3 = 2, 3, 5) |
| AK-4 | LN-3-1 |

TABLE 7-continued

| Akn | —L¹— |
|---|---|
| AK-5 | LN-3-1 |
| AK-6 | LN-3-1 |
| AK-1 | LN-4 (excluding m4 = 2, 3) |
| AK-2 | LN-4 (excluding m4 = 2, 4) |
| AK-6 | LN-4 (excluding m4 = 2, 3, 4) |
| AK-1 | LN-5 |
| AK-2 | LN-5 |
| AK-6 | LN-5 |
| AK-1 | LN-6 |
| AK-2 | LN-6 |
| AK-3 | LN-6 |
| AK-4 | LN-6 |
| AK-5 | LN-6 |
| AK-6 | LN-6 |
| AK-1 | LN-7 |
| AK-2 | LN-7 |
| AK-6 | LN-7 |
| AK-1 | LN-8 |
| AK-2 | LN-8 |
| AK-3 | LN-8 |
| AK-4 | LN-8 |
| AK-5 | LN-8 |
| AK-6 | LN-8 |
| AK-1 | LN-9 |
| AK-2 | LN-9 |
| AK-6 | LN-9 |
| AK-1 | LN-10 |
| AK-2 | LN-10 (excluding m13 = 1, m14 = 2) |
| AK-6 | LN-10 |
| AK-1 | LN-11 |
| AK-2 | LN-11 (excluding m15 = 1, m16 = 2) |
| AK-6 | LN-11 |

or more preferably, any of the combinations shown in the following table (with each formula being defined as in the Embodiments [1-1], [1-2], [1-1a], [1-2a], [1-1b] and [1-2b]):

TABLE 8

| Akn | —L¹— |
|---|---|
| AK-1 | LN-1 (excluding m1 = 2) |
| AK-6 | LN-1 |
| AK-1 | LN-2-1 |
| AK-3 | LN-2-1 |
| AK-6 | LN-2-1 |
| AK-1 | LN-3-1 |
| AK-3 | LN-3-1 (excluding m3 = 2, 3, 5) |
| AK-6 | LN-3-1 |
| AK-1 | LN-4 (excluding m4 = 2, 3) |
| AK-6 | LN-4 (excluding m4 = 2, 3, 4) |
| AK-1 | LN-5-p |
| AK-6 | LN-5-p |
| AK-1 | LN-6-p |
| AK-3 | LN-6-p |
| AK-6 | LN-6-p |
| AK-1 | LN-7-p |
| AK-6 | LN-7-p |
| AK-1 | LN-9-p |
| AK-6 | LN-9-p |
| AK-1 | LN-10 |
| AK-6 | LN-10 |
| AK-1 | LN-11 |
| AK-6 | LN-11 |

or still more preferably, any of the combinations shown in the following table (with each formula being defined as in the Embodiments [1-1], [1-2], [1-1a], [1-2a], [1-1b] and [1-2b]):

TABLE 9

| Akn | —L¹— |
|---|---|
| AK-1 | LN-1 (excluding m1 = 2) |
| AK-6 | LN-1 |
| AK-1 | LN-3-a |
| AK-3 | LN-3-1 (excluding m3 = 2, 3, 5) |
| AK-6 | LN-3-a |
| AK-1 | LN-9-p-a |
| AK-6 | LN-9-p-a |
| AK-1 | LN-10 |
| AK-6 | LN-10 |
| AK-1 | LN-11 |
| AK-6 | LN-11 |

such as those combinations represented by any of the following structural formulae:

[C84]

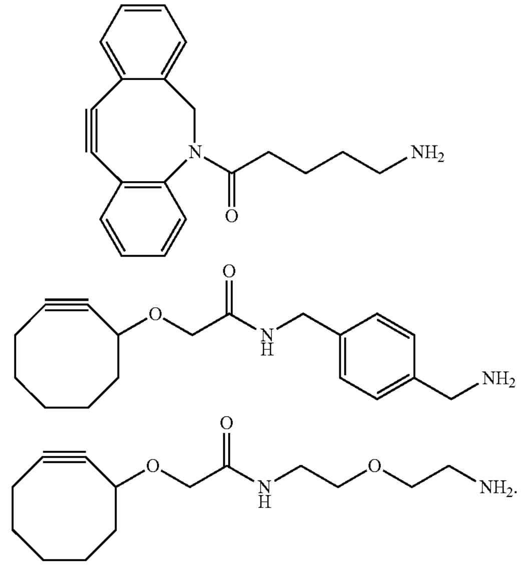

Preferred embodiments of the crosslinked alginic acid derivative of the Embodiment [16] can be formed at will by appropriately combining preferred embodiments of the Embodiment as well as the definitions of Akn and -L¹-.

[17] Embodiment 17 is as follows: An amino compound represented by the following formula (AM-2), or a pharmaceutically acceptable salt thereof or a solvate of these:

[C85]

(AM-2)

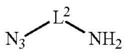

[in formula (AM-2), $-L^2-$ is formula (LK-1) (except when the substitution pattern of the phenyl ring in the formula is p-substitution, n1=1 and n2=3), formula (LK-2), formula (LK-3), formula (LK-4) (except when the substitution pattern of the phenyl ring in the formula is m-substitution and n7=3, or when the substitution pattern of the phenyl ring is p-substitution and n7=2, 3, 4 or 6), formula (LK-5) (except when the substitution pattern of the phenyl ring is p-substitution, n8=1 and n9=2), formula (LK-6) or formula (LK-7) [with each formula defined as in the Embodiment [4]]].

[17-1] In the formula (AM-2) of the Embodiment [17], preferably $-L^2-$ is formula (LK-1-1) (except when n1=1 and n2=3 in the formula), formula (LK-2-1), formula (LK-3-1), formula (LK-4-1) (except when n7=2, 3, 4 and 6 in the formula), formula (LK-5-1) (except when n8=1 and n9=2), formula (LK-6-1) or formula (LK-7-1) [with each formula defined as in the Embodiment [4-1], [4-1a] or [4-1b]]; or more preferably $-L^2-$ is formula (LK-1-1a), formula (LK-2-1-a), formula (LK-3-1-a), formula (LK-5-1-a), formula (LK-6-1-a), formula (LK-7-1-a) or formula (LK-7-1-b) [with each formula defined as in the Embodiment [4-1], [4-1a] or [4-1b]].

Preferred embodiments of the crosslinked alginic acid derivative of the Embodiment [17] can be formed at will by appropriately combining preferred embodiments of the Embodiment as well as the definitions of the azide group and $-L^2-$.

Each embodiment is explained in more detail below.

1. Alginic Acid

In the present Description, references to alginic acid refer to at least one kind of alginic acid (also called an "alginate") selected from the group consisting of alginic acid, the alginic acid esters and the salts of these (such as sodium alginate). The alginic acid used may be either naturally derived or synthetic, but a naturally derived alginic acid is preferred. A preferred alginic acid is a bioabsorbable polysaccharide that is extracted from natural brown algae such as *Lessonia, Macrocystis, Laminaria, Ascophyllum, Durvillea, Ecklonia cava, Eisenia bicyclis* and *Saccharina japonica*, and is a polymer obtained by linear polymerization of two kinds of uronic acid, D-mannuronic acid (M) and L-guluronic acid (G). More specifically, this is a block copolymer comprising a homopolymer fraction of D-mannuronic acid (MM fraction), a homopolymer fraction of L-guluronic acid (GG fraction), and a fraction of randomly arranged D-mannuronic acid and L-guluronic acid (M/G fraction) in arbitrary combination.

In this Description, alginic acid is sometimes expressed as (ALG)-COOH, where (ALG) is alginic acid and —COOH is any one carboxyl group of alginic acid.

In some embodiments, the alginic acid is sodium alginate. Commercial sodium alginate may be used as the sodium alginate. In the following examples, the sodium alginates A-1, A-2, A-3, B-1, B-2 and B-3 described in the tables below (sold by Mochida Pharmaceutical Co., Ltd.) are used as the sodium alginate. The following table shows the viscosity (1 w/w % aqueous solution), weight-average molecular weight and M/G ratio of each sodium alginate.

TABLE 10

| Sodium alginate | 1 w/w % viscosity (mPa · s) | Weight-average molecular weight GPC | GPC-MALS | M/G ratio |
|---|---|---|---|---|
| A-1 | 10 to 40 | 300,000 to 700,000 | 60,000 to 130,000 | 0.5 to 1.8 |
| A-2 | 50 to 150 | 700,000 to 1,400,000 | 130,000 to 200,000 | |
| A-3 | 300 to 600 | 1,400,000 to 2,000,000 | 200,000 to 400,000 | |
| B-1 | 10 to 40 | 150,000 to 800,000 | 60,000 to 130,000 | 0.1 to 0.5 |
| B-2 | 70 to 150 | 800,000 to 1,500,000 | 130,000 to 200,000 | |
| B-3 | 400 to 600 | 1,500,000 to 2,500,000 | 200,000 to 350,000 | |

The physical property values of the sodium alginates A-1, A-2, A-3, B-1, B-2 and B-3 were measured by the methods described below. The measurement methods are not limited to these, and the physical property values may differ from those given above depending on the measurement method.

[Measuring Viscosity of Sodium Alginate]

This was measured by the rotational viscometer method (using a cone plate rotational viscometer) according to the viscosity measurement methods of the Japanese Pharmacopoeia (16th Edition). The specific measurement conditions are as follows. The sample solution was prepared using MilliQ water. A cone plate rotational viscometer (RS600 RheoStress rheometer (Thermo Haake GmbH), sensor: 35/1) was used as the measurement equipment. The rotation was set at 1 rpm when measuring a 1 w/w % sodium alginate solution. For the read time, the solution was measured for 2 minutes and the average value from 1 to 2 minutes after starting was used. The average of three measured values was used as the measurement value. The measurement temperature was 20° C.

[Measuring Weight-Average Molecular Weight of Sodium Alginate]

This was measured by two measurement methods, (1) gel permeation chromatography (GPC) and (2) GPC-MALS. The measurement conditions are as follows.

[Pre-Treatment Method]

An eluent was added to dissolve the sample, which was then filtered through an 0.45-micron membrane filter to obtain a measurement solution.

(1) Gel Permeation Chromatography (GPC) Measurement

[Measurement Conditions (Relative Molecular Weight Distribution Measurement)]

Columns: TSKgel GMPW-XL×2+G2500PW-XL (7.8 mm I.D.×300 mm×3)

Eluent: 200 mM sodium nitrate aqueous solution

Flow rate: 1.0 ml/min

Concentration: 0.05%

Detector: RI detector

Column temperature: 40° ° C.

Injection volume: 200 μl

Molecular weight standards: Standard pullulan, glucose (2) GPC-MALS Measurement

[Refractive Index Increment (Dn/Dc) Measurement (Measurement Conditions)]

Differential refractometer: Optilab T-rEX

Measurement wavelength: 658 nm

Measurement temperature: 40° ° C.

Solvent: 200 mM sodium nitrate aqueous solution

Sample concentration: 0.5 to 2.5 mg/ml (5 concentrations)

[Measurement Conditions (Absolute Molecular Weight Distribution Measurement)]

Columns: TSKgel GMPW-XL×2+G2500PW-XL (7.8 mm I.D.×300 mm×3)

Eluent: 200 mM sodium nitrate aqueous solution

Flow rate: 1.0 ml/min

Concentration: 0.05%

Detectors: RI detector, light scattering detector (MALS)

Column temperature: 40° ° C.

Injection volume: 200 μl

In this Description, the molecular weights of alginic acid, alginic acid derivatives and crosslinked alginic acids may be given in units of Da (Daltons).

The constituent ratio of D-mannuronic acid and L-guluronic acid (M/G ratio) in an alginate differs principally according to the type of seaweed or other organism from which it is derived, and may also be affected by the organism's habitat and season, with a wide range from high-G (M/G ratio about 0.2) to high-M alginic acid (M/G ratio about 5). The gelling ability of the alginic acid and the properties of the resulting gel are affected by the M/G ratio, and in general, the gel strength is known to be greater the higher the proportion of G. The M/G ratio also affects the hardness, fragility, water absorption, flexibility and the like of the gel. The M/G ratio of the alginic acid and/or salt thereof used is normally from 0.2 to 4.0, or preferably from 0.4 to 3.0, or still more preferably from 0.5 to 3.0.

When numerical ranges are indicated with "from" and "to" this Description, the numbers after "from" and "to" are the minimum and maximum values of the range, respectively.

The "alginic acid ester" and "alginic acid salt" in this Description are not particularly limited, but because these will react with a crosslinking agent, they must have no functional groups that would impede the crosslinking reaction. Desirable examples of alginic acid esters include propylene glycol alginate and the like.

In this Description, examples of alginic acid salts include monovalent salts and divalent salts of alginic acid. Preferred examples of monovalent alginic acid salts include sodium alginate, potassium alginate and ammonium alginate, of which sodium alginate and potassium alginate are more preferred, and sodium alginate is particularly preferred. Preferred examples of divalent alginic acid salts include calcium alginate, magnesium alginate, barium alginate, strontium alginate and the like.

Alginic acid is a high-molecular-weight polysaccharide, and its molecular weight is hard to determine accurately, but generally the weight-average molecular weight is in the range of 1,000 to 10,000,000, or preferably 10,000 to 8,000,000, or more preferably 20,000 to 3,000,000. It is known that in molecular weight measurement of naturally derived high-molecular-weight substances, values may differ depending on the measurement method.

For example, the weight-average molecular weight as measured by gel permeation chromatography (GPC) or gel filtration chromatography (which together are sometimes called size exclusion chromatography) is preferably at least 100,000, or more preferably at least 500,000, and is preferably not more than 5,000,000, or more preferably not more than 3,000,000. The preferred range is 100,000 to 5,000,000, or more preferably 150,000 to 3,000,000.

The absolute weight-average molecular weight can also be measured by the GPC-MALS method. The weight-average molecular weight (absolute molecular weight) as measured by GPC-MALS is preferably at least 10,000, or more preferably at least 50,000, or still more preferably at least 60,000, and is preferably not more than 1,000,000, or more preferably not more than 800,000, or still more preferably not more than 700,000, or especially not more than 500,000. The preferred range is 10,000 to 1,000,000, or more preferably 50,000 to 800,000, or still more preferably 60,000 to 700,000, or especially 60,000 to 500,000.

When the molecular weight of a high-molecular-weight polysaccharide is calculated by such methods, a measurement error of 10% to 20% is normal. Thus, a value of 400,000 may vary in the range of 320,000 to 480,000, a value of 500,000 may vary in the range of 400,000 to 600,000, and a value of 1,000,000 may vary in the range of 800,000 to 1,200,000 for example.

The molecular weight of an alginate can be measured by ordinary methods.

Typical conditions for molecular weight measurement using gel filtration chromatography are described in the examples of this Description below. For example, a Superose 6 Increase 10/300 GL column (GE Health Care Sciences) may be used as the column, a 10 mmol/L phosphate buffer, containing 0.15 mol/L NaCl (pH 7.4) may be used as the development solvent, and blue dextran, thyroglobulin, ferritin, aldolase, conalbumin, ovalbumin, ribonuclease A and aprotinin may be used as molecular weight standards.

The viscosity of the alginic acid used in this Description is not particularly limited, but when measured in a 1 w/w % aqueous alginate solution, the viscosity is preferably 10 mPa·s to 1,000 mPa·s, or more preferably 50 mPa·s to 800 mPa·s.

The viscosity of an aqueous solution of alginic acid can be measured by ordinary methods. For example, it can be measured by rotational viscometry using a coaxial double cylindrical rotational viscometer, single cylindrical rotary viscometer (Brookfield viscometer), conical plate rotational viscometer (cone plate viscometer) or the like. Preferably it is measured following the viscosity measurement methods of the Japanese Pharmacopoeia (16th Edition). More preferably, a cone plate viscometer is used.

When first extracted from brown algae, alginates have a high molecular weight and a high viscosity, but the molecular weight and viscosity are reduced by the processes of heat drying, purification and the like. Alginic acids with different molecular weights can be manufactured by methods such as controlling the temperature and other conditions during the manufacturing process, selecting the brown algae used as raw materials, and fractioning the molecular weights in the manufacturing process. An alginic acid having the desired molecular weight can also be obtained by mixing alginic acids from different lots having different molecular weights or viscosities.

Some embodiments of the alginic acid used in this Description have been subjected to low endotoxin treatment, while others have not been subject to low endotoxin treatment. "Low endotoxin" means that the level of endotoxins is so low that there is no effective risk of inflammation or fever. An alginic acid that has been subjected to low endotoxin treatment is more preferred.

Low endotoxin treatment can be performed by known methods or analogous methods. For example, it can be performed by the methods of Kan et al for purifying sodium hyaluronate (see for example Japanese Patent Application Publication No. JP H 09-324001A, etc.), the methods of Yoshida et al for purifying β 1,3-glucan (see for example Japanese Patent Application Publication No. JP H 08-260102A), the methods of William et al for purifying biopolymer salts such as alginate and gellan gum (see for example Japanese Patent Application Publication No. JP 2002-530440A), the methods of James et al for purifying polysaccharides (see for example WO 93/13136A), the methods of Lewis et al (see for example U.S. Pat. No. 5,589,591B), and the methods of Herman Frank for purifying alginates (see for example Appl. Microbiol. Biotechnol. (1994) 40:638-643, etc.) and the like or analogous methods. Low endotoxin treatment is not limited to these methods, and may also be performed by known methods such as washing, filtration with a filter (endotoxin removal filter, charged filter or the like), ultrafiltration, column purification (using an endotoxin adsorption affinity column, gel filtration column, ion-exchange resin column or the like), adsorption by a hydrophobic substance, resin, activated carbon or the like, organic solvent treatment (organic solvent extraction, deposition/sedimentation with an organic solvent or the like), surfactant treatment (see for example Japanese Patent Application Publication No. JP 2005-036036A) or the like, or by a suitable combination of these methods. Known methods such as centrifugation may also be combined with the steps of such treatment. The treatment is preferably selected appropriately according to the type of alginic acid.

The endotoxin level can be confirmed by known methods, such as limulus reagent (LAL) methods or methods using an Endospecy (registered trademark) ES-24S set (Seikagaku Corp.).

There are no particular limitations on the endotoxin treatment method used, but the resulting endotoxin content of the treated alginate is preferably not more than 500 endotoxin units (EU)/g, or more preferably not more than 100 EU/g, or still more preferably not more than 50 EU/g, or especially not more than 30 EU/g when measured with a limulus reagent (LAL). Low endotoxin treated sodium alginate is available as a commercial product such as Sea Matrix (registered trademark) (Mochida Pharmaceutical Co., Ltd.) or Pronova (registered trademark) UP LVG (FMC BioPolymer).

2. Alginic Acid Derivative

Novel alginic acid derivatives are provided in this Description. An alginic acid derivative in this Description has a reactive group or a reactive group complementary to that reactive group in a Huisgen reaction introduced at any one or more carboxyl groups of alginic acid via an amide bond and a divalent linker.

More specifically, these are an alginic acid derivative represented by formula (I) below [in which (ALG), $-L^1-$ and Akn are defined as in Embodiment 1 above]:

[C86]

(I)

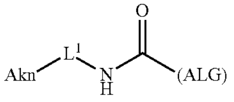

and an alginic acid derivative represented by formula (II) below [in which (ALG) and $-L^2-$ are defined as in Embodiment 4 above]:

[C87]

(II)

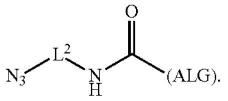

Any linear group may be used as the divalent linker ($-L^1-$ or $-L^2-$) as long as it does not impede the reaction between the reactive group and the reactive group complementary to that reactive group. Specific examples include linear alkylene groups ($-(CH_2)_n-$, n=1 to 30) (in which $-CH_2-$ may be substituted with one or more (such as 1 to 10, or 1 to 5) groups such as $-C(=O)-$, $-CONH-$, $-O-$, $-NH-$ or $-S-$ or a benzene or heterocyclic ring (5- to 6-membered aromatic or non-aromatic heterocycle such as a pyridine, piperidine or piperazine ring), and a hydrogen atom of the $-CH_2-$ may also be substituted with one or more (such as 1 to 10, or 1 to 5) groups selected from the oxo (=O), hydroxyl (—OH) and $C_{1-6}$ alkyl groups (such as methyl, ethyl, n-propyl and iso-propyl groups) and halogen atoms (such as a fluorine, chlorine, bromine and iodine atoms)).

The novel alginic acid derivatives in this Description are the alginic acid derivatives represented by formula (I) and formula (II), which can be manufactured by the methods shown in the following formulae (for details, see the general manufacturing methods described below).

[C88]

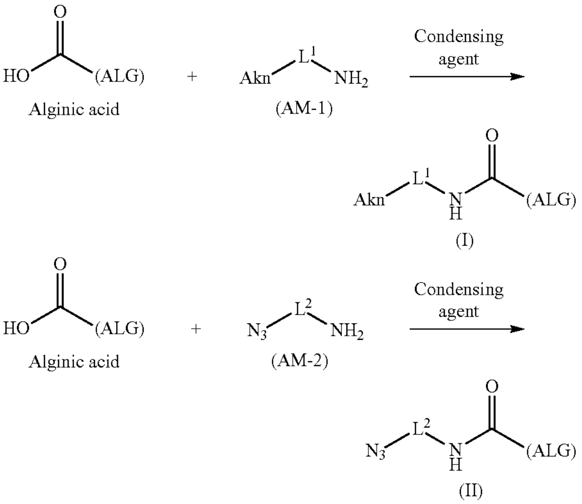

The weight-average molecular weights of the alginic acid derivatives represented by formula (I) and formula (II) in this Description are each 100,000 Da to 3,000,000 Da, or preferably 300,000 Da to 2,500,000 Da, or still more preferably 500,000 Da to 2,000,000 Da. The molecular weights of both alginic acid derivatives can be determined by the methods described below.

In this Description, the Akn-$L^1$-NH— group of formula (I) need not be bound to all of the carboxyl groups of the constituent units of alginic acid, and the $N_3$-$L^2$-NH— group of formula (II) need not be bound to all of the carboxyl groups of the constituent units of alginic acid.

In this Description, the Akn-$L^1$-NH— group of formula (I) is sometimes called a reactive group, and the $N_3$-$L^2$-NH— group of formula (II) is sometimes called a complementary reactive group. Conversely, the $N_3$-$L^2$-NH— group of formula (II) may sometimes be called a reactive group, and the Akn-$L^1$-NH— group of formula (I) may sometimes be called a complementary reactive group.

In this Description, the introduction rate of the reactive group or complementary reactive group is 0.1% to 30% or 1% to 30%, or preferably 2% to 20%, or more preferably 3% to 10% of each.

The introduction rate of the reactive group or complementary reactive group is a value representing the number of uronic acid monosaccharide units having introduced reactive groups or complementary reactive groups as a percentage of the uronic acid monosaccharide units that are repeating units of the alginate. Unless otherwise specified, the % value used as the introduction rate of the reactive group or complementary reactive group in the alginic acid derivative (formula (I) or formula (II)) in this Description is a mol % value. The introduction rate of the reactive group or complementary reactive group can be determined by the methods described in the examples below.

In this Description, the cyclic alkyne group (Akn) in formula (I) and the azide group in formula (II) form a triazole ring by a Huisgen reaction, thereby forming a crosslink.

3. Huisgen Reaction

A Huisgen reaction (1,3-dipolar cycloaddition reaction) is a condensation reaction between compounds having a terminal azide group and a terminal alkyne group as shown in the formula below. The reaction efficiently yields a disubstituted 1,2,3-triazole ring, and has the feature of producing no extra by-products. Although it is believed that the reaction may produce a 1,4- or 1,5-disubstituted triazole ring, it is possible to regioselectively obtain a triazole ring by using a copper catalyst.

[C89]

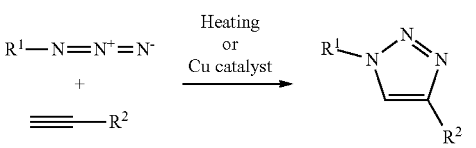

Wittig and Krebs have also reported on a Huisgen reaction that does not use a copper catalyst. For example, in this reaction a cycloadduct is obtained by simply mixing cyclooctyne and phenyl azide ($R^3$=phenyl in the formula below). Because the triple bond of cyclooctyne is greatly distorted in this reaction, elimination of the distortion caused by the reaction with the phenyl azide acts as a driving force, and the reaction progresses spontaneously without the need of a catalyst.

[C90]

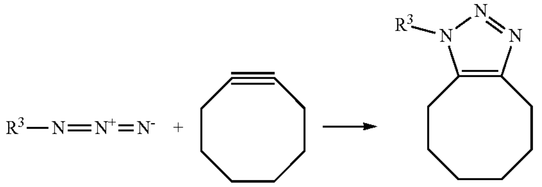

Thus, the Huisgen reaction may use an azide compound having a substituted primary azide, secondary azide, tertiary azide, aromatic azide or the like and a compound having a terminal or cyclic alkyne group, which is a reactive group complementary to the azide group. Moreover, because it is mainly only the azide and alkyne groups that react in the Huisgen reaction, various functional groups (such as ester, carboxyl, alkenyl, hydroxyl and amino groups and the like) may also be substituted in the reaction substrate.

In certain embodiments, the cyclic alkyne group (cyclooctyl group) described in the Embodiment [1] above for example is used as the alkyne group in a Huisgen reaction so that crosslinks are formed easily, efficiently and in a short amount of time by 1,2,3-triazole rings between alginic acid molecules without producing undesirable by-products and while avoiding the use of a copper catalyst so as to avoid cytotoxicity from the copper catalyst.

In a preferred embodiment of the method of crosslinking the alginic acid derivatives, almost no undesirable by-products are formed by the reaction (Huisgen reaction). In this case, when alginic acid is used to prepare novel forms of biocompatible materials or to form alginic acid hydrogels, it is possible to incorporate various bioactive molecules or to incorporate cellular materials into alginic acid hydrogels for reconstructive surgery or gene therapy.

4. Crosslinked Alginic Acid

Crosslinked alginic acids include (i) those crosslinked via divalent metal ion bonds, (ii) those crosslinked via chemical bonds, and (iii) those crosslinked via both divalent metal ion bonds and chemical bonds. All of these crosslinked alginic acids have the property of forming gels, semi-solids and in some cases sponge-like forms.

When a crosslinked alginic acid is crosslinked via divalent metal ion bonds, the reaction progresses ultra-rapidly and is reversible, while when a crosslinked alginic acid is crosslinked via chemical bonds, the reaction progresses slowly under relatively mild conditions, and is irreversible. The physical properties of a crosslinked alginic acid can be adjusted for example by such methods as changing the concentration of the aqueous solution (such as a calcium carbonate aqueous solution) containing the divalent metal ion or changing the introduction rate of the reactive group introduced into the alginic acid or the like.

A variety of alginic acid structures can be prepared using the above crosslinking reaction. For example, a specific structure can be prepared instantaneously from an alginic acid solution by an ionic crosslinking reaction, and a crosslinking reaction via chemical bonds can then be used to structurally reinforce this structure (to give it long-term stability for example). Alternatively, in a crosslinked alginic acid structure crosslinked via both divalent metal ion bonds and chemical bonds, the divalent metal ions incorporated by ionic crosslinking can be reversibly released, leaving a structure having only crosslinking via chemical bonds.

The crosslinked alginic acid of one embodiment can be obtained by mixing the alginic acid derivatives of formula (I) and formula (II) above and performing a Huisgen reaction.

The crosslinked alginic acid of one embodiment forms a three-dimensional mesh structure via chemical crosslinking (crosslinking by triazole rings formed from alkyne and azide groups). Preferred alginic acid derivatives have improved stability of the crosslinked alginic acid after crosslinking.

The crosslinked alginic acid of some embodiments is a crosslinked alginic acid in which any carboxyl group of a first alginic acid and any carboxyl group of a second alginic acid are amide bonded via the following formula (III-L):

[C91]

(III-L)

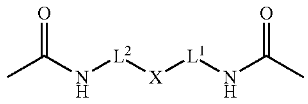

[in formula (III-L), the —CONH— and —NHCO— at either end represent amide bonds via any carboxyl group of alginic acid; and $-L^1$, $-L^2$- and X are defined as in Embodiment 7 above].

In some embodiments, the mixing ratio of the alginic acid derivative of formula (I) and the alginic acid derivative of formula (II) when preparing the crosslinked alginic acid (the weight ratio of formula (I) derivative:formula (II) derivative) is 1 to 1.5:1 for example, or preferably 1.2 to 1.5:1, or 1 to 1.2:1, or more preferably 1:1.

In terms of the mixing ratio of the alginic acid derivative of formula (II) and the alginic acid derivative of formula (I) when preparing the crosslinked alginic acid, in some embodiments the mixing ratio of the derivative of formula (II) to the derivative of formula (I) (the weight ratio of formula (II) derivative:formula (I) derivative) is 1 to 4.0:1 for example, or preferably 1.5 to 4.0:1, or 1.2 to 1.5:1, or 1 to 1.2:1, or more preferably 1:1.

In some embodiments, the mixing ratio of the alginic acid derivative of formula (I) and the alginic acid derivative of formula (II) when preparing the crosslinked alginic acid is more preferably such that the ratio of the introduction rates (mol %) of the reactive groups of the alginic acid derivative of formula (I) and the alginic acid derivative of formula (II) is 1 to 1.5:1 for example, or preferably 1.2 to 1.5:1, or 1 to 1.2:1, or more preferably 1:1.

In some embodiments, the mixing ratio of the alginic acid derivative of formula (II) and the alginic acid derivative of formula (I) when preparing the crosslinked alginic acid is more preferably such that the ratio of the introduction rates (mol %) of the reactive groups of the alginic acid derivative of formula (II) and the alginic acid derivative of formula (I) is 1 to 4.0:1 for example, or preferably 1.5 to 4.0:1, or 1.2 to 1.5:1, or 1 to 1.2:1, or more preferably 1:1.

In the mixing ratios above, the alginic acid derivative of formula (II) may be substituted for the alginic acid derivative of formula (I), and the alginic acid derivative of formula (I) may be substituted for the alginic acid derivative of formula (II).

In the crosslinked alginic acid, it is not necessary that all of the carboxyl groups of the constituent units of the alginic acid have the crosslink of formula (III-L) above. The introduction rate of the crosslink represented by formula (III-L) above in the crosslinked alginic acid (also called the crosslinking rate) is in the range of 0.1% to 80%, or 0.3% to 60%, or 0.5% to 30%, or 1.0% to 10% for example.

The concentration of the alginic acid derivative of formula (I) or (II) in the Huisgen reaction for obtaining the crosslinked alginic acid is normally 1 to 500 mg/ml, or preferably 5 to 100 mg/ml.

The reaction temperature in the Huisgen reaction is normally an external temperature of 4° C. to 60° ° C., or preferably 15° C. to 40° C.

The stirring time for forming the crosslinked alginic acid (hydrogel) is a few seconds to 24 hours, or a few seconds to 12 hours, or a few seconds to 30 minutes, or a few seconds to 10 minutes for example.

The reaction solvent or reaction solution used in the Huisgen reaction is not particularly limited, and examples include tap water, pure water (such as distilled water, ion-exchange water, RO water or RO-EDI water), ultrapure water, cell culture medium, phosphate-buffered saline (PBS) and physiological saline, and ultrapure water is preferred.

The crosslinked alginic acid of some embodiments is a crosslinked alginic acid comprising as crosslinking both chemical crosslinking by triazole rings formed from a Huisgen reaction and ionic crosslinking partially formed by calcium ions.

5. Crosslinked Alginic Acid Structure

The crosslinked alginic acid structure can be obtained by a method that includes subjecting the above alginic acid derivatives to a crosslinking reaction. It can be prepared by the following methods for example, but this is not a limitation.

[Mixing Method]

A mixed alginic acid derivative solution obtained by mixing the alginic acid derivative of formula (I) with the alginic acid derivative of formula (II) is dripped into a solution containing a divalent metal ion to obtain a crosslinked alginic acid structure, which is a specific structure formed by chemical crosslinking (crosslinking by triazole rings formed from alkyne groups and azide groups in a Huisgen reaction) and ionic crosslinking (partial crosslinking formed by divalent metal ions).

[Coating Method]

A solution containing the alginic acid derivative of formula (I) is dripped or the like into a solution containing a divalent metal ion to obtain a specific partially crosslinked structure. The resulting gel or other structure for example can then be added to a solution containing the alginic acid structure of formula (II) above to thereby perform a further crosslinking reaction (Huisgen reaction) on the surface of the like of the previous structure and obtain a crosslinked alginic acid. This method can also be implemented with the alginic acid derivative of formula (II) substituted for the alginic acid derivative of formula (I) and with the alginic acid derivative of formula (I) substituted for the alginic acid derivative of formula (II).

The divalent metal ion used in this method is not particularly limited, but examples include calcium ions, magnesium ions, barium ions, strontium ions, zinc ions and the like, and a calcium ion is preferred.

The solution containing the calcium ion used in this method is not particularly limited, but may be an aqueous solution such as a calcium chloride aqueous solution, calcium carbonate aqueous solution, calcium gluconate aqueous solution or the like for example, and a calcium chloride aqueous solution is preferred.

The calcium ion concentration of the solution containing the calcium ion used in this method is not particularly limited but may be 1 mM to 1 M for example, or preferably 5 mM to 500 mM, or more preferably 10 mM to 300 mM.

The solvent or solution used in this method is not particularly limited, but examples include tap water, pure water (such as distilled water, ion-exchange water, RO water or RO-EDI water), ultrapure water, cell culture medium, phosphate-buffered saline (PBS) and physiological saline, and ultrapure water is preferred.

Examples of specific crosslinked alginic acid structures include fibrous structures, fibers, beads, gels and nearly spherical gels. A preferred crosslinked alginic acid structure has improved stability. The crosslinked alginic acid structure may also have the ability to retain contents within the structure (content retention property).

The physical properties of the alginic acid gel can be adjusted by adjusting the physical property values such as hardness, elasticity, repulsive force, rupture force, stress at break and the like.

6. Biocompatibility of Alginic Acid Derivative and Crosslinked Alginic Acid

In this Description, the alginic acid derivative or crosslinked alginic acid structure has biocompatibility. In this Description, biocompatibility means the property of not causing reactions such as interactions between a biomaterial (in this case, an alginic acid derivative having an introduced reactive group represented by formula (I), or a crosslinked alginic acid structure manufactured using this alginic acid derivative) and a living body, or local reactions in tissue adjacent to the biomaterial, or systemic reactions and the like.

In this Description, the biocompatibility of the alginic acid derivative or crosslinked alginic acid structure is confirmed in the examples relating to biocompatibility below.

7. Stability of Crosslinked Alginic Acid Structure

The stability of the crosslinked alginic acid structure can be confirmed for example by measuring gel stability, and its permeability can be confirmed by measuring gel permeability.

[Method for Measuring Gel Stability]

Phosphate buffered saline (PBS) is added to a crosslinked alginic acid structure gel in a container, and the concentration (μg/ml) of alginic acid leaking into the PBS is measured. The measured alginic acid concentration is divided by the total alginic acid concentration obtained by decomposing the crosslinked alginic acid structure gel, and the resulting value is given as percentage and used as the gel collapse rate. Gel stability can be determined specifically by the methods described in the examples below.

In this Description, the gel collapse rate of the crosslinked alginic acid structure is preferably 0% to 90%, or more preferably 0% to 70%, or still more preferably 0% to 50%. The stability of the crosslinked alginic acid structure is greater the lower the concentration of the alginic acid leaking into an aqueous solution, or in other words the lower the gel collapse rate.

[Method for Measuring Gel Permeation Rate]

A crosslinked alginic acid structure gel containing fluorescein isothiocyanate-dextran is prepared, physiological saline is added to the gel in a container, and the concentration of dextran leaking into the physiological saline is measured. The measured dextran concentration is divided by the total dextran concentration obtained by decomposing the crosslinked alginic acid structure gel containing the fluorescein isothiocyanate-dextran, and the resulting value is given as percentage and used as the gel permeation rate. The gel permeation rate can be determined specifically by the methods described in the examples below.

The gel permeation rate of the crosslinked alginic acid 24 hours after addition of the saline is preferably 0% to 90%, or more preferably 0% to 70%, or still more preferably 0% to 50% when the gel contains dextran with a molecular weight of 2,000,000. When it contains dextran with a molecular weight of 150,000, assuming that the intended use of the crosslinked alginic acid structure gel is releasing and producing proteins and antibodies, the gel permeation rate is preferably 1% to 100%, or more preferably 10% to 100%, or still more preferably 30% to 100%, while if the intended use is as an immune barrier, the gel permeation rate is preferably 0% to 90%, or more preferably 0% to 70%, or still more preferably 0% to 50%.

The lower the permeation rate of the crosslinked alginic acid structure, the lower the permeation of the gel contents or external substances, while the higher the permeation rate, the higher the permeation of the gel contents or external substances.

The gel permeation rate can be adjusted by adjusting the molecular weight and concentration of the alginic acid used, the type and introduction rate of the crosslinking group introduced into the alginic acid, the type and concentration of the divalent metal ion used for gelling, or a combination of these.

[Method for Preparing Crosslinked Alginic Acid Structure Gel Containing Contents]

For example, a crosslinked alginic acid structure gel containing fluorescein isothiocyanate-dextran contents can be prepared by the following methods.

(1) A solution of the alginic acid derivative represented by formula (I) is mixed with a fluorescein isothiocyanate-dextran solution.

(2) The mixed solution obtained in (1) is mixed with a solution of the alginic acid derivative represented by formula (II).

(If formula (I) is substituted for formula (II) in step (1), then formula (II) is substituted for formula (I) in step (2)).

(3) The mixed solution obtained in (2) is dripped into a solution containing a calcium ion to obtain a gel that forms chemical crosslinks and ionic crosslinks in solution, thereby yielding a crosslinked alginic acid structure gel containing fluorescein isothiocyanate-dextran.

8. Methods for Synthesizing Alginic Acid Derivatives

In this Description, the alginic acid derivatives represented by formula (I) and formula (II) can each be manufactured by a condensation reaction using a condensing agent, in which an amine derivative (AM-1) represented by $H_2N-L^1-Akn$ (in which $L^1$ and Akn are defined as in the Embodiment [1]) or an amine derivative (AM-2) represented by $H_2N-L^2N_3$ (in which $L^2$ is defined as in the Embodiment [4]) is reacted with any carboxyl group of an alginate.

[C92]

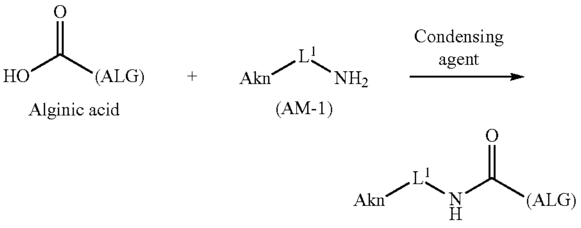

Alginic acid (AM-1)
(I)

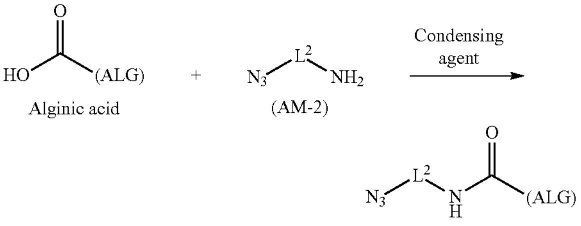

Alginic acid (AM-2)
(II)

[Method for Preparing Alginic Acid Derivative of Formula (I)]

Using a 0.5 wt % to 1 wt % aqueous alginic acid solution and the amine represented by formula (AM-I), the alginic active derivative of formula (I) can be manufactured by methods known in the literature (such as "Experimental Chemistry Course 5th Edition", Vol. 16, Synthesis of Organic Compounds IV: Carboxylic acids, derivatives and esters, pp. 35-70, Acid amides and acid imides, pp. 118-154, Amino acids and peptides, pp. 258-283, 2007 (Maruzen)) by for example performing a condensation reaction at temperatures between 0° C. and 50° C., with or without an inorganic base such as sodium hydrogen carbonate or sodium carbonate or an organic base such as triethylamine or pyridine, in a mixed solvent of water and a solvent selected from the ether solvents such as tetrahydrofuran and 1,4-dioxane, the alcohol solvents such as methanol, ethanol and 2-propanol and the polar solvents such as N,N-dimethylformamide and the like to a degree that does not cause precipitation of the alginic acid, in the presence of a condensing agent selected from 1,3-dicyclohexyl carbodiimide (DCC), 1-ethyl-3-(3-dimethylaminopropyl) carbodiimide hydrochloride (WSC·HCl), benzotriazol-1-yloxytris(dimethylamino) phosphonium hexafluorophosphate (BOP reagent), bis(2-oxo-3-oxazolidinyl) phosphinic chloride (BOP-Cl), 2-chloro-1,3-dimethylimidazolinium hexafluorophosphate (CIP), 4-(4,6-dimethoxy-1,3,5-triazin-2-yl)-4-methyl morpholinium chloride (DMT-MM) or the like.

[Method for Preparing Alginic Acid Derivative of Formula (II)]

The alginic acid derivative of formula (II) can be manufactured by performing a reaction according to the "Method for preparing alginic acid derivative of formula (I)" above using a 0.5 wt % to 1 wt % aqueous alginic acid solution and the amine derivative represented by formula (AM-2).

In the method of preparing the alginic acid derivative of formula (I) or the alginic acid derivative of formula (II) above, the introduction rate of the amine of formula (AM-1) or formula (AM-2) can be regulated by appropriately selecting and combining the reaction conditions of (i) to (v) below and the like in consideration of the properties and the like of the respective amines: (i) increasing or decreasing the equivalent amount of the condensing agent, (ii) raising or lowering the reaction temperature, (iii) lengthening or shortening the reaction time, (iv) adjusting the concentration of alginic acid as the reaction substrate, (v) adding an organic solvent miscible with water to raise the solubility of the amine of formula (AM-1) or (AM-2), etc.

Of the amines represented by formula (AM-1) and (AM-2), methods for manufacturing more specific amines are given below.

In the manufacturing methods below, $R^A$ is a $C_{1-6}$ alkyl group such as a methyl or ethyl group; $P^1$ is an amino group protecting group selected from a —C(O)O-tertBu group, —C(O)O-Bn group, —$C(O)CH_3$ group, $C(O)CF_3$ group and the like; $P^2$ is an amino group protecting group selected from a —C(O)O-tertBu group, —C(O)O-Bn group, —$C(O)CH_3$ group, —$C(O)CF_3$ group, —$SO_2Ph$ group, —$SO_2PhMe$ group, —$SO_2Ph(NO_2)$ group and the like; and E is a leaving group such as a halogen atom (fluorine atom, chlorine atom, bromine atom, iodine atom, etc.), -OTs group, -OMs group or the like.

In the manufacturing methods below, moreover, the protecting groups $P^1$ and $P^2$ can be protected and deprotected by methods known in the literature, such as the deprotection methods described in Greene et al, "Protective Groups in Organic Synthesis, 4th Edition", 2007, John Wiley & Sons.

[Manufacturing Method A]

Method for manufacturing amine represented by formula (AM-OL-1):

[C93]

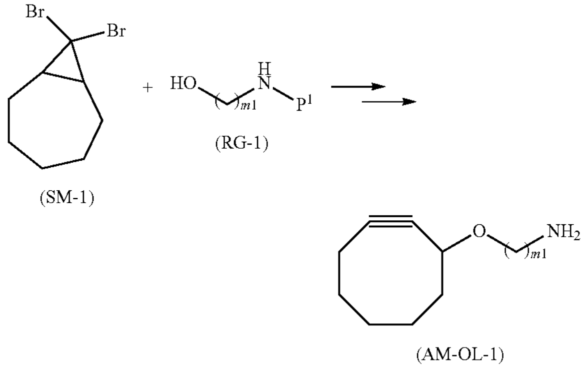

(SM-1) (RG-1) (AM-OL-1)

Using the compound of formula (SM-1) [the compound of formula (SM-1) is a commercial compound or a compound that can be manufactured by methods known in the literature from commercial compounds] and the compound of formula (RG-1) [the compound of formula (RG-1) is a commercial compound or a compound that can be manufactured by methods known in the literature from commercial compounds; m1 is an integer from 2 to 6], the amine compound represented by formula (AM-OL-1) or a salt of (AM-OL-1) can be manufactured by methods known in the literature (such as Carbohydrate Polymers, 169, pp. 332-340, 2017) by for example (i) substituting (RG-1) in the presence of $AgO_3SCF_3$ in a solvent such as toluene that does not participate in the reaction, then (ii) performing a debromination reaction with DBU to form an alkyne group, and finally (iii) deprotecting the protecting group $P^1$.

[Manufacturing Method B]

Method for manufacturing amine represented by formula (AM-OL-2):

[C94]

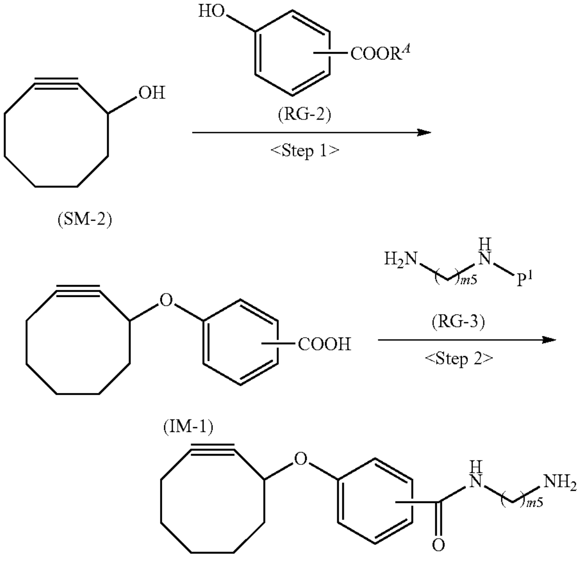

(SM-2) (RG-2) (IM-1) (RG-3) (AM-OL-2)

m5 = 2-6

<Step 1>

Using the compound of formula (SM-2) [the compound of formula (SM-2) is a commercial compound or a compound that can be manufactured by methods known in the literature from commercial compounds] and the compound of formula (RG-2) [the compound of formula (RG-2) is a commercial compound or a compound that can be manufactured by methods known in the literature from commercial compounds], the compound represented by formula (IM-1) can be manufactured by methods known in the literature (such as European Journal of Organic Chemistry, 2014 (6), pp. 1280-1286; 2014) by for example (i) performing a Mitsunobu reaction in the presence of $PPh_3$ and $N_2(CO_2CHMe_2)_2$ reagents in a solvent such as tetrahydrofuran that does not participate in the reaction, then (ii) performing hydrolysis in the presence of a base such as sodium hydroxide in a solvent such as methanol, ethanol, tetrahydrofuran or water that does not participate in the reaction, or a mixed solvent of these.

<Step 2>

Using the compound of formula (IM-1) obtained in <Step 1> of [Manufacturing Method B] and the compound of formula (RG-3) [the compound of formula (RG-3) is a commercial compound or a compound that can be manufactured by methods known in the literature from commercial compounds; m5 is an integer from 2 to 6], the amine compound represented by formula (AM-OL-2) or a salt of (AM-OL-2) can be manufactured by (iii) performing a condensation reaction as in the "Method for preparing alginic acid derivative of formula (I)" above and then (iv) deprotecting the protecting group $P^1$.

[Manufacturing Method C]

Method for manufacturing amine represented by formula (AM-OL-3):

[C95]

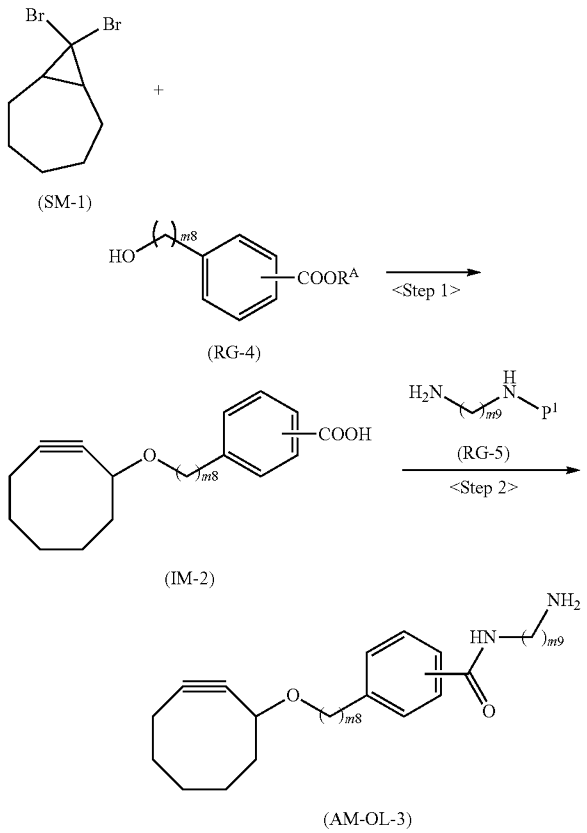

m8 = 1-6, m9 = 2-6

<Step 1>

Using the compound of formula (SM-1) and the compound of formula (RG-4) [the compound of formula (RG-4) is a commercial compound or a compound that can be manufactured by methods known in the literature from commercial compounds; m8 is an integer from 1 to 6], the compound represented by formula (IM-2) can be manufactured by methods known in the literature (such as Journal of the American Chemical Society, 126 (46), pp. 15046-15047, 2004) by for example (i) substituting the compound of formula (RG-4) in the presence of $AgClO_4$ in a solvent such as toluene that does not participate in the reaction, then (ii) performing a debromination reaction with NaOMe to form alkyne groups, and (iii) performing hydrolysis in the presence of a base such as lithium hydroxide or sodium hydroxide in a solvent such as methanol, ethanol, tetrahydrofuran or water that does not participate in the reaction, or a mixed solvent of these.

<Step 2>

Using the compound of formula (IM-2) obtained in <Step 1> of [Manufacturing Method C] and the compound of formula (RG-5) [the compound of formula (RG-5) is a commercial compound or a compound that can be manufactured by methods known in the literature from commercial compounds; m9 is an integer from 2 to 6], the amine compound represented by formula (AM-OL-3) or a salt of (AM-OL-3) can be manufactured by performing a condensation reaction as in the "Method for preparing alginic acid derivative of formula (I)" above and then deprotecting the protecting group $P^1$.

[Manufacturing Method D]

Method for manufacturing amine represented by formula (AM-OL-5):

[C96]

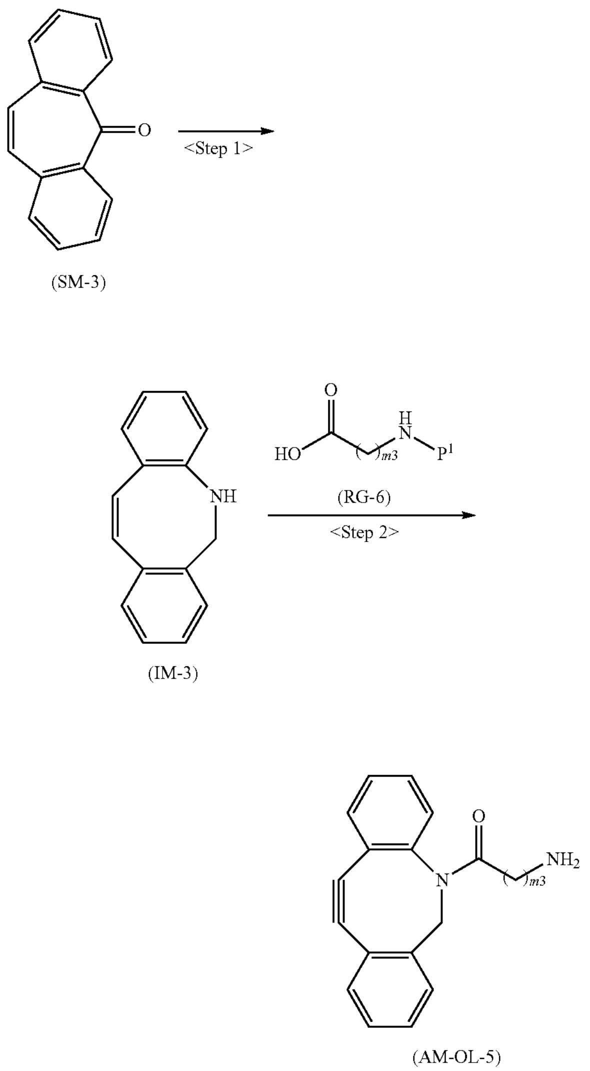

m3 = 1-6

<Step 1>

Using the compound of formula (SM-3) [the compound of formula (SM-3) is a commercial compound or a compound that can be manufactured by methods known in the literature from commercial compounds], the compound represented by formula (IM-3) can be manufactured by methods known in the literature (such as Faming Zhuanli Shenqing, 104529898, 22 Apr. 2015) by for example (i) reacting $H_2NOH$—HCl in the presence of a base such as pyridine in a solvent such as ethanol that does not participate in the reaction to form an oxime, then (ii) reacting diphosphorus pentoxide in $P_2O_5$ and methanesulfonic acid to perform Beckmann rearrangement and thereby form an 8-membered lactam, and finally (iii) reducing the amide groups with a reducing agent such as $BH_3$ or $LiAlH_4$ in a solvent such as diethyl ether that does not participate in the reaction.

<Step 2>

Using the compound of formula (IM-3) obtained in <Step 1> of [Manufacturing Method D] and the compound of formula (RG-6) [the compound of formula (RG-6) is a commercial compound or a compound that can be manufactured by methods known in the literature from commercial compounds; m3 is an integer from 1 to 6], the amine compound represented by formula (AM-OL-5) or a salt of (AM-OL-5) can be manufactured by (iv) performing a condensation reaction as in the "Method for preparing alginic acid derivative of formula (I)" above to obtain a condensate, then (v) adding bromine, and then using tert-BuOK to perform a debromination reaction and form an alkyne group, and finally (vi) deprotecting the protecting group $P^1$.

[Manufacturing Method E]

Method for manufacturing amines represented by formula (AM-OL-6) and formula (AM-OL-7):

<Step 1>

Using the compound of formula (IM-4) obtained from (ii) of <Step 1> of [Manufacturing Method D] and the compound of formula (RG-7) [the compound of formula (RG-7) is a commercial compound or a compound that can be manufactured by methods known in the literature from commercial compounds; m2' is an integer from 2 to 6], the compound represented by formula (IM-5) can be manufactured by methods known in the literature (such as Synthesis, 46 (5): pp. 669-677, 2014) by performing a reaction in the presence of a base such as sodium hydroxide and a phase transfer catalyst such as tetrabutyl ammonium bromide in a solvent such as toluene that does not participate in the reaction.

<Step 2>

The compound represented by formula (AM-OL-6) or a salt of (AM-OL-6) can be manufactured by first adding bromine to the compound of formula (IM-5) obtained in <Step 1> of [Manufacturing Method E], and then using a base such as tert-BuOK to perform a debromination reaction and form an alkyne group, and finally deprotecting the protecting group $P^2$.

<Step 3>

The compound of formula (IM-6) can be manufactured using the compound of formula (IM-5) obtained in <Step 1> of [Manufacturing Method E] by performing a reaction according to the reduction methods described in (iii) of <Step 1> of [Manufacturing Method D].

<Step 4>

The amine compound represented by formula (AM-OL-7) or a salt of (AM-OL-7) can be manufactured using the compound of formula (IM-6) obtained in <Step 3> of [Manufacturing Method E] by performing a reaction as in <Step 2> of [Manufacturing Method E].

[C97]

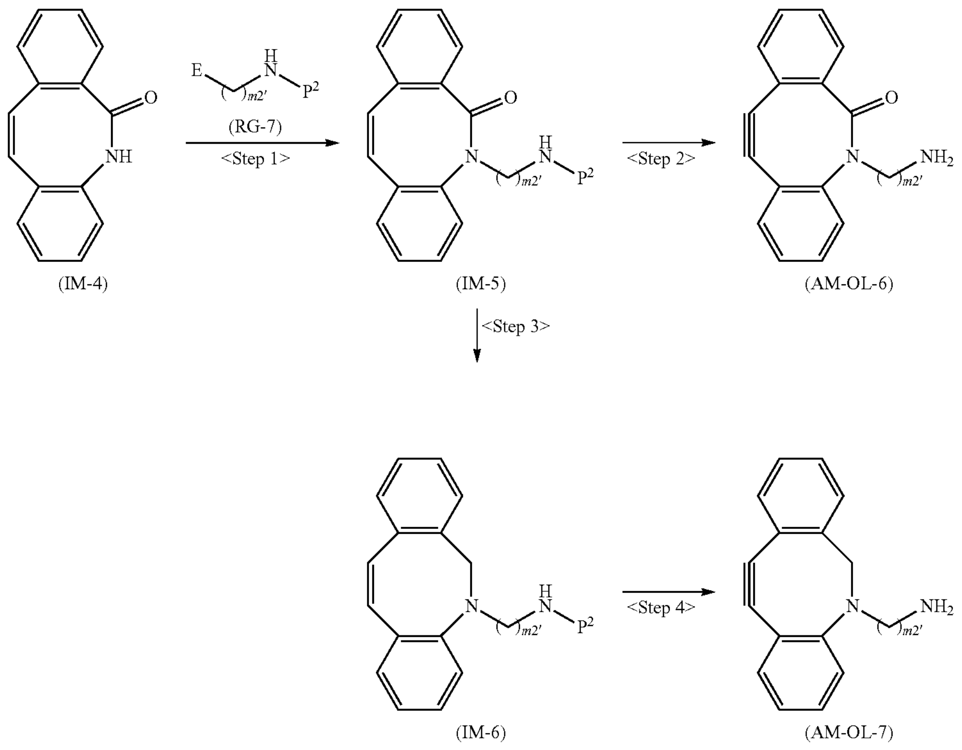

[Manufacturing Method F]

Method for manufacturing amine represented by formula (AM-OL-8):

[C98]

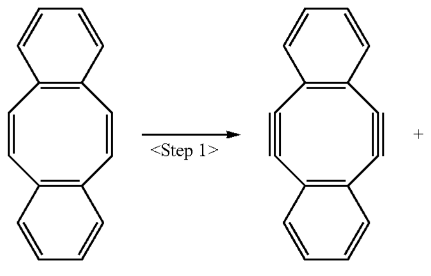

(SM-4) (IM-7)

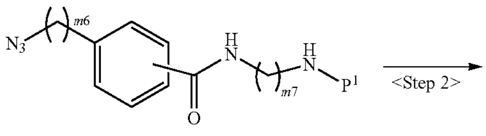

(RG-8)

-continued

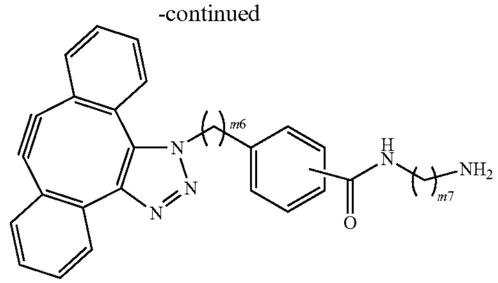

(AM-OL-8)

m6 = 1-6, m7 = 2-6

<Step 1>

Using the compound of formula (SM-4) [the compound of formula (SM-4) is a commercial compound or a compound that can be manufactured by methods known in the literature from commercial compounds], the compound represented by formula (IM-7) can be manufactured by methods known in the literature (such as Synthesis, (9), pp. 1191-1194, 2002) by first adding bromine and then performing a debromination reaction with tert-BuOK to form an alkyne group.

<Step 2>

Using the compound of formula (IM-7) obtained in <Step 1> of [Manufacturing Method F] and the compound of formula (RG-8) [the compound of formula (RG-8) is a commercial compound or a compound that can be manufactured by methods known in the literature from commercial compounds (for details, see Manufacturing Method H below); m6 is an integer from 1 to 6 and m7 is an integer from 2 to 6], the amine compound represented by formula (AM-OL-8) or a salt of (AM-OL-8) can be manufactured by methods known in the literature (such as Journal of the American Chemical Society, 126, pp. 15046-15047, 2004 or Chem. Ber. 94, pp. 3260-3275, 1961) by performing a Huisgen reaction and then deprotecting the protecting group $P^1$.

[Manufacturing Method G]

Method for manufacturing amine represented by formula (AM-OL-9):

[C99]

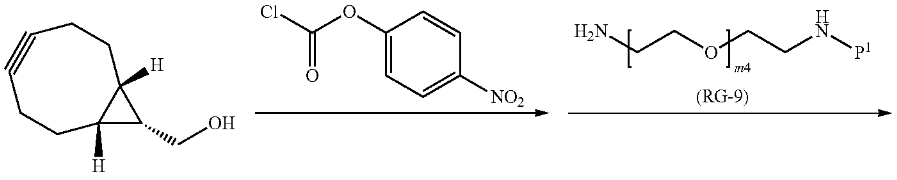

(RG-9)

(SM-5)

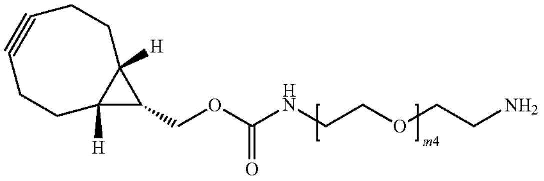

(AM-OL-9)

m4 = 1-6

Using the compound of formula (SM-5) [the compound of formula (SM-5) is a commercial compound or a compound that can be manufactured by methods known in the literature from commercial compounds] and following methods known in the literature (such as U.S. Patent Application Publication No. 2013-0137861A), a carbonate is obtained by reacting p-nitrophenyl chloroformate with or without a base such as pyridine in a solvent such as dichloromethane that does not participate in the reaction. Next, the compound of formula (RG-9) [the compound of formula (RG-9) is a commercial compound or a compound that can be manufactured by methods known in the literature from commercial compounds; m4 is an integer from 1 to 6] is reacted in a N,N-dimethylformamide solvent in the presence of triethylamine to obtain a carbamoyl body. Finally, the protecting group $P^1$ can be deprotected to obtain the amine compound represented by formula (AM-OL-9) or a salt of (AM-OL-9).

[Manufacturing Method H]

Method for manufacturing amine represented by formula (AM-LK-1) [of the amines represented by (AM-LK-1), a p-substituted amine in which n1=1 and n2=3 can also be manufactured by the methods described in WO 2016/152980A]:

[C100]

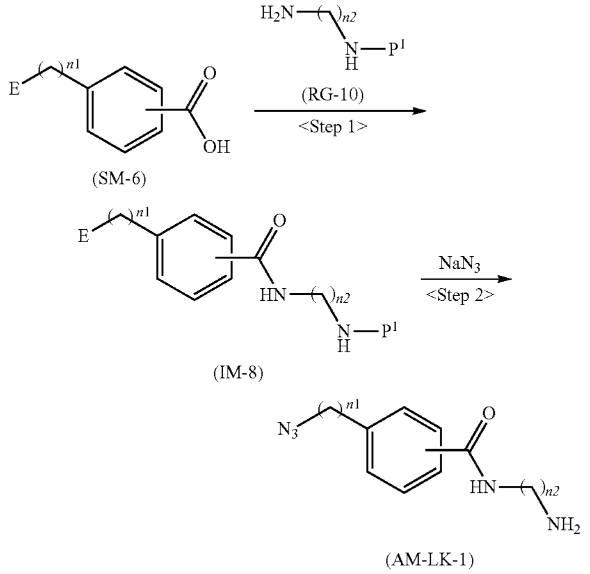

n1 = 1-6, n2 = 2-6

<Step 1>

Using the compound of formula (SM-6) [the compound of formula (SM-6) is a commercial compound or a compound that can be manufactured by methods known in the literature from commercial compounds; n1 is an integer from 1 to 6] and the compound of formula (RG-10) [the compound of formula (RG-10) is a commercial compound or a compound that can be manufactured by methods known in the literature from commercial compounds; n2 is an integer from 2 to 6], the compound of formula (IM-8) can be manufactured by performing a condensation reaction as in the "Method for preparing alginic acid derivative of formula (I)" above.

<Step 2>

Using the compound of formula (IM-8) obtained in <Step 1> of [Manufacturing Method H], the amine compound represented by formula (AM-LK-1) or a salt of (AM-LK-1) can be manufactured by methods known in the literature (such as Organometallics, 29 (23), pp. 6619-6622, 2010) by reacting $NaN_3$ in a solvent such as dimethylsulfoxide that does not participate in the reaction to thereby introduce an azide group, and then deprotecting the protecting group $P^1$.

[Manufacturing Method J]

Method for manufacturing amine represented by formula (AM-LK-2):

[C101]

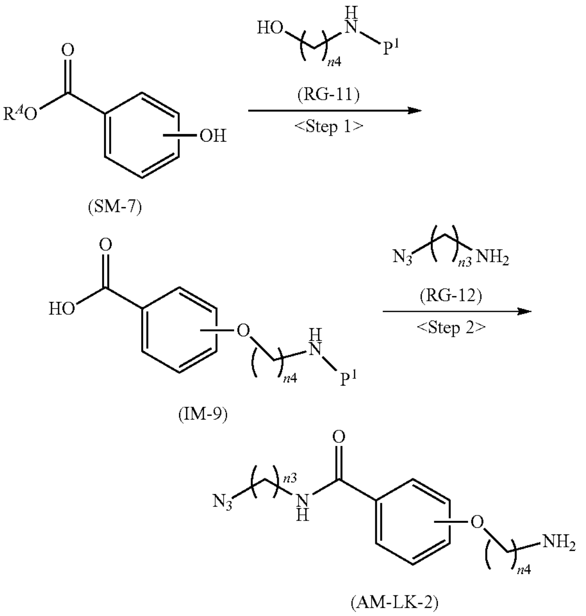

n3 = 2-6, n4 = 2-6

<Step 1>

Using the compound of formula (SM-7) [the compound of formula (SM-7) is a commercial compound or a compound that can be manufactured by methods known in the literature from commercial compounds] and the compound of formula (RG-11) [the compound of formula (RG-11) is a commercial compound or a compound that can be manufactured by methods known in the literature from commercial compounds; n4 is an integer from 2 to 6], the compound represented by formula (IM-9) can be manufactured by performing a Mitsunobu reaction according to <Step 1> of [Manufacturing Method B], and then hydrolyzing the ester groups in a solvent such as methanol, ethanol, tetrahydrofuran or water that does not participate in the reaction, or a mixed solvent of these, in the presence of a base such as sodium hydroxide.

<Step 2>

Using the compound of formula (IM-9) obtained in <Step 1> of [Manufacturing Method J] and the compound of formula (RG-12) [the compound of formula (RG-12) is a commercial compound or a compound that can be manufactured by methods known in the literature from commercial compounds; n3 is an integer from 2 to 6], the amine compound represented by formula (AM-LK-2) or a salt of (AM-LK-2) can be manufactured by performing a condensation reaction as in the "Method for preparing alginic acid derivative of formula (I)" above to obtain a condensate, and then deprotecting the protecting group $P^1$.

[Manufacturing Method K]

Method for manufacturing amine represented by formula (AM-LK-3):

[C102]

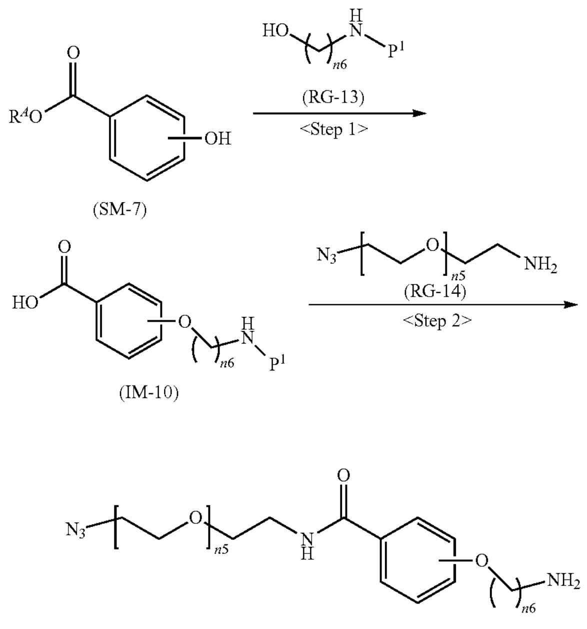

(SM-7)

(RG-13)

(IM-10)

(RG-14)

(AM-LK-3)

n5 = 1-6, n6 = 2-6

<Step 1>

Using the compound of formula (SM-7) used in <Step 1> of [Manufacturing Method J] and the compound of formula (RG-13) [the compound of formula (RG-13) is a commercial compound or a compound that can be manufactured by methods known in the literature from commercial compounds; n6 is an integer from 2 to 6], the compound represented by formula (IM-10) can be manufactured by performing a Mitsunobu reaction according to <Step 1> of [Manufacturing Method B], and then hydrolyzing the ester groups in a solvent such as methanol, ethanol, tetrahydrofuran or water that does not participate in the reaction, or a mixed solvent of these, in the presence of a base such as sodium hydroxide.

<Step 2>

Using the compound (IM-10) obtained in <Step 1> of [Manufacturing Method K] and the compound of formula (RG-14) [the compound of formula (RG-14) is a commercial compound or a compound that can be manufactured by methods known in the literature from commercial compounds; n5 is an integer from 1 to 6], the amine compound represented by formula (AM-LK-3) or a salt of (AM-LK-3) can be manufactured by performing a condensation reaction as in the "Method for preparing alginic acid derivative of formula (I)" above to obtain a condensate, and then deprotecting the protecting group $P^1$.

[Manufacturing Method L]

Method for manufacturing amine represented by formula (AM-OL-4):

[C103]

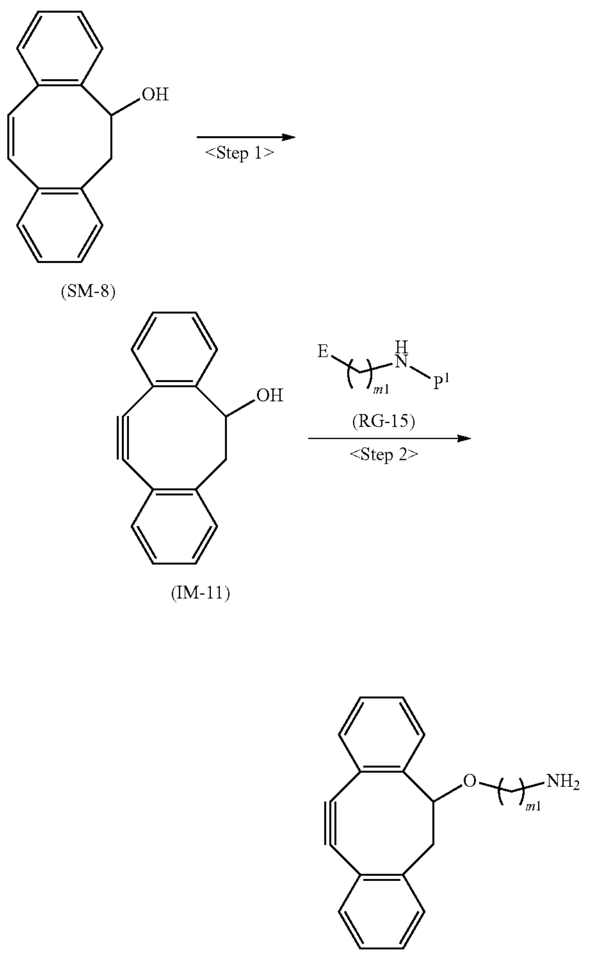

(SM-8)

(IM-11)

(RG-15)

(AM-OL-4)

n7 = 2-6

<Step 1>

Using the compound of formula (SM-8) [the compound of formula (SM-8) is a commercial compound or a compound that can be manufactured by methods known in the literature from commercial compounds], the compound represented by formula (IM-11) can be manufactured by methods known in the literature (such as the methods described in WO 2009/067663A) by first adding bromine and then performing debromination with $LiN(i\text{-}Pr)_2$.

<Step 2>

Using the compound of formula (IM-11) obtained in <Step 1> of [Manufacturing Method L] and the compound represented by formula (RG-15) [the compound of formula (RG-15) is a commercial compound or a compound that can be manufactured by methods known in the literature from commercial compounds; m1 is an integer from 2 to 6], the amine compound represented by formula (AM-OL-4) or a salt of (AM-OL-4) can be manufactured by performing a reaction in the presence of a base such as sodium hydride in a solvent such as tetrahydrofuran that does not participate in the reaction to obtain a compound with introduced side chains, and then deprotecting the protecting group $P^1$.

[Manufacturing Method M]

Method for manufacturing amine represented by formula (AM-LK-4):

[C104]

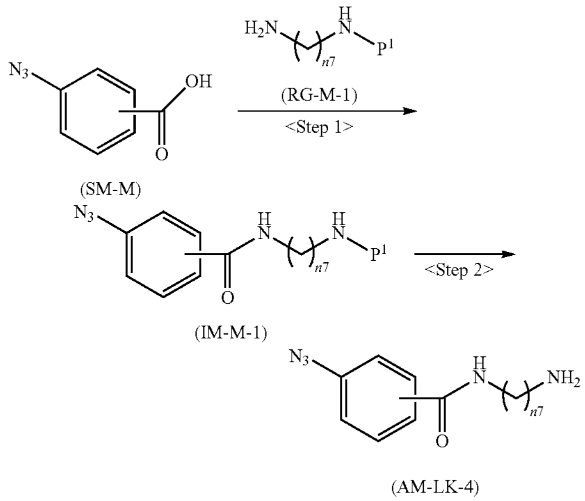

(SM-M)

(IM-M-1)

(AM-LK-4)

n7 = 2-6

<Step 1>

Using the compound of formula (SM-M) and the compound of formula (RG-M-1) [the compound of formula (SM-M) and the compound of formula (RG-M-1) are commercial compounds or compounds that can be manufactured by methods known in the literature from commercial compounds; n7 is an integer from 2 to 6], the compound represented by formula (IM-M-1) can be manufactured by performing a condensation reaction as in the "Method for preparing alginic acid derivative of formula (I)" above.

The carboxylic acid represented by formula (SM-M) can also be converted into an acid halide or acid anhydride by methods known in the literature (such as those described in "Experimental Chemistry Course 5th Edition", Vol. 16, Carboxylic acids and derivatives, acid halides and acid anhydrides, pp. 99-118, 2007, Maruzen), which can then be reacted with the compound of formula (RG-M-1) at temperatures from 0° C. to the reflux temperature of the solvent in a solvent selected from the halogen solvents such as dichloromethane and chloroform, the ether solvents such as diethyl ether and tetrahydrofuran, the aromatic hydrocarbon solvents such as toluene and benzene and the polar solvents such as N,N-dimethylformamide in the presence of a base such as triethylamine or pyridine to similarly manufacture the compound of formula (IM-M-1).

<Step 2>

Using the compound of formula (IM-M-1) obtained in <Step 1> of [Manufacturing Method M], the compound represented by formula (AM-LK-4) or a salt of (AM-LK-4) can be manufactured by methods known in the literature, such as those described in Greene et al, "Protective Groups in Organic Synthesis 4th Edition", 2007 (John Wiley & Sons), by performing a reaction by a deprotection method selected appropriately according to the type of protecting group.

[Manufacturing Method N]

Method for manufacture amine represented by formula (AM-OL-17):

[C105]

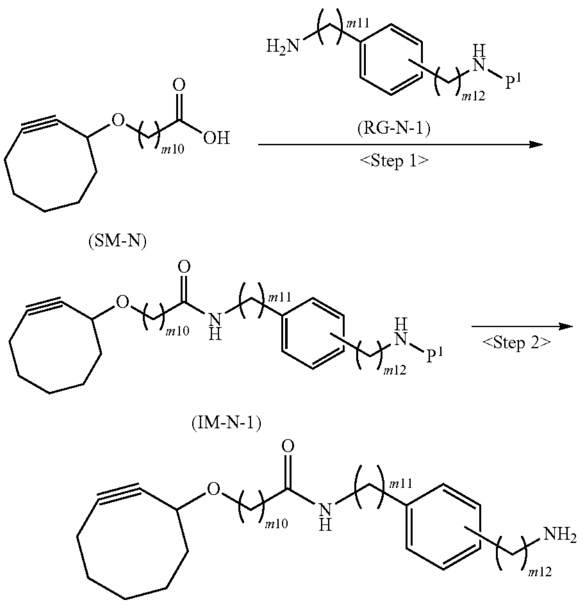

(SM-N)

(IM-N-1)

(AM-OL-17)

m10 = 1-4, m11 = 1-6, m12 = 1-6

<Step 1>

Using the compound of formula (SM-N) and the compound of formula (RG-N-1) [the compound of formula (SM-N) and the compound of formula (RG-N-1) are commercial compounds or compounds that can be manufactured by methods known in the literature from commercial compounds; m10 is an integer from 1 to 4, m11 is an integer from 1 to 6 and m12 is an integer from 1 to 6], the compound represented by formula (IM-N-1) can be manufactured by performing a condensation reaction as in <Step 1> of [Manufacturing Method M].

<Step 2>

Using the compound of formula (IM-N-1) obtained in <Step 1> of [Manufacturing Method N], the compound represented by formula (AM-OL-17) or a salt of (AM-OL-17) can be manufactured by methods known in the literature, such as those described in Greene et al, "Protective Groups in Organic Synthesis 4th Edition", 2007, John Wiley & Sons, by performing a reaction by a deprotection method selected appropriately according to the type of protecting group.

[Manufacturing Method P]

Method for manufacturing amine represented by formula (AM-OL-18) [of the amines represented by (AM-OL-18), an amine in which m13=1 and m14=2 can be manufactured by the methods described in WO 2015/143092A]:

[C106]

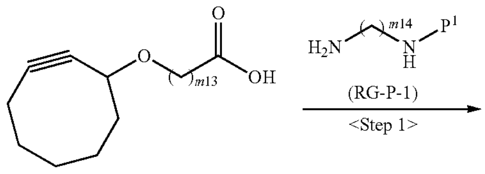

(SM-P)

-continued

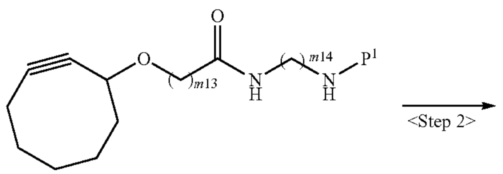

(IM-P-1)

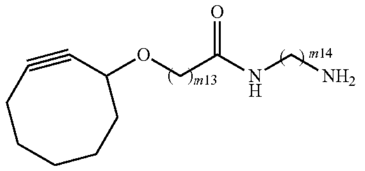

(AM-OL-18)

m13 = 1-4, m14 = 2-6

<Step 1>

Using the compound of formula (SM-P) and the compound of formula (RG-P-1) [the compound of formula (SM-P) and the compound of formula (RG-P-1) are commercial compounds or compounds that can be manufactured by methods known in the literature from commercial compounds; m13 is an integer from 1 to 4 and m14 is an integer from 2 to 6], the compound represented by formula (IM-P-1) can be manufactured by performing a condensation reaction as in <Step 1> of [Manufacturing Method M].

<Step 2>

Using the compound of formula (IM-P-1) obtained in <Step 1> of [Manufacturing Method P], the compound represented by formula (AM-OL-18) or a salt of (AM-OL-18) can be manufactured by methods known in the literature, such as those described in Greene et al, “Protective Groups in Organic Synthesis 4th Edition”, 2007, John Wiley & Sons, by performing a reaction by a deprotection method selected appropriately according to the type of protecting group.

[Manufacturing Method Q]

Method for manufacturing amine represented by formula (AM-OL-19):

[C107]

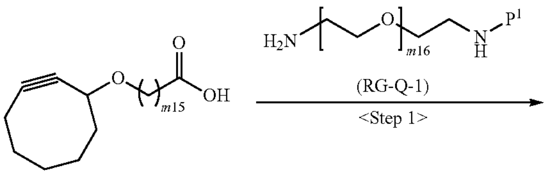

(SM-Q)

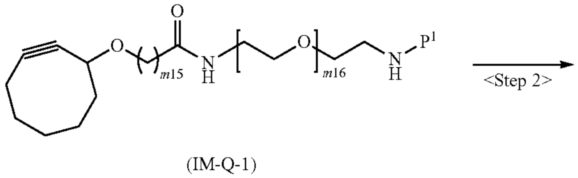

(IM-Q-1)

-continued

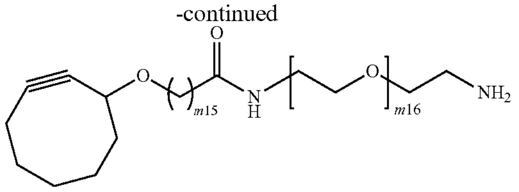

(AM-OL-19)

m15 = 1-4, m16 = 1-6

<Step 1>

Using the compound of formula (SM-Q) and the compound of formula (RG-Q-1) [the compound of formula (SM-Q) and the compound of formula (RG-Q-1) are commercial compounds or compounds that can be manufactured by methods known in the literature from commercial compounds; m15 is an integer from 1 to 4 and m16 is an integer from 1 to 6], the compound represented by formula (IM-Q-1) can be manufactured by performing a condensation reaction as in <Step 1> of [Manufacturing Method M].

<Step 2>

Using the compound of formula (IM-Q-1) obtained in <Step 1> of [Manufacturing Method Q], the compound represented by formula (AM-OL-19) or a salt of (AM-OL-19) can be manufactured by methods known in the literature, such as those described in Greene et al, “Protective Groups in Organic Synthesis 4th Edition”, 2007, John Wiley & Sons, by performing a reaction by a deprotection method selected appropriately according to the type of protecting group.

[Manufacturing Method R]

Method for manufacturing amine represented by formula (AM-LK-5) [of the amines represented by (AM-LK-5), an amine in which n8=1 and n9=2 can be manufactured by the methods described in WO 2016/152980A]:

[C108]

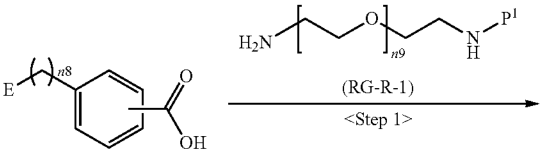

(SM-R)

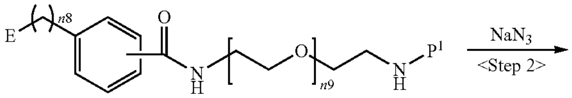

(IM-R-1)

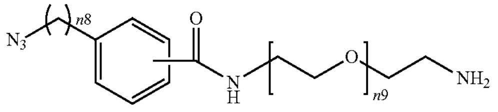

(AM-LK-5)

n8 = 1-4, n9 = 1-6

<Step 1>

Using the compound of formula (SM-R) [the compound of formula (SM-R) is a commercial compound or a compound that can be manufactured by methods known in the literature from commercial compounds; n8 is an integer from 1 to 4] and the compound of formula (RG-R-1) [the compound of formula (RG-R-1) is a commercial compound or a compound that can be manufactured by methods known in the literature from commercial compounds; n9 is an integer from 1 to 6], the compound represented by formula (IM-R-1) can be manufactured by performing a condensation reaction as in <Step 1> of [Manufacturing Method M].

<Step 2>

Using the compound of formula (IM-R-1) obtained in <Step 1> of [Manufacturing Method R], the amine compound represented by formula (AM-LK-5) or a salt of (AM-LK-5) can be manufactured by reacting $NaN_3$ as in <Step 2> of [Manufacturing Method H] to introduce an azide group, and then deprotecting the protecting group $P^1$.

[Manufacturing Method S]

Method for manufacturing amine represented by formula (AM-LK-6):

[C109]

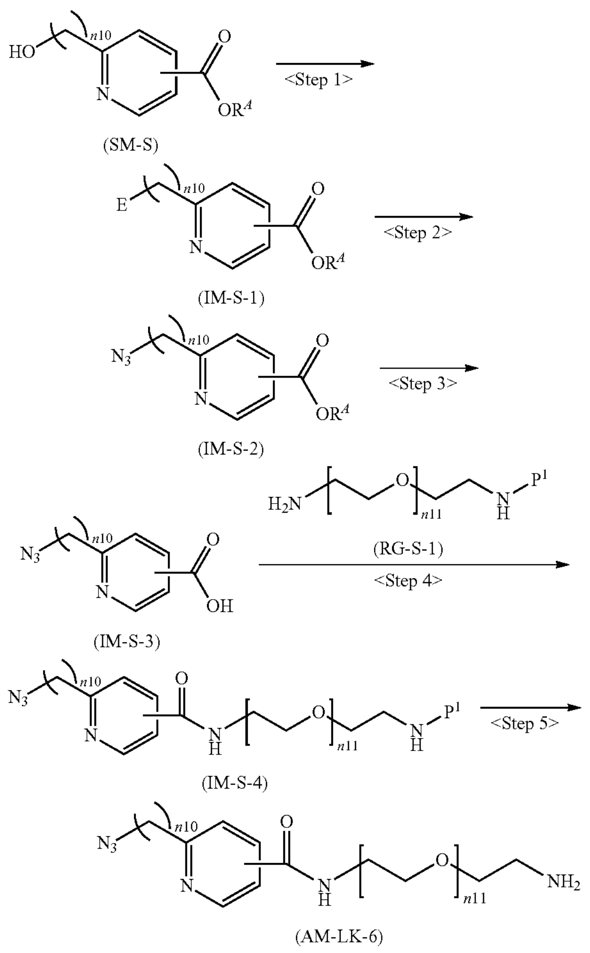

(SM-S), (IM-S-1), (IM-S-2), (RG-S-1), (IM-S-3), (IM-S-4), (AM-LK-6)

n10 = 1-4, n11 = 1-6

<Step 1>

[When E is an OTs Group or OMs Group]:

Using the compound of formula (SM-S) [the compound of formula (SM-S) is a commercial compound or a compound that can be manufactured by methods known in the literature from commercial compounds; n10 is an integer from 1 to 4] and a reagent such as methanesulfonic acid chloride, tosyl chloride or tosyl anhydride, compounds represented by formula (IM-S-1) can be manufactured by methods known in the literature (such as those described in Journal of the American Chemical Society, 136 (29): pp. 10450-10459, 2014) by performing a reaction at temperatures from −78° ° C. to the reflux temperature of the solvent in the presence of a base such as triethylamine, N,N-diisopropylethylamine or pyridine in a solvent that does not participate in the reaction, such as a halogen solvent such as dichloromethane or chloroform, an ether solvent such as diethyl ether, tetrahydrofuran, 1,2-dimethoxyethane or 1,4-dioxane or an aromatic hydrocarbon solvent such as benzene or toluene, or a mixed solvent of these, or without a solvent.

[When E is a Halogen (Chlorine, Bromine or Iodine)]:

Using the compound of formula (SM-S), halide compounds represented by formula (IM-S-1) (E=chlorine, bromine, iodine) can be manufactured by methods known in the literature (such as those described in "Experimental Chemistry Course 4th Edition", Vol. 19, Organic Synthesis I: Hydrocarbons and halide compounds, pp. 363-482, 1992, Maruzen) by appropriately selecting the halogenating agents (chlorinating agents, brominating agents, iodizing agents) shown below and solvents that do not participate in the reaction, and performing a reaction at temperatures between 0° C. and the reflux temperature of the solvent.

<When E=Chlorine>

The desired chloride can be manufactured by using a reagent such as hydrogen chloride/zinc chloride ($HCl/ZnCl_2$), hydrogen chloride/hexamethylphosphoramide (HCl/HMPA), thionyl chloride ($SOCl_2$), carbon tetrachloride/triphenylphosphine ($CCl_4/PPh_3$), triphosgene/triphenylphosphine ($(CCl_3)_2CO/PPh_3$) or triphosgene/N,N-dimethylformamide ($POCl_3$/DMF) as a chlorinating agent.

<When X=Bromine>

The desired bromide can be manufactured by using a reagent such as 48% hydrobromic acid (48% HBr), 48% hydrobromic acid/sulfuric acid (48% $HBr/H_2SO_4$), hydrogen bromide/lithium bromide (HBr/LiBr), sodium bromide/sulfuric acid ($NaBr/H_2SO_4$) or phosphorus tribromide ($PBr_3$) as a brominating agent. The desired bromide can also be manufactured by reacting sodium bromide (NaBr) with the compound of formula (IM-S-1) in which E=OTs or OMs.

<When X=Iodine>

The desired iodide can be manufactured by using a reagent such as hydroiodic acid (HI) or iodine/triphenylphosphine ($I_2/PPh_3$) as an iodizing agent. The desired iodide can also be manufactured by reacting sodium iodide (NaI) with the compound of formula (IM-S-1) in which E=OTs or OMs.

<Step 2>

Using the compound of formula (IM-S-1) obtained in <Step 1> of [Manufacturing Method S], the compound of formula (IM-S-2) can be manufactured by reacting $NaN_3$ as in <Step 2> of [Manufacturing Method H].

<Step 3>

Using the compound of formula (IM-S-2) obtained in <Step 2> of [Manufacturing Method S], the compound of formula (IM-S-3) can be manufactured by performing hydrolysis as in the ester group hydrolysis reaction of <Step 1> of [Manufacturing Method B].

<Step 4>

Using the compound of formula (IM-S-3) obtained in <Step 3> of [Manufacturing Method S] and the compound of formula (RG-S-1) [the compound of formula (RG-S-1) is a commercial compound or a compound that can be manufactured by methods known in the literature from commercial compounds; n11 is an integer from 1 to 6], the compound represented by formula (IM-S-4) can be manufactured by performing a condensation reaction as in <Step 1> of [Manufacturing Method M].

<Step 5>

The amine compound of formula (AM-LK-6) or a salt of (AM-LK-6) can be manufactured by deprotecting the protecting group $P^1$ of the compound of formula (IM-S-4) obtained in <Step 4> of [Manufacturing Method S].

[Manufacturing Method T]

Method for manufacturing amine represented by formula (AM-LK-7):

[C110]

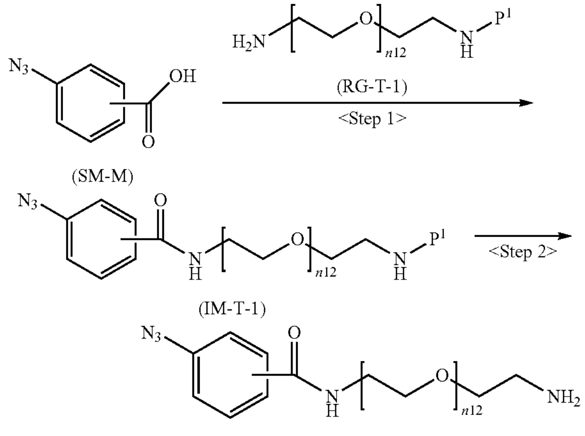

(RG-T-1)

(SM-M)

(IM-T-1)

(AM-LK-7)

n12 = 1-6

<Step 1>

Using the compound of formula (SM-M) and the compound of formula (RG-T-1) [the compound of formula (SM-M) and the compound of formula (RG-T-1) are commercial compounds or compounds that can be manufactured by methods known in the literature from commercial compounds; n12 is an integer from 1 to 6], the compound represented by formula (IM-T-1) can be manufactured by performing a condensation reaction as in <Step 1> of [Manufacturing Method M].

The carboxylic acid represented by formula (SM-M) can also be converted into an acid halide or acid anhydride by methods known in the literature (such as those described in "Experimental Chemistry Course 5th Edition", Vol. 16, Carboxylic acids and derivatives, acid halides and acid anhydrides, pp. 99-118, 2007, Maruzen), and reacted with the compound of formula (RG-T-1) at temperatures from 0° C. to the reflux temperature of the solvent in a solvent selected from the halogen solvents such as dichloromethane and chloroform, the ether solvents such as diethyl ether and tetrahydrofuran, the aromatic hydrocarbon solvents such as toluene and benzene and the polar solvents such as N,N-dimethylformamide in the presence of a base such as triethylamine or pyridine to similarly manufacture the compound of formula (IM-T-1).

<Step 2>

Using the compound of formula (IM-T-1) obtained in <Step 1> of [Manufacturing Method T], the compound represented by formula (AM-LK-7) or a salt of (AM-LK-7) can be manufactured by methods known in the literature, such as those described in Greene et al, "Protective Groups in Organic Synthesis 4th Edition", 2007 (John Wiley & Sons), by performing a reaction by a deprotection method selected appropriately according to the type of protecting group.

For the amine ($Akn-L^1-NH_2$) with introduced alkyne group and the amine ($N_3-L^2-NH_2$) with introduced azide group used in manufacturing the alginic acid derivative represented by formula (I) or (II), the desired amines can be manufactured by appropriately combining the reactions described in [Manufacturing Method A] through [Manufacturing Method N] and [Manufacturing Method P] through [Manufacturing Method T] above with methods described in known literature, such as "Experimental Chemistry Course 5th Edition", each volume, 2007, Maruzen, or "Comprehensive Organic Transformations, A Guide to Functional Group Preparations, 3rd Edition", Richard C. Larock, Ed., 2018 and "Strategic Applications of Named Reactions in Organic Synthesis", Laszlo Kurti & Barbara Czako, Eds., Academic Press, 2005. The amines in the table below can also be manufactured by the methods described in the documents of prior art shown in the table.

TABLE 11

| Amine (Akn—L1—NH2) | Akn | L1 | Conditions | Document of prior art |
|---|---|---|---|---|
| AM-K2N4 | AK-2 | LN-4 | m4 = 2 | WO 2009/067663A |
| AM-K6N4 | AK-6 | LN-4 | m4 = 2 | WO 2011/136645A |
| AM-K12N2 | AK-12 | LN-2 | m2 = 1 | WO 2013/036748A |
| AM-K1N1 | AK-1 | LN-1 | m1 = 2 | WO 2015/020206A |
| AM-K2N1 | AK-2 | LN-1 | m1 = 2 | |
| AM-K7N1 | AK-7 | LN-1 | m1 = 2 | |
| AM-K3N3 | AK-3 | LN-3 | m3 = 1 | |
| AM-K4N3 | AK-4 | LN-3 | m3 = 1 | |
| AM-K9N8 | AK-9 | LN-8 | * | |
| AM-K10N6 | AK-10 | LN-6 | p-position, m6 = 1, m7 = 2 | |
| AM-K11N3 | AK-11 | LN-3 | m3 = 1 | |
| AM-K3N3 | AK-3 | LN-3 | m3 = 2 | WO 2015/112014A |
| AM-K6N4 | AK-6 | LN-4 | m4 = 4 | WO 2016/054315A |
| AM-K6N4 | AK-6 | LN-4 | m4 = 3 | WO 2016/168766A |
| AM-K2N3 | AK-2 | LN-3 | m3 = 2 | Macromolecular Rapid Communications, 39(1), 2018 |
| AM-K2N4 | AK-2 | LN-4 | m4 = 4 | Journal of the American Chemical Society, 133(18): 7054-7064, 2011 |

TABLE 11-continued

| Amine (Akn—L1—NH2) | Akn | L1 | Conditions | Document of prior art |
|---|---|---|---|---|
| AM-K3N3 | AK-3 | LN-3 | m3 = 3 | Bioconjugate Chemistry, 23(8): 1680-1686, 2012 |
| AM-K3N3 | AK-3 | LN-3 | m3 = 5 | ACS Medicinal Chemistry Letters, 2(12), 885-889, 2011 |
| AM-K1N10 | AK-1 | LN-10 | m13 = 1, m14 = 2 | WO 2015/143092A |
| Amine (N3—L2—NH2) | L1 | Substitution position | Conditions | Document of prior art |
| AM-LK1(p) | LK-1 | p-position | n1 = 1, n2 = 3 | WO 2016/152980A |
| AM-LK4(m) | LK-4 | m-position | n7 = 3 | Journal of Medicinal Chemistry (2011), 54(18), 6319-6327 |
| AM-LK4(p) | LK-4 | p-position | n7 = 2, 3, 4, 6 | n7 = 2, 3, 4; Journal of Medicinal Chemistry, (2011), 54(18), 6319-6327. n7 = 6; Experientia, 39(10), 1063-72. |
| AM-LK5(p) | LK-5 | p-position | n8 = 1, n9 = 2 | WO 2016/152980A |

In this Description, the amine compound represented by formula (AM-1) or (AM-2) (including subordinate expressions of each expression) may sometimes form a pharmaceutically acceptable salt (such as an acid addition salt). This salt is not particularly limited as long as it is pharmaceutically acceptable, and examples include salts with inorganic acids, salts with organic acids, and salts with acidic amino acids and the like. Preferred examples of salts with inorganic acids include salts with hydrochloric acid, hydrobromic acid, hydroiodic acid, nitric acid, sulfuric acid and phosphoric acid. Preferred examples of salts with organic acids include salts with aliphatic monocarboxylic acids such as formic acid, acetic acid, trifluoroacetic acid, propionic acid, butyric acid, valeric acid, enanthic acid, capric acid, myristic acid, palmitic acid, stearic acid, lactic acid, sorbic acid and mandelic acid, salts with aliphatic dicarboxylic acids such as oxalic acid, malonic acid, succinic acid, fumaric acid, maleic acid, malic acid and tartaric acid, salts with aliphatic tricarboxylic acids such as citric acid, salts with aromatic monocarboxylic acids such as benzoic acid and salicylic acid, salts with aromatic dicarboxylic acids such as phthalic acid, salts with organic carboxylic acids such as cinnamic acid, glycolic acid, pyruvic acid, oxylic acid, salicylic acid and N-acetylcysteine, salts with organic sulfonic acids such as methanesulfonic acid, benzenesulfonic acid and p-toluenesulfonic acid, and acid addition salts with acidic amino acids such as aspartic acid and glutamic acid. Preferred examples of salts with acidic amino acids include salts with aspartic acid, glutamic acid and the like. Of these, a pharmaceutically acceptable salt is preferred.

This salt can be obtained by ordinary methods, such as for example by mixing the compound of the invention with a solution containing a suitable amount of an acid or base to form the target salt, and then either performing separation filtration or distilling off the mixed solvent. General information on salts is published in Stahl & Wermuth, “Handbook of Pharmaceutical Salts: Properties, Selection and Use” (Wiley-VCH, 2002), and details are described in this handbook.

In this Description, the amine compound represented by formula (AM-1) or (AM-2) (including subordinate expressions of each expression) or a salt thereof may form a solvate with a solvent such as water, ethanol, glycerol or the like.

In this Description, unless otherwise specified, when a variable substituent is substituted on a cyclic group this means that the variable substituent is not linked to a specific carbon atom on the cyclic group. For example, this means that the variable substituent Rs in the following formula A can be substituted on any of the carbon atoms i, ii, iii, iv and v.

[C111]

Formula A

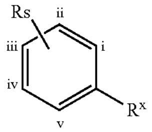

9. Use of Alginic Acid Derivatives and Crosslinked Alginic Acid Structure

The alginic acid derivatives can be used in place of conventional alginic acid in a wide range of fields including foodstuffs, medicine, cosmetics, fibers, paper and the like. Specifically, preferred uses of the alginic acid derivatives and photocrosslinked alginic acid structure include medical materials such as wound dressings, postoperative adhesion prevention materials, sustained drug release materials, cell culture substrates and cell transplant substrates.

When used as a medical material, the crosslinked alginic acid structure may be in the form of a tube, fiber, bead, gel, nearly spherical gel or the like; a bead, gel or nearly spherical gel is preferred, and a nearly spherical gel is more preferred.

The entire contents of all literature and publications cited in this Description are incorporated by reference in this Description regardless of their purpose.

Moreover, the objectives, features, advantages and ideas of the present invention are clear to a person skilled in the art from the descriptions of this Description, and the present invention can be easily implemented by a person skilled in the art based on the descriptions of this Description. The best mode and specific examples for implementing the invention are used to illustrate preferred embodiments of the present invention, and the present invention is not limited to these because they are given for purposes of example or explanation. Based on the descriptions of this Description, a person skilled in the art can understand that various modifications are possible within the intent and scope of the present invention as disclosed in this Description.

EXAMPLES

Examples and test examples are given next in order to explain the present invention in detail, but these are only examples and test examples that do not limit the present invention, and may be altered without departing from the scope of the present invention.

A JEOL JNM-ECX400 FT-NMR (JEOL) was used for nuclear magnetic resonance (NMR) spectrum measurement. Liquid chromatography-mass spectrometry (LC-Mass) was performed by the following methods. A [UPLC] Waters Aquity UPLC system and a BEH C18 column (2.1 mm×50 mm, 1.7 μm) (Waters) were used under gradient conditions with a mobile phase of acetonitrile:0.05% trifluoroacetic acid aqueous solution=5:95 (0 minutes) to 95:5 (1.0 minute) to 95:5 (1.6 minutes) to 5:95 (2.0 minutes).

In the NMR signal patterns of the $^1$H-NMR data, s means a singlet, d a doublet, t a triplet, q a quartet and m a multiplet, br means broad, J is the coupling constant, Hz means hertz, $CDCl_3$ is deuterated chloroform, DMSO-$D_6$ is deuterated dimethylsulfoxide, and $D_2O$ is deuterium. In the $^1$H-NMR data, signals that cannot be confirmed because they are broadband, such as protons of hydroxyl (OH), amino ($NH_2$) and carboxyl (COOH) groups, are not included in the data.

In the LC-Mass data, M means molecular weight, RT means retention time, and $[M+H]^+$ and $[M+Na]^+$ indicate molecular ion peaks.

"Room temperature" in the examples normally indicates a temperature from 0° C. to about 35° C.

In the examples, the introduction rate (mol %) of the reactive substituent is the molar number of introduced reactive substituents as a percentage of the molar number of monosaccharide (guluronic acid and mannuronic acid) units constituting the alginic acid as calculated by $^1$H-NMR ($D_2O$).

In the examples, sodium alginate having the physical properties shown in Table 10 above was used as the sodium alginate before introduction of the reactive group or complementary reactive group.

Table 12 shows the physical property values (specifically, reactive group introduction rates (mol %), molecular weights and weight-average molecular weights (ten thousands Da)) of the alginic acid derivatives with introduced reactive groups obtained in (Example 1) to (Example 15) (Examples 1a, 1b, 1c, 1d, 1e and 1f, Example 2, Examples 3a, 3b, 3c, 3d, 3e and 3f, Example 4, Example 5a, Example 5b, Example 6, Example 7a, Example 7b, Example 8, Examples 9a, 9b and 9c, Example 10, Example 11, Example 12, Example 13, Example 14 and Example 15.

Example 1

Synthesis of Alginic Acids Having Introduced Dibenzocyclooctyne-Amine Groups (Examples 1a, 1b, 1c, 1d, 1e, 1f and 1g)

[C112]

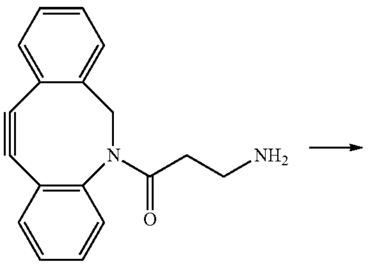

EX1-SM

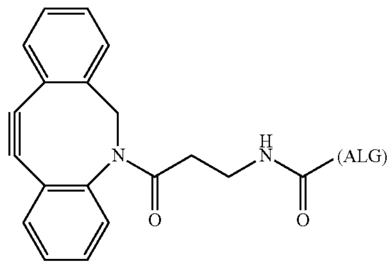

Example 1a: EX1-(I)-A-2
Example 1b: EX1-(I)-A-1
Example 1c: EX1-(I)-A-3
Example 1d: EX1-(I)-B-2a
Example 1e: EX1-(I)-B-2b
Example 1f: EX1-(I)-B-2c
Example 1g: EXI-(I)-A-2b

Example 1a

Synthesis of Alginic Acid (EX1-(I)-A-2) Having Introduced Dibenzocyclooctyne-Amine Group 4-(4,6-dimethoxy-1,3,5-triazin-2-yl)-4-methylmorpholinium chloride (DMT-MM) (111.65 mg) and 1-molar sodium bicarbonate water (403.5 μl) were added to 43.6 ml of an aqueous solution of sodium alginate (Mochida Pharmaceutical: A-2) adjusted to 1 wt %. An ethanol solution (2 ml) of commercial dibenzocyclooctyne-amine [CAS: 1255942-06-3] (EX1-SM, 83.62 mg) was dripped into this solution, and stirred for 18 hours at room temperature. Sodium chloride (400 mg) was added, ethanol (87.2 ml) was added, and the mixture was stirred for 30 minutes at room temperature. The resulting precipitate was collected by filtration, washed with ethanol, and dried under reduced pressure to obtain the title compound EX1-(I)-A-2 (376 mg) as a light yellow solid.

The introduction rate of the reactive substituent (dibenzocyclooctyne-amino group) was 6.9 mol % (NMR integration ratio).

Example 1b

Synthesis of Alginic Acid (EX1-(I)-A-1) Having Introduced Dibenzocyclooctyne-Amine Group 4-(4,6-dimethoxy-1,3,5-triazin-2-yl)-4-methylmorpholinium chloride (DMT-MM) (49.47 mg) and 1-molar sodium bicarbonate water (178.8 μl) were added to 19.32 ml of an aqueous solution of sodium alginate (Mochida Pharmaceutical: A-1) adjusted to 1 wt %. An ethanol solution (4 ml) of commercial dibenzocyclooctyne-amine [CAS: 1255942-06-3] (EX1-SM, 37.05 mg) was dripped into this solution, and stirred for 20 hours at room temperature. Sodium chloride (200 mg) was added, ethanol (38.64 ml) was added, and the mixture was stirred for 30 minutes at room temperature. The resulting precipitate was collected by filtration, washed with ethanol, and dried under reduced pressure to obtain the title compound EX1-(I)-A-1 (184 mg) as a light yellow solid.

The introduction rate of the reactive substituent (dibenzocyclooctyne-amino group) was 6.5 mol % (NMR integration ratio).

Example 1c

Synthesis of Alginic Acid (EX1-(I)-A-3) Having Introduced Dibenzocyclooctyne-Amine Group 4-(4,6-dimethoxy-1,3,5-triazin-2-yl)-4-methylmorpholinium chloride (DMT-MM) (38.57 mg) and 1-molar sodium bicarbonate water (139.4 μl) were added to 15.06 ml of an aqueous solution of sodium alginate (Mochida Pharmaceutical: A-3) adjusted to 1 wt %. An ethanol solution (2 ml) of commercial dibenzocyclooctyne-amine [CAS: 1255942-06-3] (EX1-SM, 28.88 mg) was dripped into this solution, and stirred for 23 hours at room temperature. Sodium chloride (150 mg) was added, ethanol (60.24 ml) was added, and the mixture was stirred for 30 minutes at room temperature. The resulting precipitate was collected by filtration, washed with ethanol, and dried under reduced pressure to obtain the title compound EX1-(I)-A-3 (164 mg) as a light yellow solid.

The introduction rate of the reactive substituent (dibenzocyclooctyne-amino group) was 6.6 mol % (NMR integration ratio).

Example 1d

Synthesis of Alginic Acid (EX1-(I)-B-2a) Having Introduced Dibenzocyclooctyne-Amine Group 4-(4,6-dimethoxy-1,3,5-triazin-2-yl)-4-methylmorpholinium chloride (DMT-MM) (111.0 mg), an ethanol solution (5.3 ml) of dibenzocyclooctyne-amine [CAS: 1255942-06-3] (EX1-SM, 36.9 mg), and 1-molar sodium bicarbonate water (113.7 μl) were added to 53.0 ml of an aqueous solution of sodium alginate (Mochida Pharmaceutical: B-2) adjusted to 1 wt %, and stirred for 3 hours at 30° C. Sodium chloride (530 mg) was added, ethanol (101 ml) was added, and the mixture was stirred for 30 minutes at room temperature. The resulting precipitate was collected by filtration, washed with ethanol, and dried under reduced pressure to obtain the title compound EX1-(I)-B-2a (465 mg) as a white solid.

The introduction rate of the reactive substituent (dibenzocyclooctyne-amino group) was 4.9 mol % (NMR integration ratio).

Example 1e

Synthesis of Alginic Acid (EX1-(I)-B-2b) Having Introduced Dibenzocyclooctyne-Amine Group 4-(4,6-dimethoxy-1,3,5-triazin-2-yl)-4-methylmorpholinium chloride (DMT-MM) (14.7 mg), dibenzocyclooctyne-amine [CAS: 1255942-06-3] (EX1-SM, 4.9 mg), 1-molar sodium bicarbonate water (17.7 μl) and ethanol (3.5 ml) were added to 35.0 ml of an aqueous solution of sodium alginate (Mochida Pharmaceutical: B-2) adjusted to 1 wt %, and stirred for 3.5 hours at 30° ° C. Sodium chloride (350 mg) was added, ethanol (70 ml) was added, and the mixture was stirred for 30 minutes at room temperature. The resulting precipitate was collected by filtration, washed with ethanol, and dried under reduced pressure to obtain the title compound EX1-(I)-B-2 (329 mg) as a white solid.

The introduction rate of the reactive substituent (dibenzocyclooctyne-amino group) was 0.8 mol % (NMR integration ratio).

Example 1f

Synthesis of Alginic Acid (EX1-(I)-B-2c) Having Introduced Dibenzocyclooctyne-Amine Group 4-(4,6-dimethoxy-1,3,5-triazin-2-yl)-4-methylmorpholinium chloride (DMT-MM) (67.0 mg), dibenzocyclooctyne-amine [CAS: 1255942-06-3] (EX1-SM, 16.7 mg), 1-molar sodium bicarbonate water (60.5 μl) and ethanol (6.0 ml) were added to 60.0 ml of an aqueous solution of sodium alginate (Mochida Pharmaceutical: B-2) adjusted to 1 wt %, and stirred for 3 hours at 30° C. Sodium chloride (600 mg) was added, ethanol (120 ml) was added, and the mixture was stirred for 30 minutes at room temperature. The resulting precipitate was collected by filtration, washed with ethanol, and dried under reduced pressure to obtain the title compound EX1-(I)-B-2c (558 mg) as a white solid.

The introduction rate of the reactive substituent (dibenzocyclooctyne-amino group) was 1.9 mol % (NMR integration ratio).

Example 1g

Synthesis of Alginic Acid (EX1-(I)-A-2b) Having Introduced Dibenzocyclooctyne-Amine Group The title compound (EX1-(I)-A-2b) was obtained by the same methods as (Example 1a) with an introduction rate (NMR integration ratio) of 4.9 mol % of the reactive substituent.

Example 2

Synthesis of Alginic Acid (EX2-(I)-A-2) Having Introduced N-(1R, 8S, 9s)-bicyclo[6.1.0]non-4-in-9-ylmethoxycarbonyl-1,8-diamino-3,6-dioxaoctane Group

[C113]

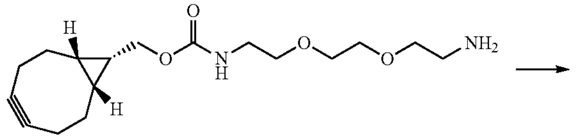

EX2-SM

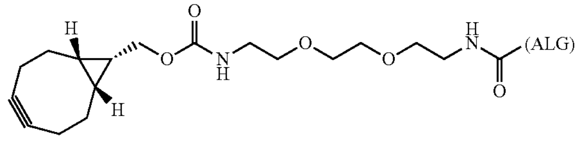

EX2-(I)-A-2

4-(4,6-dimethoxy-1,3,5-triazin-2-yl)-4-methylmorpholinium chloride (DMT-MM) (27.91 mg) and 1-molar sodium bicarbonate water (100.9 μl) were added at room temperature to 10.9 ml of an aqueous solution of sodium alginate (Mochida Pharmaceutical: A-2) adjusted to 1 wt %. An ethanol (2 ml) and water (1 ml) solution of commercial N-(1R, 8S, 9s)-bicyclo[6.1.0]non-4-in-9-ylmethoxycarbonyl-1,8-diamino-3,6-dioxaoctane [CAS: 1263166-93-3] (EX-2-SM, 24.54 mg) was dripped into this at room temperature, and stirred for 21 hours at that temperature. Sodium chloride (100 mg) was added, followed by ethanol (21.8 ml), and the mixture was stirred for 30 minutes at room temperature. The resulting precipitate was collected by filtration, washed with ethanol, and dried under reduced pressure to obtain the title compound EX2-(I)-A-2 (100 mg) as a light yellow solid.

The introduction rate of the reactive substituent (N-(1R, 8S, 9s)-bicyclo[6.1.0]non-4-in-9-ylmethoxycarbonyl-1,8-diamino-3,6-dioxaoctane group) was 5.8 mol % (NMR integration ratio).

Example 3

Synthesis of Alginic Acids Having Introduced 4-(2-aminoethoxy)-N-(3-azidopropyl)benzamide Groups (Examples 3a, 3b, 3c, 3d, 3e, 3f and 3g)

[C114]

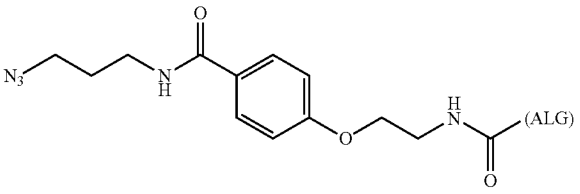

Example 3a: EX3-(II)-A-2
Example 3b:EX3-(II)-A-1
Example 3c::EX3-(II)-A-3
Example 3d::EX3-(II)-B-2a
Example 3e::EX3-(II)-B-2b
Example 3f::EX3-(II)-B-2c
Example 3g::EX3-(II)-A-2b <Step 1> Synthesis of methyl 4-(2-((tert-butoxycarbonyl)amino)ethoxy) benzoate (Compound EX3-IM-1)

[C115]

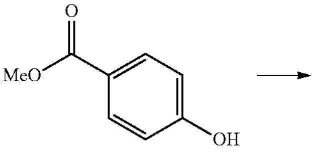

EX3-SM

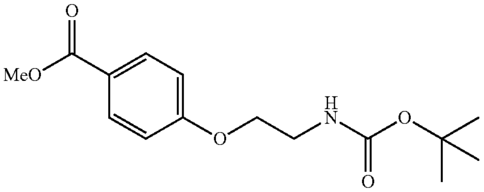

EX3-IM-1

A diethyl azodicarboxylate solution (40% toluene solution, 1.92 ml) was added under ice cooling and stirring to a tetrahydrofuran (2.59 ml) solution of triphenylphosphine (0.96 g), and stirred for 20 minutes at room temperature. A tetrahydrofuran (1.1 ml) solution of commercial methyl 4-hydroxybenzoate [CAS: 99-76-3] (Compound EX3-SM, 0.37 g) and 2-(tert-butoxycarbonyl) ethanolamine [CAS: 26690-80-2] (0.39 g) was added to this solution under ice cooling and stirring, and the mixture was stirred for 17 hours at room temperature. The reaction solution was concentrated under reduced pressure, and the residue was purified by silica gel column chromatography (5% ethyl acetate/n-heptane to 40% ethyl acetate/n-heptane) to obtain a mixture of EX3-SM and EX3-IM-1. This mixture was dissolved in methyl tert-butyl ether (20 ml) and washed twice with 1N-sodium hydroxide aqueous solution (5 ml) and once with brine (5 ml). The organic layer was dried with anhydrous sodium sulfate, and the solvent was distilled off under reduced pressure to obtain the compound EX3-IM-1 (0.45 g) as a pink oily substance.

NMR data ($CDCl_3$) (δ: ppm): 7.98 (2H, d, J=8.8 Hz), 6.90 (2H, d, J=8.8 Hz), 4.97 (1H, br s), 4.07 (2H, t, J=5.2 Hz), 3.88 (3H, s), 3.56 (2H, q, J=5.2 Hz), 1.45 (9H, s)

<Step 2> Synthesis of 4-(2-aminoethoxy)-N-(3-azidopropyl)benzamide Hydrochloride (Compound EX3-IM-3)

[C116]

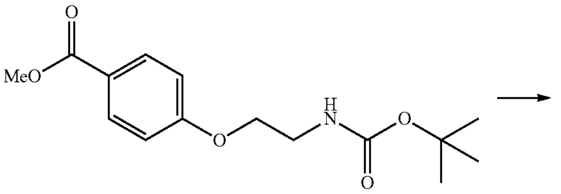

EX3-IM-1

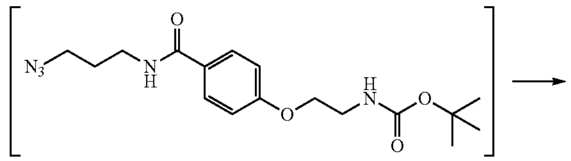

EX3-IM-2

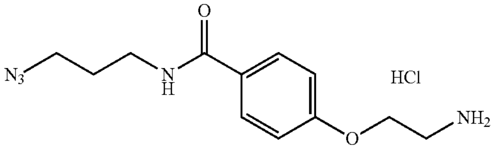

EX3-IM-3

Lithium hydroxide monohydrate (0.25 g) was added to a methanol (4.4 ml) solution of the compound EX3-IM-1 (0.44 g) obtained in <Step 1> of (Example 3), and stirred for 3 hours and 30 minutes at 60° C. 1N-hydrochloric acid (5 ml) was added to the reaction solution, which was then extracted three times with ethyl acetate (10 ml). The organic layer was washed successively with water (5 ml) and brine (5 ml) and dried with anhydrous sodium sulfate, and the solvent was distilled off under reduced pressure. The residue was dissolved in acetonitrile (4.4 ml), and 3-azido propane-1-amine [CAS: 88192-19-2] (0.15 g) and O-(7-azabenzotriazole-1-yl)-N,N,N',N'-tetramethyluronium hexafluorophosphate salt (0.57 g) were added. N,N-diisopropylethylamine (0.52 ml) was then added under ice cooling and stirring, and the mixture was stirred for 5 hours at room temperature. Water (10 ml) was added to the reaction solution, which was then extracted 3 times with ethyl acetate (15 ml), the organic layer was dried with anhydrous sodium sulfate, and the solvent was distilled off under reduced pressure. The residue was purified by silica gel column chromatography (16% ethyl acetate/n-heptane to 100% ethyl acetate) to obtain a fraction containing the compound EX3-IM-2 (0.71 g).

4N-hydrogen chloride/1,4-dioxane (4.9 ml) was added to the fraction (0.71 g) containing the compound EX3-IM-2, and stirred for 20 minutes at room temperature. Diisopropyl ether was added to the reaction solution, and the precipitate was filtered out to obtain the title compound EX3-IM-3 (0.49 g) as a white solid.

NMR data ($CDCl_3$) (δ: ppm): 7.60 (2H, d, J=8.8 Hz), 6.93 (2H, d, J=8.8 Hz), 4.19 (2H, t, J=4.8 Hz), 3.31 to 3.29 (6H, m), 1.77 to 1.71 (2H, m), LC-MS: M (free amine)=263, RT=0.54 (minutes), $[M+H]^+$=264

Example 3a

Synthesis of Alginic Acid (Compound EX3-(II)-A-2) Having Introduced 4-(2-aminoethoxy)-N-(3-azidopropyl)benzamide Group

[C117]

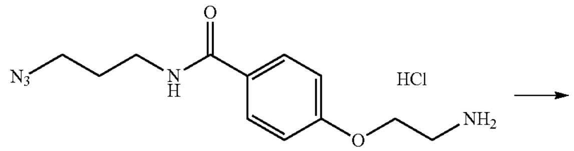

EX3-IM-3

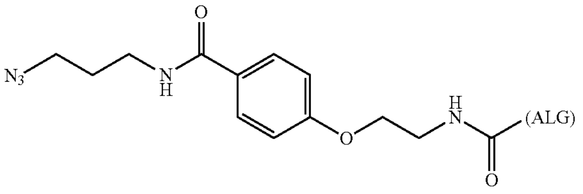

EX3-(II)-A-2

4-(4,6-dimethoxy-1,3,5-triazin-2-yl)-4-methylmorpholinium chloride (DMT-MM) (50.19 mg), the compound EX3-IM-3 (54.37 mg) obtained in <Step 2> of (Example 3), and 1-molar sodium bicarbonate water (181.4 μl) were added under ice cooling and stirring to 19.6 ml of an aqueous solution of sodium alginate (Mochida Pharmaceutical: A-2) adjusted to 1 wt %, and stirred for 5 hours at room temperature. Sodium chloride (200 mg) was added, followed by ethanol (39.2 ml), and the mixture was stirred for 30 minutes at room temperature. The resulting precipitate was collected by filtration, washed with ethanol, and dried under reduced pressure to obtain the title compound EX3-(II)-A-2 (198 mg) as a white solid.

The introduction rate of the reactive substituent (4-(2-aminoethoxy)-N-(3-azidopropyl)benzamide group) was 6.1 mol % (NMR integration ratio).

Example 3b

Synthesis of Alginic Acid (compound EX3-(II)-A-1) Having Introduced 4-(2-aminoethoxy)-N-(3-azidopropyl)benzamide Group

[C118]

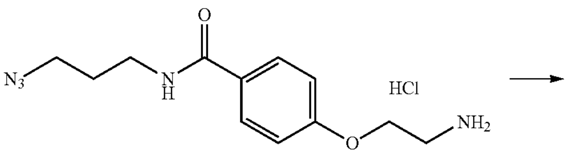

EX3-IM-3

-continued

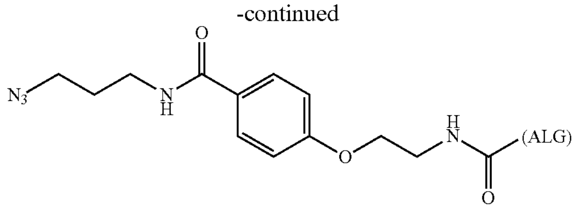

EX3-(II)-A-1

4-(4,6-dimethoxy-1,3,5-triazin-2-yl)-4-methylmorpholinium chloride (DMT-MM) (49.47 mg), the compound EX3-IM-3 (53.39 mg) obtained in <Step 2> of (Example 3), and 1-molar sodium bicarbonate water (178.8 µl) were added under ice cooling and stirring to 19.32 ml of an aqueous solution of sodium alginate (Mochida Pharmaceutical: A-1) adjusted to 1 wt %, and stirred for 20 hours at room temperature. Sodium chloride (200 mg) was added, followed by ethanol (38.64 ml), and the mixture was stirred for 30 minutes at room temperature. The resulting precipitate was collected by filtration, washed with ethanol, and dried under reduced pressure to obtain the compound EX3-(II)-A-1 (221 mg) as a white solid.

The introduction rate of the reactive substituent (4-(2-aminoethoxy)-N-(3-azidopropyl)benzamide group) was 9.4 mol % (NMR integration ratio).

Example 3c

Synthesis of Alginic Acid (Compound EX3-(II)-A-3) Having Introduced 4-(2-aminoethoxy)-N-(3-azidopropyl)benzamide Group

[C119]

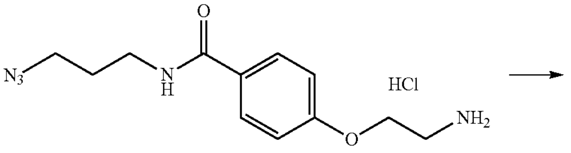

EX3-IM-3

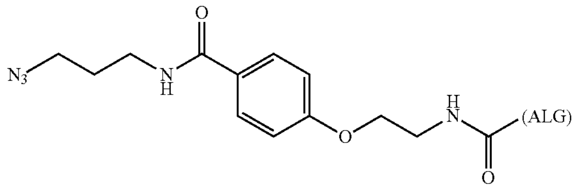

EX3-(II)-A-3

4-(4,6-dimethoxy-1,3,5-triazin-2-yl)-4-methylmorpholinium chloride (DMT-MM) (38.57 mg), the compound EX3-IM-3 (41.78 mg) obtained in <Step 2> of (Example 3), and 1-molar sodium bicarbonate water (139.4 µl) were added under ice cooling and stirring to 15.06 ml of an aqueous solution of sodium alginate (Mochida Pharmaceutical: A-3) adjusted to 1 wt %, and stirred for 5 hours at room temperature. Sodium chloride (150 mg) was added, followed by ethanol (60.24 ml), and the mixture was stirred for 30 minutes at room temperature. The resulting precipitate was collected by filtration, washed with ethanol, and dried under reduced pressure to obtain the title compound EX3-(II)-A-3 (155 mg) as a white solid.

The introduction rate of the reactive substituent (4-(2-aminoethoxy)-N-(3-azidopropyl)benzamide group) was 6.9 mol % (NMR integration ratio).

Example 3d

Synthesis of Alginic Acid (Compound EX3-(II)-B-2a) Having Introduced 4-(2-aminoethoxy)-N-(3-azidopropyl)benzamide Group

[C120]

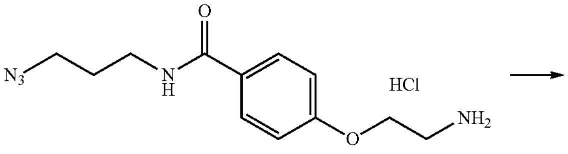

EX3-IM-3

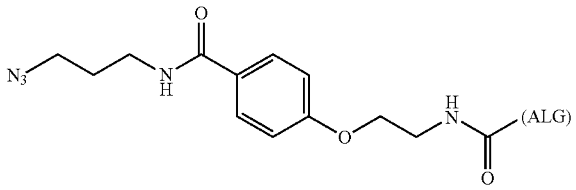

EX3-(II)-B-2a 4-(4,6-dimethoxy-1,3,5-triazin-2-yl)-4-methylmorpholinium chloride (DMT-MM) (125.6 mg), the compound EX3-IM-3 (45.4 mg) obtained in <Step 2> of (Example 3) (45.4 mg), and 1-molar sodium bicarbonate water (211.8 µl) were added to 60.0 ml of an aqueous solution of sodium alginate (Mochida Pharmaceutical: B-2) adjusted to 1 wt %, and stirred for 3 hours at 30° C. Sodium chloride (600 mg) was added, followed by ethanol (120 ml), and the mixture was stirred for 30 minutes at room temperature. The resulting precipitate was collected by filtration, washed with ethanol, and dried under reduced pressure to obtain the title compound EX3-(II)-B-2a (553 mg) as a white solid.

The introduction rate of the reactive substituent (4-(2-aminoethoxy)-N-(3-azidopropyl)benzamide group) was 3.7 mol % (NMR integration ratio).

Example 3e

Synthesis of Alginic Acid (Compound EX3-(II)-B-2b) Having Introduced 4-(2-aminoethoxy)-N-(3-azidopropyl)benzamide Group

[C121]

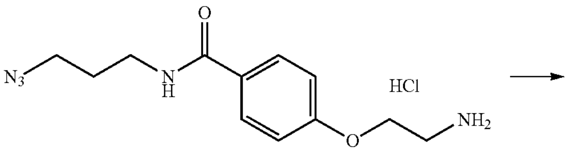

EX3-IM-3

-continued

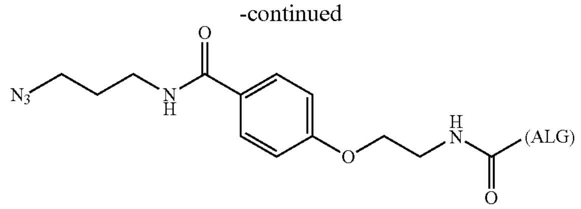

EX3-(II)-B-2b 4-(4,6-dimethoxy-1,3,5-triazin-2-yl)-4-methylmorpholinium chloride (DMT-MM) (14.7 mg), the compound EX3-IM-3 (5.3 mg) obtained in <Step 2> of (Example 3), and 1-molar sodium bicarbonate water (26.5 μl) were added to 35.0 ml of an aqueous solution of sodium alginate (Mochida Pharmaceutical: B-2) adjusted to 1 wt %, and stirred for 3.5 hours at 30° C. Sodium chloride (350 mg) was added, followed by ethanol (70 ml), and the mixture was stirred for 30 minutes at room temperature. The resulting precipitate was collected by filtration, washed with ethanol, and dried under reduced pressure to obtain the title compound EX3-(II)-B-2b (304 mg) as a white solid.

The introduction rate of the reactive substituent (4-(2-aminoethoxy)-N-(3-azidopropyl)benzamide group) was 0.6 mol % (NMR integration ratio).

Example 3f

Synthesis of Alginic Acid (Compound EX3-(II)-B-2c) Having Introduced 4-(2-aminoethoxy)-N-(3-azidopropyl)benzamide Group

[C122]

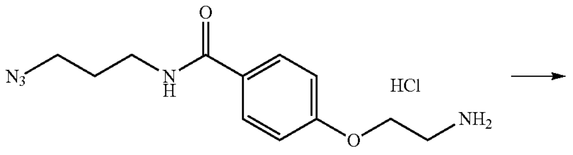

EX3-IM-3

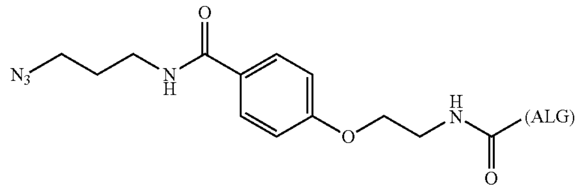

EX3-(II)-B-2c 4-(4,6-dimethoxy-1,3,5-triazin-2-yl)-4-methylmorpholinium chloride (DMT-MM) (67.0 mg), the compound EX3-IM-3 (18.1 mg) obtained in <Step 2> of (Example 3), and 1-molar sodium bicarbonate water (90.8 μl) were added to 60.0 ml of an aqueous solution of sodium alginate (Mochida Pharmaceutical: B-2) adjusted to 1 wt %, and stirred for 3 hours at 30° C. Sodium chloride (600 mg) was added, followed by ethanol (120 ml), and the mixture was stirred for 30 minutes at room temperature. The resulting precipitate was collected by filtration, washed with ethanol, and dried under reduced pressure to obtain the title compound EX3-(II)-B-2c (568 mg) as a white solid.

The introduction rate of the reactive substituent (4-(2-aminoethoxy)-N-(3-azidopropyl)benzamide group) was 1.5 mol % (NMR integration ratio).

Example 3g

Synthesis of Alginic Acid (Compound EX3-(II)-A-2b) Having Introduced 4-(2-aminoethoxy)-N-(3-azidopropyl)benzamide Group The title compound (EX3-(II)-A-2b) was obtained by the same methods as (Example 3a) with an introduction rate (NMR integration ratio) of 4.3 mol % of the reactive substituent.

Example 4

Synthesis of Alginic Acid (Compound EX4-(II)-A-2) Having Introduced 4-(3-aminopropoxy)-N-(2-(2-(2-azidoethoxy)ethoxy)ethyl)benzamide Group

[C123]

EX-4(II)-A-2

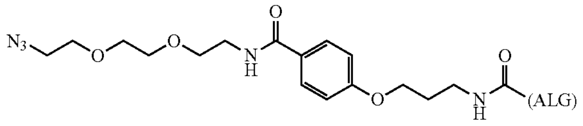

<Step 1> Synthesis of 4-(3-((tert-butoxycarbonyl)amino) propoxy) benzoic Acid (Compound EX4-IM-2)

[C124]

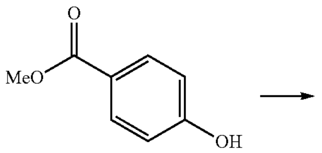

EX4-SM

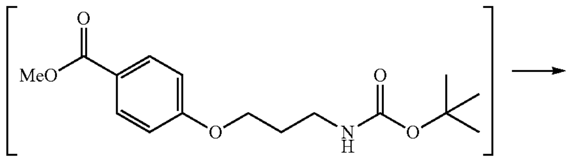

EX4-IM-1

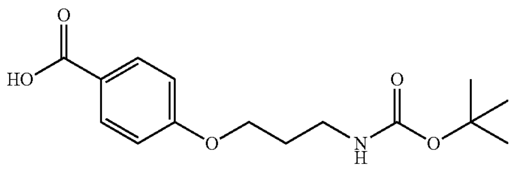

EX4-IM-2

Diisopropyl azodicarboxylate (40% toluene solution, 4.15 ml) was added to a tetrahydrofuran (7 ml) solution of triphenyl phosphine (2.07 g) and stirred until a precipitate formed. This was stirred for another 1 hour, a tetrahydrofuran (3 ml) solution of commercial tert-butyl(3-hydroxypropyl) carbamate

[CAS: 58885-58-8] (1.15 g) and 4-hydroxybenzoic acid methyl ester [CAS: 99-76-3] (compound EX4-SM, 1 g) was added, and stirred for 3 hours. The reaction solution was concentrated under reduced pressure, and the residue was purified by silica gel column chromatography (8% ethyl acetate/n-heptane to 66% ethyl acetate/n-heptane). The purified product was dissolved in methyl tert-butyl ether (20 ml) and washed twice with 1N-sodium hydroxide aqueous solution (5 ml) and then once with brine (5 ml). The organic layer was dried with anhydrous sodium sulfate, and the solvent was distilled off under reduced pressure to obtain a fraction containing the compound EX4-IM-1 (2.94 g) as a white solid.

Lithium hydroxide monohydrate (1.06 g) was added at room temperature under stirring to a methanol (15.6 ml) solution of the fraction (2.94 g) containing the compound EX4-IM-1, and the solution was stirred for 3 hours at 60° C. This was cooled to room temperature, and the solvent was distilled off under reduced pressure. Water (20 ml) was added to the residue, which was then extracted twice with methyl tert-butyl ether (20 ml). The water layer was acidified with 1N-hydrochloric acid (25 ml), extracted three times with ethyl acetate (20 ml), and washed successively with water (10 ml) and brine (10 ml). The organic layer was dried with anhydrous sodium sulfate, and the solvent was distilled off under reduced pressure. Methyl tert-butyl ether (30 ml) and 1N-sodium hydroxide aqueous solution (20 m) were added to the residue, which was then extracted twice with methyl tert-butyl ether (20 ml). The water layer was acidified with 1N-hydrochloric acid (20 ml) and extracted twice with ethyl acetate (20 ml). The organic layer was dried with anhydrous sodium sulfate, and the solvent was distilled off under reduced pressure to obtain the compound EX4-IM-2 (1.4 g) as a white solid.

NMR data ($CDCl_3$) (δ: ppm): 8.03 (2H, d, J=7.6 Hz), 6.92 (2H, d, J=8.8 Hz), 4.73 (1H, br s), 4.09 (2H, t, J=6.0 Hz), 3.34 (2H, q, J=6.3 Hz), 2.05 to 1.98 (2H, m), 1.45 (9H, s)

<Step 2> Synthesis of 4-(3-aminopropoxy)-N-(2-(2-(2-azidoethoxy)ethoxy)ethyl)benzamide Hydrochloride (compound EX4-IM-4)

[C125]

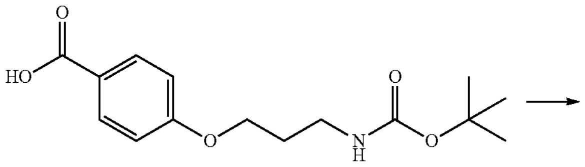

EX4-IM-2

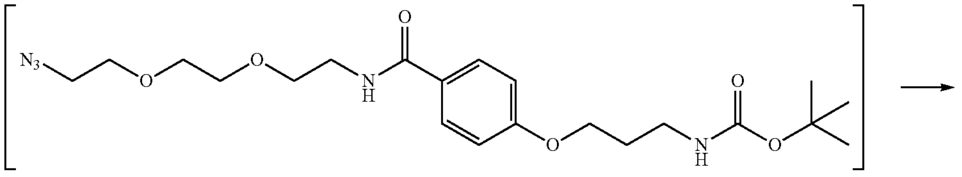

EX4-IM-3

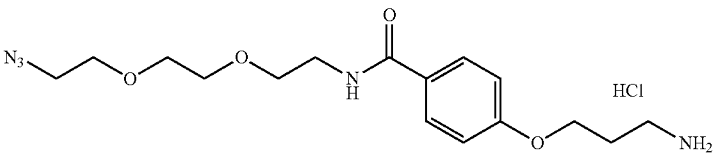

EX4-IM-4

N,N-diisopropylethylamine (1.24 ml) was dripped under ice cooling and stirring into an acetonitrile (20 ml) solution of the compound EX4-IM-2 (1 g) obtained in <Step 1> of (Example 4), commercial 2-(2-(2-azidoethoxy)ethoxy)ethane-1-amine [CAS: 166388-57-4] (0.62 g) and O-(7-azabenzotriazole-1-yl)-N,N,N',N'-tetramethyluronium hexafluorophosphate salt (1.35 g), and stirred for 1 hour at room temperature. Water (20 ml) was added to the reaction solution, which was then extracted three times with ethyl acetate (20 ml) and washed successively with water (10 ml) and brine (10 ml). The organic layer was dried with anhydrous sodium sulfate, and the solvent was distilled off under reduced pressure. The residue was purified by silica gel column chromatography (16% ethyl acetate/n-heptane to 100% ethyl acetate) to obtain a fraction containing the compound EX4-IM-3 (1.37 g).

1,4-dioxane (9.58 ml) was added to the fraction (1.37 g) containing the compound EX4-IM-3. 4N-hydrogen chloride/1,4-dioxane (9.58 ml) was added under ice cooling and stirring to this solution, which was then stirred for 1 hour at room temperature. Diisopropyl ether (100 ml) was added to the reaction solution, and the resulting suspension was stirred for 1 hour at room temperature. The solvent was distilled off under reduced pressure, and the residue was triturated with ethyl acetate (20 ml) and methyl tert-butyl ether (10 ml). The resulting solid was filtered out and dried under reduced pressure to obtain the title compound EX4-IM-4 (1.23 g) as a white solid.

NMR data ($D_2O$) (δ: ppm): 7.66 to 7.64 (2H, m), 6.98 to 6.94 (2H, m), 4.12 (2H, t, J=5.6 Hz), 3.66 to 3.57 (6H, m), 3.57 to 3.52 (2H, m), 3.47 (2H, t, J=5.2 Hz), 3.29 (2H, t, J=4.8 Hz), 3.12 (2H, t, J=7.2 Hz), 2.10 to 2.04 (2H, m), LC-MS: M (free amine)=351, RT=0.57 (minutes), $[M+H]^+$ =352

<Step 3> Synthesis of Alginic Acid (compound EX4-(II)-A-2) Having Introduced 4-(3-aminopropoxy)-N-(2-(2-(2-azidoethoxy)ethoxy)ethyl)benzamide Group

[C126]

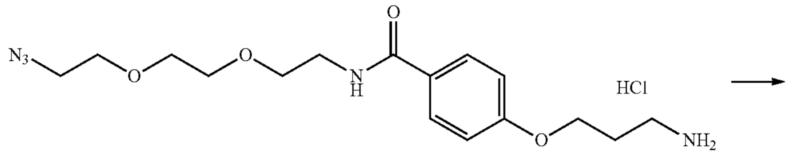

EX4-IM-4

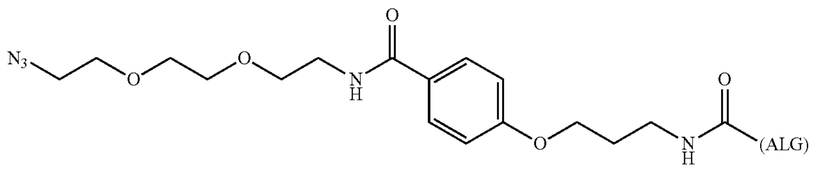

EX4-(II)-A-2

4-(4,6-dimethoxy-1,3,5-triazin-2-yl)-4-methylmorpholinium chloride (DMT-MM) (50.19 mg), the compound EX4-IM-4 (70.35 mg) obtained in <Step 2> of (Example 4), and 1-molar sodium bicarbonate water (181.4 μl) were added under ice cooling and stirring to 19.6 ml of an aqueous solution of sodium alginate (Mochida Pharmaceutical: A-2) adjusted to 1 wt %, and stirred for 5 hours at room temperature. Sodium chloride (200 mg) was added, followed by ethanol (39.2 ml), and the mixture was stirred for 30 minutes at room temperature. The resulting precipitate was collected by filtration, washed with ethanol, and dried under reduced pressure to obtain the title compound EX4-(II)-A-2 (199 mg) as a white solid.

The introduction rate of the reactive substituent (4-(3-aminopropoxy)-N-(2-(2-(2-azidoethoxy)ethoxy)ethyl)benzamide group) was 4.3 mol % (NMR integration ratio).

Example 5

Synthesis of Alginic Acids (Examples 5a, 5b and 5c) Having Introduced N-(2-aminoethyl)-4-(azidomethyl)benzamide Groups

[C127]

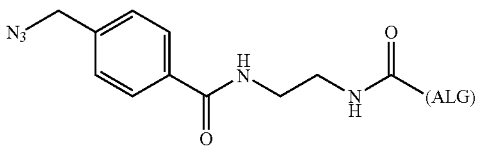

Example 5a: EX5-(II)-A-2
Example 5b: EX5-(II)-B-2
Example 5c: EX5-(II)-A-2b

<Step 1> Synthesis of tert-butyl (2-(4-(chloromethyl)benzamido)ethyl)carbamate (Compound EX5-IM-1)

[C128]

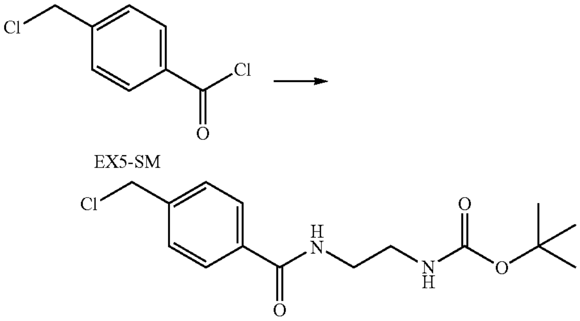

EX5-SM

EX5-IM-1

EX5-SM (4-(chloromethyl) benzoyl chloride [CAS: 876-08-4] (2.0 g) was dissolved in tetrahydrofuran (10.0 ml), a tetrahydrofuran (10.0 ml) solution of tert-butyl(2-aminoethyl) carbamate [CAS: 57260-73-8] (1.7 g) and N,N'-diisopropylethylamine (3.7 ml) was dripped in under ice-water cooling, and the mixture was stirred for 1.5 hours at room temperature. Ethyl acetate (30 ml) and water (10 ml) were added to separate the reaction solution. The organic layer was washed successively with semi-saturated sodium bicarbonate water (10 ml), water (10 ml) and brine (5 ml), dried with anhydrous sodium sulfate, and concentrated under reduced pressure. The residue was triturated with tert-butyl methyl ether, and the resulting solid was collected by filtration and washed with tert-butyl methyl ether to obtain the title compound EX5-IM-1 (2.9 g) as a white solid.

NMR data ($CDCl_3$) (δ: ppm): 7.81 (2H, d, J=8 Hz), 7.44 (2H, d, J=8 Hz), 7.24 (1H, brs), 4.96 (1H, brs), 4.60 (2H, s), 3.56 (2H, q, J=5 Hz), 3.45 to 3.38 (2H, m), 1.43 (9H, s)

<Step 2> Synthesis of tert-butyl (2-(4-(azidomethyl)benzamido)ethyl)carbamate (EX5-IM-2)

[C129]

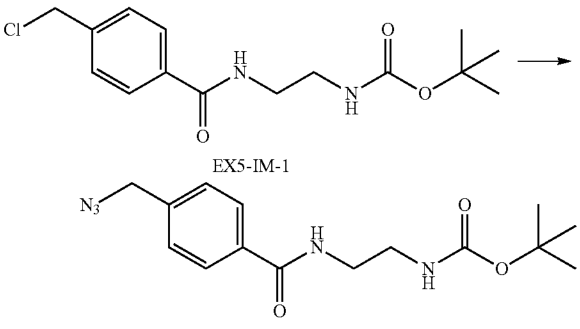

EX5-IM-1

EX5-IM-2

Sodium azide (100 mg) was dissolved in dimethylsulfoxide (6.0 ml), the compound EX5-IM-1 (400 mg) obtained in <Step 1> of (Example 5) was added, and the mixture was stirred for 2.5 hours at room temperature. Water (12 ml) was added under ice-water cooling to the reaction solution, and the precipitated solid was filtered out and water washed. The resulting solid was dried at 50° ° C. under reduced pressure to obtain the title compound EX5-IM-2 (380 mg) as a white solid.

NMR data ($CDCl_3$) (δ: ppm): 7.84 (2H, d, J=8 Hz), 7.37 (2H, d, J=8 Hz), 7.22 (1H, brs), 4.95 (1H, brs), 4.39 (2H, s), 3.56 (2H, q, J=5 Hz), 3.45 to 3.38 (2H, m), 1.43 (9H, s)

<Step 3> Synthesis of N-(2-aminoethyl)-4-(azidomethyl)benzamide Hydrochloride (Compound EX5-IM-3)

[C130]

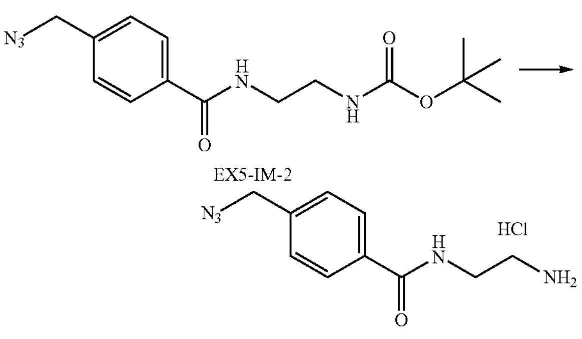

EX5-IM-2

EX5-IM-3

4N-hydrogen chloride/1,4-dioxane (1.75 ml) was added under ice-water cooling to the compound EX5-IM-2 (250 mg) obtained in <Step 2> of (Example 5), and stirred for 1 hour at room temperature. Diisopropyl ether (5.25 ml) was added to the reaction solution, and the resulting precipitate was collected by filtration, washed with diisopropyl ether, and dried under reduced pressure to obtain the title compound EX5-IM-3 (192 mg) as a white solid.

NMR data (DMSO-$d_6$) (δ: ppm): 8.68 (1H, t, J=6 Hz), 7.91 (2H, d, J=8 Hz), 7.80 (3H, brs), 7.47 (2H, d, J=8 Hz), 4.53 (2H, s), 3.51 (2H, q, J=6 Hz), 2.98 (2H, t, J=6 Hz), LC-MS: M (free amine)=219, RT=0.56 (minutes), $[M+H]^+$=220

<Step 4-1> (Example 5a) Synthesis of Alginic Acid (compound EX5-(II)-A-2) Having Introduced N-(2-aminoethyl)-4-(azidomethyl)benzamide Group

[C131]

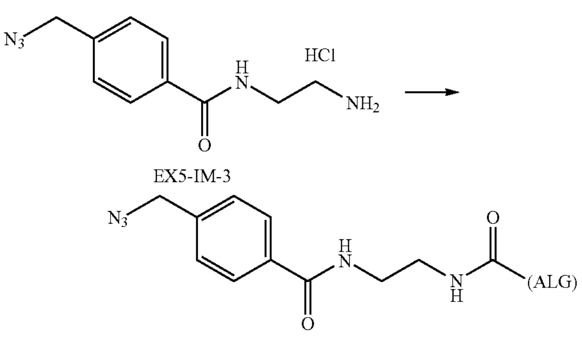

EX5-IM-3

EX5-(II)-A-2

4-(4,6-dimethoxy-1,3,5-triazin-2-yl)-4-methylmorpholinium chloride (DMT-MM) (84 mg), the compound EX5-IM-3 (52 mg) obtained in <Step 3> of (Example 5) and 1-molar sodium bicarbonate water (252 μl) were added to 20 ml of an aqueous solution of sodium alginate (Mochida Pharmaceutical: A-2) adjusted to 1 wt %, and stirred for 3 hours at 30° C. Sodium chloride (200 mg) was added, followed by ethanol (40 ml), and the mixture was stirred at room temperature for 30 minutes. The resulting precipitate was collected by filtration, washed with ethanol, and dried under reduced pressure to obtain the title compound EX5-(II)-A-2 (185 mg) as a white solid.

The introduction rate of the reactive substituent (N-(2-aminoethyl)-4-(azidomethyl)benzamide group) was 9.4 mol % (NMR integration ratio).

<Step 4-2> (Example 5b) Synthesis of Alginic Acid (Compound EX5-(II)-B-2) Having Introduced N-(2-aminoethyl)-4-(azidomethyl)benzamide Group

[C132]

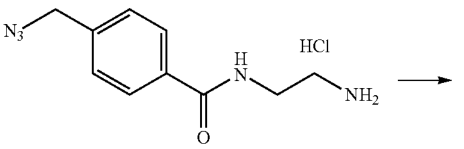

EX5-IM-3

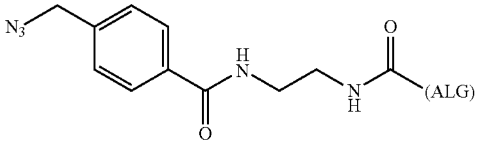

EX5-(II)-B-2

4-(4,6-dimethoxy-1,3,5-triazin-2-yl)-4-methylmorpholinium chloride (DMT-MM) (84 mg), the compound EX5-IM-3 (26 mg) obtained in <Step 3> of (Example 5) and 1-molar sodium bicarbonate water (151 μl) were added to 20 ml of an aqueous solution of sodium alginate (Mochida Pharmaceutical: B-2) adjusted to 1 wt %, and stirred for 3 hours at 30° C. Sodium chloride (200 mg) was added, followed by ethanol (40 ml), and the mixture was stirred at room temperature for 30 minutes. The resulting precipitate was collected by filtration, washed with ethanol, and dried under reduced pressure to obtain the title compound EX5-(II)-B-2 (187 mg) as a white solid.

The introduction rate of the reactive substituent (N-(2-aminoethyl)-4-(azidomethyl)benzamide group) was 11 mol % (NMR integration ratio).

Example 5c

Synthesis of Alginic Acid (EX5-(II)-A-2b) Having Introduced N-(2-aminoethyl)-4-(azidomethyl)benzamide Group The title compound (EX5-(II)-A-2b) was obtained by the same methods as (Example 5a) with an introduction rate (NMR integration ratio) of 4.9 mol % of the reactive substituent.

Example 6

Synthesis of Alginic Acid (compound EX6-(I)-B-2) Having Introduced 5-amino-1-(11, 12-didehydrodibenz[b,f]azocin-5(6H)-yl)-1-pentanone Group (ADIBO-C5-amine)

[C133]

EX6-(I)-B-2

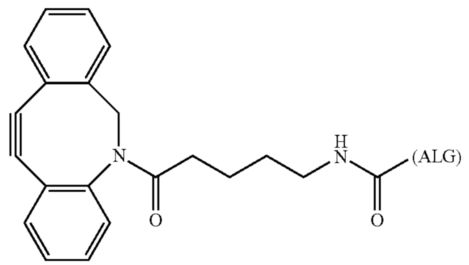

<Step 1> Synthesis of N-trifluoroacetyl-5-aminopentanoic Acid (EX6-IM-1)

[C134]

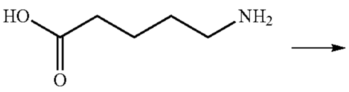

EX6-SM1

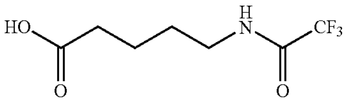

EX6-IM-1

5-aminopentanoic acid [CAS: 660-88-8] (EX6-SM1, 2.0 g), trifluoroacetic acid ethyl ester (3.1 ml) and triethylamine (3.6 ml) were dissolved in methanol (90.0 ml), and stirred for 5 hours at 40° C. The reaction solution was concentrated under reduced pressure, and the operation of adding ethanol (10 ml) to the residue and concentrating under reduced pressure was repeated twice. The concentrated residue was dissolved in ethyl acetate (200 ml), and washed three times with 0.1 molar sodium dihydrogen phosphate aqueous solution (70 ml) and once with brine (50 ml). The organic layer was dried with anhydrous sodium sulfate, concentrated under reduced pressure, and then dried under reduced pressure to obtain the title compound EX6-IM-1 (1.8 g) as a white solid.

NMR data (DMSO-$d_6$) (δ: ppm): 12.04 (1H, brs), 9.43 (1H, brs), 3.17 (2H, q, J=6 Hz), 2.22 (2H, H, tt, J=7.2 Hz), 1.51 to 1.46 (4H, m)

<Step 2> Synthesizing (Z)—N-(5-(dibenzo[b,f]azocin-5(6H)-yl)-5-oxopentyl-trifluoroacetamide (compound EX6-IM-2)

[C135]

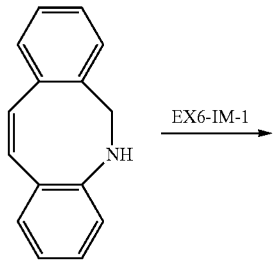

EX6-SM2

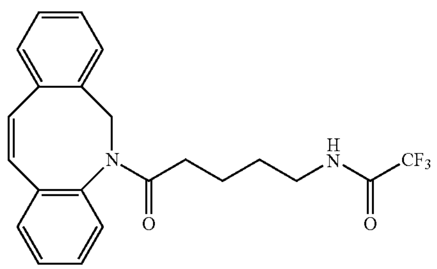

EX6-IM-2

Thionyl chloride (440 μl) and N,N-dimethylformamide (2 μl) were added to the compound (EX6-IM-1) (617 mg) obtained in <Step 1> of (Example 6) and stirred for 1.5 hours at 80° C., and the reaction solution was concentrated under reduced pressure. Following the methods described in <Step 1> of [Manufacturing Method D], a methylene chloride (1.0 ml) solution of the residue was added under ice-water cooling to a methylene chloride (5.0 ml) solution of pyridine (585 μl) and a compound EX6-SM2 [CAS: 23294-93-6] (500 mg) synthesized from 5-dibenzosuberone [CAS: 2222-33-5], and the mixture was stirred for 30 minutes at room temperature. The reaction solution was diluted with 20 ml of tert-butyl methyl ether, washed successively with water (10 ml), 1N-hydrochloric acid (10 ml), water (10 ml) and brine (5 ml), dried with anhydrous sodium sulfate, and then concentrated under reduced pressure. The resulting residue was purified by silica gel column chromatography (heptane to 60% ethyl acetate/heptane), and the resulting solid was triturated with tert-butyl methyl ether/heptane. The solid was filtered and then washed with heptane to obtain the title compound EX6-IM-2 (840 mg) as a white solid.

NMR data ($CDCl_3$) (δ: ppm): 7.37 to 7.27 (4H, m), 7.22 to 7.14 (4H, m), 7.08 (1H, brs), 6.76 (1H, d, J=13 Hz), 6.57 (1H, d, J=13 Hz), 5.43 (1H, d, J=15 Hz), 4.17 (1H, d, J=15 Hz), 3.22 (1H, dt, J=13.6 Hz), 2.83 (1H, dt, J=13.6 Hz), 2.22 to 2.12 (1H, m), 1.87 (1H, dq, J=16.5 Hz), 1.68 to 1.58 (1H, m), 1.52 to 1.36 (2H, m), 1.28 to 1.16 (1H, m), LC-MS: M=402, RT=1.05 (minutes), $[M+H]^+$=403

<Step 3> Synthesis of N-(5-(11,12-dibromo-11,12-dihydrodibenzo[b,f]azocin-5(6H)-yl)-5-oxopentyl-trifluoroacetamide (compound EX6-IM-3)

[C136]

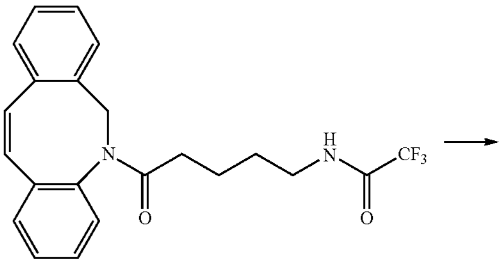

EX6-IM-2

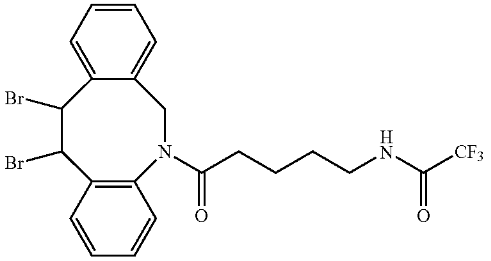

EX6-IM-3

Pyridinium bromide perbromide (612 mg) was added under ice-water cooling to a methylene chloride (2.8 ml) solution of the compound EX6-IM-2 (700 mg) obtained in <Step 2> of (Example 6), and stirred for 1.5 hours at room temperature, after which additional pyridinium bromide perbromide (111 mg) was added, and the mixture was stirred for a further 1 hour at room temperature. The reaction solution was diluted with ethyl acetate (20 ml), and washed successively with 2N-hydrochloric acid (10 ml) and brine (5 ml). The organic layer was dried with anhydrous sodium sulfate, and concentrated under reduced pressure to obtain the title crude compound EX6-IM-3 (1.03 g) as a yellow amorphous substance.

LC-MS: M=562, RT=1.10 (minutes), $[M+H]^+$=563 (561:563:565=1:2:1)

<Step 4> Synthesis of N-[5-(11, 12-didehydrodibenz[b, f]azocin-5(6H)-yl)-5-oxopentyl]-2, 2, 2-trifluoro Acetamide (EX6-IM-4)

[C137]

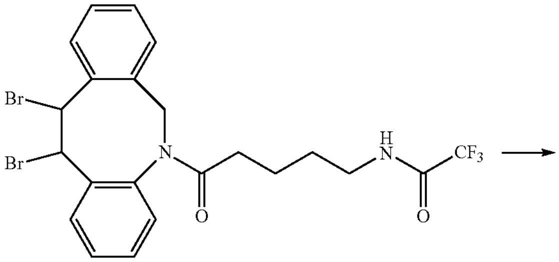

EX6-IM-3

-continued

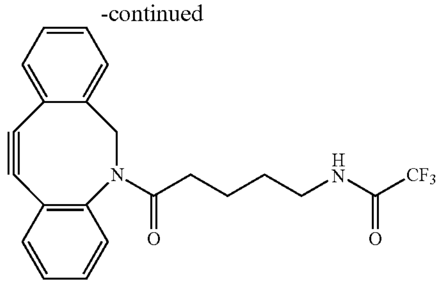

EX6-IM-4

Potassium tert-butoxide (100 mg) was added little by little over the course of 8 hours under stirring at room temperature to a tetrahydrofuran (1.5 ml) solution of the crude compound EX6-IM-3 (100 mg) obtained in <Step 3> of (Example 6). The reaction solution was diluted with ethyl acetate (15 ml), and washed successively with water (3 ml) and brine (2 ml). The organic layer was dried with anhydrous sodium sulfate, and concentrated under reduced pressure to obtain the title crude compound EX6-IM-4 (58 mg) as a light brown gummy substance.

NMR data ($CDCl_3$) (δ: ppm): 7.69 (1H, d, J=7 Hz), 7.44 to 7.23 (7H, m), 5.17 (1H, d, J=14 Hz), 3.70 (1H, d, J=14 Hz), 3.21 (1H, dt, J=13.6 Hz), 2.57 (1H, dq, J=19.5 Hz), 2.36 to 2.28 (1H, m), 1.82 (1H, dq, J=16, 5 Hz), 1.46 to 1.34 (2H, m), 1.29 to 1.24 (1H, m), 1.15 to 1.05 (1H, m), LC-MS: M=400, RT=1.08 (minutes), $[M+H]^+$=401, $[M+Na]^+$=423

<Step 5> Synthesis of 5-amino-1-(11, 12-didehydrodibenz[b,f]azocin-5(6H)-yl)-1-pentanone (compound EX6-IM-5)

[C138]

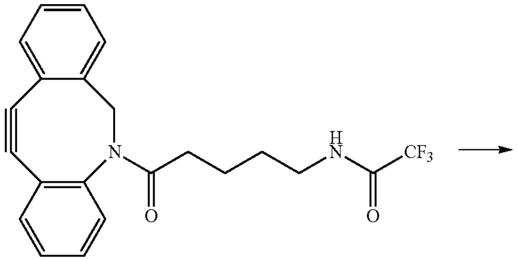

EX6-IM-4

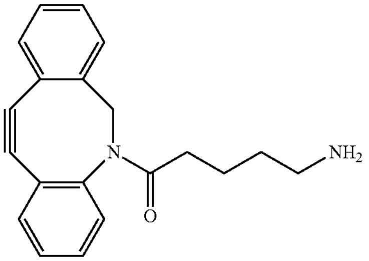

EX6-IM-5

A water (0.25 ml) solution of potassium carbonate (40 mg) was added to a methanol (1.2 ml) solution of the crude compound EX6-IM-4 (58 mg) obtained in <Step 4> of (Example 6), and stirred for 23 hours at room temperature. The reaction solution was concentrated, and separated by addition of ethyl acetate (10 ml), methylene chloride (1 ml) and semi-brine (2 ml). The organic layer was dried with anhydrous sodium sulfate, and concentrated under reduced pressure. The resulting gum was purified by silica gel chromatography (ethyl acetate to 50% methanol/ethyl acetate) to obtain the title compound EX6-IM-5 (22 mg) as a colorless gummy substance.

NMR data ($CDCl_3$) (δ: ppm): 7.70 (1H, d, J=8 Hz), 7.43 to 7.23 (7H, m), 5.18 (1H, d, J=14 Hz), 3.65 (1H, d, J=14 Hz), 2.45 (2H, t, J=7 Hz), 2.24 to 2.16 (1H, m), 1.96 to 1.89 (1H, m), 1.48 to 1.38 (2H, m), 1.21 to 1.10 (2H, m), LC-MS: M=304, RT=0.76 (minutes), $[M+H]^+$=305

<Step 6> Synthesis of Alginic Acid (EX6-(I)-B-2) Having Introduced 5-amino-1-(11,12-didehydrodibenz[b,f]azocin-5(6H)-yl)-1-pentanone (ADIBO-C5-amino) Group

[C139]

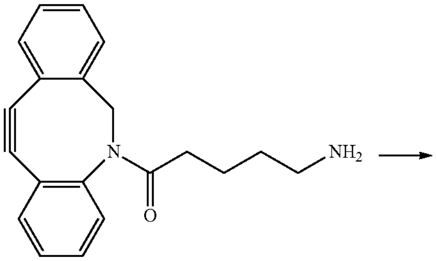

EX6-IM-5

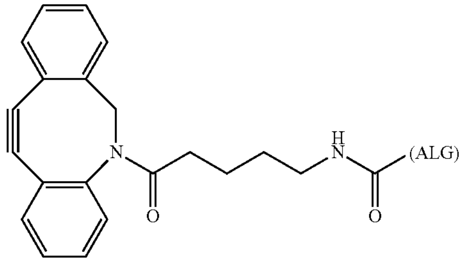

EX6-(I)-B-2

4-(4,6-dimethoxy-1,3,5-triazin-2-yl)-4-methylmorpholinium chloride (DMT-MM) (60 mg), an ethanol (2.9 ml) solution of the compound EX6-IM-5 (22 mg) obtained in <Step 5> of (Example 6), and 1-molar sodium bicarbonate water (72 μl) were added to 28.5 ml of an aqueous solution of sodium alginate (Mochida Pharmaceutical: B-2) adjusted to 1 wt %, and stirred for 3 hours at 30° C. Sodium chloride (285 mg) was added, followed by ethanol (57 ml), and the mixture was stirred at room temperature for 30 minutes. The resulting precipitate was collected by filtration, washed with ethanol, and then dried under reduced pressure to obtain the title compound EX6-(I)-B-2 (277 mg) as a white solid.

The introduction rate of the reactive group (N-(3-aminopentanyl)-5,6-dihydro-11,12-didehydrodibenzo[b,f]azocin (ADIBO-C3-amino) group) was 2.7 mol % (NMR integration ratio).

Example 7

Synthesis of Alginic Acids (Examples 7a, 7b and 7c) Having Introduced N-(2-aminoethyl)-4-azidobenzamide Groups

[C140]

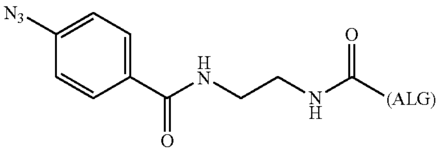

Example 7a: EX7-(II)-B-2a
Example 7b: EX7-(II)-B-2b
Example 7c: EX7-(II)-A-2

<Step 1> Synthesis of tert-butyl (2-(4-azidobenzamido)ethyl)carbamate (Compound EX7-IM-1)

[C141]

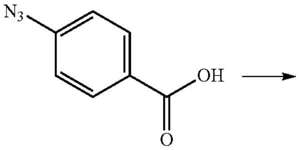

EX7-SM

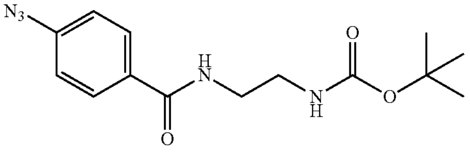

EX7-IM-1

Thionyl chloride (783 μl) and N,N-dimethylformamide (3 μl) were added to 4-azidobenzoic acid [CAS: 6427-66-3] (EX7-SM, 700 mg), and stirred for 1 hour at 70° C. The reaction solution was concentrated under reduced pressure, and the residue and methylene chloride (1 ml) were added under ice-water cooling to a methylene chloride (7.0 ml) solution of tert-butyl(2-aminoethyl) carbamate [CAS: 57260-73-8] (825 mg) and pyridine (1.04 ml), and stirred for 1 hour at room temperature. The reaction solution was diluted with tert-butyl methyl ether (30 ml), and washed successively with water (10 ml), saturated sodium bicarbonate water (5 ml), 0.5N-citric acid (5 ml, twice), water (5 ml) and brine (5 ml). The organic layer was washed with anhydrous sodium sulfate and concentrated under reduced pressure. The residue was triturated with tert-butyl methyl ether/heptane, and the solid was filtered and washed with tert-butyl methyl ether/heptane to obtain the title compound EX7-IM-1 (1.1 g) as a white solid.

NMR data ($CDCl_3$) (δ: ppm): 7.83 (2H, d, J=8 Hz), 7.26 (1H, brs), 7.05 (2H, d, J=8 Hz), 4.97 (1H, brs), 3.55 (2H, q, J=5 Hz), 3.45 to 3.37 (2H, m), 1.43 (9H, s), LC-MS: M=305, RT=0.90 (minutes), $[M+H]^+$=306, $[M+Na]^+$=328

<Step 2> Synthesis of N-(2-aminoethyl)-4-azidobenzamide Hydrochloride (Compound EX7-IM-2)

[C142]

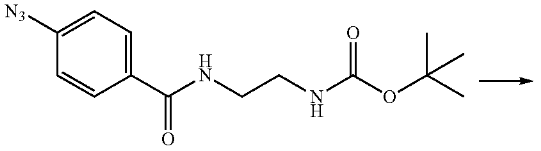

EX7-IM-1

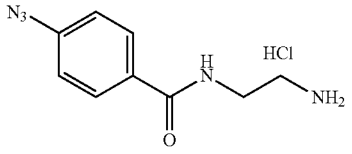

EX7-IM-2

The compound (EX7-IM-1, 500 mg) obtained in <Step 1> of (Example 7) was suspended in 1, 4-dioxane (1.5 ml). 4N-hydrogen chloride/dioxane solution (3.5 ml) was added under ice-water cooling, and stirred for 1 hour at room temperature. Diisopropyl ether (10.5 ml) was added to the reaction solution, which was then stirred for 50 minutes at room temperature. The solid was filtered out, washed with diisopropyl ether, and dried under reduced pressure to obtain the title compound EX7-IM-2 (365 mg) as a light beige solid.

NMR data (DMSO-$d_6$) (δ: ppm): 8.68 (1H, t, J=6 Hz), 7.93 (2H, d, J=9 Hz), 7.82 (1H, brs), 7.22 (2H, d, J=9 Hz), 3.49 (2H, q, J=6 Hz), 2.97 (2H, t, J=6 Hz), LC-MS: M (free amine)=205, RT=0.56 (minutes), $[M+H]^+$=206

<Step 3-1> (Example 7a) Synthesis of Alginic Acid (EX7-(II)-B-2a) Having Introduced N-(2-aminoethyl)-4-azidobenzamide Group

[C143]

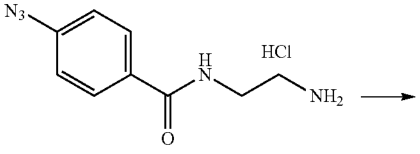

EX7-IM-2

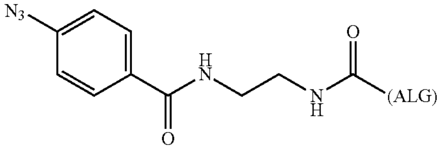

EX7-(II)-B-2a 4-(4,6-dimethoxy-1,3,5-triazin-2-yl)-4-methylmorpholinium chloride (DMT-MM) (63 mg), the compound EX7-IM-2 (18 mg) obtained in <Step 2> of (Example 7), and 1-molar sodium bicarbonate water (114 μl) were added to 30.0 ml of an aqueous solution of sodium alginate (Mochida Pharmaceutical: B-2) adjusted to 1 wt %, and stirred for 3 hours at 30° C. Sodium chloride (300 mg) was added, ethanol (60 ml) was added, and the mixture was stirred at room temperature for 30 minutes. The resulting precipitate was collected by filtration, washed with ethanol, and dried under reduced pressure to obtain the title compound EX7-(II)-B-2a (282 mg) as a white solid.

The introduction rate of the reactive substituent (N-(2-aminoethyl)-4-azidobenzamide group) was 5.1 mol % (NMR integration ratio).

<Step 3-2> (Example 7b) Synthesis of Alginic Acid (EX7-(II)-B-2b) Having Introduced N-(2-aminoethyl)-4-azidobenzamide Group

[C144]

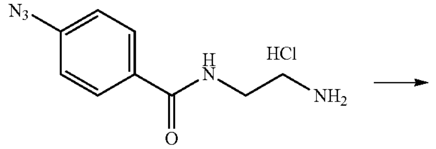

EX7-IM-2

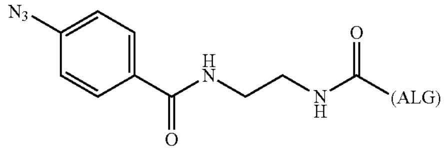

EX7-(II)-B-2b 4-(4,6-dimethoxy-1,3,5-triazin-2-yl)-4-methylmorpholinium chloride (DMT-MM) (67 mg), the compound EX7-IM-2 (15 mg) obtained in <Step 2> of (Example 7), and 1-molar sodium bicarbonate water (91 μl) were added to 60.0 ml of an aqueous solution of sodium alginate (Mochida Pharmaceutical: B-2) adjusted to 1 wt %, and stirred for 3 hours at 30° C. Sodium chloride (600 mg) was added, followed by ethanol (120 ml), and the mixture was stirred at room temperature for 30 minutes. The resulting precipitate was collected by filtration, washed with ethanol, and dried under reduced pressure to obtain the title compound EX7-(II)-B-2b (560 mg) as a white solid.

The introduction rate of the reactive substituent (N-(2-aminoethyl)-4-azidobenzamide group) was 2.0 mol % (NMR integration ratio).

Example 7c

Synthesis of Alginic Acid (EX7-(II)-A-2) Having Introduced N-(2-aminoethyl)-4-azidobenzamide Group The title compound (EX7-(II)-A-2) was obtained with an introduction rate (NMR integration ratio) of 5.0 mol % of the reactive substituent by the same methods as (Example 7a) using the alginic acid A-2 in place of B-2.

Example 8

Synthesis of Alginic Acid (EX8-(I)-B-2) Having Introduced N-(4-(aminomethyl)benzyl)-2-(cyclooct-2-yn-1-yloxy)acetamide Group

[C145]

EX8-(I)-B-2

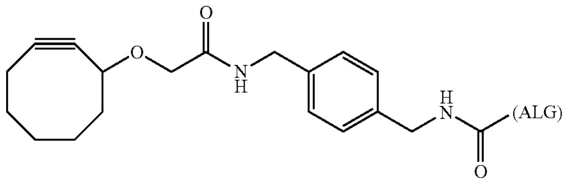

<Step 1> Synthesis of tert-butyl(4-((2,2,2-trifluoroacetamido)methyl)benzyl)carbamate (Compound EX8-IM-1)

[C146]

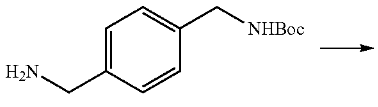

EX8-SM1

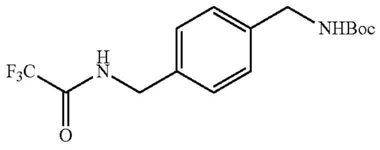

EX8-IM-1

With reference to methods known in the literature (Bioorganic & Medicinal Chemistry (2003) 11: 4189-4206), ethyl trifluoroacetate (0.44 ml) was dipped under ice cooling and stirring into a mixture of triethylamine (0.39 ml), methanol (6.67 ml) and tert-butyl (4-(aminomethyl)benzyl) carbamate [CAS: 108468-80-4] (EX8-SM1, 0.67 g) synthesized from 1,4-bis(aminomethyl)-benzene [CAS: 539-48-0]. The reaction mixture was warmed to room temperature and stirred for 5 hours at that temperature. The reaction was stopped with water (10 ml), and the mixture was extracted 3 times with ethyl acetate (10 ml). The collected organic layer was washed with brine (5 ml) and dried with anhydrous sodium sulfate, and the dried organic layer was filtered and then concentrated to obtain the title compound EX8-IM-1 (0.671 g) as a light-yellow amorphous substance.

NMR data ($CDCl_3$) (δ: ppm): 7.29 (2H, d, J=8.4 Hz), 7.25 (2H, d, J=7.6 Hz), 6.51 (1H, br s), 4.86 (1H, br s), 4.51 (2H, d, J=5.2 Hz), 4.31 (2H, d, J=6.0 Hz), 1.46 (9H, s), LC-MS: M=332, RT=0.97 (minutes), $[M+Na]^+$=355

<Step 2> Synthesis of N-(4-(aminomethyl)benzyl)-2,2,2-trifluoroacetamide Hydrochloride (Compound EX8-IM-2)

[C147]

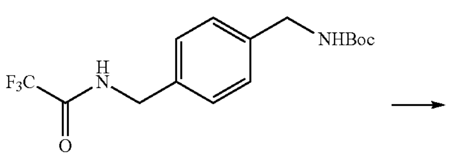

EX8-IM-1

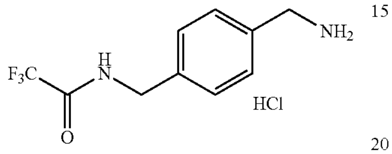

EX8-IM-2

4N-hydrogen chloride/1,4-dioxane (3.5 ml) was added under water cooling and stirring to a 1,4-dioxane solution (3.5 ml) of the compound EX8-IM-1 (0.5 g) obtained in <Step 1> of (Example 8), and stirred for 3 hours at room temperature. Diisopropyl ether (40 ml) was added to the reaction solution, and the precipitate was filtered out to obtain the title compound EX8-IM-2 (0.36 g) as a white solid.

NMR data ($D_2O$) (δ: ppm): δ: 7.29 (2H, d, J=8.0 Hz), 7.25 (2H, d, J=8.4 Hz), 4.38 (2H, s), 4.02 (2H, s), LC-MS: M (free amine)=232, RT=0.53 (minutes), $[M+H]^+$=233

<Step 3> Synthesis of N-(4-((2-(cyclooct-2-yn-1-yloxy)acetamido)methyl)benzyl)-2,2,2-trifluoroacetamide (Compound EX8-IM-3)

[C148]

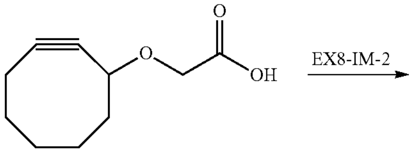

EX8-SM2

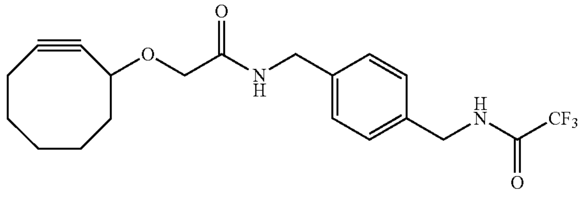

EX8-IM-3

Following methods known in the literature (Org. Process Res. Dev. (2018) 22: 108-110), the compound EX8-IM-2 (0.26 g) obtained in <Step 2> of (Example 8) and N,N-diisopropylethylamine (0.51 ml) were dripped under ice-cooling and stirring into an acetonitrile (1.7 ml) solution of O-(7-azabenzotriazol-1-yl)-N,N,N',N'-tetramethyluronium hexafluorophosphate salt (0.26 g) and a carboxylic acid [CAS: 917756-42-4] (EX8-SM2, 0.17 g) synthesized from cycloheptene [CAS: 628-92-2], and stirred for 1 hour and 30 minutes at room temperature. Water (5 ml) was added to stop the reaction, and the mixture was extracted 3 times with ethyl acetate (5 ml). The organic layer was washed with brine (3 ml) and dried with anhydrous sodium sulfate. The dried organic layer was filtered, and the solvent was distilled off under reduced pressure. The residue was purified by silica gel column chromatography (12% ethyl acetate/n-heptane to 100% ethyl acetate) to obtain the title compound EX8-IM-3 (0.189 g) as a white amorphous substance.

NMR data ($CDCl_3$) (δ: ppm): δ: 7.31 (2H, d, J=8.4 Hz), 7.26 (2H, d, J=8.0 Hz, overlapped with solvent peak), 6.84 (1H, br s), 6.52 (1H, br s), 4.52 (2H, d, J=6.0 Hz), 4.49 (2H, d, J=6.4 Hz), 4.26 to 4.23 (1H, m), 4.11 (1H, d, J=15.2 Hz), 3.94 (1H, d, J=15.2 Hz), 2.26 to 2.09 (3H, m), 2.00 to 1.58 (6H, m), 1.48 to 1.44 (1H, m), LC-MS: M=396, RT=0.99 (minutes), $[M+H]^+$=397

<Step 4> Synthesis of N-(4-(aminomethyl)benzyl)-2-(cyclooct-2-yn-1-yloxy)acetoamide (Compound EX8-IM-4)

[C149]

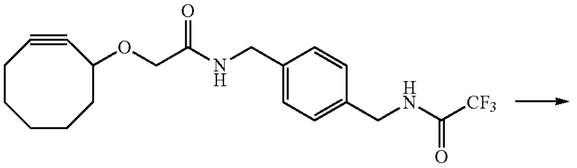

EX8-IM3

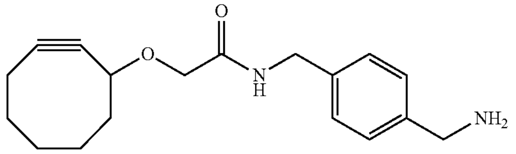

EX8-IM4

A potassium carbonate (0.126 g) aqueous solution (0.9 ml) was dripped under ice cooling and stirring into a mixture of the compound EX8-IM-3 (0.18 g) obtained in <Step 3> of (Example 8) and methanol (1.8 ml), and stirred for 17 hours and 30 minutes at room temperature. The methanol was distilled off under reduced pressure, and the mixture was extracted 3 times with ethyl acetate (5 ml). The organic layer was washed with brine (5 ml), and dried with anhydrous sodium sulfate. The organic layer was filtered and the solvent was distilled off under reduced pressure to obtain the title crude compound EX8-IM-4 (0.13 g) as a light yellow oily substance.

NMR data ($CDCl_3$) (δ: ppm): 7.28 to 7.28 (4H, m), 6.80 (1H, br s), 4.48 (2H, d, J=6.0 Hz), 4.26 to 4.21 (1H, m), 4.11 (1H, d, J=15.2 Hz), 3.93 (1H, d, J=15.2 Hz), 3.86 (2H, s), 2.28 to 2.07 (3H, m), 1.99 to 1.40 (7H, m, overlapped with solvent peak), LC-MS: M=300, RT=0.68 (minutes), $[M+H]^+$= 301

<Step 5> Synthesis of Alginic Acid (EX8-(I)-B-2) Having Introduced N-(4-(aminomethyl)benzyl)-2-(cyclooct-2-yn-1-yloxy)acetamide Group

[C150]

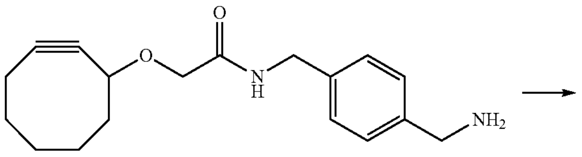

EX8-IM4

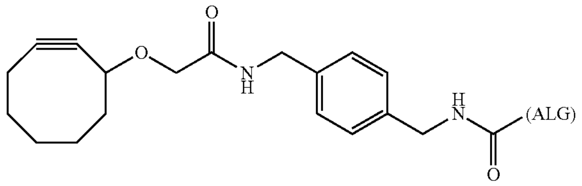

EX8-(I)-B-2

4-(4,6-dimethoxy-1,3,5-triazin-2-yl)-4-methylmorpholinium chloride (DMT-MM) (0.118 g) was added under stirring at room temperature to 50.86 ml of an aqueous solution of sodium alginate (Mochida Pharmaceutical: B-2) adjusted to 1 wt %. An ethanol (3 ml) solution of the compound EX8-IM-4 (0.035 g) obtained in <Step 4> of (Example 8) was then dripped in at the same temperature, and the mixture was stirred for 4 hours at 40° C. This was cooled to room temperature and sodium chloride (500 mg) was added, followed by ethanol (101.72 ml), and the mixture was stirred for 30 minutes. The resulting precipitate was collected by filtration, washed 3 times with ethanol (2 ml), and dried under reduced pressure to obtain the title compound EX8-(I)-B-2 (521 mg) as a white solid.

The introduction rate of the reactive substituent (N-(4-(aminomethyl)benzyl)-2-(cyclooct-2-yn-1-yloxy)acetamide group) was 4.46 mol % (NMR integration ratio).

Example 8b

Synthesis of Alginic Acid (EX8-(I)-A-2) Having Introduced N-(4-(aminomethyl)benzyl)-2-(cyclooct-2-yn-1-yloxy)acetamide Group The title compound (EX8-(I)-A-2) was obtained with an introduction rate of 4.4 mol % (NMR integration ratio) of the reactive substituent by the same methods as (Example 8), with A-2 substituted for B-2 as the alginic acid.

Example 9

Synthesis of Alginic Acids (9a, 9b, 9c) Having Introduced N-(2-aminoethyl)-2-(cyclooct-2-yn-1-yloxy)acetamide Groups

[C151]

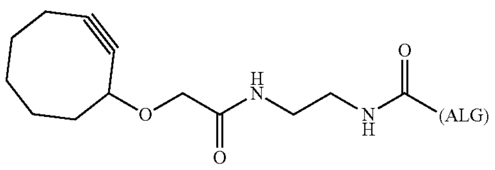

Example 9a: EX9-(I)-A-2
Example 9b: EX9-(I)-B-2a
Example 9c: EX9-(I)-B-2b

Example 9a

Synthesis of Alginic Acid (EX9-(I)-A-2) Having Introduced N-(2-aminoethyl)-2-(cyclooct-2-yn-1-yloxy)acetamide Group <Step 1> Synthesis of tert-butyl (2-(2,2,2-trifluoroacetamido)carbamate (EX9-IM-1)

[C152]

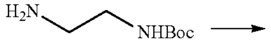

EX9-SM1

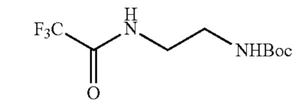

EX9-IM-1

Ethyl trifluoroacetate (2.24 ml) was dripped into a tetrahydrofuran (12.0 ml) solution of commercial tert-butyl(2-aminoethyl) carbamate (EX9-SM1, 3.00 g, [CAS: 57260-73-8]). The reaction mixture was stirred for 14.5 hours at room temperature, the reaction solution was concentrated under reduced pressure, and the residue was triturated by addition of tert-butyl methyl ether (5 ml) and heptane (25 ml). The solid was filtered out and washed with heptane to obtain the title compound EX9-IM-1 (4.36 g) as a white solid.

NMR data ($CDCl_3$) (δ: ppm): 7.80 (1H, brs), 4.93 (1H, brs), 3.45 (2H, q, J=5 Hz), 3.41 to 3.34 (2H, m), 1.44 (9H, s)

<Step 2> Synthesis of N-(2-aminoethyl)-2,2,2-trifluoroacetamide Hydrochloride (EX9-IM-2)

[C153]

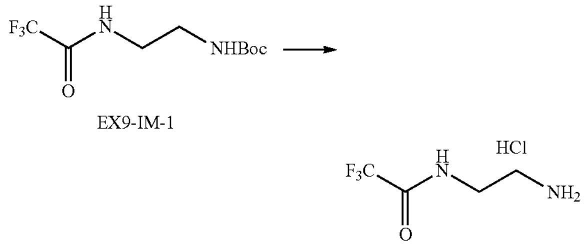

EX9-IM-1

EX9-IM-2

Formic acid (3.1 ml) was added to the compound EX9-IM-1 (0.50 g) obtained in <Step 1> of (Example 9a), and stirred for 22.5 hours at room temperature. The formic acid was distilled off, and the mixture was azeotropically distilled with toluene. Hydrogen chloride/methanol was added to the resulting oily substance, which was then concentrated under reduced pressure. This was azeotropically distilled successively with ethyl acetate and tert-butyl methyl ether, and dried under reduced pressure to obtain the title compound EX9-IM-2 (0.35 g) as a colorless oily substance.

NMR data (DMSO-$d_6$) (δ: ppm): 3.42 (2H, d, J=6 Hz), 2.92 (2H, d, J=6 Hz)

<Step 3> Synthesis of N-(2-(2-(cyclooct-2-yn-1-yloxy)acetamido)ethyl)-2,2,2-trifluoroacetamide (EX9-IM-3)

[C154]

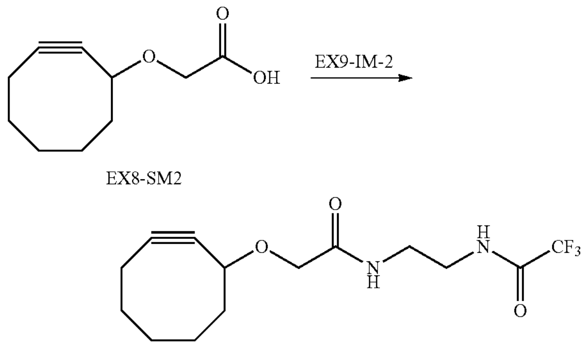

EX8-SM2

EX9-IM-3

Ethanol (1.0 ml), 4-(4,6-dimethoxy-1,3,5-triazin-2-yl)-4-methylmorpholinium chloride (DMT-MM) (304 mg), the compound EX9-IM-2 (159 mg) obtained in <Step 2> of (Example 9a) and triethylamine (153 μl) were added to a carboxylic acid (EX8-SM2, 100 mg) synthesized according to methods known in the literature (Org. Process Res. Dev. (2018) 22: 108-110), and stirred for 3.5 hours at room temperature. Water (4 ml) was added, and the mixture was extracted with ethyl acetate (15 ml, 5 ml). The organic layer was washed successively with 0.5N-citric acid (5 ml), water (5 ml×2) and brine (3 ml) and then dried with anhydrous sodium sulfate, and the solvent was distilled off under reduced pressure. The residue was purified by silica gel column chromatography (10% ethyl acetate/n-heptane to 60% ethyl acetate/n-heptane) to obtain the title compound EX9-IM-3 (103 mg) as a white solid.

NMR data (DMSO-$d_6$) (δ: ppm): 9.42 (1H, brs), 7.83 (1H, brs), 4.29 to 4.24 (1H, m), 3.87 (2H, d, J=15 Hz), 3.73 (1H, d, J=15 Hz), 3.28 to 3.20 (4H, m), 2.27 to 2.04 (3H, m), 1.96 to 1.70 (4H, m), 1.67 to 1.50 (2H, m), 1.43 to 1.34 (1H, m)

<Step 4> Synthesis of N-(2-aminoethyl)-2-(cyclooct-2-yn-1-yloxy)acetamide (EX9-IM-4)

[C155]

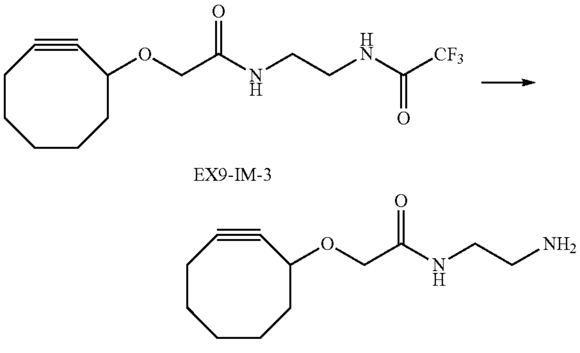

EX9-IM-3

EX9-IM-4

A water (515 μl) solution of potassium carbonate (89 mg) was added to a methanol (1.55 ml) solution of the compound EX9-IM-3 (103 mg) obtained in <Step 3> of (Example 9a), and stirred for 6 hours at room temperature. The methanol was distilled off under reduced pressure, water (2 ml) was added, and the mixture was saturated with sodium chloride. This was extracted with ethyl acetate (15 ml, 10 ml×5) and dried with anhydrous sodium sulfate, after which the solvent was distilled off under reduced pressure to obtain the title compound EX9-IM-4 (75 mg) as a colorless oily substance.

NMR data ($CDCl_3$) (δ: ppm): 6.83 (1H, brs), 4.28 to 4.22 (1H, m), 4.06 (1H, d, J=15 Hz), 3.90 (1H, d, J=15 Hz), 3.42 to 3.30 (2H, m), 2.86 (2H, t, J=6 Hz), 2.31 to 2.12 (3H, m), 2.04 to 1.78 (4H, m), 1.75 to 1.57 (2H, m), 1.51 to 1.43 (1H, m)

<Step 5> Synthesis of Alginic Acid (EX9-(I)-A-2) Having Introduced N-(2-aminoethyl)-2-(cyclooct-2-yn-1-yloxy)acetamide Group

[C156]

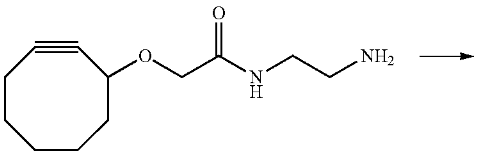

EX9-IM-4

-continued

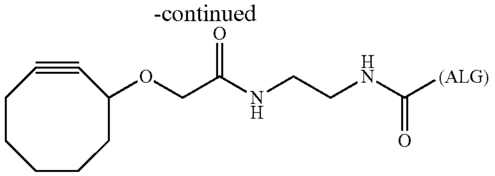

EX9-(I)-A-2

4-(4,6-dimethoxy-1,3,5-triazin-2-yl)-4-methylmorpholinium chloride (DMT-MM) (84 mg), an ethanol (3 ml) solution of the compound EX9-IM-4 (17 mg) obtained in <Step 4> of (Example 9a), and 1 mol % sodium bicarbonate water (76 μl) were added in that order under stirring at room temperature to 30 ml of an aqueous solution of sodium alginate (Mochida Pharmaceutical: A-2) adjusted to 1 wt %, and stirred for 3 hours at 30° C. Sodium chloride (0.3 g) and then ethanol (60 ml) were added to the reaction solution, which was then stirred for 1.5 hours. The resulting precipitate was collected by filtration, washed with ethanol (10 ml×5), and dried under reduced pressure to obtain the title compound EX9-(I)-A-2 (290 mg) as a white solid.

The introduction rate of the reactive substituent (N-(2-aminoethyl)-2-(cyclooct-2-yn-1-yloxy)acetamide group) was 4.3 mol % (NMR integration ratio).

Example 9b

Synthesis of Alginic Acid (EX9-(I)-B-2a) Having Introduced N-(2-aminoethyl)-2-(cyclooct-2-yn-1-yloxy)acetamide Group

<Step 1> Synthesis of N-(2-aminoethyl)-2,2,2-trifluoroacetamide hydrochloride (EX9-IM-2)

[C157]

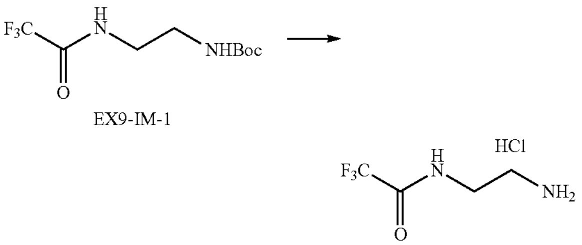

EX9-IM-1

EX9-IM-2

The compound EX9-IM-1 (0.50 g) obtained in <Step 1> of (Example 9a) was suspended in 1,4-dioxane (3.0 ml). 4N-hydrogen chloride/1,4-dioxane (7.0 ml) was added under ice-water cooling, and the mixture was stirred for 3 hours at room temperature. Diisopropyl ether (30.0 ml) was added to the reaction solution, which was then stirred for 50 minutes at room temperature. A solid was collected by filtration, washed with diisopropyl ether, and dried under reduced pressure to obtain the title compound EX9-IM-2 (0.70 g) as a white solid.

NMR data (DMSO-$d_6$) (δ: ppm): 9.56 (1H, brs), 8.00 (3H, brs), 3.45 (2H, d, J=6 Hz), 2.95 (2H, d, J=6 Hz)

<Step 2> Synthesis of N-(2-(2-(cyclooct-2-yn-1-yloxy)acetamido)ethyl)-2,2,2-trifluoroacetamide (EX9-IM-3)

[C158]

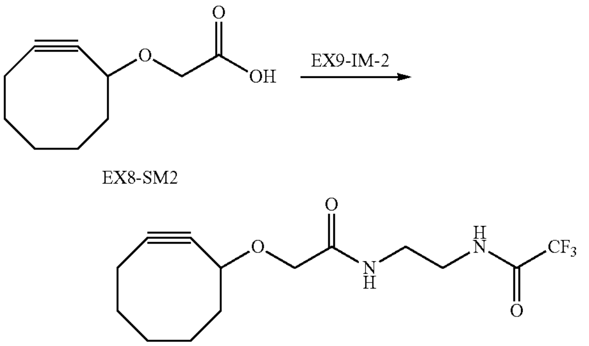

EX8-SM2

EX9-IM-3

The title compound EX9-IM-3 (322 mg) was obtained as a white solid by the same operations as in <Step 3> of (Example 9a) using a carboxylic acid (EX8-SM2, 300 mg) synthesized by methods known in the literature (Org. Process Res. Dev. (2018) 22: 108-110) and the compound EX9-IM-2 (380 mg) obtained in <Step 1> of (Example 9b).

NMR data ($CDCl_3$) (δ: ppm): 7.95 (1H, brs), 6.95 (1H, brs), 4.28 to 4.23 (1H, m), 4.08 (2H, d, J=15 Hz), 3.91 (1H, d, J=15 Hz), 3.56 to 3.50 (4H, m), 2.31 to 2.12 (3H, m), 2.03 to 1.78 (4H, m), 1.75 to 1.61 (2H, m), 1.52 to 1.42 (1H, m)

<Step 3> Synthesis of N-(2-aminoethyl)-2-(cyclooct-2-yn-1-yloxy)acetamide (EX9-IM-4)

[C159]

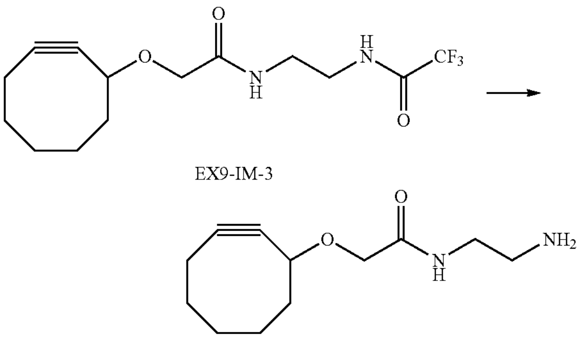

EX9-IM-3

EX9-IM-4

The title compound EX9-IM-4 (238 mg) was obtained as a colorless oily substance by the same operations as in <Step 4> of (Example 9b) using the compound EX9-IM-3 (322 mg) obtained in <Step 2> of (Example 9b).

NMR data ($CDCl_3$) (δ: ppm): 6.82 (1H, brs), 4.28 to 4.22 (1H, m), 4.06 (1H, d, J=15 Hz), 3.90 (1H, d, J=15 Hz), 3.40 to 3.31 (2H, m), 2.86 (2H, t, J=6 Hz), 2.31 to 2.12 (3H, m), 2.02 to 1.78 (4H, m), 1.75 to 1.57 (2H, m), 1.52 to 1.41 (1H, m)

<Step 4> Synthesis of Alginic Acid (EX9-(I)-B-2a) Having Introduced N-(2-aminoethyl)-2-(cyclooct-2-yn-1-yloxy)acetamide Group

[C160]

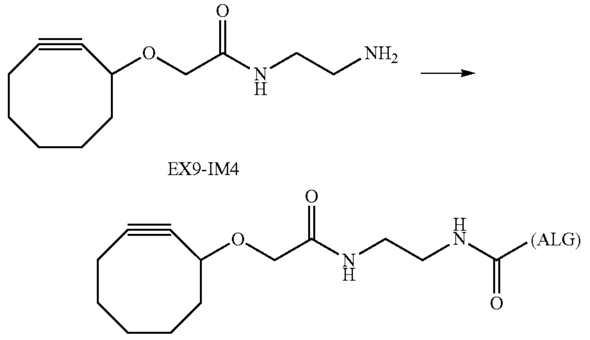

EX9-IM4

EX9-(I)-B-2a 4-(4,6-dimethoxy-1,3,5-triazin-2-yl)-4-methylmorpholinium chloride (DMT-MM) (335 mg), an ethanol (12 ml) solution of the compound EX9-IM-4 (68 mg) obtained in <Step 3> of (Example 9b) and 1 mol % sodium bicarbonate water (303 μl) were added in that order at room temperature under stirring to 120 ml of an aqueous solution of sodium alginate (Mochida Pharmaceutical: B-2) adjusted to 1 wt %, and stirred for 3 hours at 30° C. Sodium chloride (1.2 g) and then ethanol (240 ml) were added to the reaction solution, which was then stirred for 1.5 hours. The resulting precipitate was collected by filtration, washed with ethanol (20 ml×5), and dried under reduced pressure to obtain the title compound EX9-(I)-B-2a (1.16 g) as a white solid.

The introduction rate of the reactive substituent (N-(2-aminoethyl)-2-(cyclooct-2-yn-1-yloxy)acetamide group) was 4.2 mol % (NMR integration ratio).

Example 9c

Synthesis of Alginic Acid (EX9-(I)-B-2b) Having Introduced N-(2-aminoethyl)-2-(cyclooct-2-yn-1-yloxy)acetamide Group

[C161]

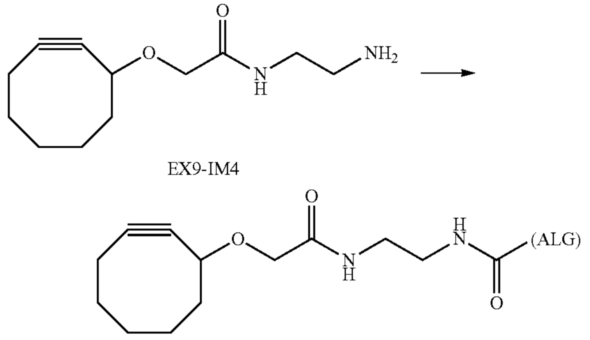

EX9-IM4

EX9-(I)-B-2b 4-(4,6-dimethoxy-1,3,5-triazin-2-yl)-4-methylmorpholinium chloride (DMT-MM) (167 mg), an ethanol (12 ml) solution of the compound EX9-IM-4 (34 mg) obtained in <Step 3> of (Example 9b), and 1 mol % sodium bicarbonate water (151 μl) were added in that order at room temperature under stirring to 120 ml of an aqueous solution of sodium alginate (Mochida Pharmaceutical: B-2) adjusted to 1 wt %, and stirred for 3 hours at 30° C. Sodium chloride (1.2 g) and then ethanol (240 ml) were added to the reaction solution, which was then stirred for 1.5 hours. The resulting precipitate was collected by filtration, washed with ethanol (20 ml×5), and dried under reduced pressure to obtain the title compound EX9-(I)-B-2b (1.12 g) as a white solid.

The introduction rate of the reactive substituent (N-(2-aminoethyl)-2-(cyclooct-2-yn-1-yloxy)acetamide group) was 2.1 mol % (NMR integration ratio).

Example 10

Synthesis of Alginic Acid (EX10-(II)-A-2) Having Introduced N-(2-(2-aminoethoxy)ethyl)-4-(azidomethyl)benzamide Group

[C162]

EX10-(II)-A-2

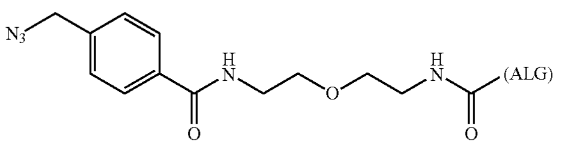

<Step 1> Synthesis of tert-butyl (2-(2-(4-(chloromethyl)benzamido)ethoxy)ethyl) carbamate (EX10-IM-1)

[C163]

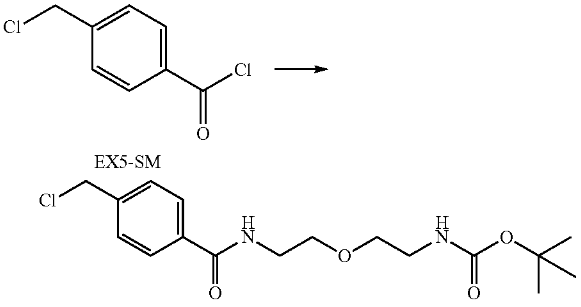

EX5-SM

EX10-IM-1

EX5-SM (4-(chloromethyl)benzoyl chloride, 0.50 g) was dissolved in tetrahydrofuran (5.0 ml), a tetrahydrofuran (5.0 ml) solution of tert-butyl(2-(2-aminoethoxy)ethyl)carbamate (0.54 g [CAS: 127828-22-2]) and N, N-diisopropylethylamine (0.92 ml) was added, and the mixture was stirred for 3 hours at room temperature. Ethyl acetate (25 ml) and water (10 ml) were added to separate the reaction solution. The organic layer was washed successively with water (5 ml) and brine (5 ml), dried with anhydrous sodium sulfate, and concentrated under reduced pressure. The residue was triturated with a mixed tert-butyl methyl ether/n-heptane solvent, and the resulting solid was collected by filtration and washed with n-heptane to obtain the title compound EX10-IM-1 (0.79 g) as a white solid.

NMR data ($CDCl_3$) (δ: ppm): 7.79 (2H, d, J=8 Hz), 7.46 (2H, d, J=8 Hz), 6.62 (1H, brs), 4.83 (1H, brs), 4.61 (2H, s), 3.68 to 3.62 (4H, m), 3.55 (2H, t, J=5 Hz), 3.33 (2H, t, J=5 Hz), 1.42 (9H, s)

<Step 2> Synthesis of tert-butyl (2-(2-(4-(azidomethyl)benzamido)ethoxy)ethyl) carbamate (EX10-IM-2)

[C164]

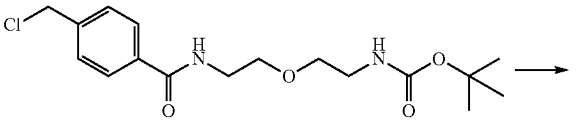

EX10-IM-1

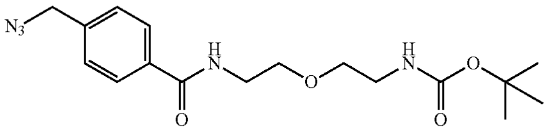

EX10-IM-2

Sodium azide (109 mg) was dissolved in dimethylsulfoxide (7.5 ml), the compound EX10-IM-1 (500 mg) obtained in <Step 1> of (Example 10) was added, and the mixture was stirred for 3 hours at room temperature. Water (15 ml) was added under ice-water cooling to the reaction solution, and the precipitated solid was filtered out and washed with water. The resulting solid was dried to obtain the title compound EX10-IM-2 (478 mg) as a white solid.

NMR data ($CDCl_3$) (δ: ppm): 7.82 (2H, d, J=8 Hz), 7.39 (2H, d, J=8 Hz), 6.63 (1H, brs), 4.83 (1H, brs), 4.40 (2H, s), 3.68 to 3.62 (4H, m), 3.55 (2H, t, J=5 Hz), 3.33 (2H, q, J=5 Hz), 1.42 (9H, s)

<Step 3> Synthesis of N-(2-(2-aminoethoxy)ethyl)-4-(azidomethyl)benzamide Hydrochloride (EX10-IM-3)

[C165]

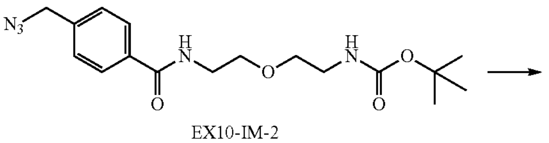

EX10-IM-2

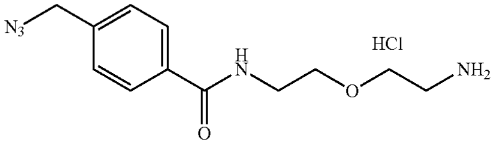

EX10-IM-3

4N-hydrogen chloride/1,4-dioxane (2.8 ml) was added under ice-water cooling to the compound EX10-IM-2 (400 mg) obtained in <Step 2> of (Example 10), and stirred for 1.75 hours at room temperature. Diisopropyl ether (8.4 ml) was added to the reaction solution to obtain a gummy substance. The supernatant was removed by decantation, and the product was decantation washed with diisopropyl ether and dried under reduced pressure to obtain the title compound EX10-IM-3 (298 mg) as a beige solid.

NMR data (DMSO-$d_6$) (δ: ppm): 8.60 (1H, t, J=6 Hz), 7.89 (2H, d, J=8 Hz), 7.90 (3H, brs), 7.45 (2H, d, J=8 Hz), 4.52 (2H, s), 3.62 (2H, t, J=5 Hz), 3.58 (2H, t, J=6 Hz), 3.47 (2H, q, J=6 Hz), 2.98 (2H, t, J=5 Hz), LC-MS (free amine): RT=0.58 (minutes), [M+H]+=264

<Step 4> Synthesis of Alginic Acid (EX10-(II)-A-2) Having Introduced N-(2-(2-aminoethoxy)ethyl)-4-(azidomethyl)benzamide Group

[C166]

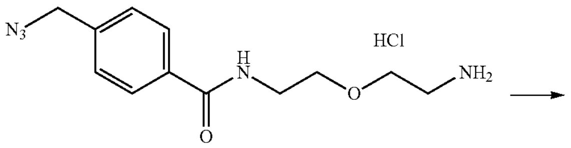

EX10-IM-3

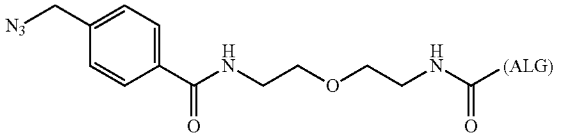

EX10-(II)-A-2

4-(4,6-dimethoxy-1,3,5-triazin-2-yl)-4-methylmorpholinium chloride (DMT-MM) (112 mg), the compound EX10-IM-3 (30 mg) obtained in <Step 3> of (Example 10) and 1-molar sodium bicarbonate water (151 μl) were added to 40 ml of an aqueous solution of sodium alginate (Mochida Pharmaceutical: A-2) adjusted to 1 wt %, and stirred for 3 hours at 30° C. Sodium chloride (400 mg) was added, ethanol (80 ml) was added, and the mixture was stirred at room temperature for 30 minutes. The resulting precipitate was collected by filtration, washed with ethanol, and dried under reduced pressure to obtain the title compound EX10-(II)-A-2 (408 mg) as a white solid.

The introduction rate of the reactive substituent (N-(2-(2-aminoethoxy)ethyl)-4-(azidomethyl)benzamide group) was 4.7 mol % (NMR integration ratio).

Example 11

Synthesis of Alginic Acid (EX11-(II)-A-2) Having Introduced N-(2-(2-(2-aminoethoxy)ethoxy)ethyl)-4-(azidomethyl)benzamide Group

[C167]

EX11-(II)-A-2

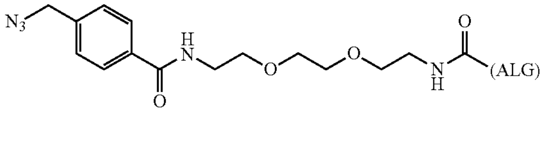

<Step 1> Synthesis of tert-butyl (2-(2-(2-(4-(chloromethyl)benzamido)ethoxy)ethoxy)ethyl)carbamate (EX11-IM-1)

[C168]

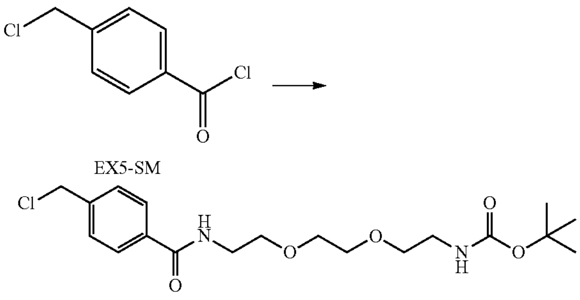

EX5-SM

EX11-IM-1

EX5-SM (4-(chloromethyl)benzoyl chloride, 0.50 g) was dissolved in tetrahydrofuran (5.0 ml), and a tetrahydrofuran (5.0 ml) solution of tert-butyl(2-(2-(2-aminoethoxy)ethoxy)ethyl)carbamate (0.66 g) and N, N-diisopropylethylamine (0.92 ml) was dripped in and stirred for 4.7 hours at room temperature. Ethyl acetate (25 ml) and water (10 ml) were added to separate the reaction solution. The organic layer was washed successively with semi-saturated sodium bicarbonate water (10 ml), water (10 ml) and brine (5 ml), dried with anhydrous sodium sulfate, and then concentrated under reduced pressure. Tert-butyl methyl ether was added to the residue, and the solid was removed by filtration. The resulting filtrate was concentrated under reduced pressure, and purified by silica gel column chromatography (20% ethyl acetate/n-heptane to ethyl acetate) to obtain the title compound EX11-IM-1 (0.82 g) as a colorless oily substance.

NMR data ($CDCl_3$) (δ: ppm): 7.79 (2H, d, J=8 Hz), 7.45 (2H, d, J=8 Hz), 6.71 (1H, brs), 4.97 (1H, brs), 4.60 (2H, s), 3.70 to 3.60 (8H, m), 3.55 (2H, t, J=5 Hz), 3.31 (2H, q, J=6 Hz), 1.43 (9H, s)

<Step 2> Synthesis of tert-butyl (2-(2-(2-(4-(azidomethyl)benzamido)ethoxy)ethoxy)ethyl)carbamate (EX11-IM-2)

[C169]

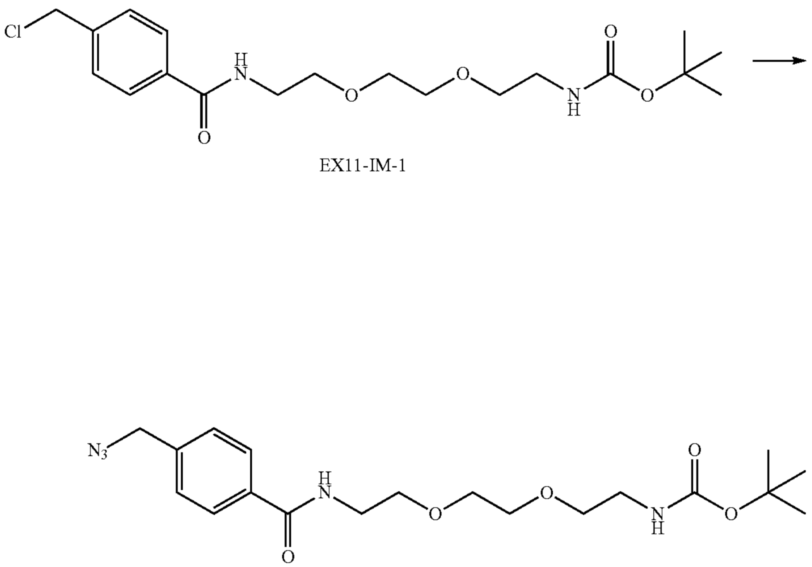

EX11-IM-1

EX11-IM-2

Sodium azide (152 mg) was added to a dimethylsulfoxide (11.7 ml) solution of the compound EX11-IM-1 (0.82 g) obtained in <Step 1> of (Example 11), and stirred for 3.5 hours at room temperature. Water (23 ml) was added under ice-water cooling to the reaction solution, which was then stirred for 30 minutes at that temperature. This was extracted with ethyl acetate (30 ml, 10 ml), and the organic layer was washed successively with water (10 ml×3) and brine (5 ml). The organic layer was dried with anhydrous sodium sulfate, and the precipitated solid was filtered out and dried under reduced pressure to obtain the title compound EX11-IM-2 (0.80 g) as a colorless oily substance.

NMR data ($CDCl_3$) (δ: ppm): 7.81 (2H, d, J=8 Hz), 7.39 (2H, d, J=8 Hz), 6.73 (1H, brs), 4.97 (1H, brs), 4.40 (2H, s), 3.72 to 3.60 (8H, m), 3.55 (2H, t, J=5 Hz), 3.31 (2H, q, J=5 Hz), 1.43 (9H, s)

<Step 3> Synthesis of N-(2-(2-(2-aminoethoxy)ethoxy)ethyl)-4-(azidomethyl)benzamide Hydrochloride (EX11-IM-3)

[C170]

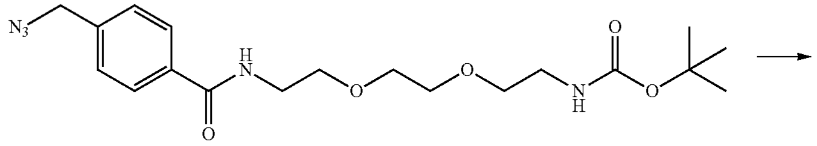

EX11-IM-2

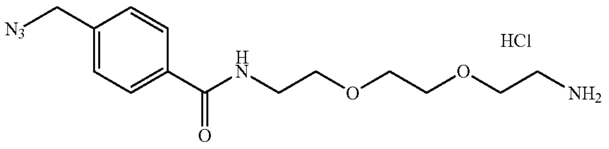

EX11-IM-3

4N-hydrogen chloride/1,4-dioxane (5.3 ml) was added under ice-water cooling to the compound EX11-IM-2 (0.80 g) obtained in <Step 2> of (Example 11), and stirred for 1.75 hours at room temperature. Diisopropyl ether (16.0 ml) was added to the reaction solution, which was then stirred for 30 minutes. The solvent was removed by decantation, and the residue was washed with diisopropyl ether. The resulting residue was dried under reduced pressure to obtain the title compound EX11-IM-3 (0.73 g) as a colorless gummy substance.

NMR data (DMSO-$d_6$) (δ: ppm): 8.62 (1H, t, J=6 Hz), 7.95 (3H, brs), 7.88 (2H, d, J=8 Hz), 7.45 (2H, d, J=8 Hz), 4.52 (2H, s), 3.62 to 3.52 (8H, m), 3.43 (2H, q, J=6 Hz), 2.98 to 2.89 (2H, m), LC-MS (free amine): RT=0.59 (minutes), $[M+H]^+$=308

<Step 4> Synthesis of Alginic Acid (EX11-(II)-A-2) Having Introduced N-(2-(2-(2-aminoethoxy)ethoxy)ethyl)-4-(azidomethyl)benzamide Group

[C171]

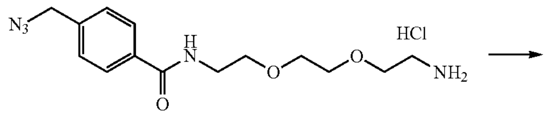

EX11-IM-3

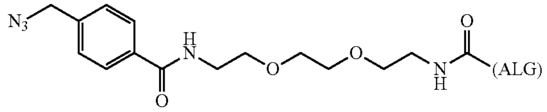

EX11-(II)-A-2

4-(4,6-dimethoxy-1,3,5-triazin-2-yl)-4-methylmorpholinium chloride (DMT-MM) (112 mg), an ethanol (4.0 ml) solution of the compound EX11-IM-3 (38 mg) obtained in <Step 3> of (Example 11), and 1-molar sodium bicarbonate water (151 μl) were added to 40 ml of an aqueous solution of sodium alginate (Mochida Pharmaceutical: A-2) adjusted to 1 wt %, and stirred for 3 hours at 30° C. Sodium chloride (0.4 g) was added, ethanol (80 ml) was added, and the mixture was stirred for 30 minutes at room temperature. The resulting precipitate was collected by filtration, washed with ethanol, and dried under reduced pressure to obtain the title compound EX11-(II)-A-2 (416 mg) as a white solid.

The introduction rate of the reactive substituent (N-(2-(2-(2-aminoethoxy)ethoxy)ethyl)-4-(azidomethyl)benzamide group) was 4.2 mol % (NMR integration ratio).

Example 12

Synthesis of Alginic Acid (EX12-(II)-A-2) Having Introduced N-(2-(2-aminoethoxy)ethyl)-6-(azidomethyl)nicotinamide Group

[C172]

EX12-(II)-A-2

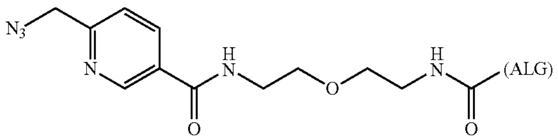

<Step 1> Synthesis of methyl 6-(azidomethyl)nicotinate (EX12-IM-1)

[C173]

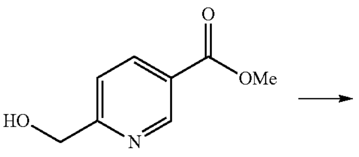

EX12-SM1

-continued

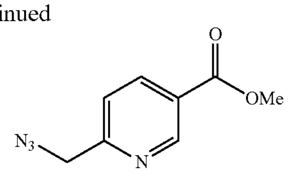

EX12-IM-1

With reference to methods known in the literature (Angew. Chem. Int. Ed. (2012) 51: 5852-5856), p-toluenesulfonyl chloride (0.68 g) and triethylamine (0.63 ml) were added under ice cooling and stirring to a mixture of commercial methyl 6-(hydroxymethyl) nicotinate [CAS: 56026-36-9] (EX12-SM1, 0.5 g) and tetrahydrofuran (5 ml). This reaction mixture was stirred for 20 hours and 30 minutes at room temperature, sodium azide (0.29 g) was added at that temperature, and the mixture was stirred for 4 hours at room temperature. After completion of the reaction, ethyl acetate (10 ml) and water (10 ml) were added to dilute the reaction solution, and the water layer was extracted 3 times with ethyl acetate (10 ml). The combined organic layer was washed successively with water (5 ml) and brine (5 ml), and dried with anhydrous sodium sulfate. The organic layer was filtered, and concentrated under reduced pressure to obtain a crude product. This crude product was purified by silica gel column chromatography (n-heptane/ethyl acetate) to obtain the title compound EX12-IM-1 (0.34 g) as a light-yellow amorphous substance.

NMR data ($CDCl_3$) (δ: ppm): 9.18 (1H, d, J=2.0 Hz), 8.33 (1H, dd, J=8.0, 2.0 Hz), 7.45 (1H, d, J=8.0 Hz), 4.57 (2H, s), 3.96 (3H, s), LC-MS: M=192, RT=0.78 (minutes), $[M+H]^+$=193

<Step 2> Synthesis of 6-(azidomethyl)nicotinic Acid (EX12-IM-2)

[C174]

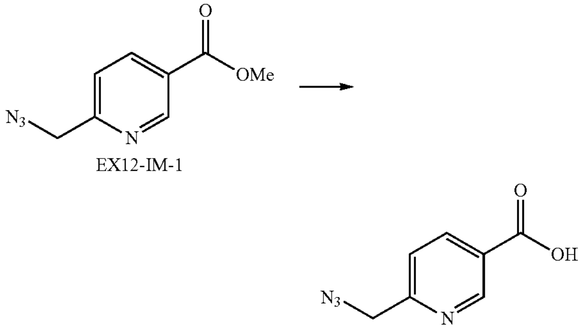

EX12-IM-1

EX12-IM-2

1-molar lithium hydroxide monohydrate (5.34 ml) was added at room temperature to a mixture of the compound EX12-IM-1 (0.342 g) obtained in <Step 1> of (Example 12) and methanol (6.84 ml), and stirred for 30 minutes at room temperature. After completion of the reaction, acetic acid (0.41 ml) was added, and the reaction solution was concentrated under reduced pressure. The residue was purified by silica gel column chromatography (n-heptane/ethyl acetate to ethyl acetate/methanol) to obtain the title compound EX12-IM-2 (0.28 g) as a light-yellow amorphous substance.

NMR data ($CD_3OD$) (δ: ppm): 9.09 (1H, d, J=2.4 Hz), 8.38 (1H, dd, J=8.0, 2.4 Hz), 7.56 (1H, d, J=8.0 Hz), 4.57 (2H, s), LC-MS: M=178, RT=0.60 (minutes), [M+H]+=179

<Step 3> Synthesis of tert-butyl (2-(2-(6-(azidomethyl)nicotinamido)ethoxy)ethyl)carbamate (EX12-IM-3)

[C175]

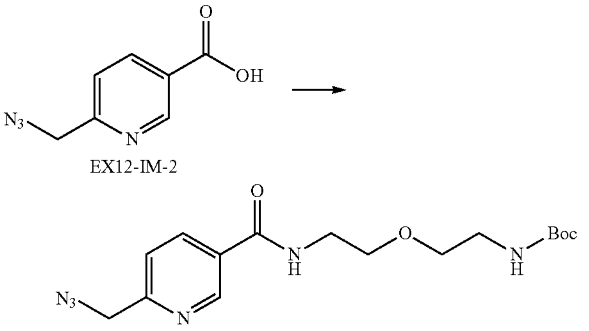

EX12-IM-2

EX12-IM-3

O-(7-azabenzotriazol-1-yl)-N,N,N'N'-tetramethyluronium hexafluorophosphate (213.43 mg) and triethylamine (156.48 µl) were added under ice cooling and stirring to a mixture of the compound 12-IM-2 (100 mg) obtained in <Step 2> of (Example 12), commercial N-(tert-butoxycarbonyl)-2-(2-aminoethoxy)ethylamine [CAS: 127828-22-2] (108.07 µl) and acetonitrile (2,000 µl), and stirred for 1 hour and 45 minutes at room temperature. N-(tert-butoxycarbonyl)-2-(2-aminoethoxy) ethylamine (54 µl) and O-(7-azabenzotriazol-1-yl)-N,N,N'N'-tetramethyluronium hexafluorophosphate (106.7 mg) were further added under stirring at room temperature, and the mixture was stirred for 17 hours at that temperature. Water (5 ml) was added to stop the reaction, and ethyl acetate (10 ml) was added. The water layer was extracted 3 times with ethyl acetate (10 ml), and dried with anhydrous sodium sulfate. The organic layer was filtered and concentrated under reduced pressure to obtain a crude product. This crude product was purified by silica gel column chromatography (n-heptane/ethyl acetate) to obtain the title compound EX12-IM-3 (187 mg) as a colorless oily compound.

NMR data ($CDCl_3$) (δ: ppm): 9.00 (1H, d, J=2.0 Hz), 8.18 (1H, dd, J=8.0, 2.0 Hz), 7.43 (1H, d, J=8.0 Hz), 6.83 (1H, br s), 4.82 (1H, br s), 4.55 (2H, s), 3.69 to 3.65 (4H, m), 3.56 (2H, t, J=5.2 Hz), 3.34 (1H, d, J=5.6 Hz), 3.32 (1H, d, J=5.6 Hz), 1.41 (9H, s), LC-MS: M=364, RT=0.78 (minutes), $[M+H]^+$=365

<Step 4> Synthesis of N-(2-(2-aminoethoxy)ethyl)-6-(azidomethyl)nicotinamide Dihydrochloride (EX12-IM-4)

[C176]

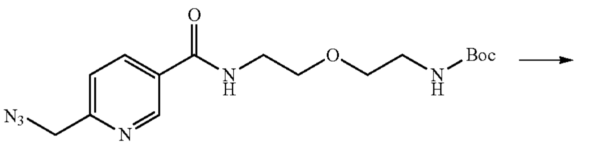

EX12-IM-3

-continued

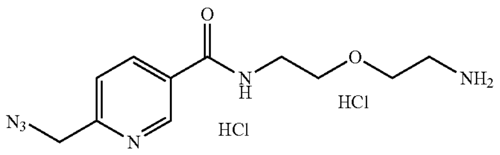

EX12-IM-4

4N-hydrogen chloride/1,4-dioxane (1.31 ml) was added under water cooling and stirring to a mixture of the compound EX12-IM-3 (0.187 g) obtained in <Step 3> of (Example 12) and 1,4-dioxane solution (1.31 ml), and stirred for 3 hours at room temperature. Diisopropyl ether (20 ml) was added to the reaction solution, and the precipitate was filtered out to obtain the title compound EX12-IM-4 (0.16 g) as an off-white solid.

NMR data (DMSO-$d_6$) (δ: ppm): 9.02 to 9.02 (1H, m), 8.80 (1H, br s), 8.27 to 8.25 (1H, m), 7.89 (3H, br s), 7.54 (1H, d, J=8.4 Hz), 4.59 (2H, s), 3.64 to 3.57 (4H, m), 3.51 to 3.47 (2H, m), 3.01 to 2.97 (2H, m), LC-MS (free amine): M=264, RT=0.49 (minutes), [M+H]+=265

<Step 5> Synthesis of Alginic Acid (EX12-(II)-A-2) Having Introduced N-(2-(2-aminoethoxy)ethyl)-6-(azidomethyl)nicotinamide Group

[C177]

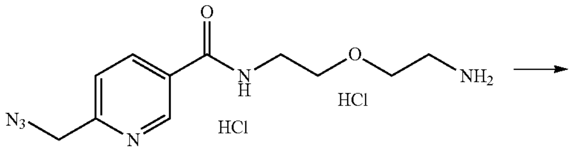

EX12-IM-4

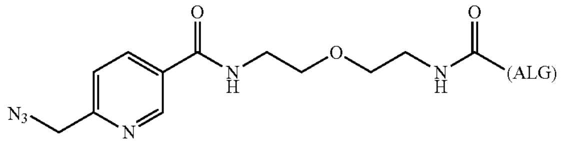

EX12-(II)-A-2

4-(4,6-dimethoxy-1,3,5-triazin-2-yl)-4-methylmorpholinium chloride (DMT-MM) (91.52 mg) and 1-molar sodium bicarbonate water (183 μl) were added under stirring at room temperature to 39.55 ml of an aqueous solution of sodium alginate (Mochida Pharmaceutical: A-2) adjusted to 1 wt %. A mixture of the compound EX12-IM-4 (30 mg) obtained in <Step 4> of (Example 12), water (1 ml) and ethanol (1 ml) was then added at the same temperature, and stirred for 4 hours at 40° C. Sodium chloride (400 mg) was added, followed by ethanol (79.1 ml), and the mixture was stirred for 30 minutes at room temperature. The resulting precipitate was collected by filtration, washed with ethanol, and dried under reduced pressure to obtain the title compound EX12-(II)-A-2 (378 mg) as a white solid.

The introduction rate of the reactive substituent (N-(2-(2-aminoethoxy)ethyl)-6-(azidomethyl)nicotinamide group) was 4.8 mol % (NMR integration ratio).

Example 13

Synthesis of Alginic Acid (EX13-(II)-A-2) Having Introduced N-(2-(2-aminoethoxy)ethyl)-4-azidobenzamide Group

[C178]

EX13-(II)-A-2

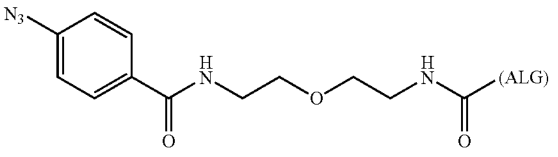

<Step 1> Synthesis of tert-butyl (2-(2-(4-azidobenzamido)ethoxy)ethyl)carbamate (EX13-IM-1)

[C179]

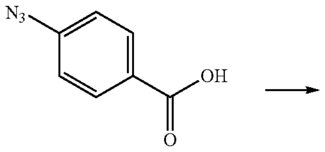

EX7-SM

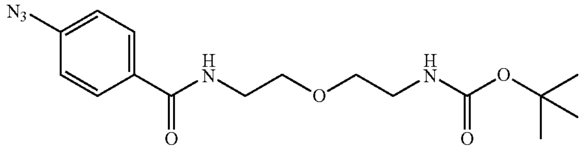

EX13-IM-1

4-azidobenzoic acid (EX7-SM, 300 mg) and tert-butyl(2-(2-aminoethoxy)ethyl)carbamate [CAS: 127828-22-2] (376 mg) were dissolved in acetonitrile (6.0 ml). O-(7-azabenzotriazol-1-yl)-N,N,N'N'-tetramethyluronium hexafluorophosphate (0.77 g) and N, N-diisopropylethylamine (707 μl) were added, and the mixture was stirred for 16 hours at room temperature. Ethyl acetate (20 ml) and water (10 ml) were added to separate the reaction solution. The organic layer was washed successively with water (10 ml) and brine (5 ml), dried with anhydrous sodium sulfate, and then concentrated under reduced pressure. The residue was purified by silica gel column chromatography (20% ethyl acetate/n-heptane to 70% ethyl acetate/n-heptane) to obtain the title compound EX13-IM-1 (673 mg) as a light-yellow gummy substance.

NMR data ($CDCl_3$) (δ: ppm): 7.83 (2H, d, J=9 Hz), 7.08 (2H, d, J=9 Hz), 6.61 (1H, brs), 4.84 (1H, brs), 3.68 to 3.64 (4H, m), 3.56 (2H, t, J=5 Hz), 3.34 (2H, q, J=5 Hz), 1.44 (9H, s)

<Step 2> Synthesis of N-(2-(2-aminoethoxy)ethyl)-4-azidobenzamide Hydrochloride (EX13-IM-2)

[C180]

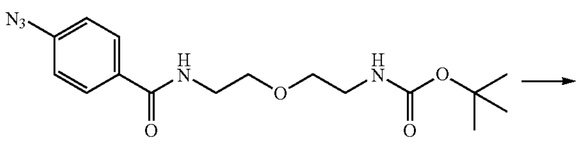

EX13-IM-1

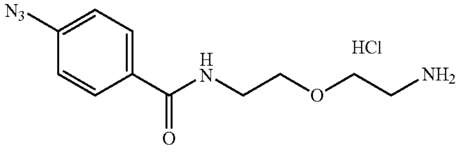

EX13-IM-2

4N-hydrogen chloride/1,4-dioxane (4.7 ml) was added under ice-water cooling to the compound EX13-IM-1 (670 mg) obtained in <Step 1> of (Example 13), and stirred for 2 hours at room temperature. Diisopropyl ether (14.0 ml) was added to the reaction solution, which was then stirred for 30 minutes. The resulting solid was collected by filtration, washed with diisopropyl ether, and dried under reduced pressure to obtain the title compound EX13-IM-2 (604 mg) as a light beige solid.

NMR data (DMSO-$d_6$) (δ: ppm): 8.61 (1H, t, J=6 Hz), 7.95 (3H, brs), 7.93 (2H, d, J=9 Hz), 7.20 (2H, d, J=9 Hz), 3.62 (2H, t, J=5 Hz), 3.57 (2H, t, J=6 Hz), 3.46 (2H, q, J=6 Hz), 3.02 to 2.93 (2H, m), LC-MS (free amine): RT=0.57 (minutes), $[M+H]^+$=250

<Step 3> Synthesis of Alginic Acid (EX13-(II)-A-2) Having Introduced N-(2-(2-aminoethoxy)ethyl)-4-azidobenzamide Group

[C181]

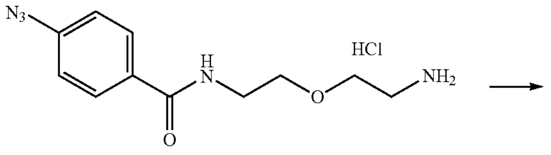

EX13-IM-2

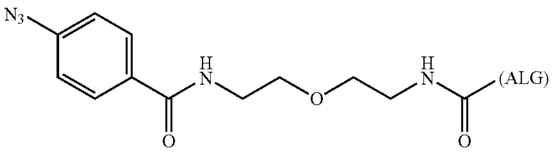

EX13-(II)-A-2

4-(4,6-dimethoxy-1,3,5-triazin-2-yl)-4-methylmorpholinium chloride (DMT-MM) (112 mg), the compound EX13-IM-2 (31 mg) obtained in <Step 2> of (Example 13) and 1-molar sodium bicarbonate water (151 μl) were added to 40 ml of an aqueous solution of sodium alginate (Mochida Pharmaceutical: A-2) adjusted to 1 wt %, and stirred for 3 hours at 30° C. Sodium chloride (0.4 g) was added, followed by ethanol (80 ml), and the mixture was stirred for 30 minutes at room temperature. The resulting precipitate was collected by filtration, washed with ethanol, and dried under reduced pressure to obtain the title compound EX13-(II)-A-2 (400 mg) as a white solid.

The introduction rate of the reactive substituent (N-(2-(2-aminoethoxy)ethyl)-4-azidobenzamide group) was 3.9 mol % (NMR integration ratio).

Example 14

Synthesis of Alginic Acid (EX14-(II)-A-2) Having Introduced N-(2-(2-(2-aminoethoxy)ethoxy)ethyl)-4-azidobenzamide Group

[C182]

EX14-(II)-A-2

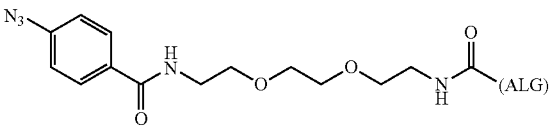

<Step 1> Synthesis of tert-butyl (2-(2-(2-(4-azidobenzamido)ethoxy)ethoxy)ethyl)carbamate (EX14-IM-1)

[C183]

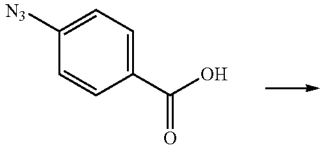

EX7-SM

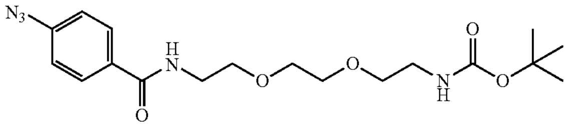

EX14-IM-1

4-azidobenzoic acid (EX7-SM, 300 mg) and tert-butyl(2-(2-(2-aminoethoxy)ethoxy)ethyl)carbamate (457 mg) were dissolved in acetonitrile (6.0 ml). O-(7-azabenzotriazol-1-yl)-N,N,N'N'-tetramethyluronium hexafluorophosphate (0.77 g) and N, N-diisopropylethylamine (707 μl) were added, and the mixture was stirred for 16 hours at room temperature. Ethyl acetate (20 ml) and water (10 ml) were added to separate the reaction solution. The organic layer was washed successively with water (10 ml) and brine (5 ml), dried with anhydrous sodium sulfate, and then concentrated under reduced pressure. The residue was purified by silica gel column chromatography (40% ethyl acetate/n-heptane to 90% ethyl acetate/n-heptane) to obtain the title compound EX14-IM-1 (603 mg) as a light-yellow oily substance.

NMR data (DMSO-$d_6$) (δ: ppm): 8.53 (1H, t, J=6 Hz), 7.89 (2H, d, J=9 Hz), 7.19 (2H, d, J=9 Hz), 6.76 (1H, t, J=5 Hz), 3.55 to 3.47 (6H, m), 3.42 to 3.33 (4H, m), 3.04 (2H, q, J=6 Hz), 1.36 (9H, s)

<Step 2> Synthesis of N-(2-(2-(2-aminoethoxy)ethoxy)ethyl)-4-azidobenzamide Hydrochloride (EX14-IM-2)

[C184]

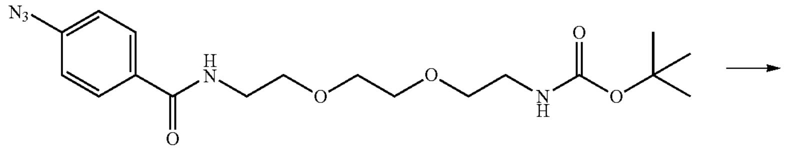

EX14-IM-1

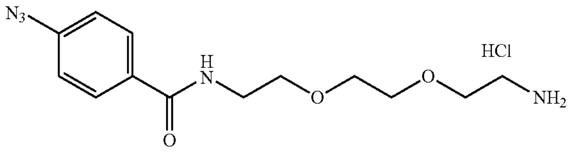

EX14-IM-2

4N-hydrogen chloride/1,4-dioxane solution (4.2 ml) was added under ice-water cooling to the compound (EX14-IM-1, 600 mg) obtained in <Step 1> of (Example 14), and stirred at room temperature for 2 hours. Diisopropyl ether (12.0 ml) was added to the reaction solution, which was then stirred for 30 minutes at room temperature. The solvent was removed by decantation, and the residue was washed with diisopropyl ether. The resulting residue was dried under reduced pressure to obtain the title compound EX14-IM-2 (596 mg) as a beige gummy substance.

NMR data (DMSO-$d_6$) (δ: ppm): 8.62 (1H, t, J=6 Hz), 7.97 (3H, brs), 7.91 (2H, d, J=9 Hz), 7.20 (2H, d, J=9 Hz), 3.62 to 3.51 (8H, m), 3.42 (2H, q, J=6 Hz), 2.97 to 2.89 (2H, m), LC-MS (free amine): RT=0.58 (minutes), $[M+H]^+$=294

<Step 3> Synthesis of Alginic Acid (EX14-(II)-A-2) Having Introduced N-(2-(2-(2-aminoethoxy)ethoxy)ethyl)-4-azidobenzamide Group

[C185]

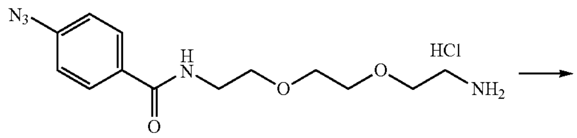

EX14-IM-2

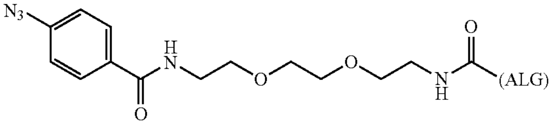

EX14-(II)-A-2

4-(4,6-dimethoxy-1,3,5-triazin-2-yl)-4-methylmorpholinium chloride (DMT-MM) (112 mg), an ethanol (4.0 ml) solution of the compound EX14-IM-2 (45 mg) obtained in <Step 2> of (Example 14), and 1-molar sodium bicarbonate water (151 μl) were added to 40 ml of an aqueous solution of sodium alginate (Mochida Pharmaceutical: A-2) adjusted to 1 wt %, and stirred for 3 hours at 30° C. Sodium chloride (0.4 g) was added, followed by ethanol (80 ml), and the mixture was stirred for 30 minutes at room temperature. The resulting precipitate was collected by filtration, washed with ethanol, and dried under reduced pressure to obtain the title compound EX14-(II)-A-2 (408 mg) as a white solid.

The introduction rate of the reactive substituent (N-(2-(2-(2-aminoethoxy)ethoxy)ethyl)-4-azidobenzamide group) was 4.2 mol % (NMR integration ratio).

Example 15

Synthesis of Alginic Acid (EX15-(I)-A-2) Having Introduced N-(2-(2-aminoethoxy)ethyl)-2-(cyclooct-2-yn-1-yloxy)acetamide Group

[C186]

EX15-(I)-A-2

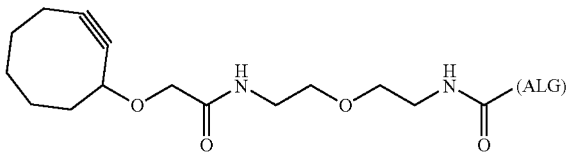

<Step 1> Synthesis of tert-butyl (2-(2-(2,2,2-trifluoroacetamido)ethoxy)ethyl)carbamate (EX15-IM-1)

[C187]

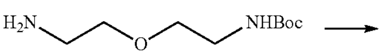

EX9-SM1

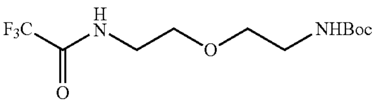

EX15-IM-1

Ethyl trifluoroacetate (0.6 ml) was dripped into a tetrahydrofuran (4.0 ml) solution of tert-butyl(2-aminoethyl)carbamate (EX9-SM1, 1.0 g) [CAS: 57260-73-8]. The reaction mixture was stirred for 3.5 hours at room temperature.

The reaction solution was concentrated under reduced pressure to obtain the title compound EX15-IM-1 (1.5 g) as a colorless oily substance.

NMR data ($CDCl_3$) (δ: ppm): 7.01 (1H, brs), 4.84 (1H, brs), 3.62 to 3.51 (6H, m), 3.31 (2H, q, J=5 Hz), 1.45 (9H, s)

<Step 2> Synthesis of N-(2-(2-aminoethoxy)ethyl)-2,2,2-trifluoroacetamide Hydrochloride (EX15-IM-2)

[C188]

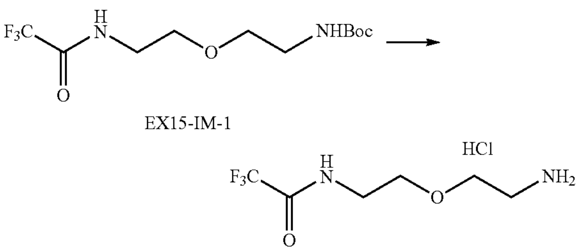

EX15-IM-1

EX15-IM-2

4N-hydrogen chloride/1,4-dioxane solution (10.3 ml) was added under ice-water cooling to the compound EX15-IM-1 (1.5 g) obtained in <Step 1> of (Example 15), and stirred for 1 hour at room temperature. Diisopropyl ether (30 ml) was added to the reaction solution, which was then stirred for 30 minutes at room temperature. The solvent was distilled off under reduced pressure, and the reaction solution was azeotropically distilled with diisopropyl ether and dried under reduced pressure to obtain the title compound EX15-IM-2 (1.3 g) as a colorless oily substance.

NMR data (DMSO-$d_6$) (δ: ppm): 9.55 (1H, brs), 8.05 (3H, brs), 3.61 (2H, d, J=5 Hz), 3.54 (2H, t, J=6 Hz), 3.39 (2H, q, J=6 Hz), 3.00 to 2.91 (2H, m)

<Step 3> Synthesis of N-(2-(2-(2-(cyclooct-2-yn-1-yloxy)acetamido)ethoxy)ethyl)-2,2,2-trifluoroacetamide (EX15-IM-3)

[C189]

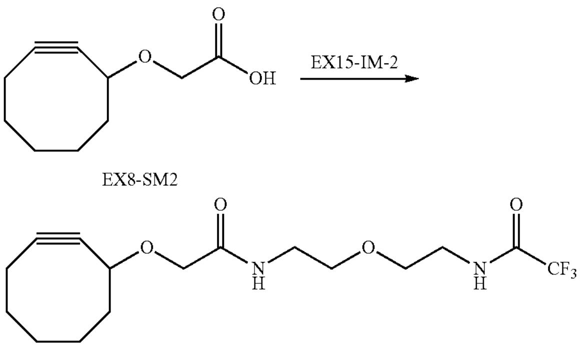

EX8-SM2

EX15-IM-3

A carboxylic acid (EX8-SM2, 300 mg) synthesized according to methods known in the literature (Org. Process Res. Dev. (2018) 22: 108-110) and the compound (443 mg) obtained in <Step 2> of (Example 14) were dissolved in acetonitrile (6.0 ml). O-(7-azabenzotriazol-1-yl)-N,N,N'N'-tetramethyluronium hexafluorophosphate (0.75 g) and N,N-diisopropylethylamine (920 μl) were added, and the mixture was stirred for 2.5 hours at room temperature. Ethyl acetate (20 ml) and water (10 ml) were added to separate the reaction solution. The organic layer was washed successively with water (10 ml) and brine (5 ml), dried with anhydrous sodium sulfate, and then concentrated under reduced pressure. The residue was purified by silica gel column chromatography (50% ethyl acetate/n-heptane to 70% ethyl acetate/n-heptane) to obtain the title compound EX15-IM-3 (469 mg) as a colorless gummy substance.

NMR data (DMSO-$d_6$) (δ: ppm): 9.45 (1H, brs), 7.61 (1H, t, J=6 Hz), 4.29 to 4.25 (1H, m), 3.87 (2H, d, J=15 Hz), 3.75 (1H, d, J=15 Hz), 3.50 (2H, t, J=6 Hz), 3.43 (2H, t, J=6 Hz), 3.37 to 3.31 (2H, m), 3.24 (2H, q, J=6 Hz), 2.27 to 2.03 (3H, m), 1.96 to 1.69 (4H, m), 1.67 to 1.50 (2H, m), 1.43 to 1.35 (1H, m)

<Step 4> Synthesis of N-(2-(2-aminoethoxy)ethyl)-2-(cyclooct-2-yn-1-yloxy) acetamide (EX15-IM-4)

[C190]

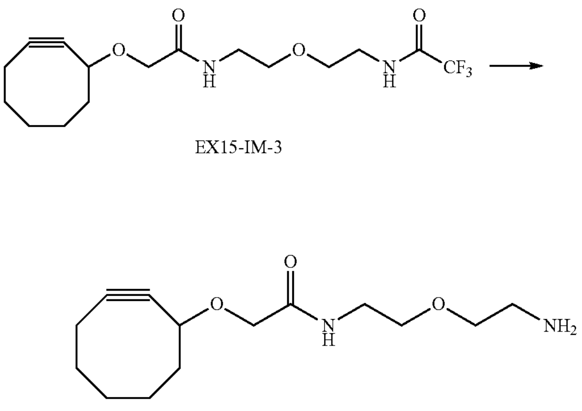

EX15-IM-3

EX15-IM-4

A water (0.99 ml) solution of potassium carbonate (103 mg) was added to a methanol (3.0 ml) solution of the compound EX15-IM-3 (220 mg) obtained in <Step 3> of (Example 15), and stirred for 4.5 hours at room temperature. The methanol was distilled off under reduced pressure, water (2 ml) was added, and the mixture was saturated with sodium chloride. This was extracted with ethyl acetate (15 ml, 10 ml×4) and dried with anhydrous sodium sulfate, and the solvent was distilled off under reduced pressure. The residue was dissolved in ethyl acetate (10 ml), insoluble matter was removed by filtration, and the product was concentrated under reduced pressure to obtain the title compound EX15-IM-4 (140 mg) as a light yellow gummy substance.

NMR data ($CDCl_3$) (δ: ppm): 6.89 (1H, brs), 4.27 to 4.22 (1H, m), 4.07 (1H, d, J=15 Hz), 3.88 (1H, d, J=15 Hz), 3.58 to 3.47 (6H, m), 2.87 (2H, t, J=5 Hz), 2.31 to 2.10 (3H, m), 2.03 to 1.77 (4H, m), 1.73 to 1.59 (2H, m), 1.51 to 1.43 (1H, m), LC-MS: RT=0.60 (minutes), $[M+H]^+$=269

<Step 5> Synthesis of Alginic Acid (EX15-(I)-A-2) Having Introduced N-(2-(2-aminoethoxy)ethyl)-2-(cyclooct-2-yn-1-yloxy)acetamide Group

[C191]

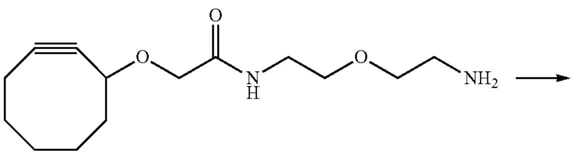

EX15-IM-4

-continued

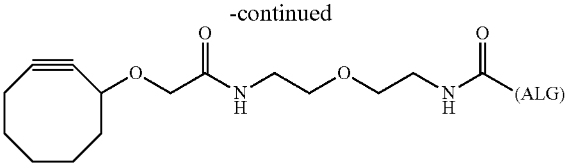

EX15-(I)-A-2

4-(4,6-dimethoxy-1,3,5-triazin-2-yl)-4-methylmorpholinium chloride (DMT-MM) (112 mg), an ethanol (4.0 ml) solution of the compound EX15-IM-4 (30 mg) obtained in <Step 4> of (Example 15), and 1-molar sodium bicarbonate water (101 µl) were added in that order under stirring at room temperature to 40 ml of an aqueous solution of sodium alginate (Mochida Pharmaceutical: A-2) adjusted to 1 wt %, and stirred for 3 hours at 30° C. Sodium chloride (0.4 g) was added to the reaction solution, followed by ethanol (80 ml), and the reaction solution was stirred for 30 minutes. The resulting precipitate was collected by filtration, washed with ethanol, and dried under reduced pressure to obtain the title compound EX15-(I)-A-2 (410 mg) as a white solid.

The introduction rate of the reactive substituent (N-(2-(2-aminoethoxy)ethyl)-2-(cyclooct-2-yn-1-yloxy)acetamide group) was 3.2 mol % (NMR integration ratio).

TABLE 12

| Example | Measurement wavelength (nm) | Molecular weight (Da) | Weight-average molecular weight (Da) | Introduction rate (mol %) |
|---|---|---|---|---|
| 1a | 280 | 12,000 to 2,650,000 | 1,530,000 | 6.9 (*) |
| 1b | 280 | 5,000 to 2,620,000 | 1,150,000 | 6.5 (*) |
| 1c | 280 | 27,000 to 2,660,000 Da | 1,710,000 | 6.6 (*) |
| 1d | 288 | 3,730 to 2,850,000 | 1,410,000 | 4.9 (*) |
| 1e | 287 | 13,700 to 2,520,000 | 1,400,000 | 0.8 (*) |
| 1f | 287 | 2,230 to 2,570,000 | 1,420,000 | 1.9 (*) |
| 2 | Differential refractometer | 6,000 to 2,350,000 Da | 920,000 Da | 5.8 (*) |
| 3a | 255 | 15,000 to 2,530,000 | 1,510,000 | 6.1 (*) |
| 3b | 255 | 5,000 to 2,590,000 | 1,140,000 | 9.4 (*) |
| 3c | 255 | 18,000 to 2,690,000 | 1,650,000 | 6.9 (*) |
| 3d | 249 | 7,630 to 2,590,000 | 1,420,000 | 3.7 (*) |
| 3e | 249 | 2,290 to 2,560,000 | 1,410,000 | 0.6 (*) |
| 3f | 249 | 11,800 to 2,540,000 | 1,420,000 | 1.5 (*) |
| 4 | 255 | 10,000 to 2,850,000 | 1,460,000 | 4.3 (*) |
| 5a | 255 | 11,000 to 2,660,000 | 1,530,000 | 9.4 (*) |
| 5b | 232 | 5,190 to 2,660,000 | 1,390,000 | 11 (*) |
| 6 | 287 | 2,080 to 2,570,000 | 1,400,000 | 2.7 (*) |
| 7a | 267 | 6,430 to 2,590,000 | 1,410,000 | 5.1 (*) |
| 7b | 267 | 1,820 to 2,560,000 | 1,410,000 | 2.0 (*) |
| 8 | 215 | 1,850 to 2,830,000 | 1,380,000 | 4.46 (*) |
| 9a | Differential refractometer | 13,000 to 2,820,000 | 1,420,000 | 4.3 (*) |
| 9b | Differential refractometer | 13,000 to 2,590,000 | 1,410,000 | 4.2 (*) |
| 9c | Differential refractometer | 13,000 to 2,670,000 | 1,410,000 | 2.1 (*) |
| 10 | 230 | 7,740 to 2,660,000 | 1,430,000 | 4.7 (*) |
| 11 | 230 | 7,120 to 2,710,000 | 1,450,000 | 4.2 (*) |
| 12 | 270 | 7,680 to 2,590,000 | 1,410,000 | 4.8 (*) |
| 13 | 270 | 5,130 to 2,690,000 | 1,410,000 | 3.9 (*) |
| 14 | 270 | 5,020 to 2,670,000 | 1,430,000 | 4.2 (*) |
| 15 | Differential refractometer | 13,000 to 3,640,000 | 1,400,000 | 3.2 (*) |

(*) NMR integration ratio

[Measuring Introduction Rate of Reactive Group or Complementary Reactive Group]

The introduction rate of the reactive group or complementary reactive group is a percentage value representing the number of introduced reactive groups or complementary reactive groups relative to the total uronic acid monosaccharide units that are repeating units of the alginic acid.

In these examples, the introduction rate of the reactive group or complementary reactive group (mol %) is calculated based on the 1H-NMR integration ratio. An amount of alginic acid necessary for calculating the introduction rate is measured by the carbazole-sulfuric acid method using a calibration curve, and the amount of the reactive group or complementary reactive group is measured by the absorbance measurement method using a calibration curve.

[Molecular Weight Measurement]

The alginic acid solids having introduced reactive groups or complementary reactive groups obtained in the examples were each dissolved in 10 mmol/L phosphate buffer, (pH 7.4) containing 0.15 mol/L NaCl to prepare 0.1% or 0.2% solutions, which were then passed through a polyether sulfone filter (Minisart High Flow Filter, Sartorius) with a pore size of 0.22 microns to remove insoluble matter, after which samples for gel filtration were prepared. The spectrum of each sample was measured with a DU-800 spectrophotometer (Beckman-Coulter), and the measurement wavelength for each compound in gel filtration was determined. A differential refractometer was used for compounds lacking characteristic absorption wavelengths.

200 μl of each sample for gel filtration was supplied to a Superose 6 Increase 10/300 GL column (GE Health Care Sciences). Gel filtration was performed at room temperature at a flow rate of 0.8 ml/min using an AKTA Explorer 10S as the chromatograph unit and 10 mmol/L phosphate buffer, (pH 7.4) containing 0.15 mol/L NaCl as the developing solvent. An elution profile was prepared for each sample by monitoring absorbance at the wavelength determined for that compound. The resulting chromatogram was analyzed with Unicorn 5.31 software (GE Health Care Sciences) to determine the peak range.

To determine the molecular weights of the alginic acids having introduced reactive groups or complementary reactive groups, gel filtration was performed using blue dextran (molecular weight 2,000,000 Da, SIGMA), thyroglobulin (molecular weight 669,000 Da, GE Health Care Sciences), ferritin (molecular weight 440,000 Da, GE Health Care Sciences), aldolase (molecular weight 158,000 Da, GE Health Care Sciences), conalbumin (molecular weight 75,000 Da, GE Health Care Sciences), ovalbumin (molecular weight 44,000 Da, GE health Care Sciences), ribonuclease A (molecular weight 13,700 Da, GE Health Care Sciences) and aprotinin (molecular weight 6,500 Da, GE Health Care Sciences) as standard substances under the same conditions used for the alginic acids having introduced reactive groups or complementary reactive groups, and the elution volume of each component was determined with Unicorn software. The elution volume of each component was plotted on the horizontal axis and the logarithm of the molecular weight on the vertical axis, and a calibration curve was prepared by linear regression. Two curves were prepared, one for blue dextran to ferritin and one for ferritin to aprotinin.

The calibration curves were used to calculate the molecular weight (Mi) at elution time i in the chromatogram obtained above. Absorbance at elution time i was then read and given as Hi. The weight-average molecular weight (Mw) was determined by the following formula from these data.

$$Mw = \frac{\sum_{i=1}^{\infty}(Hi \times Mi)}{\sum_{i=1}^{\infty} Hi} \quad \text{[Math. 1]}$$

[Measuring Gel Stability]

(Measuring Gel Stability (1))

The alginic acid derivative (EX1-(I)-A-2) obtained in (Example 1a) and the alginic acid derivative (EX3-(II)-A-2) obtained in (Example 3a) were each dissolved in water to a concentration of 1 wt % to obtain an aqueous alginic acid solution 1-1 and an aqueous alginic acid solution 2-1. The aqueous alginic acid solution 1-1 and aqueous alginic acid solution 2-1 were mixed in equal amounts, this mixed aqueous solution was placed in a syringe equipped with an 18-gauge needle, this syringe was attached to a syringe pump set to a flow rate of 1 ml/minute, and the solution was dripped for 30 seconds into a 30 mmol/L calcium chloride solution, which was then stirred for 5 minutes to obtain an alginic acid gel. This gel was washed once with 10 ml of phosphate-buffered saline (PBS), and then left standing for 10 minutes at 37° C. in PBS to perform chemical crosslinking and obtain a chemically crosslinked and ionically crosslinked alginic acid gel. 20 ml of PBS was added to this gel and shaken at 37° C., the aqueous solution was collected over time, and PBS was supplemented in the same amount as the collected amount. Upon completion of testing, 5 μl of alginate lyase (Nippon Gene, 319-08261) was added to the test solution, which was then shaken for 2 hours at 37° ° C. to completely collapse the gel, and the aqueous solution was collected. The alginic acid concentration in the collected aqueous solution was measured by the carbazole-sulfuric acid method, the alginic acid concentration in the aqueous solution at each point in time was corrected by the previously collected alginic acid concentration, the resulting value was divided by the total alginic acid concentration calculated from the alginic acid concentration at all time points and the alginic acid concentration after completion of testing, and the resulting value represented as a percentage was given as the gel collapse rate and used as an indicator of gel stability. Crosslinked alginic acid gels (beads) were also prepared in the same way as controls using alginic acid (A-2), (EX1-(I)-A-2) with (A-2), and (A-2) with (EX3-(II)-A-2), and the gel collapse rate of each was measured.

The results are shown in FIG. 1. While the crosslinked alginic acid gels prepared as controls using (A-2), (EX1-(I)-A-2) with (A-2), and (A-2) with (EX3-(II)-A-2) dissolved almost completely within 4 hours, the crosslinked alginic acid prepared using the alginic acid derivatives (EX1-(I)-A-2) and (EX3-(II)-A-2) had further improved gel stability, and did not collapse even after 144 hours. This suggests that when crosslinks are formed by a Huisgen reaction, the resulting structure maintains its structure long-term even in a solution lacking calcium ions (below the physiological concentration for a living body).

In FIG. 1, the collapse rate on the vertical axis is the relative collapse rate (%). Given 100% as the maximum value of the actual measured collapse rate (alginic acid gel prepared with only (A-2): measured value after 8 hours), the collapse rate at each point is given as a relative value relative to this maximum collapse rate.

(Measuring Gel Stability (2))

The alginic acid derivative (EX1-(I)-B-2a) obtained in (Example 1d), the alginic acid derivative (EX3-(II)-B-2a) obtained in (Example 3d), the alginic acid derivative (EX7-(II)-B-2a) obtained in (Example 7a) and the alginic acid derivative (EX8-(I)-B-2) obtained in (Example 8) were each dissolved in water to a concentration of 1.0 w/w % to obtain aqueous alginic acid solutions (1d-1), (3d-1), (7a-1) and (8a-1). Next, an equivalent mixed solution of the aqueous alginic acid solutions (1d-1) and (3d-1), an equivalent mixed solution of the aqueous alginic acid solutions (1d-1) and (7a-1), an equivalent mixed solution of the aqueous alginic acid solutions (8a-1) and (3d-1) and an equivalent mixed solution of the aqueous alginic acid solutions (8a-1) and (7a-1) were prepared, and these mixed solutions were used to prepare chemically and ionically crosslinked alginic acid gels (beads) (A1, B1, C1 and D1) by the alginic acid gel (bead) preparation method described below (see Table 13).

[Alginic Acid Gel (Bead) Preparation Method]

Each of the mixed solutions prepared above was placed in a syringe equipped with an 18-gauge needle, this syringe was attached to a syringe pump set to a flow rate of 1 ml/minute, and the solution was dripped for 30 seconds into a 30 mmol/L calcium chloride solution, which was then stirred for 5 minutes to obtain an alginic acid gel (bead). This gel was washed once with 10 ml of phosphate-buffered saline (PBS), and then chemically crosslinked by still standing for 10 minutes at 37° C. in pure water to obtain a chemically and ionically crosslinked alginic acid gel (bead).

TABLE 13

| Chemically and ionically crosslinked alginic acid gel (bead) | Contents of mixed alginate solution |
|---|---|
| A1 | Aqueous alginic acid solution (1d-1) and Aqueous alginic acid solution (3d-1) |
| B1 | Aqueous alginic acid solution (1d-1) and Aqueous alginic acid solution (7a-1) |
| C1 | Aqueous alginic acid solution (8a-1) and Aqueous alginic acid solution (3d-1) |
| D1 | Aqueous alginic acid solution (8a-1) and Aqueous alginic acid solution (7a-1) |

[Measuring Stability of Alginic Acid Gels (A1 to D1)]

19.5 ml of PBS was added to each of the chemically and ionically crosslinked alginic acid gels (beads) A1 to D1 obtained above and shaken at 37° C., the aqueous solution was collected after 1, 2, 4, 8, 24, 48, 72 and 144 hours, and PBS was supplemented in the same amount as the collected amount. After completion of testing, 20 μl of alginate lyase (Creative Enzymes, NATE-1563) was added to the test solution, which was then shaken overnight at 37° ° C. to completely collapse the gel, and the aqueous solution was collected. The alginic acid concentration in the collected aqueous solution was measured by the carbazole-sulfuric acid method, the alginic acid concentration in the aqueous solution at each point in time was divided by the total alginic acid concentration calculated from the alginic acid concentration at all time points and the alginic acid concentration after completion of testing, and the resulting value represented as a percentage was given as the gel collapse rate and used as an indicator of gel stability. An alginic acid gel (bead) (REF) was also prepared as a control by the above methods using an alginic acid (B-2) having no introduced reactive group, and the collapse rate was measured.

Figure 4:
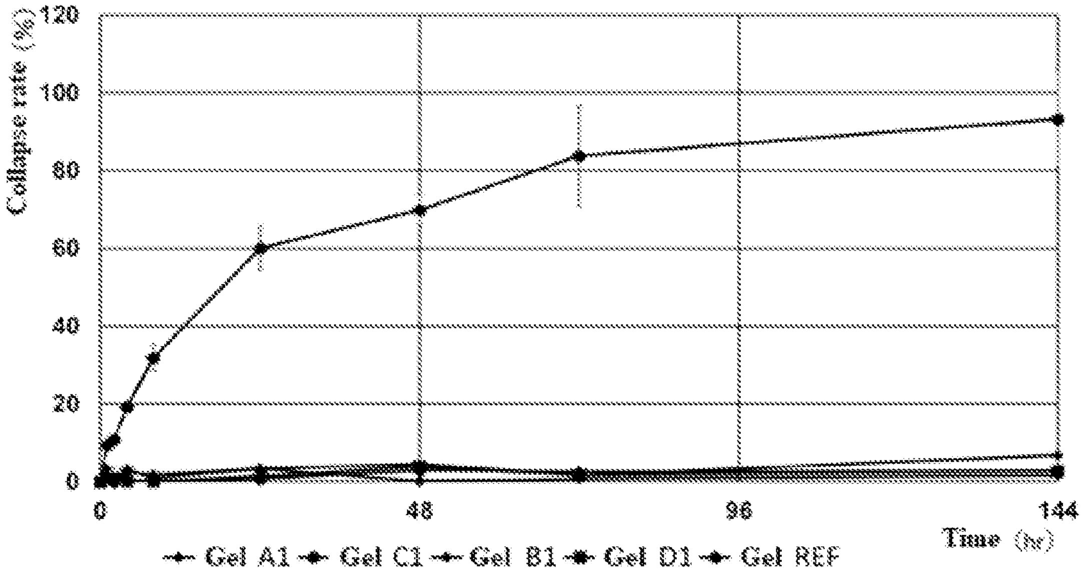
FIG. 4 shows an evaluation of the stability of gels of crosslinked alginic acid structures.

The results are shown in FIG. 4. While the alginic acid gel (gel REF) prepared as a control using an alginic acid (B-2) having no introduced reactive group exhibited at least 90% collapse after 144 hours, the crosslinked alginic acid gels (beads) (A1 to D1) obtained using the alginic acid derivatives (EX1-(I)-B-2a, EX3-(II)-B-2a, EX7-(II)-B-2a and EX8-(I)-B-2) had more improved gel stability, and did not collapse even after 144 hours. This suggests that when crosslinks are formed by a Huisgen reaction, the resulting structure maintains its structure long-term even in a solution lacking calcium ions (below the physiological concentration for a living body).

(Measuring Gel Stability (3): Measuring Gel Stability in the Presence of EDTA)

19.5 ml of 5 mM ethylenediamine tetraacetic acid dipotassium salt dihydrate (EDTA·2K)/PBS solution was added to each of the chemically and ionically crosslinked alginic acid gels (beads) (A1 to D1) obtained by the method of measuring gel stability (2) above and shaken at 37° ° C., and the aqueous solution was collected after 24 hours to obtain EDTA-treated crosslinked alginic acid gels (beads) (A2 to D2). Upon completion of testing 10 μl of alginate lyase (Creative Enzymes, NATE-1563) was added to the test solution, which was then shaken overnight at 37° C. to completely collapse the gel, and the aqueous solution was collected. The alginic acid concentration in the collected aqueous solution was measured by the carbazole-sulfuric acid method, the alginic acid concentration in the aqueous solution after 24 hours was divided by the total alginic acid concentration calculated from the alginic acid concentration after 24 hours and the alginic acid concentration after completion of testing, and the resulting value represented as a percentage was given as the gel collapse rate and used as an indicator of gel stability. An alginic acid gel (bead) (REF2) was also prepared as a control by the above methods using an alginic acid (B-2) having no introduced reactive group, and the collapse rate was measured.

TABLE 14

| Alginic acid gel | | A2 | B2 | C2 | D2 | REF2 |
|---|---|---|---|---|---|---|
| Collapse rate | 0 (h) | 0 | 0 | 0 | 0 | 0 |
| (%) | After 24 (h) | 1 | 0.3 | 0 | 1.3 | 121.8 |

The results are shown in Table 14. While the crosslinked alginic acid gel (bead) (REF2) obtained by EDTA treating an alginic acid gel prepared as a control using an alginic acid (B-2) with no introduced reactive group collapsed 100% within 24 hours, the crosslinked alginic acid gels (beads) (A2 to D2) obtained by EDTA treating the crosslinked alginic acid gels (beads) (A1 to D1) obtained using the alginic acid derivatives (EX1-(I)-B-2a, EX3-(II)-B-2a, EX7-(II)-B-2a and EX8-(I)-B-2) had more improved gel stability, and did not collapse even after 24 hours. This suggests that when chemical crosslinks are formed by a Huisgen reaction, the resulting structure (bead) maintains its structure long-term even without ionic crosslinking by calcium ions.

(Measuring Gel Stability (4))

The alginic acid with introduced reactive substituent (EX1-(I)-A-2b) obtained in (Example 1g), the alginic acid with introduced reactive substituent (EX3-(II)-A-2b) obtained in (Example 3g), the alginic acid with introduced reactive substituent (EX5-(II)-A-2b) obtained in (Example 5c), the alginic acid with introduced reactive substituent (EX7-(II)-A-2) obtained in (Example 7c) and the alginic acid with introduced reactive substituent (EX9-(I)-A-2) obtained in (Example 9a) were each dissolved in water to a concentration of 1.0% to prepare aqueous alginic acid solutions (1g-1), (3g-1), (5c-1), (7c-1) and (9a-1). The aqueous alginic acid solutions were mixed in equal amounts combining (9a-1) with (5c-1), (9a-1) with (7c-1), (9a-1) with (3g-1) and (1g-1) with (3g-1), each mixed solution was placed in a separate syringe equipped with an 18-gauge needle, this syringe was attached to a syringe pump set to a flow rate of 1 ml/minute, and the solution was dripped for 30 seconds into a 30 mmol/L calcium chloride solution, which was then stirred for 5 minutes to obtain an alginic acid gel. Each gel was washed once with 10 ml of PBS, and then left standing for 10 minutes at 37° C. in PBS to perform chemical crosslinking and obtain a chemically crosslinked alginic acid gel. 19.5 ml of PBS was added to each gel and shaken at 37° ° C., the aqueous solution was collected over time, and PBS was supplemented in the same amount as the collected amount. Upon completion of testing, 10 μl of alginate lyase (Nippon Gene, 319-08261) was added to the test solution, which was then shaken overnight at 37° C. to completely collapse the gel, and the aqueous solution was collected. The alginic acid concentration in the collected aqueous solution was measured by the carbazole-sulfuric acid method, the alginic acid concentration in the aqueous solution at each point in time was corrected by the previously collected alginic acid concentration, the resulting value was divided by the total alginic acid concentration calculated from the alginic acid concentration at all time points and the alginic acid concentration after completion of testing, and the resulting value represented as a percentage was given as the gel collapse rate and used as an indicator of gel stability.

Figure 8:
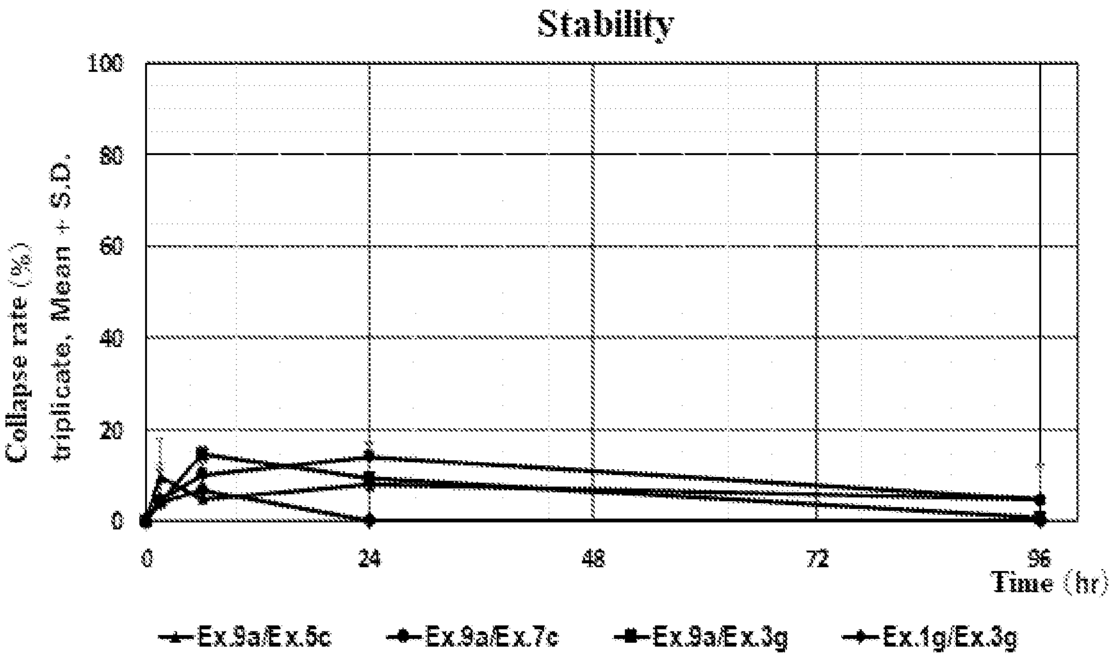
FIG. 8 shows an evaluation of the stability of gels of crosslinked alginic acid structures.

The results are shown in FIG. 8. The stability (gel collapse rate) of each of the above crosslinked alginic acid gels (beads) was 0.3% to 4.8% after 96 hours, suggesting that they maintained their structures long-term (the gel prepared using (Example 1g) and (Example 3g) was used as a control, and had a value of 0.3% after 96 hours).

Measuring Gel Stability (5): Measuring Gel Stability in the Presence of EDTA

The alginic acid with introduced reactive substituent (EX1-(I)-A-2b) obtained in (Example 1g), the alginic acid with introduced reactive substituent (EX3-(II)-A-2b) obtained in (Example 3g), the alginic acid with introduced reactive substituent (EX5-(II)-A-2b) obtained in (Example 5c), the alginic acid with introduced reactive substituent (EX7-(II)-A-2) obtained in (Example 7c) and the alginic acid with introduced reactive substituent (EX9-(I)-A-2) obtained in (Example 9a) were each dissolved in water to a concentration of 1.0% to prepare aqueous alginic acid solutions (1g-1), (3g-1), (5c-1), (7c-1) and (9a-1). The aqueous alginic acid solutions were mixed in equal amounts combining (9a-1) with (5c-1), (9a-1) with (7c-1), (9a-1) with (3g-1) and (1g-1) with (3g-1), each mixed solution was placed in a separate syringe equipped with an 18-gauge needle, this syringe was attached to a syringe pump set to a flow rate of 1 ml/minute, and the solution was dripped for 30 seconds into a 30 mmol/L calcium chloride solution, which was then stirred for 5 minutes to obtain an alginic acid gel. Each gel was washed once with 10 ml of PBS, and then left standing for 10 minutes at 37° C. in PBS to perform chemical crosslinking and obtain a chemically crosslinked alginic acid gel.

19.5 ml of 5 mM ethylenediamine tetraacetic acid dipotassium salt dihydrate (EDTA·2K)/physiological saline was added to each gel and shaken at 37° C., the aqueous solution was collected over time, and the gel was replenished with 5 mM EDTA·2K/physiological saline in the same amount as the collected amount. Upon completion of testing (after 24 hours), 30 μl of alginate lyase (Nippon Gene, 319-08261) was added to the test solution, which was then shaken overnight at 37° ° C. to completely collapse the gel, and the aqueous solution was collected. The alginic acid concentration in the collected aqueous solution was measured by the carbazole-sulfuric acid method, the alginic acid concentration in the aqueous solution at each point in time was corrected by the alginic acid concentration of the previously collected solution, the resulting value was divided by the total alginic acid concentration calculated from the alginic acid concentration at all time points and the alginic acid concentration after completion of testing, and the resulting value represented as a percentage was given as the gel collapse rate and used as an indicator of gel stability.

Figure 9:
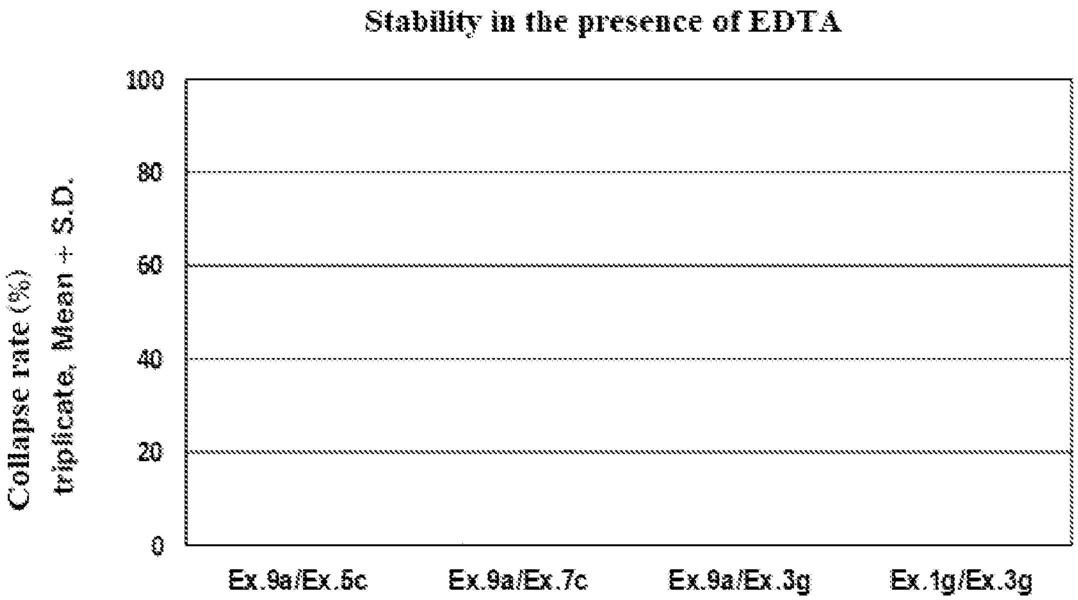
FIG. 9 shows an evaluation of the stability of gels of crosslinked alginic acid structures in the presence of EDTA.

The results are shown in FIG. 9. The crosslinked alginic acid gels (beads) did not collapse even after 24 hours, confirming gel stability. This suggests that when chemical crosslinks are formed by a Huisgen reaction, the resulting structure (bead) maintains its structure long-term.

(Measuring Gel Stability (6))

The alginic acid with introduced reactive substituent (EX1-(I)-A-2b) obtained in (Example 1g), the alginic acid with introduced reactive substituent (EX3-(II)-A-2b) obtained in (Example 3g), the alginic acid with introduced reactive substituent (EX5-(II)-A-2b) obtained in (Example 5c), the alginic acid with introduced reactive substituent (EX7-(II)-A-2) obtained in (Example 7c) and the alginic acid with introduced reactive substituent (EX8-(I)-A-2) obtained in (Example 8b) were each dissolved in water to a concentration of 1.0% to prepare aqueous alginic acid solutions (1g-1), (3g-1), (5c-1), (7c-1) and (8b-1). The aqueous alginic acid solutions were mixed in equal amounts combining (1g-1) with (5c-1), (1g-1) with (7c-1), (8b-1) with (5c-1), (8b-1) with (7c-1), (8b-1) with (3g-1), and (1g-1) with (3g-1), each mixed solution was placed in a separate syringe equipped with an 18-gauge needle, this syringe was attached to a syringe pump set to a flow rate of 1 ml/minute, and the solution was dripped for 30 seconds into a 30 mmol/L calcium chloride solution, which was then stirred for 5 minutes to obtain an alginic acid gel. Each gel was washed once with 10 ml of PBS, and then left for 10 minutes at 37° C. in PBS to perform chemical crosslinking and obtain a chemically crosslinked alginic acid gel. 19.5 ml of PBS was added to each gel and shaken at 37° C., the aqueous solution was collected over time, and PBS was supplemented in the same amount as the collected amount. Upon completion of testing, 10 μl of alginate lyase (Nippon Gene, 319-08261) was added to the test solution, which was then shaken overnight at 37° C. to completely collapse the gel, and the aqueous solution was collected. The alginic acid concentration in the collected aqueous solution was measured by the carbazole-sulfuric acid method, the amount of alginic acid eluted up to each point in time was divided by the total amount of alginic acid calculated from the alginic acid concentration at all time points and the alginic acid concentration after completion of testing, and the resulting value represented as a percentage was given as the gel collapse rate and used as an indicator of gel stability.

Figure 10:
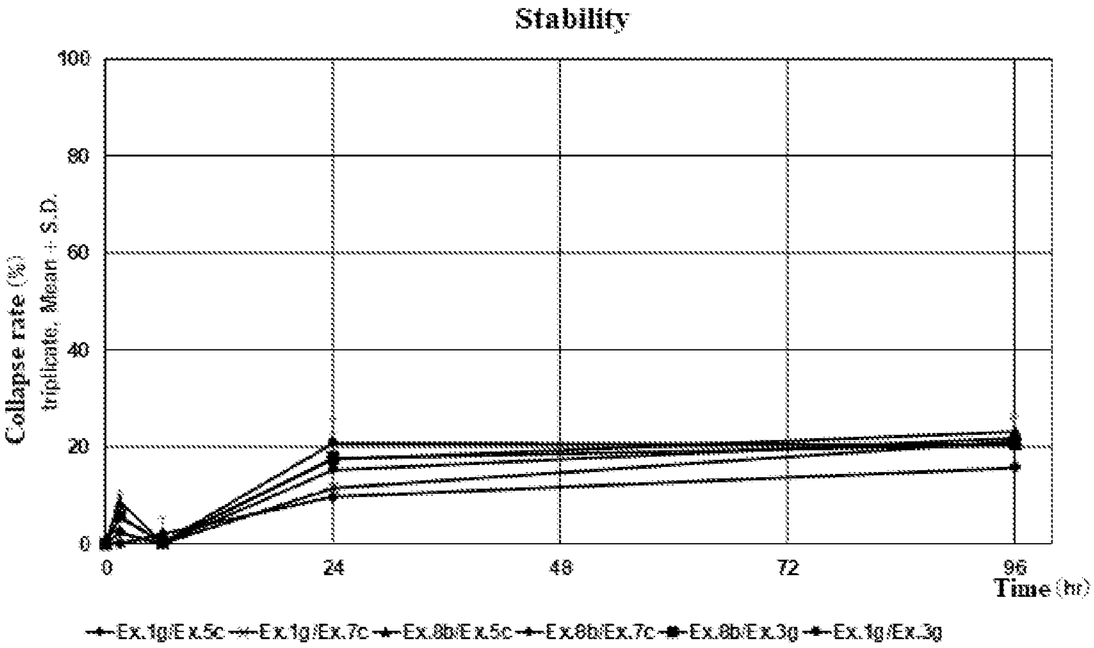
FIG. 10 shows an evaluation of the stability of gels of crosslinked alginic acid structures.

The results are shown in FIG. 10. The stability (gel collapse rate) of each of the crosslinked alginic acid gels (beads) was about 20% after 96 hours, suggesting that they maintained their structures long term (the stability of the gel prepared with (Example 1g) and (Example 3g) as a control was 20.4% after 96 hours).

(Measuring Gel Stability (7): Measuring Gel Stability in the Presence of EDTA)

The alginic acid with introduced reactive substituent (EX1-(I)-A-2b) obtained in (Example 1g), the alginic acid with introduced reactive substituent (EX3-(II)-A-2b) obtained in (Example 3g), the alginic acid with introduced reactive substituent (EX5-(II)-A-2b) obtained in (Example 5c), the alginic acid with introduced reactive substituent (EX7-(II)-A-2) obtained in (Example 7c) and the alginic acid with introduced reactive substituent (EX8-(I)-A-2) obtained in (Example 8b) were each dissolved in water to a concentration of 1.0% to prepare aqueous alginic acid solutions (1g-1), (3g-1), (5c-1), (7c-1) and (8b-1). These aqueous alginic acid solutions were mixed in equal amounts combining (1g-1) with (5c-1), (1g-1) with (7c-1), (8b-1) with (5c-1), (8b-1) with (7c-1), (8b-1) with (3g-1), and (1g-1) with (3g-1), each mixed solution was placed in a separate syringe equipped with an 18-gauge needle, this syringe was attached to a syringe pump set to a flow rate of 1 ml/minute, and the solution was dripped for 30 seconds into a 30 mmol/L calcium chloride solution, which was then stirred for 5 minutes to obtain an alginic acid gel. 19.5 ml of 5 mM ethylenediamine tetraacetic acid dipotassium salt dihydrate (EDTA·2K)/physiological saline was added to each gel and shaken at 37° ° C., the aqueous solution was collected over time, and EDTA·2K/physiological saline was supplemented in the same amount as the collected amount. Upon completion of testing (after 24 hours), 30 μl of alginate lyase (Nippon Gene, 319-08261) was added to the test solution, which was then shaken overnight at 37° C. to completely collapse the gel, and the aqueous solution was collected. The alginic acid concentration in the collected aqueous solution was measured by the carbazole-sulfuric acid method, the amount of alginic acid eluted up to each point in time was divided by the total amount of alginic acid calculated from the alginic acid concentration at all time points and the alginic acid concentration after completion of testing, and the resulting value represented as a percentage was given as the gel collapse rate and used as an indicator of gel stability.

Figure 11:
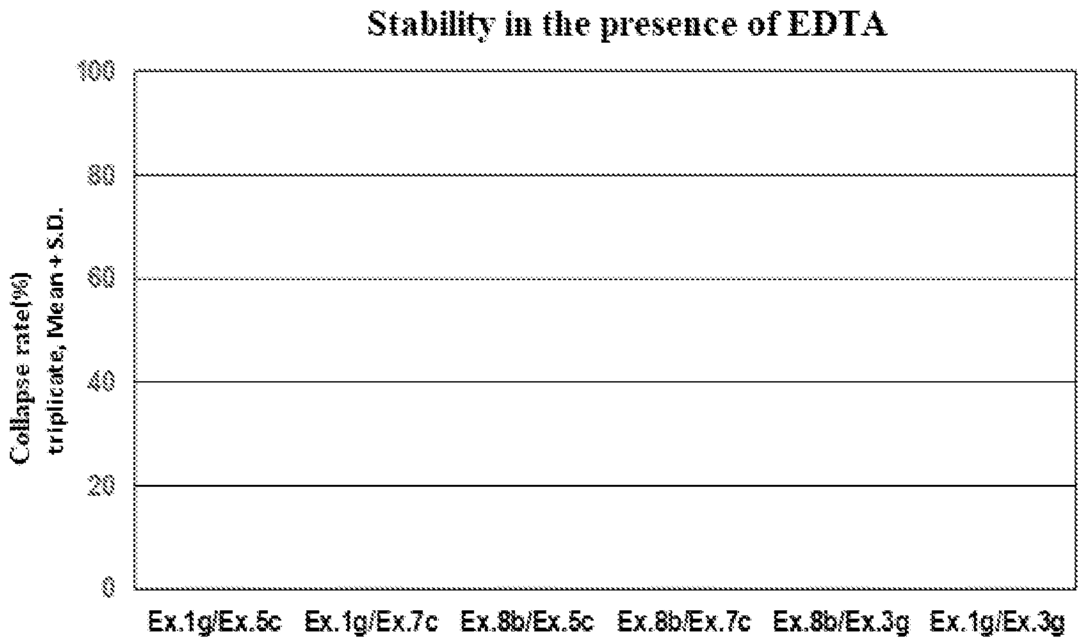
FIG. 11 shows an evaluation of the stability of gels of crosslinked alginic acid structures in the presence of EDTA.

The results are shown in FIG. 11. The crosslinked alginic acid gels (beads) did not collapse even after 24 hours, confirming gel stability. This suggests that when chemical crosslinks are formed by a Huisgen reaction, the resulting structure (bead) maintains its structure long-term.

(Measuring Gel Stability (8))

The alginic acid with introduced reactive substituent (EX1-(I)-A-2b) obtained in (Example 1g), the alginic acid with introduced reactive substituent (EX3-(II)-A-2b) obtained in (Example 3g), the alginic acid with introduced reactive substituent (EX10-(II)-A-2) obtained in (Example 10), the alginic acid with introduced reactive substituent (EX11-(II)-A-2) obtained in (Example 11), the alginic acid with introduced reactive substituent (EX12-(II)-A-2) obtained in (Example 12), the alginic acid with introduced reactive substituent (EX13-(II)-A-2) obtained in (Example 13), the alginic acid with introduced reactive substituent (EX14-(II)-A-2) obtained in (Example 14) and the alginic acid with introduced reactive substituent (EX15-(I)-A-2) obtained in (Example 15) were each dissolved in water to a concentration of 1.0% to prepare aqueous alginic acid solutions (1g-1), (3g-1), (10-1), (11-1), (12-1), (13-1), (14-1) and (15-1). The aqueous alginic acid solutions were mixed in equal amounts combining (3g-1) with (15-1), (1g-1) with (10-1), (1g-1) with (11-1), (1g-1) with (12-1), (1g-1) with (13-1), (1g-1) with (14-1) and (1g-1) with (3g-1), each mixed solution was placed in a separate syringe equipped with an 18-gauge needle, this syringe was attached to a syringe pump set to a flow rate of 1 ml/minute, and the solution was dripped for 30 seconds into a 30 mmol/L calcium chloride solution, which was then stirred for 5 minutes to obtain an alginic acid gel. Each gel was washed once with 10 ml of PBS, and then left standing for 10 minutes at 37° C. in PBS to perform chemical crosslinking and obtain a chemically crosslinked alginic acid gel. 19.5 ml of PBS was added to each gel and shaken at 37° C., the aqueous solution was collected over time, and PBS was supplemented in the same amount as the collected amount. Upon completion of testing, 10 μl of alginate lyase (Nippon Gene, 319-08261) was added to the test solution, which was then shaken overnight at 37° C. to completely collapse the gel, and the aqueous solution was collected. The alginic acid concentration in the collected aqueous solution was measured by the carbazole-sulfuric acid method, the amount of alginic acid eluted up to each point in time was divided by the total amount of alginic acid calculated from the alginic acid concentration at all time points and the alginic acid concentration after completion of testing, and the resulting value represented as a percentage was given as the gel collapse rate and used as an indicator of gel stability.

Figure 12:
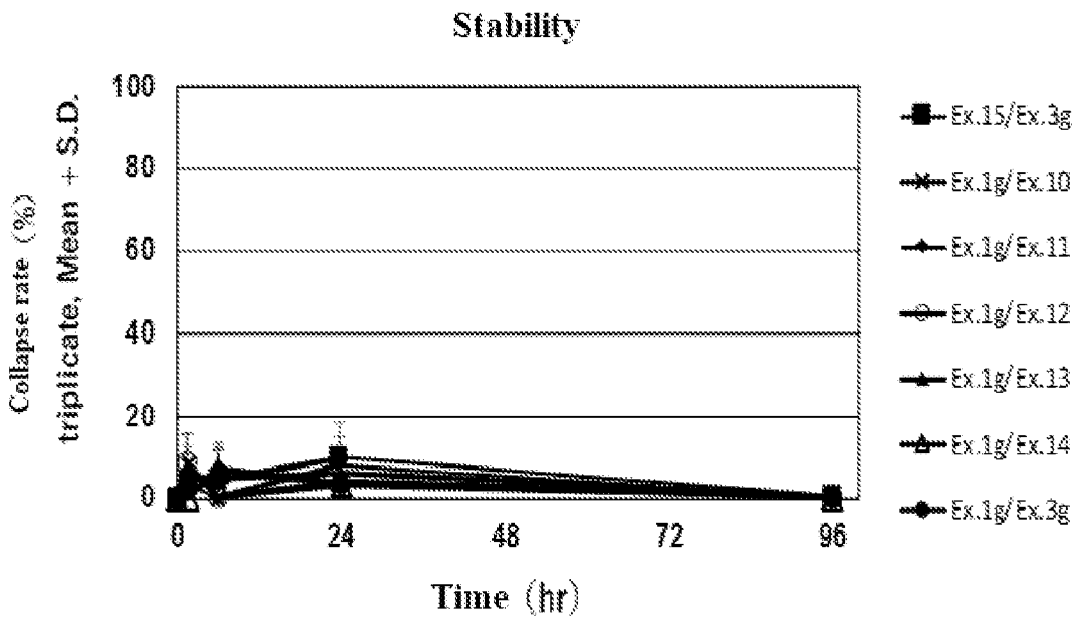
FIG. 12 shows an evaluation of the stability of gels of crosslinked alginic acid structures.

The results are shown in FIG. 12. The stability (gel collapse rate) of each of the crosslinked alginic acid gels (beads) was not more than 0.5% after 96 hours, suggesting that they maintained their structures long term (the stability of the gel prepared with (Example 1g) and (Example 3g) as a control was 0.3% after 96 hours).

(Measuring Gel Stability (9): Measuring Gel Stability in the Presence of EDTA

The alginic acid with introduced reactive substituent (EX1-(I)-A-2b) obtained in (Example 1g), the alginic acid with introduced reactive substituent (EX3-(II)-A-2b) obtained in (Example 3g), the alginic acid with introduced reactive substituent (EX10-(II)-A-2) obtained in (Example 10), the alginic acid with introduced reactive substituent (EX11-(II)-A-2) obtained in (Example 11), the alginic acid with introduced reactive substituent (EX12-(II)-A-2) obtained in (Example 12), the alginic acid with introduced reactive substituent (EX13-(II)-A-2) obtained in (Example 13), the alginic acid with introduced reactive substituent (EX14-(II)-A-2) obtained in (Example 14) and the alginic acid with introduced reactive substituent (EX15-(I)-A-2) obtained in (Example 15) were each dissolved in water to a concentration of 1.0% to prepare aqueous alginic acid solutions (1g-1), (3g-1), (10-1), (11-1), (12-1), (13-1), (14-1) and (15-1). The aqueous alginic acid solutions were mixed in equal amounts in the combinations (3g-1) with (15-1), (1g-1) with (10-1), (1g-1) with (11-1), (1g-1) with (12-1), (1g-1) with (13-1), (1g-1) with (14-1) and (1g-1) with (3g-1), each mixed solution was placed in a separate syringe equipped with an 18-gauge needle, this syringe was attached to a syringe pump set to a flow rate of 1 ml/minute, and the solution was dripped for 30 seconds into a 30 mmol/L calcium chloride solution, which was then stirred for 5 minutes to obtain an alginic acid gel.

19.5 ml of 5 mM ethylenediamine tetraacetic acid dipotassium salt dihydrate (EDTA·2K)/physiological saline was added to each gel and shaken at 37° ° C., the aqueous solution was collected over time, and the gel was replenished with 5 mM EDTA·2K/physiological saline in the same amount as the collected amount. Upon completion of testing (after 24 hours), 30 μl of alginate lyase (Nippon Gene, 319-08261) was added to the test solution, which was then shaken overnight at 37° C. to completely collapse the gel, and the aqueous solution was collected. The alginic acid concentration in the collected aqueous solution was measured by the carbazole-sulfuric acid method, the amount of alginic acid eluted up to each point in time was divided by the total amount of alginic acid calculated from the alginic acid concentration at all time points and the alginic acid concentration after completion of testing, and the resulting value represented as a percentage was given as the gel collapse rate and used as an indicator of gel stability.

Figure 13:
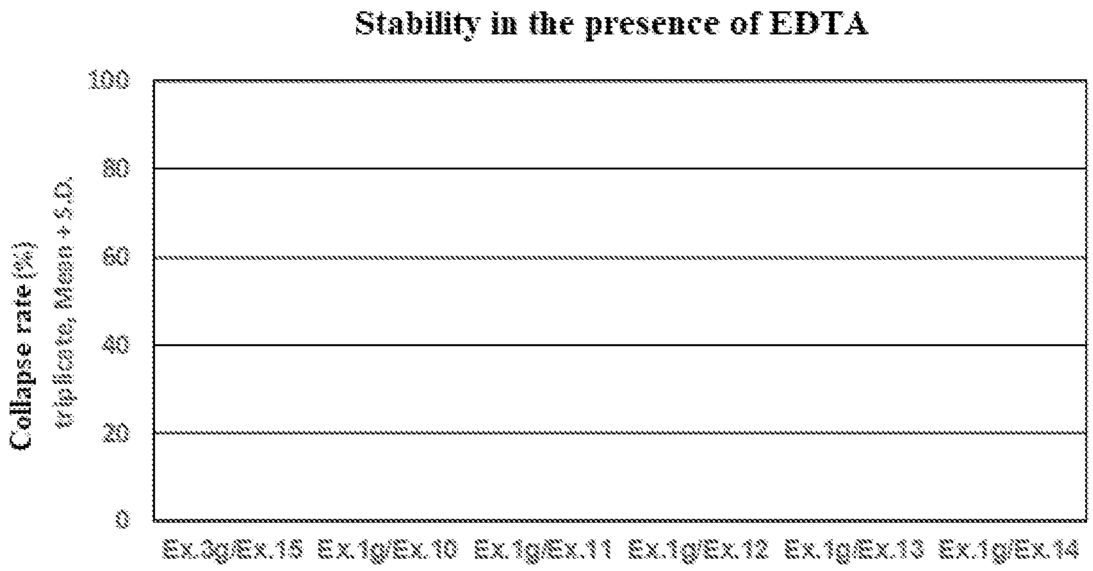
FIG. 13 shows an evaluation of the stability of gels of crosslinked alginic acid structures in the presence of EDTA.

The results are shown in FIG. 13. The crosslinked alginic acid gels (beads) did not collapse even after 24 hours, confirming gel stability. This suggests that when chemical crosslinks are formed by a Huisgen reaction, the resulting structure (bead) maintains its structure long-term.

[Measuring Gel Permeability]

(Measuring Gel Permeability (1))

The alginic acid derivative (EX1-(I)-A-2) obtained in (Example 1a) and the alginic acid derivative (EX3-(II)-A-2) obtained in (Example 3a) were each dissolved in water to a concentration of 2% to obtain (an aqueous alginic acid solution 1-2) and (an aqueous alginic acid solution 2-2). An equal amount of fluorescein isothiocyanate-dextran with a molecular weight of 2,000,000 (Sigma Aldrich, FD2000S) adjusted to 1 mg/ml or an equal amount of fluorescein isothiocyanate-dextran with a molecular weight of 150,000 (Sigma Aldrich, FD150S) adjusted to 1 mg/ml was then added to (the aqueous alginic acid solution 1-2), to obtain (an aqueous alginic acid solution 3) or (an aqueous alginic acid solution 4). An equal amount of physiological saline was also added to (the aqueous alginic acid solution 2-2) to obtain (an aqueous alginic acid solution 5).

(The aqueous alginic acid solution 3) and (the aqueous alginic acid solution 5) were mixed in equal amounts, this mixed aqueous solution was placed in a syringe equipped with an 18-gauge needle, the syringe was attached to a syringe pump set to a flow rate of 1 ml/minute, and the solution was dripped for 30 seconds into a 30 mmol/L calcium chloride solution, which was then stirred for about 20 minutes to obtain an alginic acid gel. This gel was washed once with 10 ml of physiological saline to obtain a chemically crosslinked alginic acid gel (bead) containing fluorescein-isothiocyanate (mw 2,000,000)-dextran. (The aqueous alginic acid solution 4) and (the aqueous alginic acid solution 5) were also mixed in equal amounts, and a chemically crosslinked alginic acid gel (bead) containing fluorescein-isothiocyanate (mw 150,000)-dextran was obtained by the same methods.

20 ml of physiological saline was added to each resulting gel (bead) and shaken at 37° C., and the aqueous solution was collected over time. After completion of testing, 10 μl of alginate lyase (Nippon Gene, 319-08261) was added to each test solution, which was then shaken for 2 hours at 37° ° C. to completely collapse the gel, and the aqueous solution was collected. The dextran concentration in the collected aqueous solution was measured by fluorescence assay (excitation light: 485 nm, fluorescence: 535 nm), and the value of the dextran concentration at each point of time divided by the dextran concentration after completion of testing was represented as a percentage and given as the permeation rate.

Figure 2:
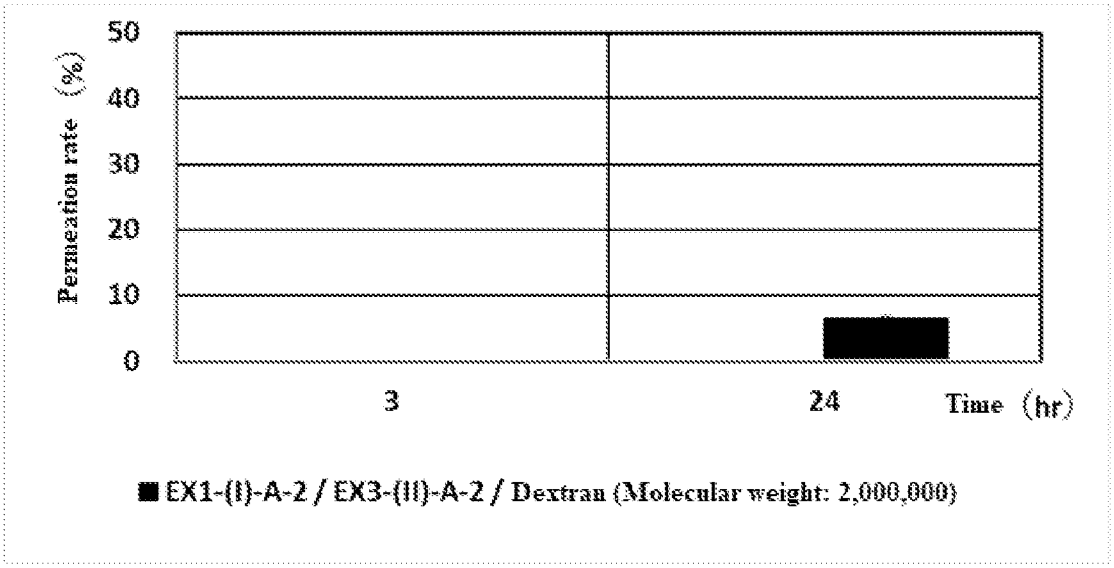
FIG. 2 shows an evaluation of the permeability of a gel of a crosslinked alginic acid structure.

FIG. 2 shows the results for the gel obtained by mixing equal amounts of (the aqueous alginic acid solution 3) and (the aqueous alginic acid solution 5) (EX1-(I)-A-2/EX3-(II)-A-2/dextran (MW 2,000,000)). Permeation was 6.4% after 24 hours.

Figure 3:
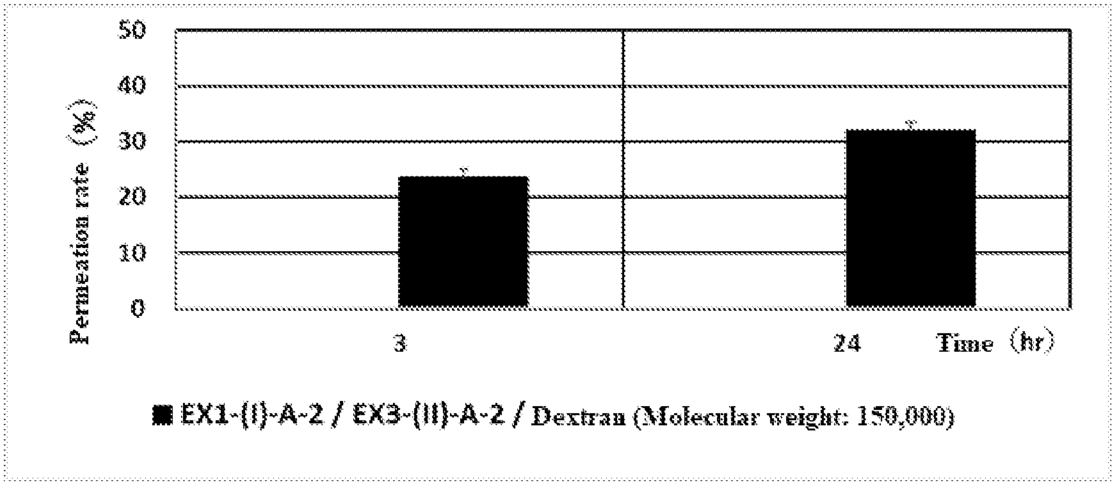
FIG. 3 shows an evaluation of the permeability of a gel of a crosslinked alginic acid structure.

FIG. 3 shows the results for the gel obtained by mixing equal amounts of (the aqueous alginic acid solution 4) and (the aqueous alginic acid solution 5) (EX1-(I)-A-2/EX3-(II)-A-2/dextran (MW 150,000)). Permeation was 23.6% after 3 hours and 31.9% after 24 hours.

(Measuring Gel Permeability (2))

The alginic acid derivative (EX1-(I)-B-2a) obtained in (Example 1d), the alginic acid derivative (EX3-(II)-B-2a) obtained in (Example 3d), the alginic acid derivative (EX7-(II)-B-2a) obtained in (Example 7a) and the alginic acid derivative (EX8-(I)-B-2) obtained in (Example 8) were each dissolved in water to a concentration of 1.5 w/w % to obtain aqueous alginic acid solutions (1d-2), (3d-2), (7a-2) and (8a-2). Fluorescein isothiocyanate-dextran with a molecular weight of 2,000,000 (Sigma Aldrich, FD2000S) adjusted to 1 mg/ml or fluorescein isothiocyanate-dextran with a molecular weight of 150,000 (Sigma Aldrich, FD150S) adjusted to 1 mg/ml was then added to (the aqueous alginic acid solution 3d-2), to obtain (an aqueous alginic acid solution 3d-2-A) or (an aqueous alginic acid solution 3d-2-B). Similarly, fluorescein isothiocyanate-dextran with a molecular weight of 2,000,000 (Sigma Aldrich, FD2000S) adjusted to 1 mg/ml or fluorescein isothiocyanate-dextran with a molecular weight of 150,000 (Sigma Aldrich, FD150S) adjusted to 1 mg/ml was also added to (the aqueous alginic acid solution 7a-2), to obtain (an aqueous alginic acid solution 7a-2-A) or (an aqueous alginic acid solution 7a-2-B).

These aqueous alginic acid solutions were mixed in the combinations shown in Table 15 to obtain final alginic acid concentrations of 1.0 w/w % and final fluorescein isothiocyanate-dextran concentrations of 100 g/ml. Each mixed aqueous solution was placed in a syringe equipped with an 18-gauge needle, the syringe was attached to a syringe pump set to a flow rate of 1 ml/minute, and the solution was dripped for 30 seconds into a 30 mmol/L calcium chloride solution, which was then stirred for 5 minutes to obtain an alginic acid gel. These gels were each washed once with 10 ml of phosphate-buffered saline (PBS), and then left standing for 10 minutes at 37° ° C. in pure water to perform chemical crosslinking and obtain chemically crosslinked alginic acid gels (beads) containing fluorescein isothiocyanate (MW 2,000,000)-dextran and chemically crosslinked alginic acid gels (beads) containing fluorescein isothiocyanate (MW 150,000)-dextran (gels a to h).

TABLE 15

| | (1d-2) | (8a-2) |
|---|---|---|
| (3d-2-A) | gel a | gel b |
| (7a-2-A) | gel c | gel d |
| (3d-2-B) | gel e | gel f |
| (7a-2-B) | gel g | gel h |

19.5 ml of physiological saline was added to each of the gels a to h and shaken at 37° ° C., the aqueous solution was collected after 3 and 24 hours, and with physiological saline was supplemented in the same amount as the collected amount. After completion of testing, 20 μl of alginate lyase (Creative Enzymes, NATE-1563) was added to each test solution, which was then shaken overnight at 37° C. to completely collapse the gel, and the aqueous solution was collected. The dextran concentration in the collected aqueous solution was measured by fluorescence assay (excitation light: 485 nm, fluorescence: 535 nm), and the value of the dextran concentration at each point of time divided by the total dextran concentration calculated from the dextran concentration at all time points and the dextran concentration after completion of testing was represented as a percentage and given as the permeation rate.

Figure 5:
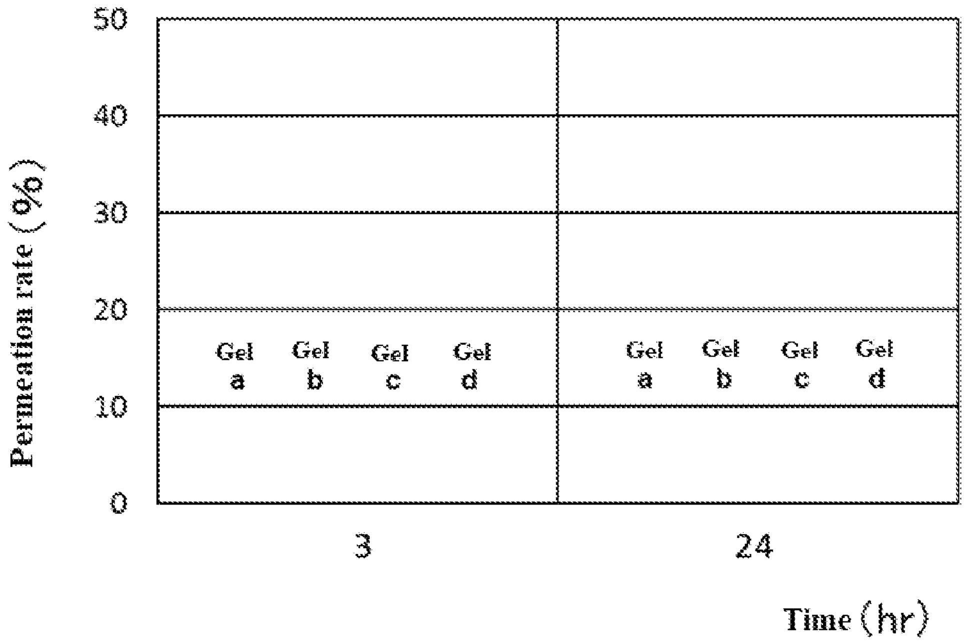
FIG. 5 shows an evaluation of the permeability of gels of crosslinked alginic acid structures.
Figure 6:
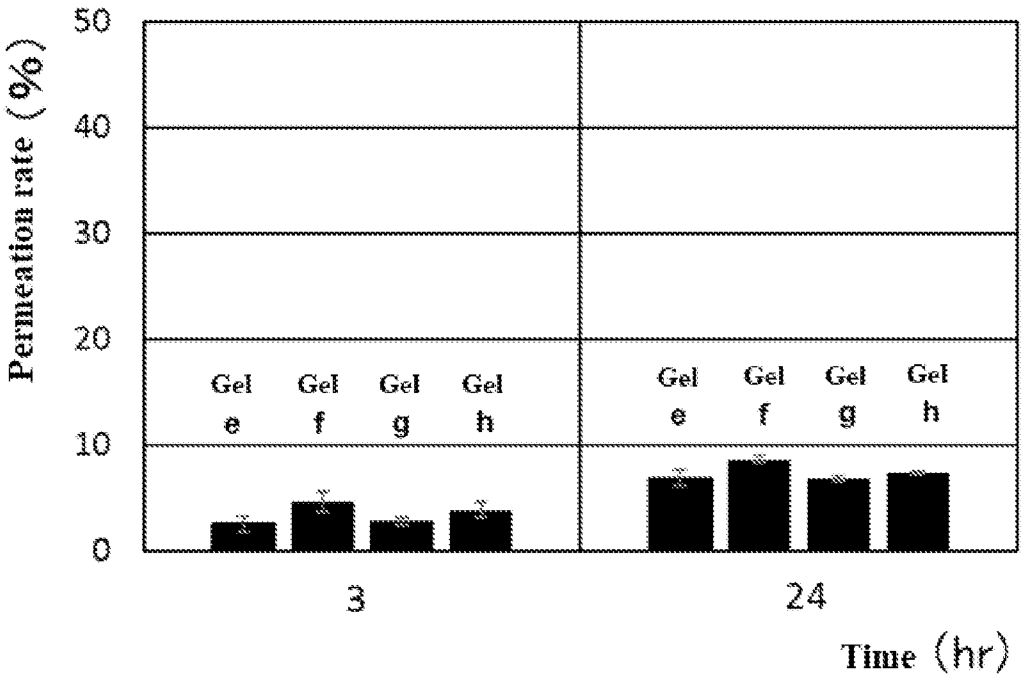
FIG. 6 shows an evaluation of the permeability of gels of crosslinked alginic acid structures.

FIG. 5 shows the results for the gels (gel a, gel b, gel c and gel d in Table 15) obtained by mixing (the aqueous alginic acid solution 3d-2-A) and (the aqueous alginic acid solution 7a-2-A) with (the aqueous alginic acid solution 1d-2) and (the aqueous alginic acid solution 8a-2). The permeation rates after 3 hours and 24 hours were 0% in all cases. FIG. 6 shows the results for the gels (gel e, gel f, gel g and gel h in Table 15) obtained by mixing (the aqueous alginic acid solution 3d-2-B) and (the aqueous alginic acid solution 7a-2-B) with (the aqueous alginic acid solution 1d-2) and (the aqueous alginic acid solution 8a-2). The permeation rates were 2.5% to 4.6% after 3 hours and 6.8% to 8.6% after 24 hours.

(Measuring Gel Permeability (3))

The alginic acid with introduced reactive substituent (EX3-(II)-A-2b) obtained in (Example 3g), the alginic acid with introduced reactive substituent (EX5-(II)-A-2b) obtained in (Example 5c) and the alginic acid with introduced reactive substituent (EX7-(II)-A-2) obtained in (Example 7c) were each dissolved in water to a concentration of 2.0% to prepare aqueous alginic acid solutions, and ⅖ the volume of fluorescein isothiocyanate-dextran with a molecular weight of 150,000 (Sigma Aldrich, FD150S) adjusted to 1 mg/ml and ⅗ the volume of water were added to these aqueous alginic acid solutions to obtain 1.0% aqueous alginic acid solutions (3g-2), (5c-2) and (7c-2) containing 0.2 mg/ml fluorescein isothiocyanate-dextran. The alginic acid with introduced reactive substituent (EX1-(I)-A-2b) obtained in (Example 1g) and the alginic acid with introduced reactive substituent (EX9-(I)-A-2) obtained in (Example 9a) were also each dissolved in water to a concentration of 1.0% to prepare aqueous alginic acid solutions (1g-1) and (9a-1). These aqueous alginic acid solutions were then mixed in equal amounts combining (9a-1) with (5c-2), (9a-1) with (7c-2), (9a-1) with (3g-2) and (1g-1) with (3g-2), and 40 ml of 30 mmol/L calcium chloride solution was added to each and shaken for 5 minutes to obtain alginic acid gels. These gels were washed once with 10 ml of physiological saline, and then left standing for 10 minutes at 37° C. in physiological saline to perform chemical crosslinking and obtain chemically crosslinked alginic acid gels containing fluorescein isothiocyanate-dextran. 19.5 ml of physiological saline was added to each gel and shaken at 37° ° C., the aqueous solution was collected over time, and physiological saline was supplemented in the same amount as the collected amount. After completion of testing (after 24 hours), 10 μl of alginate lyase (Nippon Gene, 319-08261) was added to each test solution, which was then shaken for at least 3 hours at 37° C. to completely collapse the gel, and the aqueous solution was collected. The dextran concentration in the collected aqueous solution was measured by fluorescence assay (excitation light: 485 nm, fluorescence: 535 nm), and the value of the dextran concentration at each point of time divided by the dextran concentration upon completion of testing was represented as a percentage and given as the permeation rate.

Figure 14:
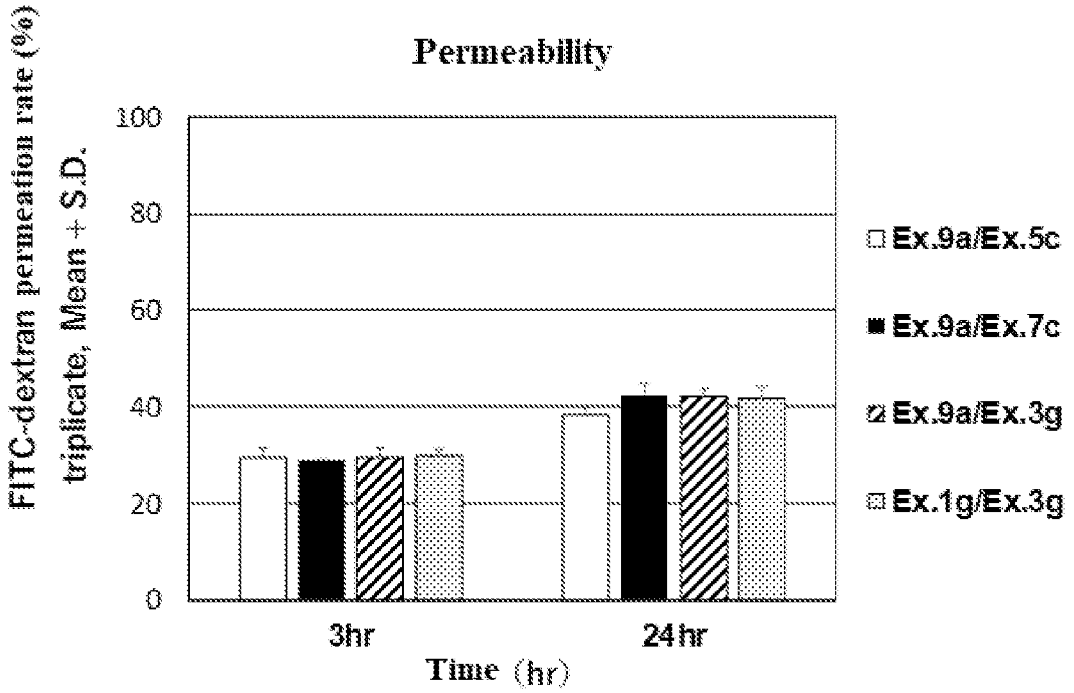
FIG. 14 shows an evaluation of the permeability of gels of crosslinked alginic acid structures.

The results are shown in FIG. 14. The permeation rate after 3 hours was about 30% in all cases, and the permeation rate after 24 hours was about 40% in all cases.

(Measuring Gel Permeability (4))

The alginic acid with introduced reactive substituent (EX3-(II)-A-2b) obtained in (Example 3g), the alginic acid with introduced reactive substituent (EX5-(II)-A-2b) obtained in (Example 5c) and the alginic acid with introduced reactive substituent (EX7-(II)-A-2) obtained in (Example 7c) were each dissolved in water to a concentration of 2.0% to prepare aqueous alginic acid solutions, and ⅖ the volume of fluorescein isothiocyanate-dextran with a molecular weight of 150,000 (Sigma Aldrich, FD150S) adjusted to 1 mg/ml and ⅗ the volume of water were added to these aqueous alginic acid solutions to obtain 1.0% aqueous alginic acid solutions (3g-2), (5c-2) and (7c-2) each containing 0.2 mg/ml fluorescein isothiocyanate-dextran. The alginic acid with introduced reactive substituent (EX1-(I)-A-2b) obtained in (Example 1g) and the alginic acid with introduced reactive substituent (EX8-(I)-A-2) obtained in (Example 8b) were also dissolved in water to a concentration of 1.0% to prepare aqueous alginic acid solutions (1g-1) and (8b-1). These were then mixed in equal amounts combining (1g-1) with (5c-2), (1g-1) with (7c-2), (8b-1) with (5c-2), (8b-1) with (7c-2), (8b-1) with (3g-2) and (1g-1) with (3g-2), and 40 ml of 30 mmol/L calcium chloride solution was added to each and shaken for 5 minutes to obtain alginic acid gels. These gels were washed once with 10 ml of physiological saline, and then left standing for 10 minutes at 37° C. in physiological saline to perform chemical crosslinking and obtain chemically crosslinked alginic acid gels containing fluorescein isothiocyanate-dextran. 19.5 ml of physiological saline was added to each gel and shaken at 37° ° C., the aqueous solution was collected over time, and physiological saline was supplemented in the same amount as the collected amount. After completion of testing (after 24 hours), 10 μl of alginate lyase (Nippon Gene, 319-08261) was added to each test solution, which was then shaken for at least 3 hours at 37° ° C. to completely collapse the gel, and the aqueous solution was collected. The dextran concentration in the collected aqueous solution was measured by fluorescence assay (excitation light: 485 nm, fluorescence: 535 nm), and the value of the dextran concentration at each point of time divided by the dextran concentration upon completion of testing was represented as a percentage and given as the permeation rate.

Figure 15:
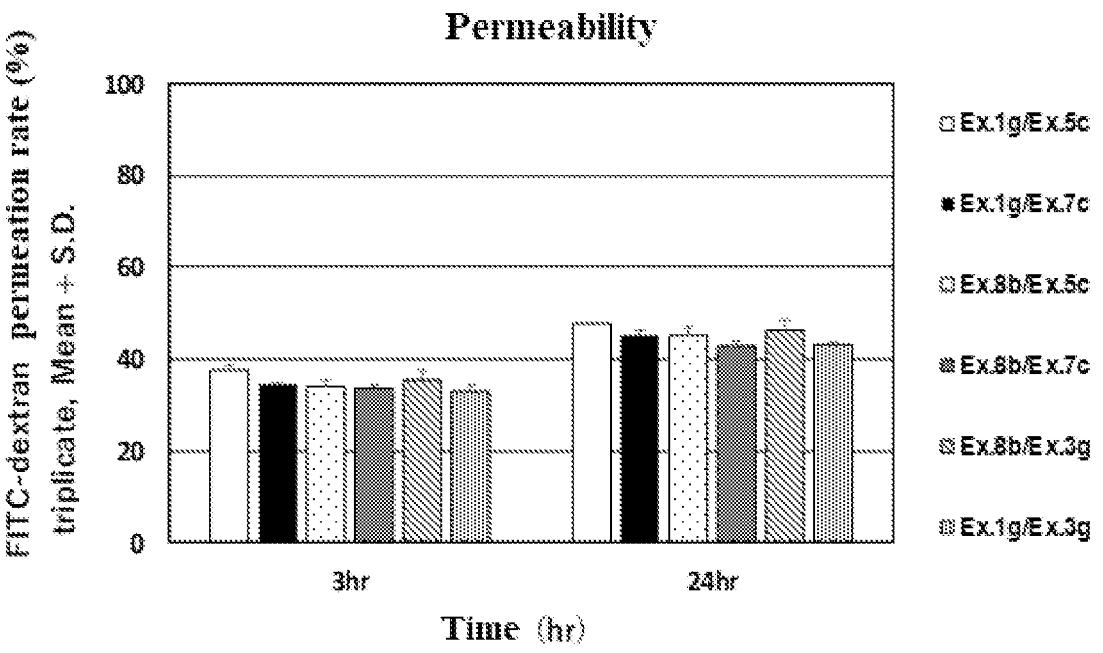
FIG. 15 shows an evaluation of the permeability of gels of crosslinked alginic acid structures.

The results are shown in FIG. 15. The permeation rate after 3 hours was about 35% in all cases, and the permeation rate after 24 hours was about 45% in all cases.

(Measuring Gel Permeability (5))

The alginic acid with introduced reactive substituent (EX3-(II)-A-2b) obtained in (Example 3g), the alginic acid with introduced reactive substituent (EX10-(II)-A-2) obtained in (Example 10), the alginic acid with introduced reactive substituent (EX11-(II)-A-2) obtained in (Example 11), the alginic acid with introduced reactive substituent (EX12-(II)-A-2) obtained in (Example 12), the alginic acid with introduced reactive substituent (EX13-(II)-A-2) obtained in (Example 13) and the alginic acid with introduced reactive substituent (EX14-(II)-A-2) obtained in (Example 14) were each dissolved in water to a concentration of 2.0% to prepare aqueous alginic acid solutions, and ⅖ the volume of fluorescein isothiocyanate-dextran with a molecular weight of 150,000 (Sigma Aldrich, FD150S) adjusted to 1 mg/ml and ⅗ the volume of water were added to these aqueous alginic acid solutions to prepare 1.0% aqueous alginic acid solutions (3g-2), (10-2), (11-2), (12-2), (13-2) and (14-2) containing 0.2 mg/ml fluorescein isothiocyanate-dextran. The alginic acid with introduced reactive substituent (EX1-(I)-A-2b) obtained in (Example 1g) and the alginic acid with introduced reactive substituent (EX15-(I)-A-2) obtained in (Example 15) were also dissolved in water to a concentration of 1.0% to prepare aqueous alginic acid solutions (1g-1) and (15-1). These were then mixed in equal amounts combining (15-1) with (3g-2), (1g-1) with (10-2), (1g-1) with (11-2), (1g-1) with (12-2), (1g-1) with (13-2), (1g-1) with (14-2) and (1g-1) with (3g-2), and 40 ml of 30 mmol/L calcium chloride solution was added to each and shaken for 5 minutes to obtain alginic acid gels. These gels were each washed once with 10 ml of physiological saline, and then left standing for 10 minutes at 37° C. in physiological saline to perform chemical crosslinking and obtain chemically crosslinked alginic acid gels containing fluorescein isothiocyanate-dextran. 19.5 ml of physiological saline was added to each gel and shaken at 37° C., the aqueous solution was collected over time, and physiological saline was supplemented in the same amount as the collected amount. After completion of testing (after 24 hours), 10 μl of alginate lyase (Nippon Gene, 319-08261) was added to each test solution, which was then shaken for at least 3 hours at 37° C. to completely collapse the gel, and the aqueous solution was collected. The dextran concentration in the collected aqueous solution was measured by fluorescence assay (excitation light: 485 nm, fluorescence: 535 nm), and the value of the dextran concentration at each point of time divided by the dextran concentration upon completion of testing was represented as a percentage and given as the permeation rate.

Figure 16:
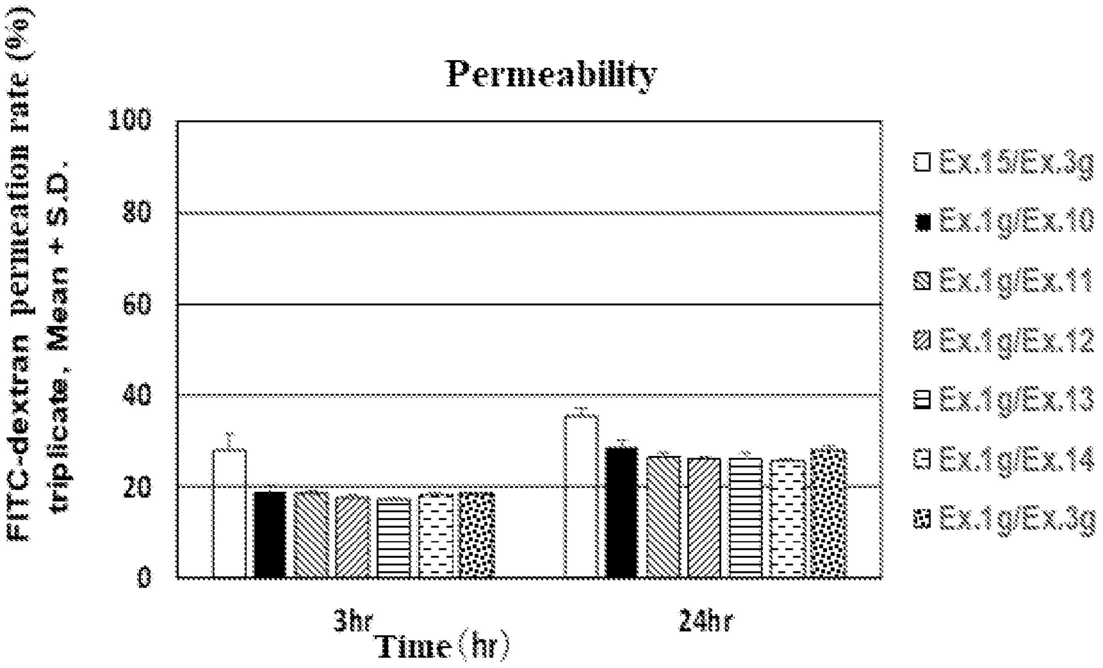
FIG. 16 shows an evaluation of the permeability of gels of crosslinked alginic acid structures.

The results are shown in FIG. 16. The permeation rates after 3 hours were about 17% to 28%, and the permeation rates after 24 hours were about 25% to 35%.

[Evaluating Biocompatibility of Crosslinked Alginic Acid Derivatives (Gels)]

An alginic acid derivative (EX1-(I)-B-2-L) with an introduction rate (NMR integration ratio) of 0.9 mol % prepared in a similar manner to (Example 1d), an alginic acid derivative (EX3-(II)-B-2-L) with an introduction rate (NMR integration ratio) of 0.6 mol % prepared in a similar manner to (Example 3d), an alginic acid derivative (EX7-(II)-B-2-L)

with an introduction rate (NMR integration ratio) of 0.9 mol % prepared by a similar manner to (Example 7a) and an alginic acid derivative (EX8-(I)-B-2-L) with an introduction rate (NMR integration ratio) of 0.3 mol % prepared in a similar manner to (Example 8) were each dissolved in physiological saline to a concentration of 1.5 w/w % to obtain aqueous alginic acid solutions (1d-L), (3d-L), (7α-L) and (8α-L).

A PBS suspension of CHO cells adjusted to $1.5\times10^7$ cells/ml was also added to both (the aqueous alginic acid solution 3d-L) and (the aqueous alginic acid solution 7α-L) to prepare (an aqueous alginic acid solution 3d-LC) and (an aqueous alginic acid solution 7a-LC).

These aqueous solutions were then mixed in the combinations shown in Table 16 so that the final alginic acid concentration was 1.0 w/w % and the final concentration of CHO cells was $5.0\times10^6$ cells/ml. Each of these mixed aqueous solutions was placed in a syringe equipped with an 18-gauge needle, this syringe was attached to a syringe pump set to a flow rate of 1 ml/minute, and the solution was dripped for 30 seconds into a 50 mmol/L calcium chloride solution, stirred for 5 minutes, and washed once with 10 ml of phosphate-buffered saline (PBS) to obtain alginic acid gels (beads) containing CHO cells (gel CHO-1 to gel CHO-4).

TABLE 16

| | 1d-L | 8a-L |
|---|---|---|
| 3d-LC | gel CHO-1 | gel CHO-2 |
| 7a-LC | gel CHO-3 | gel CHO-4 |

(The gel CHO-1) to (the gel CHO-4) were seeded onto 6-well plates (Falcon, Cat #351146), and 5 ml/well of medium with the composition shown in Table 17 below was added to impregnate the gels, which were then cultured for 2 days with shaking at 125 rpm in an incubator set to 37° C., 5% $CO_2$. After testing the gels were collected and impregnated with 5 ml of fresh medium, 50 μl of alginate lyase (Creative Enzymes, NATE-1563) was added, the gels were completely collapsed by being shaken for 1 hour at 37° C., and the medium was collected. The numbers of live and dead cells in the collected medium were measured by Trypan blue staining, and the live cell count divided by the combined count of live and dead cells represented as a percentage was given as the cell survival rate and used as an indicator of gel biocompatibility. An alginic acid gel (bead) (REF-CHO) containing CHO cells was also prepared in the same way as a control using an alginic acid (B-2) having no introduced reactive group, and the cell survival rate was measured.

TABLE 17

| | Sample | Manufacturer | Added amount (ml) | Final concentration |
|---|---|---|---|---|
| Medium | GO16 Medium | Irvine | 950 | |
| Additive | L-Glutamine 200 mM | SIGMA | 40 | 8 mM |
| | Penicillin Streptomycin | Invitrogen | 10 | 1% |

Figure 7:
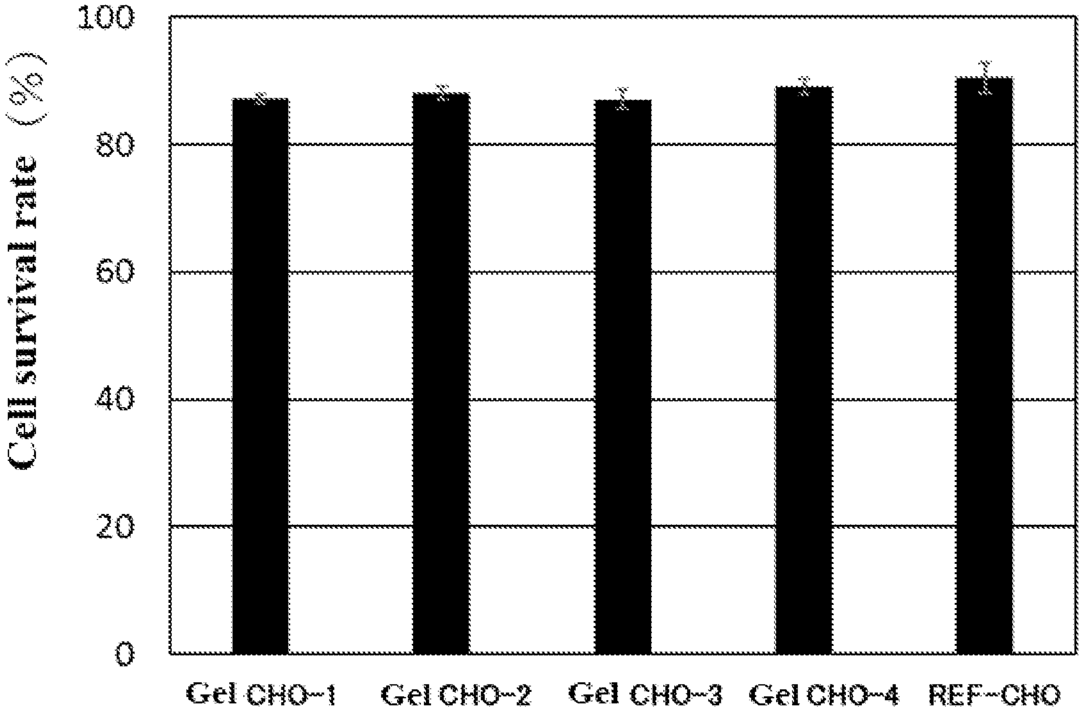
FIG. 7 shows a biocompatibility evaluation of gels of crosslinked alginic acid structures.

The results are shown in FIG. 7. The cell survival rates in the alginic acid gels (gel CHO-1) to (gel CHO-4) obtained by combining the alginic acid derivatives shown in Table 16 above were 87.2% to 89.0%. The cell survival rate in the alginic acid gel (REF-CHO) prepared as a control using an alginic acid (B-2) having no introduced reactive group was 90.5%. These results suggest that alginic acid derivatives having introduced reactive groups and alginic acid structures (beads) formed by chemical crosslinking through a Huisgen reaction have high biocompatibility equivalent to that of alginic acid having no introduced reactive group.

[Evaluating Biocompatibility of Crosslinked Alginic Acid Derivatives (Gels) (2)]

The alginic acid with introduced reactive substituent (EX1-(I)-A-2b) obtained in (Example 1g), the alginic acid with introduced reactive substituent (EX3-(II)-A-2b) obtained in (Example 3g), the alginic acid with introduced reactive substituent (EX5-(II)-A-2b) obtained in (Example 5c), the alginic acid with introduced reactive substituent (EX7-(II)-A-2) obtained in (Example 7c), the alginic acid with introduced reactive substituent (EX8-(I)-A-2) obtained in (Example 8b), the alginic acid with introduced reactive substituent (EX9-(I)-A-2) obtained in (Example 9a), the alginic acid with introduced reactive substituent (EX10-(II)-A-2) obtained in (Example 10), the alginic acid with introduced reactive substituent (EX11-(II)-A-2) obtained in (Example 11), the alginic acid with introduced reactive substituent (EX12-(II)-A-2) obtained in (Example 12), the alginic acid with introduced reactive substituent (EX13-(II)-A-2) obtained in (Example 13), the alginic acid with introduced reactive substituent (EX14-(II)-A-2) obtained in (Example 14) and the alginic acid with introduced reactive substituent (EX15-(I)-A-2) obtained in (Example 15) were each dissolved in water to obtain alginic acid solutions with introduced crosslinking groups. These were filter sterilized with a Minisart High Flow (Sartorius, 16532GUK), and 1.0% crosslinking group-introduced alginic acid/aqueous physiological saline solutions were then prepared. The 1.0% crosslinking group-introduced alginic acid/aqueous physiological saline solutions were added in the combination of (Example 3g)+(Example 1g), (Example 8b), (Example 9a) or (Example 15) and the combination of (Example 1g)+(Example 5c), (Example 7c), (Example 10), (Example 11), (Example 12), (Example 13) or (Example 14) to a final concentration of 0.1% to HeLa cells that had been cultured for 1 day after being seeded on 96-well plates to a cell concentration of $5\times10^3$ cells/well. These were then cultured for 1 day, after which ATP activity was evaluated by a Cell Titer-Glo Luminescent Cell Viability Assay (Promega, G7571) as a measure of cell toxicity.

Figure 17:
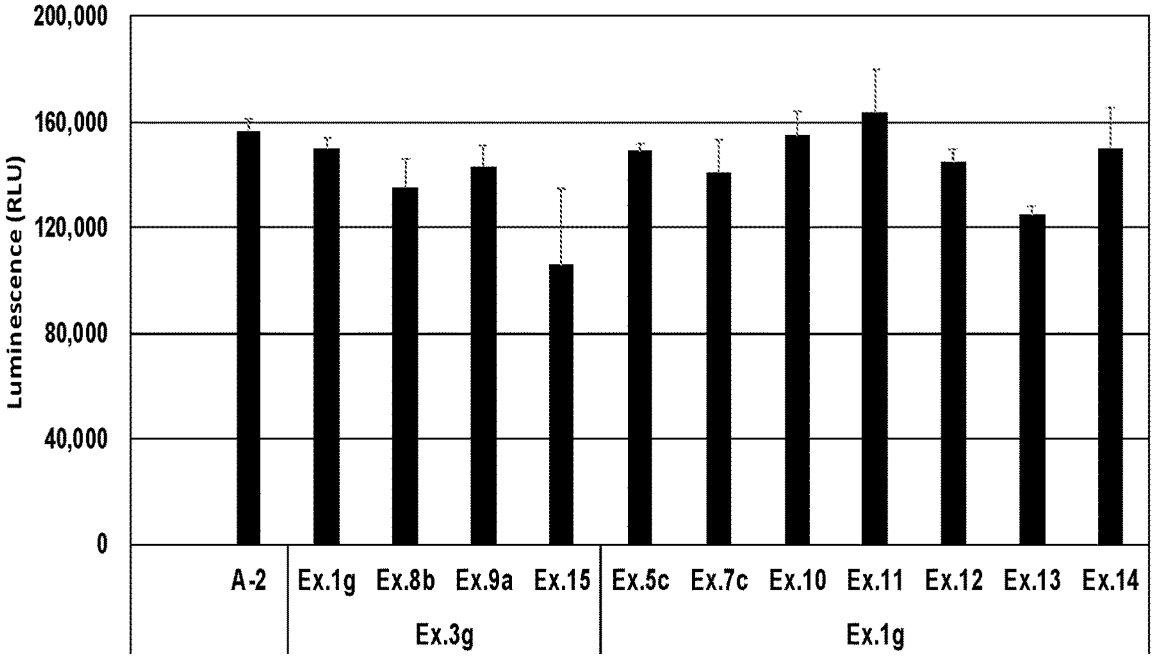
FIG. 17 shows a biocompatibility evaluation of gels of crosslinked alginic acid derivatives.

The results are shown in FIG. 17. ATP activity was confirmed in all of the above crosslinked alginic acid gels, suggesting that these crosslinked alginic acid gels lacked cell toxicity, and thus that alginic acid structures (beads) formed by chemical crosslinking through a Huisgen reaction have biocompatibility.

The invention claimed is:

1. An alginic acid derivative of formula (II) below, consisting of an azide group introduced via an amide bond and a divalent linker ($-L^2-$) at any one or more carboxyl groups of alginic acid:

(II)

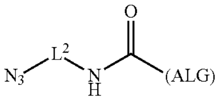

in formula (II), (ALG) is alginic acid; —NHCO— is an amide bond via any carboxyl group of alginic acid; and $-L^2-$ is a divalent linker selected from the group consisting of the following partial structural formula, excluding the parts outside the cutting lines at both ends of each formula:

(LK-1)

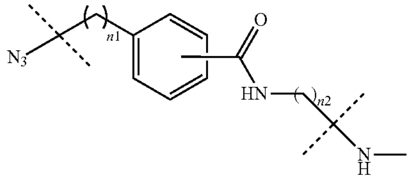

n1 = 1-6, n2 = 2-6

(LK-2)

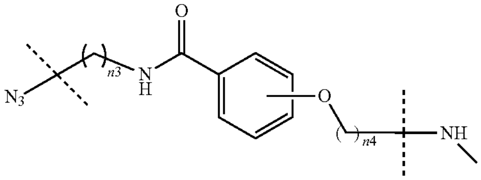

n3 = 2-6, n4 = 2-6

(LK-3)

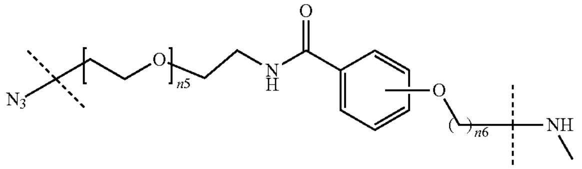

n5 = 1-6, n6 = 2-6

(LK-4)

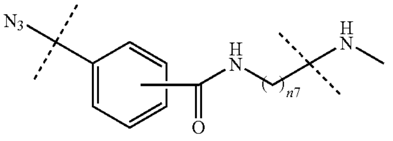

n7 = 2-6

(LK-5)

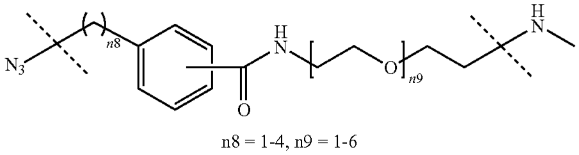

n8 = 1-4, n9 = 1-6

(LK-6)

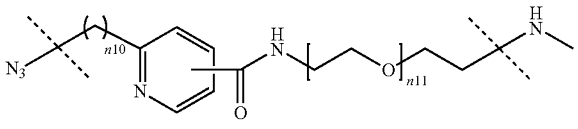

n10 = 1-4, n11 = 1-6

-continued (LK-7)

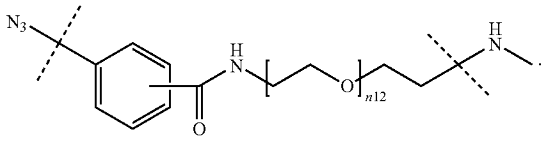

n12 = 1-6

2. The alginic acid derivative of formula (II) according to claim 1, wherein the introduction rate of the $N_3$-$L^2$-$NH_2$ group is 0.1% to 30%, wherein $-L^2-$ is defined as in claim 1.

3. The alginic acid derivative of formula (II) according to claim 1, wherein the weight-average molecular weight as measured by gel filtration chromatography of the alginic acid derivative is 100,000 Da to 3,000,000 Da.

4. The alginic acid derivative according to claim 1, wherein the alginic acid derivative has biocompatibility.

5. An alginic acid derivative selected from the group consisting of the following formula:

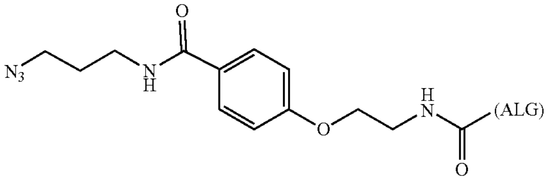

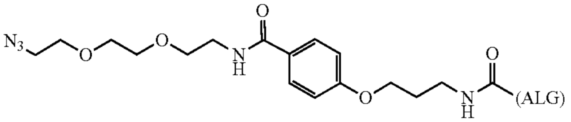

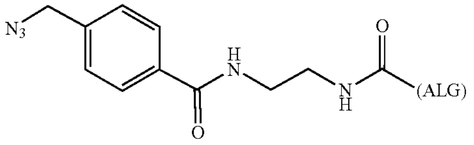

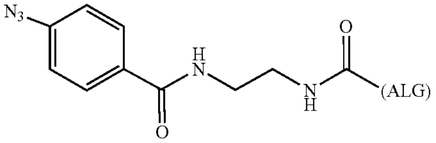

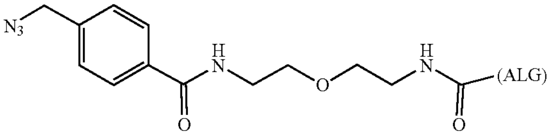

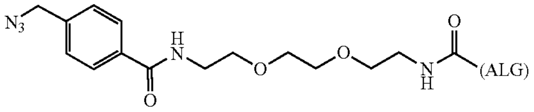

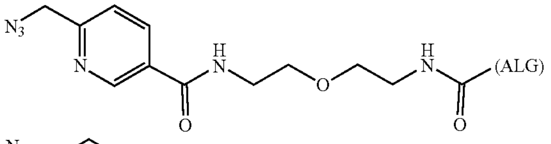

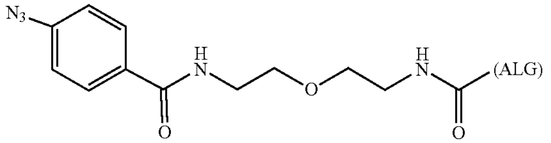

-continued

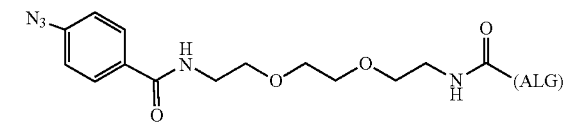

wherein in each formula, (ALG) is alginic acid; —NHCO— bound to (ALG) is an amide bond via any carboxyl group of alginic acid.

6. The alginic acid derivative according to claim 5, wherein the introduction rate of the azide-containing group is 0.1% to 30%.

7. The alginic acid derivative according to claim 5, wherein the weight-average molecular weight as measured by gel filtration chromatography of the alginic acid derivative is 100,000 Da to 3,000,000 Da.

8. The alginic acid derivative according to claim 5, wherein the alginic acid derivative has biocompatibility.

9. A method for producing the alginic acid derivative of formula (II) according to claim 1 or a salt thereof, the method comprising:

causing a condensation reaction of an alginic acid or a salt thereof with an amine derivative of Formula (AM-2) or a salt thereof by using a condensing agent to obtain the alginic acid derivative of formula (II) or a salt thereof, wherein Formula (II):

(II)

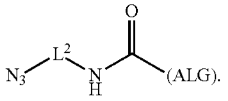

in formula (II), (ALG) is alginic acid; —NHCO— is an amide bond via any carboxyl group of alginic acid; and -$L^2$- is a divalent linker selected from the group consisting of the following partial structural formula, excluding the parts outside the cutting lines at both ends of each formula:

(LK-1)

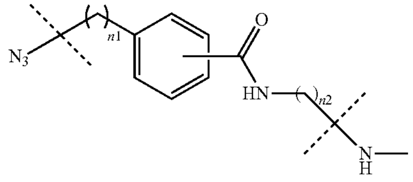

n1 = 1-6, n2 = 2-6

(LK-2)

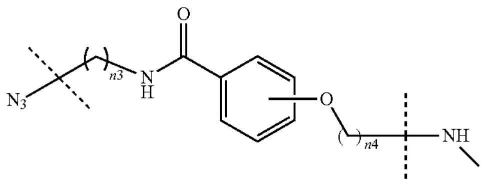

n3 = 2-6, n4 = 2-6

-continued (LK-3)

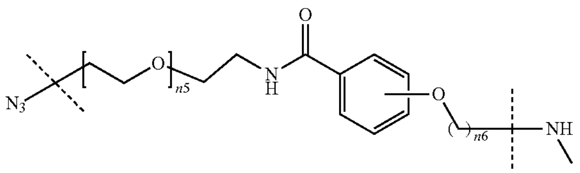

n5 = 1-6, n6 = 2-6

(LK-4)

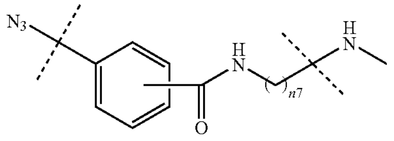

n7 = 2-6

(LK-5)

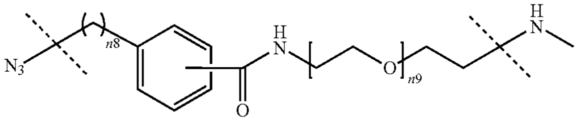

n8 = 1-4, n9 = 1-6

(LK-6)

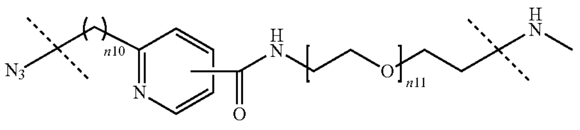

n10 = 1-4, n11 = 1-6

(LK-7)

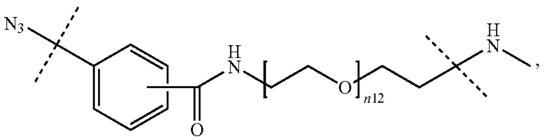

n12 = 1-6

Formula (AM-2):

(AM-2)

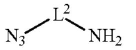

in formula (AM-2), -$L^2$- is defined as in formula (II).

10. The method for producing the alginic acid derivative of formula (II) or a salt thereof according to claim 9, wherein the condensing agent is 4-(4,6-dimethoxy-1,3,5-triazin-2-yl)-4-methyl morpholinium chloride (DMT-MM).

11. The method for producing the alginic acid derivative represented by formula (II) or a salt thereof according to claim 9, wherein a solvent in the reaction is a mixed solvent of water and a solvent selected from the ether solvents, the alcohol solvents and the polar solvents.

12. The method for producing the alginic acid derivative of formula (II) or a salt thereof according to claim 9, wherein a solvent in the reaction is a mixed solvent of water and ethanol.

13. The method for producing the alginic acid derivative of formula (II) or a salt thereof according to claim 9, wherein the condensation reaction is performed with an inorganic base or an organic base.

14. The method for producing the alginic acid derivative of formula (II) or a salt thereof according to claim 9, wherein the condensation reaction is performed with an inorganic base.

15. The method for producing the alginic acid derivative of formula (II) or a salt thereof according to claim 9, wherein the condensation reaction is performed with sodium hydrogen carbonate.

16. The method for producing the alginic acid derivative of formula (II) or a salt thereof according to claim 9, wherein the salt of alginic acid is sodium alginate.

17. The method for producing the alginic acid derivative of formula (II) or a salt thereof according to claim 9, wherein the introduction rate of the $N_3$-$L^2$-$NH_2$ group in the alginic acid derivative of formula (II) or a salt thereof is 0.1% to 30%, and -$L^2$- is defined as in claim 9.

18. The method for producing the alginic acid derivative of formula (II) or a salt thereof according to claim 9, wherein the weight-average molecular weight as measured by gel filtration chromatography of the alginic acid derivative represented by formula (II) or a salt thereof is 100,000 Da to 3,000,000 Da.

* * * * *